United States Patent
Anthony et al.

(10) Patent No.: US 11,827,610 B2
(45) Date of Patent: Nov. 28, 2023

(54) PROTOPORPHYRINOGEN OXIDASE INHIBITORS

(71) Applicant: Enko Chem, Inc., Mystic, CT (US)

(72) Inventors: Neville John Anthony, Northborough, MA (US); Paul Galatsis, Newton, MA (US); David Jeffrey Lauffer, Stow, MA (US); Peter Stchur, III, Waterford, CT (US)

(73) Assignee: Enko Chem, Inc., Mystic, CT (US)

( * ) Notice: Subject to any disclaimer, the term of this patent is extended or adjusted under 35 U.S.C. 154(b) by 0 days.

(21) Appl. No.: 18/122,583

(22) Filed: Mar. 16, 2023

(65) Prior Publication Data

US 2023/0265060 A1  Aug. 24, 2023

Related U.S. Application Data

(63) Continuation of application No. PCT/US2022/076458, filed on Sep. 14, 2022.

(60) Provisional application No. 63/400,365, filed on Aug. 23, 2022, provisional application No. 63/299,855, filed on Jan. 14, 2022, provisional application No. 63/244,586, filed on Sep. 15, 2021.

(51) Int. Cl.
*C07D 265/38* (2006.01)
*A01P 13/02* (2006.01)
*A01N 43/84* (2006.01)

(52) U.S. Cl.
CPC .......... *C07D 265/38* (2013.01); *A01N 43/84* (2013.01); *A01P 13/02* (2021.08)

(58) Field of Classification Search
None
See application file for complete search history.

(56) References Cited

U.S. PATENT DOCUMENTS

| | | | |
|---|---|---|---|
| 2,891,855 A | 6/1959 | Hans et al. |
| 3,060,084 A | 10/1962 | Littler |
| 3,235,361 A | 2/1966 | Loux |
| 3,299,566 A | 1/1967 | Macmullen |
| 3,309,192 A | 3/1967 | Luckenbaugh |
| 3,920,442 A | 11/1975 | Albert et al. |
| 4,144,050 A | 3/1979 | Frensch et al. |
| 4,172,714 A | 10/1979 | Albert |
| 4,514,574 A | 4/1985 | Inoue et al. |
| 4,761,373 A | 8/1988 | Anderson et al. |
| 4,782,086 A | 11/1988 | Lunkenheimer et al. |
| 4,816,533 A | 3/1989 | McLean et al. |
| 4,940,835 A | 7/1990 | Shah et al. |
| 5,013,659 A | 5/1991 | Bedbrook et al. |
| 5,180,587 A | 1/1993 | Moore |
| 5,188,642 A | 2/1993 | Shah et al. |
| 5,208,030 A | 5/1993 | Hoy et al. |
| 5,232,701 A | 8/1993 | Ogawa et al. |
| 5,304,732 A | 4/1994 | Anderson et al. |
| 5,561,236 A | 10/1996 | Leemans et al. |
| 5,608,147 A | 3/1997 | Kaphammer |
| 5,627,061 A | 5/1997 | Barry et al. |
| 5,633,435 A | 5/1997 | Barry et al. |
| 5,646,024 A | 7/1997 | Leemans et al. |
| 5,670,454 A | 9/1997 | Grossmann et al. |
| 5,804,425 A | 9/1998 | Barry et al. |
| 6,100,446 A | 8/2000 | Streber et al. |
| 6,153,401 A | 11/2000 | Streber et al. |
| 6,211,438 B1 | 4/2001 | Anderson et al. |
| 6,211,439 B1 | 4/2001 | Anderson et al. |
| 6,222,100 B1 | 4/2001 | Anderson et al. |
| 6,376,754 B1 | 4/2002 | Schillinger et al. |
| 6,791,014 B2 | 9/2004 | Garcon et al. |
| 7,105,724 B2 | 9/2006 | Weeks et al. |
| 7,384,967 B2 | 6/2008 | Polisetti et al. |
| 7,897,628 B2 | 3/2011 | Polisetti et al. |
| 8,063,081 B2 | 11/2011 | Polisetti et al. |
| 8,237,002 B2 | 8/2012 | Asaumi et al. |
| 8,669,208 B2 | 3/2014 | Newton et al. |
| 8,846,742 B2 | 9/2014 | Ambron et al. |

(Continued)

FOREIGN PATENT DOCUMENTS

| | | |
|---|---|---|
| CN | 1952792 A | 4/2007 |
| CN | 101463019 A | 6/2009 |

(Continued)

OTHER PUBLICATIONS

Fernandez-Moreno et al., (2018). "Abstract: A Novel Amino Acid Substitution (Arg-132-His) In Protoporphyrinogen Oxidase 2 Confers Broad Spectrum Ppo-Inhibitor Resistance In Lolium Rigidum," Weed Science Society of America (WSSA) annual meeting, 1 page.

(Continued)

*Primary Examiner* — Erin E Hirt
(74) *Attorney, Agent, or Firm* — Morrison & Foerster LLP

(57) ABSTRACT

The present invention relates to protoporphyrinogen oxidase inhibitors of the general formula (I)

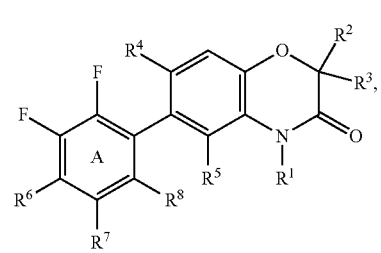

where the variables are defined herein. The invention features processes and intermediates for preparing the benzoxazinones of formula (I), compositions comprising them, and their use as herbicides—i.e. for controlling harmful plants. The invention also features methods for controlling unwanted vegetation comprising allowing an herbicidal effective amount of at least one benzoxazinone of formula (I) to act on plants, their seed, and/or their habitat.

25 Claims, 2 Drawing Sheets

(56) References Cited

U.S. PATENT DOCUMENTS

| | | | |
|---|---|---|---|
| RE45,670 E | 9/2015 | Polisetti et al. | |
| 9,220,268 B2 | 12/2015 | Witschel et al. | |
| 9,402,826 B2 | 8/2016 | Ambron et al. | |
| 9,487,529 B2 | 11/2016 | Breslin et al. | |
| 10,026,906 B2 | 7/2018 | Jung et al. | |
| 10,584,093 B2 | 3/2020 | Jia et al. | |
| 2003/0217381 A1 | 11/2003 | Croughan | |
| 2004/0158065 A1 | 8/2004 | Barth et al. | |
| 2005/0209242 A1 | 9/2005 | Chen | |
| 2006/0019967 A1 | 1/2006 | Wu et al. | |
| 2006/0094747 A1 | 5/2006 | Van Zandt et al. | |
| 2006/0141377 A1 | 6/2006 | Kuboshima et al. | |
| 2006/0160005 A1 | 7/2006 | Kuboshima et al. | |
| 2006/0224011 A1 | 10/2006 | Ishikawa et al. | |
| 2007/0054209 A1 | 3/2007 | Azuma et al. | |
| 2007/0078129 A1 | 4/2007 | Lagu et al. | |
| 2008/0153020 A1 | 6/2008 | Hamasaki et al. | |
| 2008/0293739 A1 | 11/2008 | Trede | |
| 2009/0076266 A1 | 3/2009 | Daugulis et al. | |
| 2010/0258765 A1 | 10/2010 | Dabrowski et al. | |
| 2014/0171525 A1 | 6/2014 | Yu et al. | |
| 2016/0133845 A1 | 5/2016 | Jung et al. | |
| 2016/0204353 A1 | 7/2016 | Jung et al. | |
| 2016/0206605 A1 | 7/2016 | Madden et al. | |
| 2019/0100486 A1 | 4/2019 | Jia et al. | |
| 2020/0187499 A1 | 6/2020 | Hoffmann et al. | |
| 2020/0259103 A1 | 8/2020 | Park | |
| 2020/0295269 A1 | 9/2020 | Lee et al. | |
| 2020/0313096 A1 | 10/2020 | Kim et al. | |

FOREIGN PATENT DOCUMENTS

| | | |
|---|---|---|
| CN | 102086179 A | 6/2011 |
| CN | 102153429 A | 8/2011 |
| CN | 102241553 A | 11/2011 |
| CN | 102464611 A | 5/2012 |
| CN | 102731317 A | 10/2012 |
| CN | 102898284 A | 1/2013 |
| CN | 103003240 A | 3/2013 |
| CN | 103772138 A | 5/2014 |
| CN | 104045552 A | 9/2014 |
| CN | 104046369 A | 9/2014 |
| CN | 104058909 A | 9/2014 |
| CN | 104058993 A | 9/2014 |
| CN | 104059227 A | 9/2014 |
| CN | 104262071 A | 1/2015 |
| CN | 104817438 A | 8/2015 |
| CN | 105175202 A | 12/2015 |
| CN | 105198682 A | 12/2015 |
| CN | 106146454 A | 11/2016 |
| CN | 106187656 A | 12/2016 |
| CN | 106905227 A | 6/2017 |
| CN | 107033149 A | 8/2017 |
| CN | 108484372 A | 9/2018 |
| CN | 108623439 A | 10/2018 |
| CN | 109293493 A | 2/2019 |
| CN | 109574853 A | 4/2019 |
| CN | 109796349 A | 5/2019 |
| CN | 110240593 A | 9/2019 |
| CN | 110683925 A | 1/2020 |
| CN | 112094165 A | 12/2020 |
| CN | 112552279 A | 3/2021 |
| DE | 3246493 A1 | 6/1984 |
| DE | 4323916 A1 | 1/1995 |
| EP | 1707263 A1 | 10/2006 |
| EP | 3051352 A1 | 8/2016 |
| FR | 2846656 A1 | 5/2004 |
| GB | 2095558 A | 10/1982 |
| JP | 05017433 A | 1/1993 |
| JP | 06-321920 A | 11/1994 |
| JP | 2004189599 A | 7/2004 |
| JP | 2005330204 A | 12/2005 |
| JP | 2006036752 A | 2/2006 |
| JP | 2006151946 A | 6/2006 |
| JP | 2006305558 A | 11/2006 |
| JP | 2006306758 A | 11/2006 |
| JP | 2007121819 A | 5/2007 |
| JP | 2007147824 A | 6/2007 |
| JP | 2007187787 A | 7/2007 |
| JP | 2007199271 A | 8/2007 |
| JP | 2007206130 A | 8/2007 |
| JP | 2007238448 A | 9/2007 |
| JP | 2007248733 A | 9/2007 |
| JP | 2007256768 A | 10/2007 |
| JP | 2007316097 A | 12/2007 |
| JP | 2007316099 A | 12/2007 |
| JP | 2008050281 A | 3/2008 |
| JP | 2008115142 A | 5/2008 |
| JP | 2008203766 A | 9/2008 |
| JP | 2009023986 A | 2/2009 |
| JP | 2009298727 A | 12/2009 |
| JP | 2010138088 A | 6/2010 |
| JP | 2010208977 A | 9/2010 |
| JP | 2012201602 A | 10/2012 |
| JP | 2013023466 A | 2/2013 |
| JP | 2015100999 A | 2/2015 |
| JP | 2017002002 A | 1/2017 |
| JP | 2020158422 A | 10/2020 |
| KR | 20150136294 A | 12/2015 |
| KR | 20160075059 A | 7/2016 |
| WO | WO-1991013546 A1 | 9/1991 |
| WO | WO-1993010095 A1 | 5/1993 |
| WO | WO-1995002580 A2 | 1/1995 |
| WO | WO-1995004049 A1 | 2/1995 |
| WO | WO-1996038567 A2 | 12/1996 |
| WO | WO-1997049816 A1 | 12/1997 |
| WO | WO-2002042275 A1 | 5/2002 |
| WO | WO-2003019696 A2 | 3/2003 |
| WO | WO-2003024222 A1 | 3/2003 |
| WO | WO-2004002481 A1 | 1/2004 |
| WO | WO-2004017920 A2 | 3/2004 |
| WO | WO-2004055191 A1 | 7/2004 |
| WO | WO-2005005382 A2 | 1/2005 |
| WO | WO-2005020673 A1 | 3/2005 |
| WO | WO-2005049620 A1 | 6/2005 |
| WO | WO-2005060692 A2 | 7/2005 |
| WO | WO-2005060956 A1 | 7/2005 |
| WO | WO-2005062847 A2 | 7/2005 |
| WO | WO-2005092326 A1 | 10/2005 |
| WO | WO-2005107437 A2 | 11/2005 |
| WO | WO-2006020358 A2 | 2/2006 |
| WO | WO-2006025783 A1 | 3/2006 |
| WO | WO-2006055625 A2 | 5/2006 |
| WO | WO-2006058648 A2 | 6/2006 |
| WO | WO-2006060634 A2 | 6/2006 |
| WO | WO-2006076529 A1 | 7/2006 |
| WO | WO-2006080884 A1 | 8/2006 |
| WO | WO-2006084663 A1 | 8/2006 |
| WO | WO-2006089221 A2 | 8/2006 |
| WO | WO-2006107115 A1 | 10/2006 |
| WO | WO-2006122926 A1 | 11/2006 |
| WO | WO-2007020381 A2 | 2/2007 |
| WO | WO-2007038452 A1 | 4/2007 |
| WO | WO-2007051408 A1 | 5/2007 |
| WO | WO-2007052516 A1 | 5/2007 |
| WO | WO-2007064809 A2 | 6/2007 |
| WO | WO-2007082873 A1 | 7/2007 |
| WO | WO-2007082878 A1 | 7/2007 |
| WO | WO-2007082880 A1 | 7/2007 |
| WO | WO-2007082882 A1 | 7/2007 |
| WO | WO-2007095586 A2 | 8/2007 |
| WO | WO-2007138089 A1 | 12/2007 |
| WO | WO-2007142206 A1 | 12/2007 |
| WO | WO-2008024963 A1 | 2/2008 |
| WO | WO-2008037266 A1 | 4/2008 |
| WO | WO-2008047707 A1 | 4/2008 |
| WO | WO-2008051633 A2 | 5/2008 |
| WO | WO-2008122603 A2 | 10/2008 |
| WO | WO-2008150093 A2 | 12/2008 |
| WO | WO-2008156656 A2 | 12/2008 |
| WO | WO-2009025484 A2 | 2/2009 |
| WO | WO-2009027679 A1 | 3/2009 |
| WO | WO-2009101082 A1 | 8/2009 |
| WO | WO-2009136646 A1 | 11/2009 |

(56) References Cited

FOREIGN PATENT DOCUMENTS

| | | |
|---|---|---|
| WO | WO-2009144159 A1 | 12/2009 |
| WO | WO-2009156359 A2 | 12/2009 |
| WO | WO-2010072632 A1 | 7/2010 |
| WO | WO-2010136144 A1 | 12/2010 |
| WO | WO-2011085221 A2 | 7/2011 |
| WO | WO-2011099832 A2 | 8/2011 |
| WO | WO-2011160548 A1 | 12/2011 |
| WO | WO-2012041789 A1 | 4/2012 |
| WO | WO-2012059050 A1 | 5/2012 |
| WO | WO-2012080975 A1 | 6/2012 |
| WO | WO-2012125603 A1 | 9/2012 |
| WO | WO-2013032907 A1 | 3/2013 |
| WO | WO-2013093497 A1 | 6/2013 |
| WO | WO-2013144628 A1 | 10/2013 |
| WO | WO-2013155047 A2 | 10/2013 |
| WO | WO-2014030090 A1 | 2/2014 |
| WO | WO-2014186450 A2 | 11/2014 |
| WO | WO-2015003146 A1 | 1/2015 |
| WO | WO-2015022636 A2 | 2/2015 |
| WO | WO-2015022639 A2 | 2/2015 |
| WO | WO-2015022640 A2 | 2/2015 |
| WO | WO-2015025960 A1 | 2/2015 |
| WO | WO-2015054120 A1 | 4/2015 |
| WO | WO-2015064326 A1 | 5/2015 |
| WO | WO-2015071087 A1 * | 5/2015 ............... A01C 1/06 |
| WO | WO-2015082411 A1 | 6/2015 |
| WO | WO-2015092706 A1 | 6/2015 |
| WO | WO-2015115556 A1 | 8/2015 |
| WO | WO-2015134973 A1 | 9/2015 |
| WO | WO-2015191988 A1 | 12/2015 |
| WO | WO-2016203377 A1 | 12/2016 |
| WO | WO-2017023778 A1 | 2/2017 |
| WO | WO-2017039969 A1 | 3/2017 |
| WO | WO-2017087672 A1 | 5/2017 |
| WO | WO-2017112589 A1 | 6/2017 |
| WO | WO-2017174207 A1 | 10/2017 |
| WO | WO-2017198859 A1 | 11/2017 |
| WO | WO-2018019860 A1 | 2/2018 |
| WO | WO-2018022777 A1 | 2/2018 |
| WO | WO-2019106156 A1 | 6/2019 |
| WO | WO-2020097408 A1 | 5/2020 |
| WO | WO-2020226150 A1 | 11/2020 |
| WO | WO-2021049470 A1 | 3/2021 |
| WO | WO-2023001679 A1 | 1/2023 |

OTHER PUBLICATIONS

Fu et al., (2014). "Hot Fusion: An Efficient Method to Clone Multiple DNA Fragments as Well as Inverted Repeats without Ligase," PLoS One, 9(12):e115318, 20 pages.

Giacomini et al., (2017). "Two New PPX2 Mutations Associated with Resistance to PPO-Inhibiting Herbicides in *Amaranthus palmeri*," Pest Management Science, 73:1559-1563, 16 pages.

Hao et al., (2011). "Protoporphyrinogen oxidase inhibitor: an ideal target for herbicide discovery," Chimia, 65(12):961-969.

International Search Report and Written Opinion received for International Patent Application No. PCT/US2022/076458 dated Dec. 8, 2022, 14 pages.

Jacobs et al., (1982). "Assay for enzymatic protoporphyrinogen oxidation, a late step in heme-synthesis," Enzyme, 28:206-217.

Jiang et al., (2013). "Grafting Imparts Glyphosate Resistance in Soybean," Weed Technology, 27:412-416.

Lee et al., (1993). "Cellular Localization of Protoporphyrinogen-Oxidizing Activities of Etiolated Barley (*Hordeum vulgare* L.) Leaves (Relationship to Mechanism of Action of Protoporphyrinogen Oxidase-Inhibiting Herbicides)," Plant Physiology, 102(3):881-889.

Li et al., (2005). "Development of PPO inhibitor-resistant cultures and crops," Pest Management Science, 61:277-285. Abstract Only.

Matringe et al., (1989). "Protoporphyrinogen oxidase as a molecular target for diphenyl ether herbicides," Biochemistry Journal, 260(1):231-235.

Patzoldt et al., (2006). "A codon deletion confers resistance to herbicides inhibiting protoporphyrinogen oxidase," Proc. Natl. Acad. Sci. USA, 103:12329-12334.

Rangani et al., (2018). "A Novel Mutation in Protoporphyrinogen Oxidase IX (PPO) Confers Broad Resistance to PPO inhibitors," Weed Science Society of America (WSSA) annual meeting, 1 page.

Rousonelos et al., (2012). "Characterization of a common ragweed (*Ambrosia artemisiifolia*) population resistant to ALS- and PPO-inhibiting herbicides," Weed Sci., 60(3):335-344.

Shoup et al., (2003). "Common waterhemp (*Amaranthus rudis*) resistance to protoporphyrinogen oxidase-inhibiting herbicides," Weed Sci., 51:145-150.

Artamkina et al., (1998). "The Reaction of the [CpFe(CO)2]— Anion with Pentafluorochlorobenzene: Nucleophilic Aromatic Substitution by Halogen-Metal Exchange," A European Journal, 4(7):1169-1178. Abstract Only.

Breslin et al., (2012). "Design, Synthesis, and Anaplastic Lymphoma Kinase (ALK) Inhibitory Activity for a Novel Series of 2,4,8,22-Tetraazatetracyclo[14.3.1.13,7.19, 13]docosa-1(20),3(22),4,6,9(21), 10, 12, 16, 18-nonaene Macrocycles," Journal of Medicinal Chemistry, 55(1):449-464. Abstract Only.

Chen et al., (2005). "Design, synthesis, and biological evaluation of N-acetyl-2-carboxybenzenesulfonamides: a novel class of cyclooxygenase-2 (COX-2) inhibitors," Bioorganic & medicinal Chemistry, 13(7):2459-2468. Abstract Only.

DiMauro et al., (2016). "Application of a Parallel Synthetic Strategy in the Discovery of Biaryl Acyl Sulfonamides as Efficient and Selective Nav1.7 Inhibitors," Journal of Medicinal Chemistry, 59(17):7818-7839. Abstract Only.

Lin et al., (1977). "Decomposition and byproducts from reactions involving pentafluorophenyl-grignard and lithium reagents. a GC/MS study," Journal of Fluorine Chemistry, 9(2):161-9. Abstract Only.

Nikul'shin et al., (2021). "Synthesis of Bromochloropolyfluorobiphenyls Containing Bromine and Chlorine Atoms in the 4 and 4,4' Positions," Russian Journal of General Chemistry, 91(7):1316-1324. 10 pages. Abstract Only.

* cited by examiner

Compound 2      920-4      920-6

Compound 2      920-4      920-6

PROTOPORPHYRINOGEN OXIDASE INHIBITORS

CROSS-REFERENCE TO RELATED APPLICATIONS

This application is a continuation application of PCT/US2022/076458, which claims priority to U.S. Provisional Patent Application No. 63/244,586, filed Sep. 15, 2021, U.S. Provisional Patent Application No. 63/299,855, filed Jan. 14, 2022, and U.S. Provisional Patent Application No. 63/400,365, filed Aug. 23, 2022, each of which is incorporated herein by reference in its entirety

FIELD

The present invention relates to protoporphyrinogen IX oxidase (PPO) inhibitors useful as herbicides. In particular, the present invention relates to certain benzoxazinone compounds, including for example 5-tetrafluorophenyl benzoxazinone and 6-pentafluorophenyl benzoxazinone; compositions comprising such compounds; processes for making such compounds and compositions; and methods for using such compounds for crop protection and to control unwanted vegetation.

BACKGROUND

Herbicides that inhibit protoporphyrinogen oxidase (hereinafter referred to as Protox or PPO; EC:1.3.3.4), a key enzyme in the biosynthesis of protoporphyrin IX, have been used for selective weed control since the 1960s. PPO catalyzes the last common step in chlorophyll and heme biosynthesis, which is the oxidation of protoporphyrinogen IX to protoporphyrin IX [Matringe M. et al., Protoporphyrinogen oxidase as a molecular target for diphenyl ether herbicides, *Biochemistry Journal* (1989) 260: 231-235]. Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death [Lee H. J. et al., Cellular localization of protoporphyrinogen-oxidizing activities of etiolated barley leaves, *Plant Physiology* (1993) 102: 881].

To date, thousands of PPO inhibitors have been reported in the literature, with about 30 currently used as herbicides to decimate weeds in fields [Hao, G. F., et al., Protoporphyrinogen oxidase inhibitor: an ideal target for herbicide discovery, *Chimia* (2011) 961-969]. PPO-inhibiting herbicides include many different structural classes of molecules, including diphenyl ethers (e.g. lactofen, acifluorfen, acifluorfen methyl ester, or oxyfluorfen); oxadiazoles (e.g. oxadiazon); cyclic imides [e.g. S-23142, N-(4-chloro-2-fluoro-5-propargyloxyphenyl)-3,4,5,6-tetrahydrophthalimide, chlorophthalim, N-(4-chlorophenyl)-3,4,5,6-tetrahydrophthalimide)]; phenyl pyrazoles (e.g. TNPP-ethyl, ethyl 2-[1-(2,3,4-trichlorophenyl)-4-nitropyrazolyl-5-oxy]propionate, M&B 39279); pyridine derivatives (e.g. LS 82-556); and phenopylate and its O-phenylpyrrolidino- and piperidinocarbamate analogs (Kramer W., ed., *Modern Crop Protection Compounds*, 2$^{nd}$ Ed., Vol 1: *Herbicides*, (2012) Wiley-VCH, Weinheim, Germany). Many of these compounds competitively inhibit the normal reaction catalyzed by the enzyme, apparently acting as substrate analogs.

The herbicidal properties of these known compounds towards harmful plants, however, are not always entirely satisfactory. Herbicide resistant weeds present a serious problem for efficient weed control because such resistant weeds are increasingly widespread and thus weed control by the application of herbicides is no longer effective, causing a huge problem to farmers. Resistance to PPO herbicides has been slow to evolve (about four decades from first commercialization), and to date has been confirmed in 13 weed species [Heap I, *The International Survey of Herbicide Resistant Weeds*. Available online: http://www.weedscience.org/ (October 2019)]. The first weed to evolve resistance to PPO herbicides was waterhemp (*Amaranthus tuberculatus*) in 2001 [Shoup D. E., et al., Common waterhemp (*Amaranthus rudis*) resistance to protoporphyrinogen oxidase-inhibiting herbicides *Weed Sci.* (2003) 51:145-150]. Resistance to PPO herbicides in weedy species has been attributed to target-site mutation in the PPX2 gene. For example, a unique target-site amino acid deletion ($Gly_{210}$) and Arg98Leu substitution confer PPO resistance in waterhemp [Patzoldt W. L., et al., A codon deletion confers resistance to herbicides inhibiting protoporphyrinogen oxidase. *Proc. Natl. Acad. Sci. USA* (2006) 103:12329-12334] and common ragweed [Rousonelos, et al., Characterization of a common ragweed (*Ambrosia artemisiifolia*) population resistant to ALS- and PPO-inhibiting herbicides, *Weed Sci.* (2012) 60:335-344], respectively.

Thus, there is a need for novel methods to effectively control weeds, including herbicide resistant weeds and in particular PPO resistant weeds, which at the same time is tolerated by the useful plants (crops) in question.

BRIEF SUMMARY

In some aspects, provided herein are novel PPO inhibitors that have high herbicidal activity, even at low application rates. In some embodiments, improved leaf and root penetration, improved translocation, improved spectrum, and selectivity are achieved by the benzoxazinones of the invention, defined below, and by their agriculturally suitable salts and formulations.

Accordingly, in one aspect, provided are benzoxazinones having formula I:

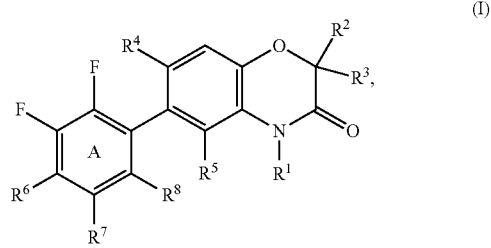

or a salt thereof, wherein Ring A and $R^1$-$R^8$ are as defined herein. In some embodiments, Ring A contains at least 4 F atom substituents.

In certain embodiments, provided are benzoxazinones having formula II:

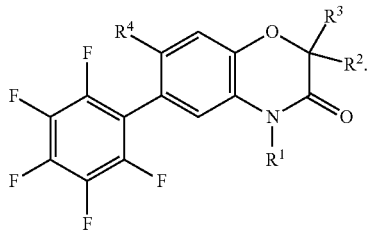

or a salt thereof, wherein $R^1$-$R^4$ as are defined herein.

In certain embodiments, provided are benzoxazinones having formula III:

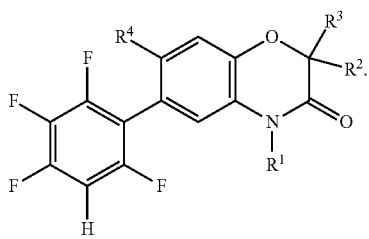

or a salt thereof, wherein $R^1$-$R^4$ as are defined herein.

In certain embodiments, provided are benzoxazinones having formula IV:

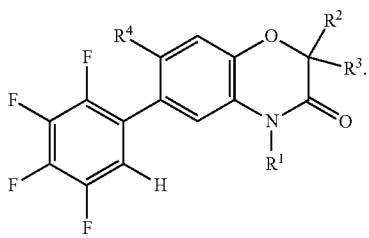

or a salt thereof, wherein $R^1$-$R^4$ as are defined herein.

In other aspects, provided is also an agricultural composition (including, in some variations, herbicidal compositions) that includes a compound of formulas I, II, III, or IV, or a salt thereof, in a herbicidally effective amount and at least one component selected from the group consisting of surfactants, solid diluents and liquid diluents (e.g., formulations). In some variations, the salt is an agriculturally suitable salt. In some embodiments, the composition optionally further includes at least one additional active ingredient. In one variation, the additional active ingredient may be an herbicide and/or herbicide safener.

In yet another aspect, provided are also processes for making the above-identified compounds, salts, and compositions.

In certain aspects, provided are compounds that are intermediates for making one or more compounds of the invention, including one or more compounds of Table 1, or a salt thereof.

In yet other aspects, provided are also methods for controlling the growth of undesired vegetation comprising contacting the vegetation or its environment with a herbicidally effective amount of a compound of the invention, its salt, or a composition that includes a compound of the invention as described herein.

BRIEF DESCRIPTION OF THE FIGURES

The present application can be understood by reference to the following description taken in conjunction with the accompanying figures.

In FIG. 1A, for each compound, 2 six-plant trays are represented. Plants on the left side of the tray were treated with penetrant (COC) and on the right side were treated without COC. In FIG. 1B, the effect of 3×2 µL droplets without penetrant on the adaxial surface of emerged *Setaria Italica* leaf for Compound 2, compound 920-4, and compound 920-6.

DETAILED DESCRIPTION

Benzoxazinone Compounds

Figure 1A:
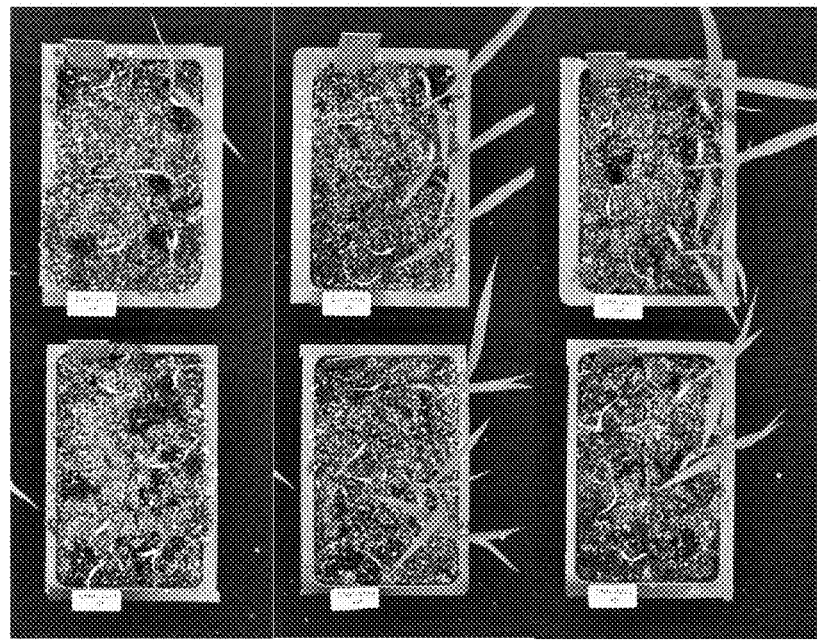
FIGS. 1A and 1B show percent growth inhibition, necrosis at application, xylem, and phloem mobility for compounds of the invention vs. known compounds.
Figure 1B:

In one aspect, provided are benzoxazinones having formula I:

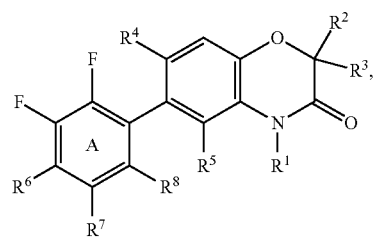

or a suitable salt thereof, wherein:
$R^1$ is H or alkyl optionally substituted with $R^{1a}$, phenyl, or benzyl, wherein each of said alkyl, phenyl or benzyl is optionally substituted with up to 3 halo atoms, an OH group, or an group;
$R^{1a}$ is

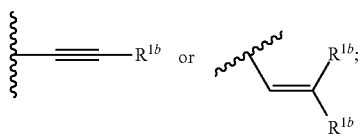

each $R^{1b}$ is, independently, H, alkyl, or cyclopropyl;
each of $R^2$ and $R^3$ is, independently, H, Cl, F, alkyl, or $R^2$ and $R^3$ together with the intervening carbon is cyclopropyl;
$R^4$ is H or F;
$R^5$ is H or F;

each of $R^6$ and $R^7$ is, independently, halo, H, alkyl, alkenyl, OH, O-alkyl, O-cyclopropyl, $OCH_2CCH$, $NHCH_2Ph$, $N(R^x)_2$, or S-(alkyl),
 wherein the alkyl is optionally substituted with at least one —OH;

$R^8$ is H or halo;

each $R^x$ is, independently, H, alkyl, or C(O)alkyl; and wherein Ring A contains at least 4 halo substituents.

In some variations of the foregoing:

$R^1$ is H or C1-4alkyl optionally substituted with $R^{1a}$, phenyl, or benzyl, wherein each of said alkyl, phenyl or benzyl is optionally substituted with up to 3 F atoms, an OH group, or an $OC_{1-4}$alkyl group;

$R^{1a}$ is

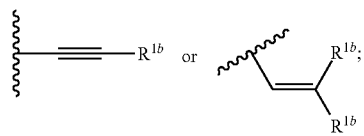

each $R^{1b}$ is, independently, H, $C_{1-4}$alkyl, or cyclopropyl;

each of $R^2$ and $R^3$ is, independently, H, Cl, F, $CH_3$, or $R^2$ and $R^3$ together with the intervening carbon is cyclopropyl;

$R^4$ is H, Cl or F;

$R^5$ is H or F;

each of $R^6$ and $R^7$ is, independently, F, H, $C_{1-2}$alkyl, alkenyl, OH, $OC_{1-2}$alkyl, O-cyclopropyl, $OCH_2CCH$, $NHCH_2Ph$, $N(R^x)_2$, or $SCH_3$,
 wherein the $C_{1-2}$alkyl is optionally substituted with at least one —OH;

$R^8$ is H or F;

each $R^x$ is, independently, H, $CH_3$, or $C(O)CH_3$; and wherein Ring A contains at least 4 F atom substituents.

In one embodiment, each of $R^2$, $R^3$, and $R^4$ of a compound of formula I is F. In another embodiment, each of $R^2$, $R^3$, and $R^4$ of a compound of formula I is F, and $R^1$ is $CH_2CCH$ (i.e., $C_{1-4}$alkyl substituted with lea, wherein $R^{1a}$ is

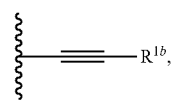

and $R^{1b}$ is H).

In some variations, each of $R^2$ and $R^3$ is, independently, H, F, $CH_3$, or $R^2$ and $R^3$ together with the intervening carbon is cyclopropyl.

In some variations, each of $R^4$ and $R^5$ is, independently, H or F.

In another further embodiment, each of $R^2$ and $R^3$ in a compound of formula I is H and $R^4$ is F.

In one embodiment, each of $R^2$ and $R^3$ in a compound of formula I is F, and each of $R^4$ and $R^5$ is H.

In certain variations, each of $R^6$ and $R^7$ is, independently, F, H, $C_{1-2}$alkyl optionally substituted with OH, alkenyl, OH, $OC_{1-2}$alkyl, O-cyclopropyl, $OCH_2CCH$, $NHCH_2Ph$, $N(R^x)_2$, or $SCH_3$. In one variation, each of $R^6$ and $R^7$ is, independently, F, H, $C_{1-2}$alkyl, alkenyl, OH, $OC_{1-2}$alkyl, $N(R^x)_2$, $N(R^x)C(O)CH_3$, or $SCH_3$.

In some variations, each IV is, independently, H or $CH_3$.

In another embodiment, the invention features benzoxazinones having formula II:

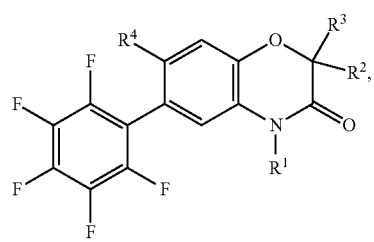

(II)

or a salt thereof.

In a further embodiment, each of $R^2$, $R^3$, and $R^4$ in a compound of formula II is F. In another embodiment, each of $R^2$, $R^3$, and $R^4$ of a compound of formula II is F, and $R^1$ is $CH_2CCH$ (i.e., $C_{1-4}$alkyl substituted with $R^{1a}$, wherein $R^{1a}$ is

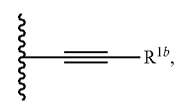

and $R^{1b}$ is H).

In another further embodiment, each of $R^2$ and $R^3$ in a compound of formula II is H and $R^4$ is F.

In another embodiment, the invention features benzoxazinones having formula II:

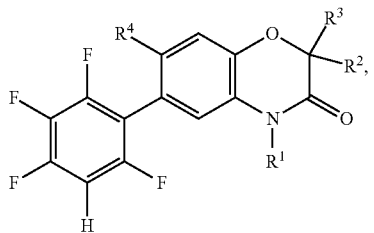

(III)

or a salt thereof.

In a further embodiment, each of $R^2$, $R^3$, and $R^4$ of a compound of formula III is F. In another embodiment, each of $R^2$, $R^3$, and $R^4$ of a compound of formula III is F, and $R^1$ is $CH_2CCH$ (i.e., $C_{1-4}$alkyl substituted with $R^{1a}$, wherein $R^{1a}$ is

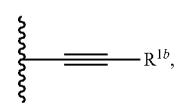

and $R^{1b}$ is H).

In another further embodiment, each of $R^2$ and $R^3$ in a compound of formula III is H and $R^4$ is F.

In another embodiment, the invention features benzoxazinones having formula IV:

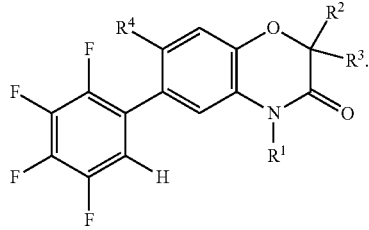

(IV)

or a salt thereof.

In a further embodiment, each of $R^2$, $R^3$, and $R^4$ in a compound of formula IV is F. In another embodiment, each of $R^2$, $R^3$, and $R^4$ of a compound of formula IV is F, and $R^1$ is $CH_2CCH$ (i.e., $C_{1-4}$alkyl substituted with $R^{1a}$, wherein $R^{1a}$ is

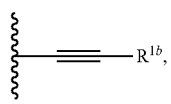

and $R^{1b}$ is H).

In another further embodiment, each of $R^2$ and $R^3$ in a compound of formula IV is H and $R^4$ is F.

In one aspect, the compounds of formula (I) are 6-pentafluorophenyl benzoxazinones.

In some variations of the foregoing, the salt may be an agriculturally suitable salt. In certain variations, the agriculturally suitable salt is a salt that exhibits herbicidal activity, or that is or can be converted in plants, water, or soil into a compound or salt with herbicidal activity.

In some aspects, provided is a compound selected from the compounds listed in Table 1 below, or a salt thereof (including an agriculturally suitable salt thereof).

TABLE 1

Exemplary Compounds

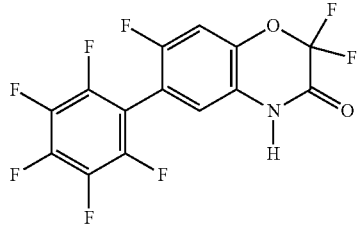 [SMILES: O=C1Nc2cc(-c3c(F)c(F)c(F)c(F)c3F)c(F)cc2OC1(F)F]

1

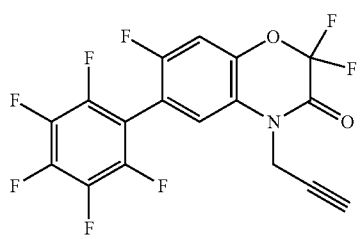 [SMILES: C#CCN1C(=O)C(F)(F)Oc2cc(F)c(-c3c(F)c(F)c(F)c(F)c3F)cc21]

2

TABLE 1-continued

Exemplary Compounds

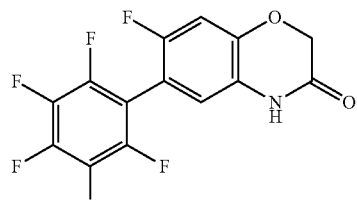

3

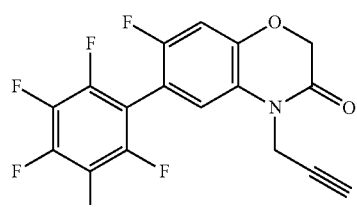

4

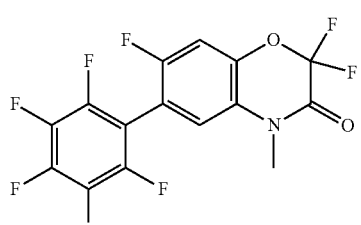

5

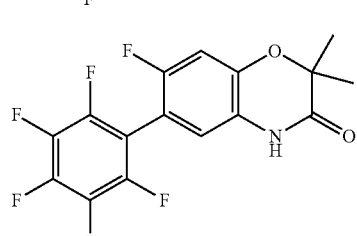

6

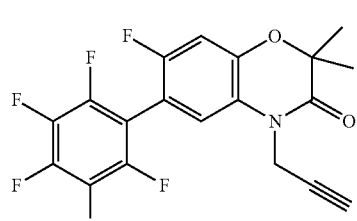

7

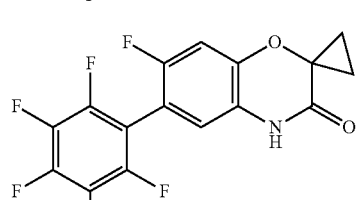

8

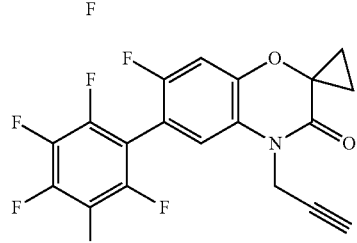

9

TABLE 1-continued
Exemplary Compounds
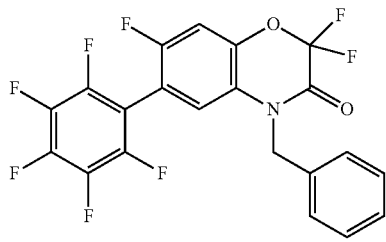 [SMILES: O=C1N(Cc2ccccc2)c2cc(-c3c(F)c(F)c(F)c(F)c3F)c(F)cc2OC1(F)F] 10
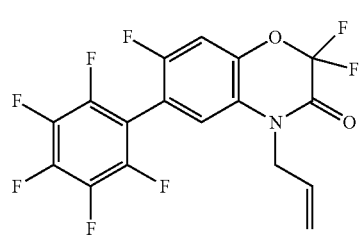 [SMILES: C=CCN1C(=O)C(F)(F)Oc2cc(F)c(-c3c(F)c(F)c(F)c(F)c3F)cc21] 11
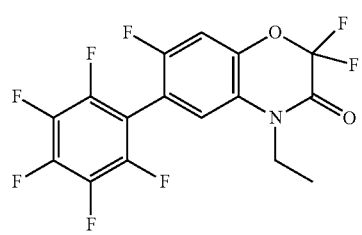 [SMILES: CCN1C(=O)C(F)(F)Oc2cc(F)c(-c3c(F)c(F)c(F)c(F)c3F)cc21] 12
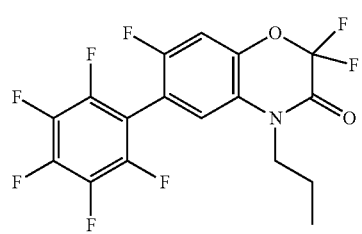 [SMILES: CCCN1C(=O)C(F)(F)Oc2cc(F)c(-c3c(F)c(F)c(F)c(F)c3F)cc21] 13
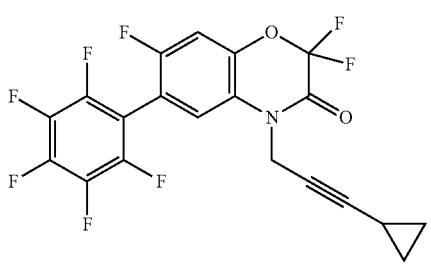 [SMILES: O=C1N(CC#CC2CC2)c2cc(-c3c(F)c(F)c(F)c(F)c3F)c(F)cc2OC1(F)F] 14
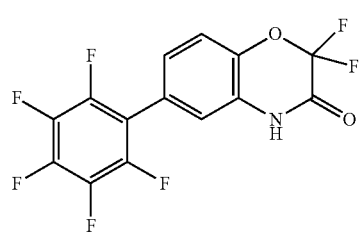 [SMILES: O=C1Nc2cc(-c3c(F)c(F)c(F)c(F)c3F)ccc2OC1(F)F] 15
TABLE 1-continued
Exemplary Compounds
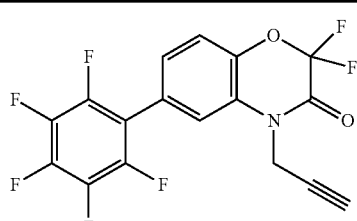 16
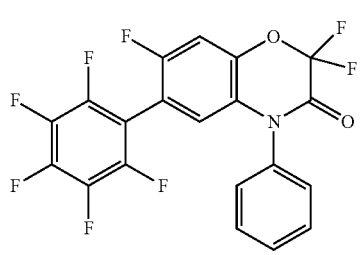 [SMILES: O=C1N(c2ccccc2)c2cc(-c3c(F)c(F)c(F)c(F)c3F)c(F)cc2OC1(F)F] 17
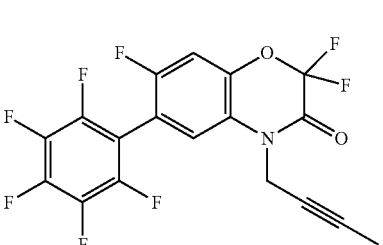 18
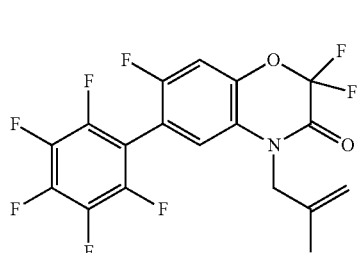 19
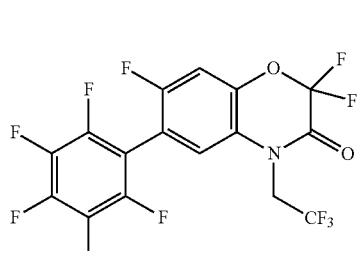 20
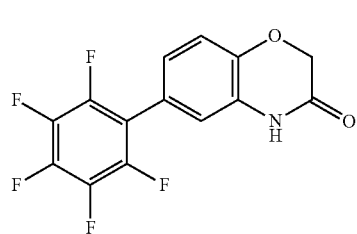 [SMILES: O=C1COc2ccc(-c3c(F)c(F)c(F)c(F)c3F)cc2N1] 21

TABLE 1-continued

Exemplary Compounds

| No. | Structure |
|---|---|
| 22 | (structure) |
| 23 | (structure) |
| 24 | (structure) |
| 25 | (structure) |
| 26 | (structure) |
| 27 | (structure) |
| 28 | (structure) |
| 29 | (structure) |
| 30 | (structure) |
| 31 | (structure) |
| 32 | (structure) |
| 33 | (structure) |
| 34 | (structure) |

TABLE 1-continued

Exemplary Compounds

TABLE 1-continued

Exemplary Compounds

TABLE 1-continued

Exemplary Compounds

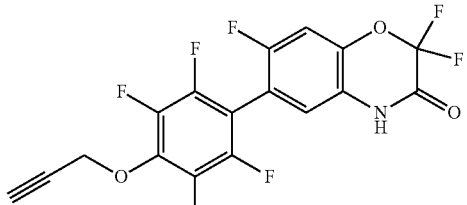

In some variations, provided is Compound 1-53 or 56-68, or a salt thereof (including an agriculturally suitable salt thereof). In some variations, provided is Compound 1-29, or a salt thereof (including an agriculturally suitable salt thereof). In some variations, provided is Compound 1-62, or a salt thereof (including an agriculturally suitable salt thereof). In one variation, provided is Compound 2, or a salt thereof (including an agriculturally suitable salt thereof). In another variation, provided is Compound 37, or a salt thereof (including an agriculturally suitable salt thereof). In another variation, provided is Compound 52, or a salt thereof (including an agriculturally suitable salt thereof).

Definitions

As used herein, the terms "comprises," "comprising," "includes," "including," "has," "having," "contains," "containing," "characterized by," or any other variation thereof, are intended to cover a non-exclusive inclusion, subject to any limitation explicitly indicated. For example, a composition, mixture, process, or method that includes or comprises a list of elements is not necessarily limited to only those elements but may include other elements not expressly listed or inherent to such composition, mixture, process, or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

Further, unless expressly stated to the contrary, "or" refers to an inclusive 'or' and not to an exclusive 'or.' For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an"

should be read to include one or at least one, and the singular word form of the element or component also includes the plural unless the number is obviously meant to be singular.

As referred to herein, the term "seedling," used either alone or in a combination of words means a young plant developing from the embryo of a seed.

As referred to herein, the term "broadleaf," used either alone or in terms such as "broadleaf weed" means dicot or dicotyledon, a term used to describe a group of angiosperms characterized by embryos having two cotyledons.

In the above recitations, the term "alkyl," used either alone or in compound words such as "alkylthio" or "haloalkyl" includes straight-chain or branched alkyl, such as, methyl, ethyl, n-propyl, i-propyl, or the different butyl, pentyl, or hexyl isomers. "Alkenyl" includes straight-chain or branched alkenes such as ethenyl, 1-propenyl, 2-propenyl, and the different butenyl, pentenyl, and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl, and the different butynyl, pentynyl, and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy, and hexyloxy isomers.

"Cycloalkyl" includes, for example, cyclopropyl, cyclobutyl, cyclopentyl, and cyclohexyl.

The term "halogen" or "halo" either alone or in compound words such as "haloalkyl," or when used in descriptions such as "alkyl substituted with halogen" includes fluorine, chlorine, bromine, or iodine.

The total number of carbon atoms in a substituent group is indicated by the "$C_i$-$C_j$" or "$C_{i-j}$" prefix, where i and j are numbers from 1 to 10. For example, $C_{1-4}$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$—, or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a compound is substituted with a substituent bearing a subscript that indicates the number of said substituents can exceed 1, the substituents (when they exceed 1) are independently selected from the group of defined substituents, e.g., $(R^1)_m$, where m is 0, 1, 2 or 3. Further, when the subscript indicates a range, e.g. $(R)_{i-j}$, then the number of substituents may be selected from the integers between 'i' and 'j' inclusive. When a group contains a substituent, which can be hydrogen (H), for example, then when this substituent is taken as hydrogen, it is recognized that this is equivalent to the group being unsubstituted. When a variable group is shown to be optionally attached to a position, then hydrogen may be at the position even if not recited in the variable group definition. When one or more positions on a group are said to be "not substituted" or "unsubstituted," then hydrogen atoms are attached to take up any free valency.

Unless otherwise indicated, a "ring" or "ring system" as a component of a compound of the invention, is carbocyclic or heterocyclic.

"Aromatic" indicates that each of the ring atoms is essentially in the same plane and has a p-orbital perpendicular to the ring plane, and that (4n+2) π electrons, where n is a positive integer, are associated with the ring to comply with Hackers rule. The term "aromatic ring system" denotes a carbocyclic or heterocyclic ring system in which at least one ring of the ring system is aromatic.

The term "nonaromatic ring system" denotes a carbocyclic or heterocyclic ring system that may be fully saturated, as well as partially or fully unsaturated, provided that none of the rings in the ring system are aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "acceptable salt" or "salt" when related to a compound of the invention includes cations or anions. Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl, or benzyl— preferably ammonium, methylammonium, isopropylammonium, dimethyl ammonium, diethylammonium, diisopropylammonium, trimethylammonium, triethylammonium, tris (isopropyl)ammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzylthmethylammonium, benzyltriethylammonium, N,N,N-trimethyl ethanol ammonium (choline salt), furthermore phosphonium ions, sulfonium ions, preferably tri($C_1$-$C_4$-alkyl)sulfonium, such as trimethylsulfonium, and sulfoxonium ions, preferably tri ($C_1$-$C_4$-alkyl)sulfoxonium, and finally the salts of polybasic amines such as N,N-bis-(3-aminopropyl)methylamine, and diethylenetriamine.

Anions of useful acid addition salts are primarily chloride, bromide, fluoride, iodide, hydrogensulfate, methyl sulfate, sulfate, dihydrogenphosphate, hydrogenphosphate, nitrate, bicarbonate, carbonate, hexafluorosilicate, hexafluorophosphate, benzoate, and also the anions of $C_1$-$C_4$-alkanoic acids—preferably formate, acetate, propionate, and butyrate.

As used herein, the terms "undesirable vegetation" and "harmful plants" are synonyms.

Preparation of Compounds of the Invention

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve-volume set of *Comprehensive Heterocyclic Chemistry* II, A. R. Katritzky, C. W. Rees and E. F. V. Scriven editors-in-chief, Pergamon Press, Oxford, 1996.

Compounds of the invention can exist as one or more stereoisomers. The various stereoisomers include enantiomers, diastereomers, atropisomers, and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. For a comprehensive discussion of all aspects of stereoisomerism, see Ernest L. Eliel and Samuel H. *Stereochemistry of Organic Compounds*, John Wiley & Sons, New York, 1994. Compounds of the invention typically exist in more than one form, and the formulas of the invention thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical, and biological properties as crystal shape, density, hardness, color, chemical stability, melting point, hygroscopicity, suspensibility, dissolution rate, and biological availability. One skilled in the art will appreciate that a polymorph of a compound of the invention can exhibit beneficial effects (e.g., suitability for preparation of useful formulations, improved biological performance) relative to another polymorph or a mixture of polymorphs of the same compound. Preparation and isolation of a particular polymorph of a compound of a compound of the invention can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art recognizes that because in the environment and under physiological conditions salts of chemical compounds are in equilibrium with their corresponding nonsalt forms, salts share the biological utility of the nonsalt forms. Thus, a wide variety of salts of compounds of the invention are useful for control of undesired vegetation (i.e. are agriculturally suitable). The salts of compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic, or valeric acids. When a compound of the invention contains an acidic moiety such as a carboxylic acid or phenol, salts also include those formed with organic or inorganic bases such as pyridine, triethylamine, or ammonia, or amides, hydrides, hydroxides or carbonates of sodium, potassium, lithium, calcium, magnesium, or barium.

Moreover, the invention features processes and intermediates for preparing compounds of the invention. These compounds can be prepared by general methods known in the art of synthetic organic chemistry. One or more of the following methods and variations as described in Schemes 1a, 1b, & 2 can be used.

In one general example, the compounds of formula I can be prepared as shown in Scheme 1a.

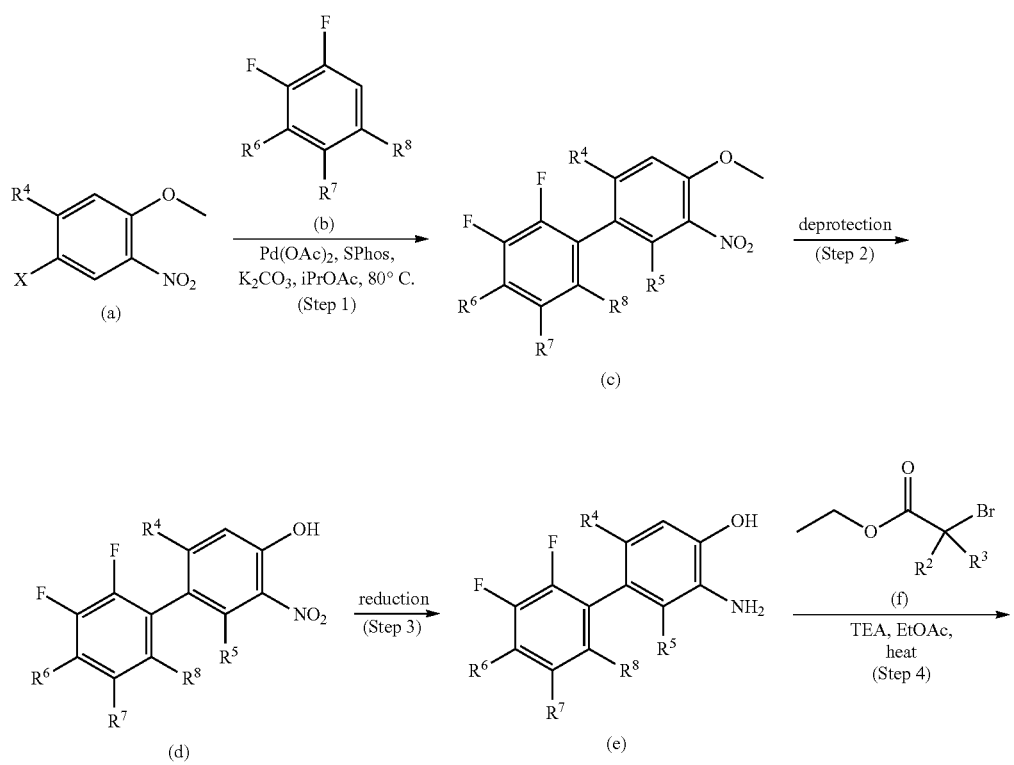

-continued

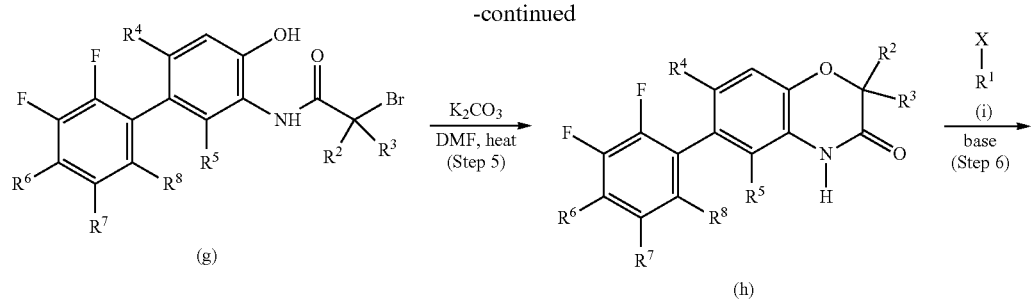

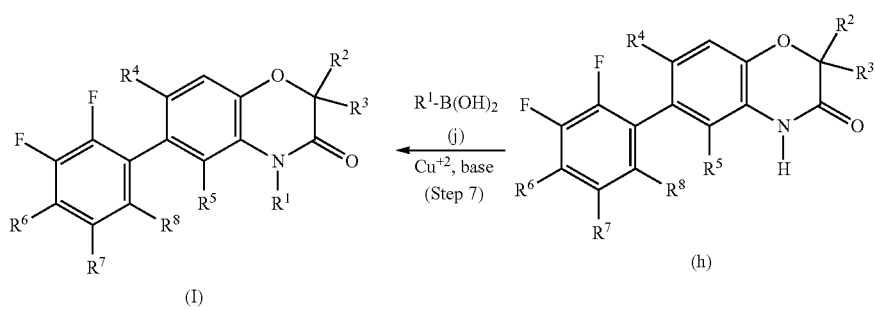

Accordingly, compounds of formula c can be prepared by reaction of a compound of formula a, where X is Br or I, with a substituted phenyl of formula b using cross-coupling reaction conditions with the aid of a metal catalyst as shown in Step 1 of Scheme 1a. Suitable catalysts include palladium catalysts, such as Pd(OAc)$_2$ combined with 2-dicyclohexylphosphino-2',6'-dimethoxybiphenyl (SPhos). As shown in Step 2 of Scheme 1a, compounds of formula d can be prepared by demethylation of the aryl methyl ether of a compound of formula c under acidic conditions. In one example, a Lewis acid such as boron tribromide can be used. As shown in Step 3 of Scheme 1a, compounds of formulae e can be prepared by reduction of the nitro group of a compound of formula d. Several methods for this are known to those skilled in the art, including the use of catalytic hydrogenation, sodium sulfide, or sodium hydrosulfite. As shown in Step 4 of Scheme 1a, compounds of formula g can be prepared by condensing the amino group of a compound of formula e with a suitable haloacetate of formula f under basic conditions in an organic solvent. In one example, the base is a trialkylamine such as triethylamine or diisopropylethylamine. As shown in Step 5 of Scheme 1a, benzoxazinones of formula h (a compound of formula I, wherein R$^1$ is H) can be prepared via intramolecular ring closure between the phenolic hydroxyl group and N-acyl halide of a compound of formula g in a suitable polar organic solvent such as DMF or DMSO. As shown in Step 6 of Scheme 1a, a compound of formula I (wherein R$^1$ is, for example, an optionally substituted C$_{1-4}$alkyl) can be formed by reacting the benzoxazinone amino group of a compound of formula h with an alkyl or aryl halide of formula i under conditions suitable for bond formation. Alternatively, a compound of formula h can be reacted with a boronic acid of formula j using a Chan-Lam type coupling to form a compound of formula I.

In another general example, the compounds of formula I can be prepared as shown in Scheme 1b.

Scheme 1b

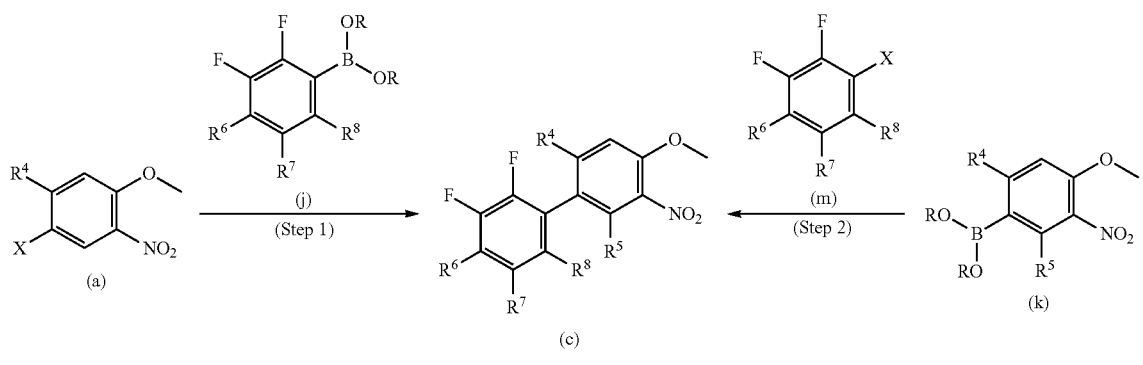

Steps 2 to 6 from Scheme 1a

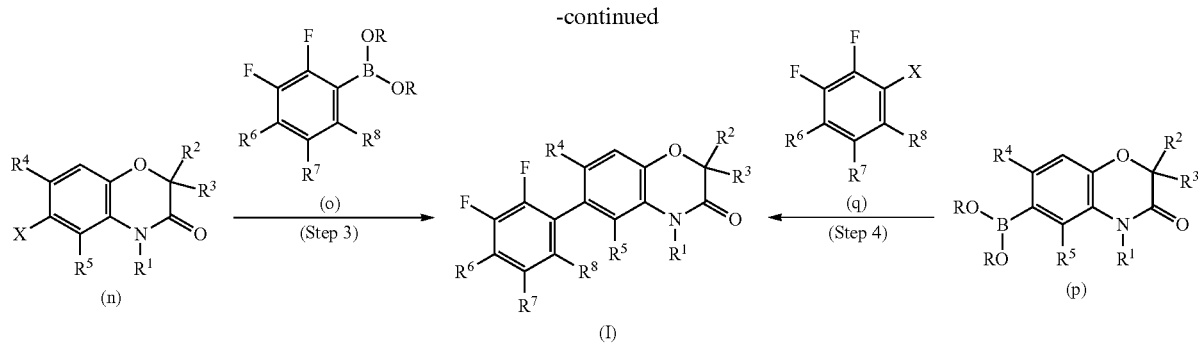

Accordingly, phenyl boronic acids (where R=H) or phenyl boronates (e.g., where —B(OR)$_2$ represents a pinacol ester) of formula j can be coupled to a suitably substituted phenyl bromide or iodide in a Suzuki-Miyaura-type reaction using a suitable catalyst to produce a compound of formula c (Step 1). This can also be accomplished under similar conditions by reacting a compound for formula k with a compound m (Step 2). Employing steps analogous to Steps 2 to 6 as described in Scheme 1 can then be used to transform a compound of formula c to a compound of formula I. Alternatively, a compound of formula n can be reacted with a compound of formula o (Step 3) or a compound of formula p can be reacted with a compound of formula q (Step 4) under Suzuki conditions to produce a compound of formula I.

In yet another general example, the compounds of formula I can be prepared as shown in Scheme 2.

Accordingly, as shown in Step 1 of Scheme 2, a fluorinated phenyl compound of formula r, where L is a leaving group such as Br, I, or OTf (triflate), is reacted with a compound of formula s, where M' is an alkali metal such as Li, or is MgBr such as found in Grignard reagents, to produce a compound of formula v. Alternatively, as shown in Step 2 of Scheme 2, a compound of formula v is produced by reacting a compound of formula t, where L is a leaving group such as Br or I, with a compound of formula u under conditions suitable for Cu-mediated aryl-aryl cross coupling known to those skilled in the art. The compound of formula v can then be nitrated, as shown in Step 3 of Scheme 2, followed by carrying out Steps 2 to 6 of Scheme 1a to produce a compound of formula I.

In one aspect, provided is a method of preparing a compound of formula (I) as described herein, or a salt thereof, comprising:

deprotecting a compound of formula (c), or a salt thereof, to yield a compound of formula (d), or a salt thereof, Scheme 2

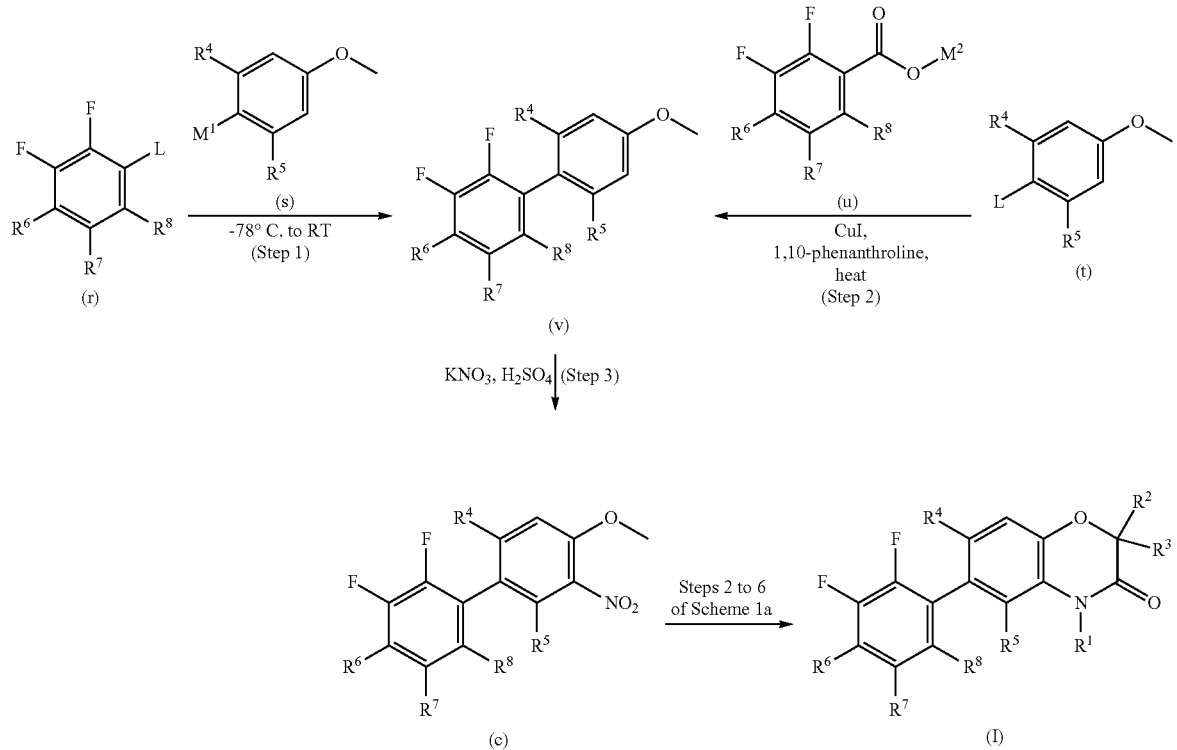

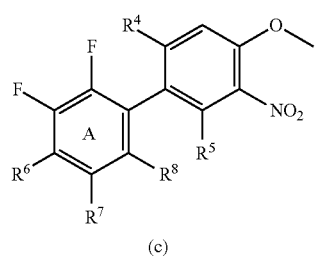

(c)

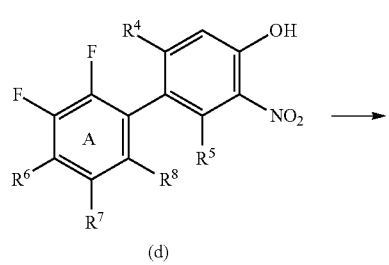

(d)

reducing a compound of formula (d), or a salt thereof, to yield a compound of formula (e), or a salt thereof,

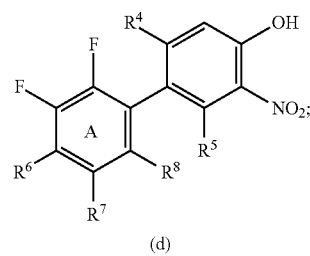

(d)

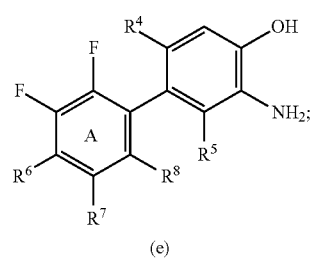

(e)

reacting a compound of formula (e), or a salt thereof, with a compound of formula (f), or a salt thereof, to yield a compound of formula (g), or a salt thereof,

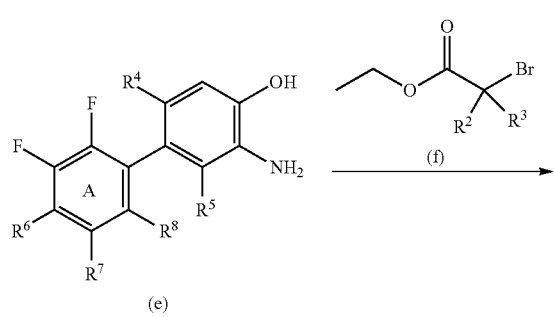

(e)    (f)

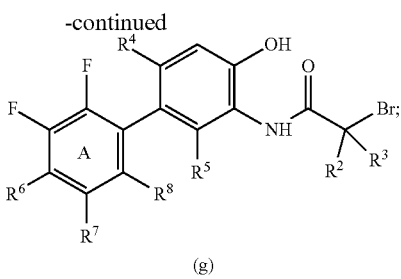

(g)

cyclizing a compound of formula (g), or a salt thereof, to yield a compound of formula (h), or a salt thereof,

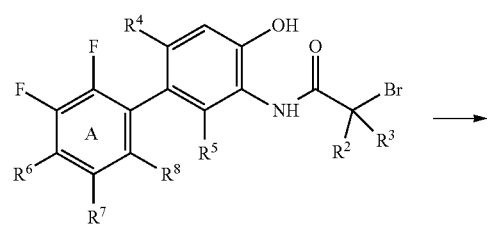

(g)

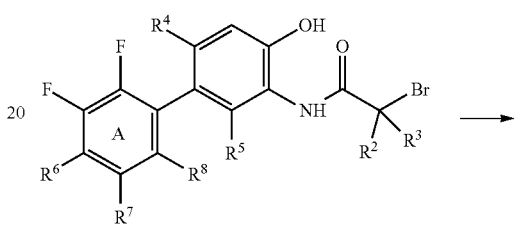

(h)

and
reacting a compound of formula (h), or a salt thereof, with a compound of formula (i), or a salt thereof, to yield a compound of formula (I), or a salt thereof,

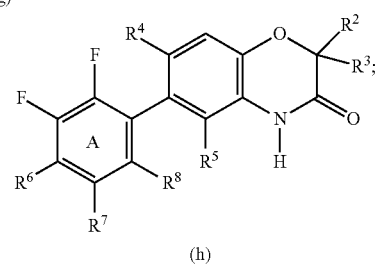

(h)

(I)

wherein:
Y is X or $B(OH)_2$;
X is Br or I; and
$R^1$-$R^8$, and ring A are as defined herein for formula (I).

In some embodiments, the compound of formula (c), or a salt thereof, is prepared according to a process comprising reacting a compound of formula (a), or a salt thereof, with a compound of formula (b), or a salt thereof, to yield a compound of formula (c), or a salt thereof,

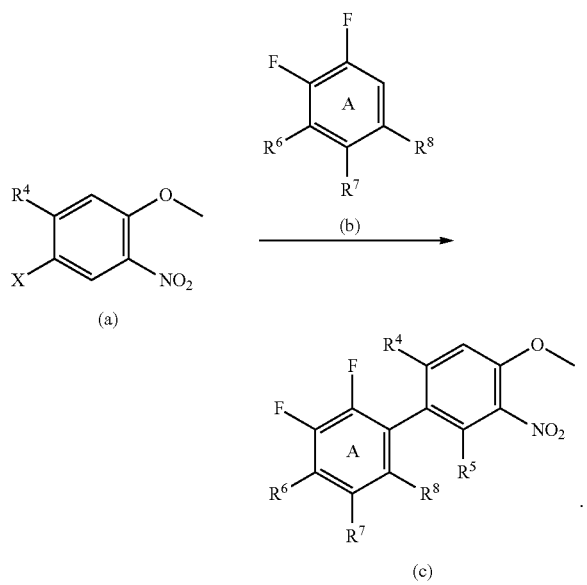

In some embodiments, the compound of formula (c), or a salt thereof, is prepared according to a process comprising reacting a compound of formula (a), or a salt thereof, with a compound of formula (j), or a salt thereof, to yield a compound of formula (c), or a salt thereof,

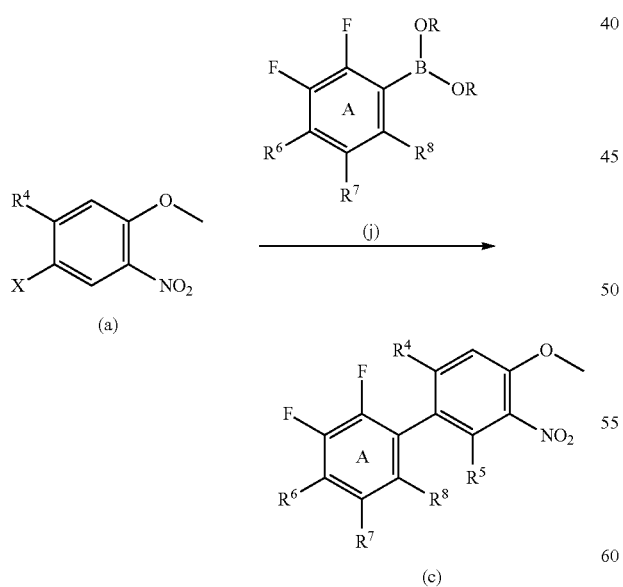

wherein R is H or phenyl.

In some embodiments, the compound of formula (c), or a salt thereof, is prepared according to a process comprising reacting a compound of formula (k), or a salt thereof, with a compound of formula (m), or a salt thereof, to yield a compound of formula (c), or a salt thereof,

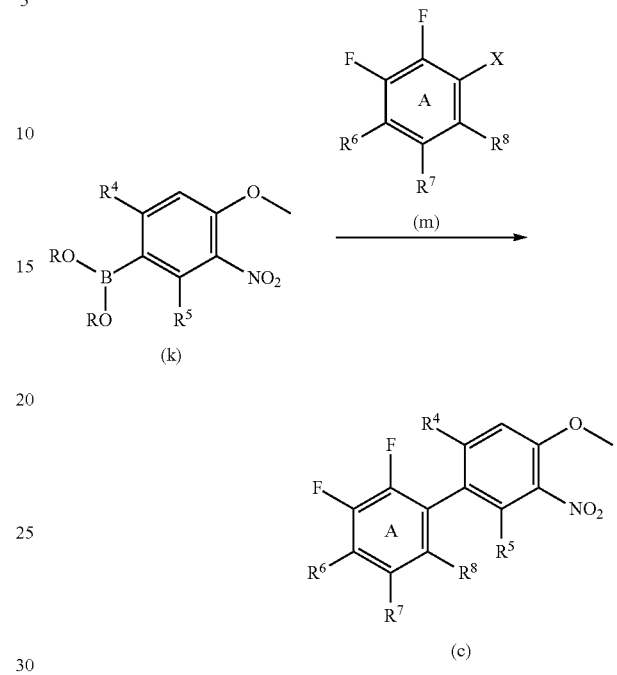

In some embodiments, the compound of formula (c), or a salt thereof, is prepared according to a process comprising reacting a compound of formula (v), or a salt thereof, to yield a compound of formula (c), or a salt thereof,

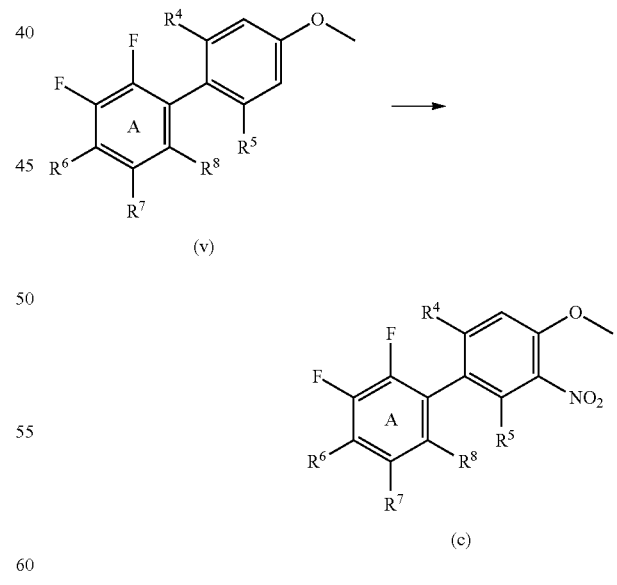

In some embodiments, the compound of formula (v), or a salt thereof, is prepared according to a process comprising reacting a compound of formula (r), or a salt thereof, with a compound of formula (s), or a salt thereof, to yield a compound of formula (v), or a salt thereof,

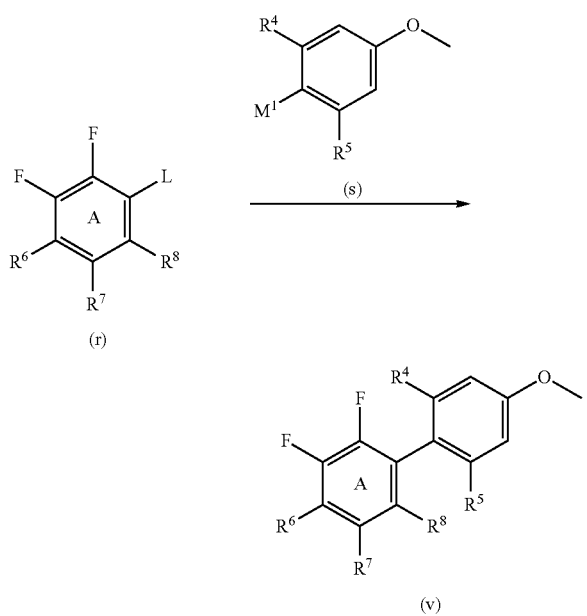

(r)

(s)

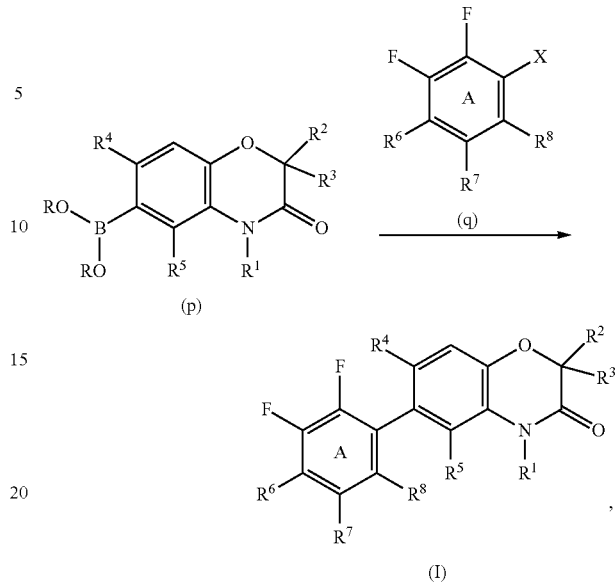

(p)

(q)

(v)

(I)

wherein L is Br, I, or OTf, and M¹ is an alkali metal.

In some embodiments, the compound of formula (v), or a salt thereof, is prepared according to a process comprising reacting a compound of formula (t), or a salt thereof, with a compound of formula (u), or a salt thereof, to yield a compound of formula (v), or a salt thereof, wherein:
R is H or phenyl;
X is Br or I; and
$R^1$-$R^8$, and ring A are as defined herein for formula (I).

In one aspect, provided is a method of preparing a compound of formula (I), or a salt thereof, comprising reacting a compound of formula (n), or a salt thereof, with a compound of formula (o), or a salt thereof, to form a compound of formula (I), or a salt thereof,

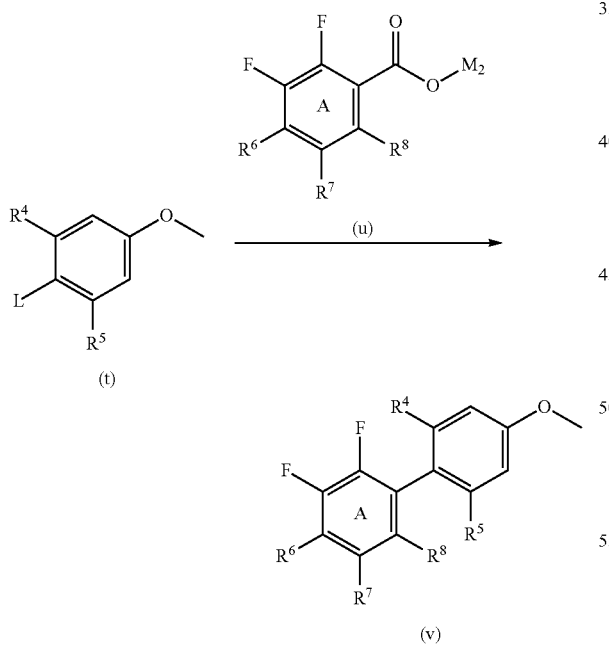

(t)

(u)

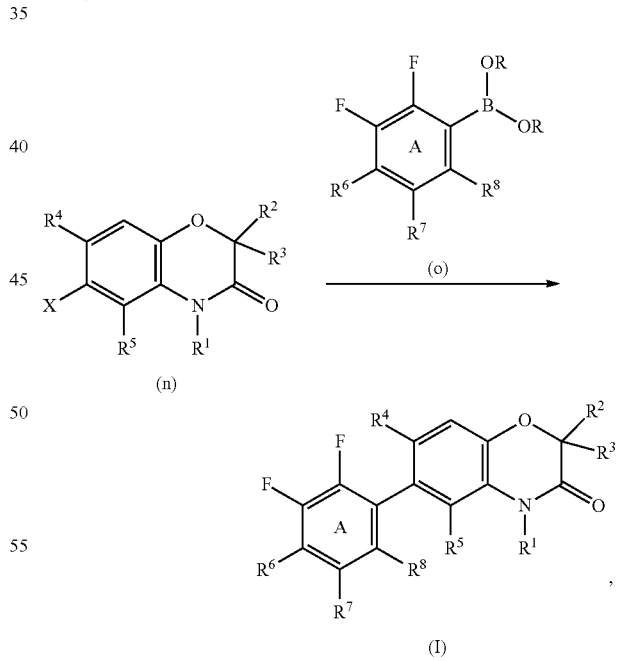

(n)

(o)

(v)

(I)

wherein L is Br, I, or OTf; and M 2 is an alkali metal.

In one aspect, provided is a method of preparing a compound of formula (I), or a salt thereof, comprising reacting a compound of formula (p), or a salt thereof, with a compound of formula (q), or a salt thereof, to form a compound of formula (I), or a salt thereof, wherein:
R is H or phenyl;
X is Br or I; and
$R^1$-$R^8$, and ring A are as defined herein for formula (I).

In another aspect, provided is a compound of formula (a), or a salt thereof,

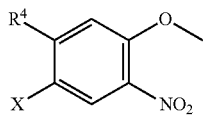

(a)

wherein X is Br or I, and $R^4$ is as defined for formula (I).

In another aspect, provided is a compound of formula (b), or a salt thereof,

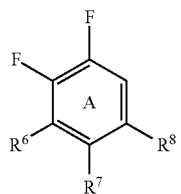

(b)

wherein $R^6$-$R^8$ and Ring A are as defined for formula (I).

In another aspect, provided is a compound of formula (c), or a salt thereof,

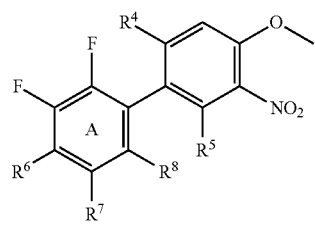

(c)

wherein $R^4$-$R^8$ and Ring A are as defined for formula (I).

In one embodiment, the compound of formula (c) is

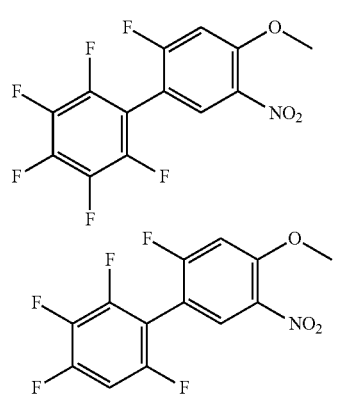

or

In another aspect, provided is a compound of formula (d), or a salt thereof,

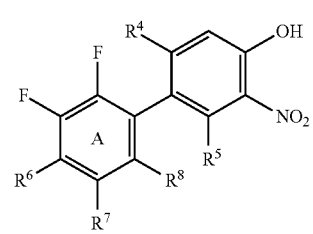

(d)

wherein $R^4$-$R^8$ and Ring A are as defined for formula (I).

In one embodiment, the compound of formula (d) is

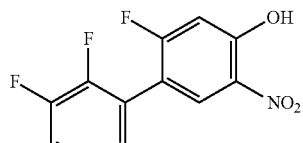

or

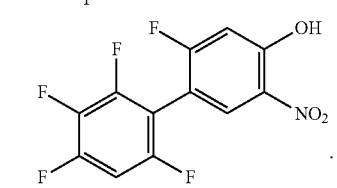

In another aspect, provided is a compound of formula (e), or a salt thereof,

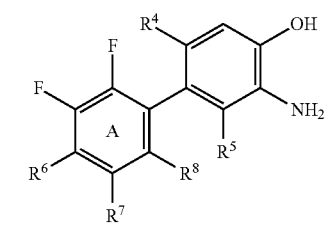

(e)

wherein $R^4$-$R^8$ and Ring A are as defined for formula (I).

In one embodiment, the compound of formula (e) is

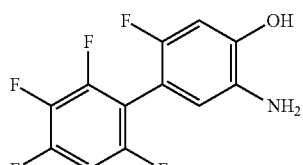

or

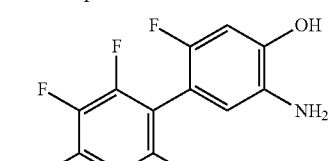

In another aspect, provided is a compound of formula (f), or a salt thereof,

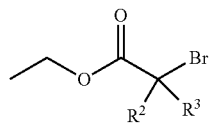

(f)

wherein $R^2$ and $R^3$ are as defined for formula (I).

In another aspect, provided is a compound of formula (g), or a salt thereof,

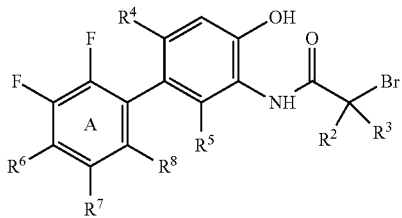
(g)

wherein $R^4$-$R^8$ and Ring A are as defined for formula (I).

In one embodiment, the compound of formula (g) is

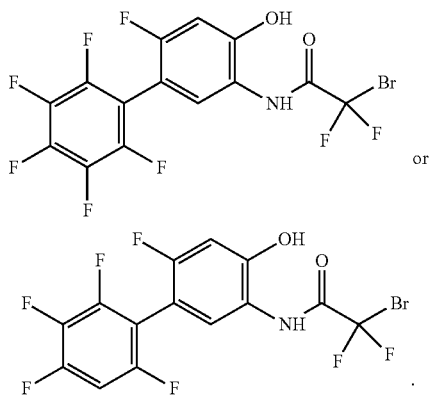

In another aspect, provided is a compound of formula (h), or a salt thereof,

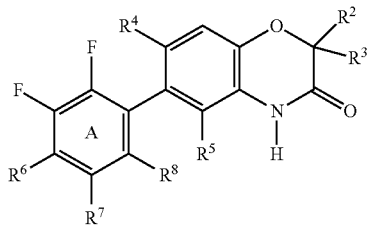
(h)

wherein $R^2$-$R^8$ and Ring A are as defined for formula (I).

In another aspect, provided is a compound of formula (i), or a salt thereof, $$\underset{R^1}{\overset{Y}{|}}$$
(i)

wherein Y is X or B(OH)$_2$; X is Br or I; and $R^1$ is as defined for formula (I).

In another aspect, provided is a compound of formula (j), or a salt thereof,

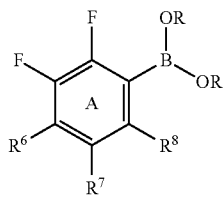
(j)

wherein $R^6$-$R^8$ and Ring A are as defined for formula (I).

In another aspect, provided is a compound of formula (k), or a salt thereof,

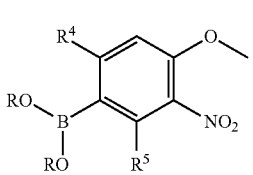
(k)

wherein $R^4$ and $R^5$ are as defined for formula (I).

In another aspect, provided is a compound of formula (m), or a salt thereof,

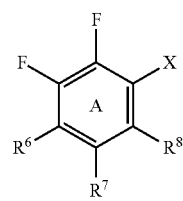
(m)

wherein $R^6$-$R^8$ and Ring A are as defined for formula (I).

In another aspect, provided is a compound of formula (n), or a salt thereof,

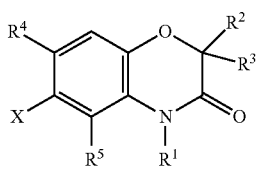
(n)

wherein X is Br or I, and are as defined for formula (I).

In one embodiment, the compound of formula (n) is

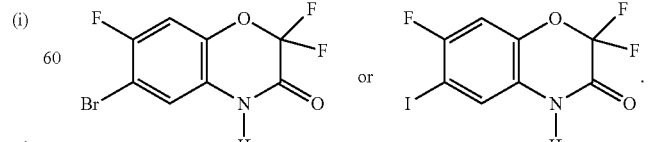

In another aspect, provided is a compound of formula (o), or a salt thereof,

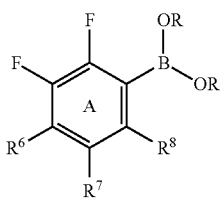

wherein R is H or phenyl, and $R^6$-$R^8$ and Ring A are as defined for formula (I).

In another aspect, provided is a compound of formula (p), or a salt thereof,

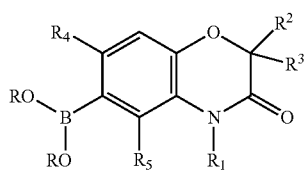

wherein R is H or phenyl, and $R^1$-$R^5$ are as defined for formula (I).

In another aspect, provided is a compound of formula (q), or a salt thereof,

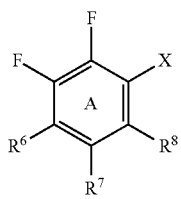

wherein X is Br or I; and $R^6$-$R^8$ and Ring A are as defined for formula (I).

In another aspect, provided is a compound of formula (r), or a salt thereof,

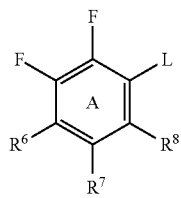

wherein L is Br, I, or OTf; and $R^6$-$R^8$ and Ring A are as defined for formula (I).

In another aspect, provided is a compound of formula (s), or a salt thereof,

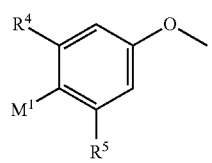

wherein $M^1$ is an alkali metal, and $R^1$, $R^4$, and $R^5$ are as defined for formula (I).

In another aspect, provided is a compound of formula (t), or a salt thereof,

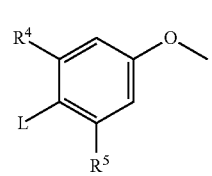

wherein L is Br, I, or OTf; and $R^4$-$R^5$ are as defined for formula (I).

In another aspect, provided is a compound of formula (u), or a salt thereof,

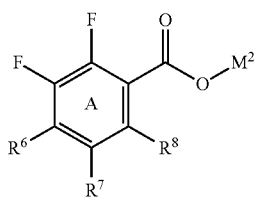

wherein $M^2$ is an alkali metal; and $R^6$-$R^8$ and Ring A are as defined for formula (I).

In another aspect, provided is a compound of formula (v), or a salt thereof,

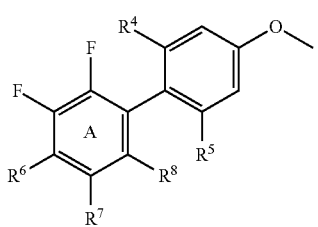

wherein $R^4$-$R^8$ and Ring A are as defined for formula (I).

Any of the embodiments and variations described herein for formula (I) also applies to intermediates of formulae (a), (b), (c), (d), (e), (f), (g), (h), (i), (j), (k), (l), (m), (n), (o), (p), (q), (r), (s), (t), (u), or (v).

It is recognized by one skilled in the art that various functional groups can be converted into others to provide different compounds of the invention. For a valuable resource that illustrates the interconversion of functional groups in a simple and straightforward fashion, see Larock, R. C, *Comprehensive Organic Transformations: A Guide to Functional Group Preparations*, $2^{nd}$ Ed., Wiley-VCH, New York, 1999.

It is recognized that some reagents and reaction conditions described above for preparing compounds of the invention may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M., *Protective Groups in Organic Synthesis*, 2$^{nd}$ ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of the invention. One skilled in the art will also recognize that it may be necessary to perform a combination of the steps illustrated in the above schemes in an order other than that implied by the particulars presented to prepare the compounds of the invention.

One skilled in the art will also recognize that compounds of the invention and the intermediates described herein can be subjected to various electrophilic, nucleophilic, radical, organometallic, oxidation, and reduction reactions to add substituents or modify existing substituents.

Compositions

In certain aspects, a compound of this disclosure, including an agriculturally suitable salt thereof, may be used as an herbicidal active ingredient in a formulation, with at least one additional component selected from the group consisting of surfactants, solid diluents, and liquid diluents, which serves as a carrier. The formulation ingredients are selected to be consistent with the physical properties of the active ingredient, mode of application, and environmental factors such as soil type, moisture, and temperature.

In some variations, the compositions provided here are herbicides. In some variations, the compositions comprise a compound of this disclosure that controls or modifies the growth of plants. In certain variations, the compositions comprise a herbicidally effective amount of the compound, such that the quantity of such compound is capable of producing a controlling or modifying effect on the growth of plants. Controlling or modifying effects include all deviation from natural development, for example killing, retardation, leaf burn, albinism, dwarfing and the like.

Liquid formulations include solutions (including emulsifiable concentrates), suspensions, emulsions (including microemulsions, oil-in-water emulsions, flowable concentrates and/or suspoemulsions), and the like, which optionally can be thickened into gels. The general types of aqueous liquid formulations are soluble concentrate, suspension concentrate, capsule suspension, concentrated emulsion, microemulsion, oil-in-water emulsion, flowable concentrate, and suspoemulsion. The general types of nonaqueous liquid formulations are emulsifiable concentrate, microemulsifiable concentrate, dispersible concentrate, and oil dispersion.

The general types of solid formulations are dusts, powders, granules, pellets, prills, pastilles, tablets, filled films (including seed coatings), and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation. Alternatively, the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength formulations are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant.

Liquid and dry formulations can be metered directly into drip irrigation systems or metered into the furrow during planting.

The formulations will typically contain effective amounts of active ingredient, diluent, and surfactant within the following approximate ranges, shown in Table 2, which add up to 100 percent by weight.

TABLE 2

Formulation Ratios

| | Weight Percent | | |
|---|---|---|---|
| | Active Ingredient | Diluent | Surfactant |
| Water-Dispersible and Water-Soluble Granules, Tablets, and Powders | 0.001-90 | 0-99.999 | 0-15 |
| Oil Dispersions, Suspensions, Emulsions Solutions (including emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Formulations | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, New Jersey.

Liquid diluents include, for example, water; N,N-dimethylalkanamides (e.g., N,N-dimethylformamide); limonene; dimethyl sulfoxide; N-alkylpyrrolidones (e.g., N-methylpyrrolidinone); alkyl phosphates (e.g., triethyl phosphate); ethylene glycol; triethylene glycol; propylene glycol; dipropylene glycol; polypropylene glycol; propylene carbonate; butylene carbonate; paraffins (e.g., white mineral oils, normal paraffins, isoparaffins); alkylbenzenes; alkylnaphthalenes; glycerine; glycerol triacetate; sorbitol; aromatic hydrocarbons; dearomatized aliphatics; alkylbenzenes; alkylnaphthalenes; ketones such as cyclohexanone, 2-heptanone, isophorone, and 4-hydroxy-4-methyl-2-pentanone; acetates such as isoamyl acetate, hexyl acetate, heptyl acetate, octyl acetate, nonyl acetate, tridecyl acetate, and isobornyl acetate; other esters such as alkylated lactate esters, dibasic esters, alkyl and aryl benzoates, and γ-butyrolactone; and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol, and benzyl alcohol. Liquid diluents also include glycerol esters of saturated and unsaturated fatty acids (typically $C_6$-$C_{22}$) such as plant seed and fruit oils (e.g., oils of olive, castor, linseed, sesame, corn (maize), peanut, sunflower, grapeseed, safflower, cottonseed, soybean, rapeseed, coconut, and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources and can be purified by distillation. Typical liquid diluents are described in C. Marsden & S. Mann, *Solvents Guide*, Cleaver-Hume Press, London, 1963.

The solid and liquid formulations of the present disclosure often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers, or defoaming agents.

Surfactants can be classified as nonionic, anionic, or cationic. Nonionic surfactants useful for the present formulations include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides, and ethoxylated alkanolamides; alkoxylated triglycerides such as ethoxylated soybean, castor, and rapeseed oils; alkylphenol alkoxylates such as octylphenol ethoxylates, nonylphenol ethoxylates, dinonyl phenol ethoxylates, and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide, or mixtures thereof); fatty acid esters, glycerol esters, lanolin-based derivatives, polyethoxylate esters such as polyethoxylated sorbitan fatty acid esters, polyethoxylated sorbitol fatty acid esters, and polyethoxylated glycerol fatty acid esters; other sorbitan derivatives such as sorbitan esters; polymeric surfactants such as random copolymers, block copolymers, alkyd PEG (polyethylene glycol) resins, graft or comb polymers and star polymers; polyethylene glycols (PEGs); polyethylene glycol fatty acid esters; silicone-based surfactants; and sugar-derivatives such as sucrose esters, alkyl polyglycosides, and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines, and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts, and diquaternary salts; and amine oxides such as alkyldimethylamine oxides and bis-(2-hydroxyethyl)-alkylamine oxides.

Also useful for the present formulations are mixtures of nonionic and anionic surfactants or mixtures of nonionic and cationic surfactants. Nonionic, anionic, and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Formulations of the present invention may also contain formulation auxiliaries and additives, known to those skilled in the art as formulation aids (some of which may be considered to also function as solid diluents, liquid diluents, or surfactants). Such formulation auxiliaries and additives may control the following: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers, and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compounds of the invention and any other active ingredients are typically incorporated into the present formulations by dissolving the active ingredient in a solvent or by grinding in a liquid or dry diluent. Solutions, including emulsifiable concentrates, can be prepared by simply mixing the ingredients. If the solvent of a liquid formulations intended for use as an emulsifiable concentrate is water-immiscible, an emulsifier is typically added to emulsify the active-containing solvent upon dilution with water. Active ingredient slurries, with particle diameters of up to 2,000 microns can be wet milled using media mills to obtain particles with average diameters below 3 microns. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 micron to 10 micron range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration," *Chemical Engineering*, Dec. 4, 1967, pp 147-48, *Perry's Chemical Engineer's Handbook*, 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. Nos. 4,144,050 and 3,920,442 and German Pat. No. 3,246,493. Tablets can be prepared as taught in U.S. Pat. Nos. 5,180,587, 5,232,701, and 5,208,030. Films can be prepared as taught in Great Britain Pat. No. 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

Biological Activity

Test results indicate that the compounds of the present invention are highly active preemergent and/or postemergent herbicides and/or plant growth regulants. The compounds of the invention generally show highest activity for postemergence weed control (e.g., applied after weed seedlings emerge from the soil) and preemergence weed control (e.g., applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, airfields, riverbanks, irrigation, and other waterways, around billboards and highway and railroad structures. Many of the compounds of this disclosure, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays.

In some variations, provided herein is a method of controlling undesired vegetation, comprising applying a compound of formula I, II, III or IV, or a salt thereof (including an agriculturally suitable salt thereof). In some variations, the compound is applied at low application rates. In certain variations, the compound is applied at a rate of 1 to 10,000 g per 10,000 $m^2$, 2 to 5,000 g per 10,000 $m^2$, 5 to 2,000 g per 10,000 $m^2$, 1 to 1000 g per 10,000 $m^2$, 1 to 500 g per 10,000 $m^2$, 1 to 100 g per 10,000 $m^2$, 1 to 75 g per 10,000 $m^2$, to 1000 g per 10,000 $m^2$, 15 to 100 g per 10,000 $m^2$, 15 to 75 g per 10,000 $m^2$, or 15 to 60 g per 10,000 $m^2$. In certain variations of the foregoing, the application of the compound at the aforementioned application rates leads to postemergence control of the undesired vegetation and/or preemergence control of the undesired vegetation.

In certain variations, the application of the compound, including at the aforementioned application rate, leads to burndown. In one variation, burndown refers to when an herbicide is used to reduce weed presence at the time of treatment. Burndown is often used in minimum or no-till fields because the weeds cannot be managed by tilling the soil. The burndown application may be used post-harvest and/or prior to crop emergence. Burndown may be useful against weeds that emerge between growing seasons.

In certain variations, the application of the compound, including at the aforementioned application rate, imparts residual control. The compounds described herein may be used as pre-emergence herbicides, which may be applied after crop planting, but prior to crop and/or weed emergence. Herbicides considered pre-emergence also may be referred to as those imparting "residual control," and provide extended control of germinating or newly emerged weeds In one variation, the undesired vegetation is at least 50%, at least 55%, at least 60%, at least 65%, at least 70%, at least 75%, at least 80%, at least 85%, at least 90%, at least 95%, at least 96%, at least 97%, at least 98%, at least 99%, or about 100% controlled. In some variations of the foregoing, the undesired vegetation is a weed. In one variation, the undesired vegetation is a PPO inhibitor-resistant weed.

Examples of crop fields treated by the compounds in the present invention include edible crop fields such as peanut fields, soybean fields, corn fields, and wheat fields, feed crop fields such as sorghum fields and oat fields, industrial crop fields such as cotton fields and rape fields, and sugar crop fields such as sugarcane fields and sugar beet fields. In one variation, crop fields treated by the compounds herein include corn, soybean, wheat, and cotton fields.

Examples of vegetable fields treated by the compounds in the present invention include fields for cultivation of solanaceous vegetables (eggplants, tomatoes, bell peppers, capsicums, potatoes, and the like), fields for cultivation of cucurbitaceous vegetables (cucumbers, pumpkins, zucchini, watermelons, melons, and the like), fields for cultivation of cruciferous vegetables (radishes, turnips, horseradishes, kohlrabies, Chinese cabbages, cabbages, mustard, broccoli s, cauliflowers, and the like), fields for cultivation of asteraceous vegetables (burdocks, garland chrysanthemums, artichokes, lettuces, and the like), fields for cultivation of liliaceous vegetables (leeks, onions, garlics, and asparagus), fields for cultivation of apiaceous vegetables (carrots, parsley, celery, parsnips, and the like), fields for cultivation of chenopodiaceous vegetables (spinach, chards, and the like), fields for cultivation of lamiaceous vegetables (perilla, mint, basil, and lavender), strawberry fields, sweet potato fields, yam fields, and taro fields.

Examples of the land under perennial crops in the present invention include orchards, tea fields, mulberry fields, coffee fields, banana fields, palm fields, flowering tree firms, flowering tree fields, planting stock fields, nursery fields, forest lands, and gardens. Examples of the orchard trees in the present invention include pomaceous fruits (apples, pears, Japanese pears, Chinese quinces, quinces, and the like), stone fruits (peaches, plums, nectarines, Japanese apricots, cherries, apricots, prunes, and the like), citrus fruits (Citrus unshiu, oranges, lemons, limes, grapefruits, and the like), nut trees (chestnuts, walnuts, hazelnut trees, almonds, pistachios, cashew nut trees, macadamia nut trees, and the like), berry fruits (grapes, blueberries, cranberries, blackberries, raspberries, and the like), Japanese persimmons, olives, and loquats.

Examples of the non-crop land in the present invention include athletic fields, empty lots, railroad edges, parks, parking lots, road edges, dry riverbeds, lands under a power line, residential lands, and factory sites.

The crop cultivated in the crop field in the present invention is not limited as long as the crop is a variety generally cultivated as a crop.

The plant of the above-mentioned variety may be a plant that can be produced by natural crossing, a plant that can be generated by mutation, an F1 hybrid plant, or a transgenic plant (also referred to as a genetically-modified plant). The plant generally has properties such as obtaining of the tolerance to an herbicide, accumulation of a toxic substance against a pest, suppression of the susceptibility to a disease, increase in the yield potential, improvement in the tolerance to a biotic and an abiotic stressors, accumulation of a substance, and improvement in the preservability and the processability.

An F1 hybrid plant is a first-generation hybrid obtained by crossing varieties of two different strains, and generally has a heterotic property with a trait superior to that of either of the parents. A transgenic plant has a foreign gene introduced from another organism or the like such as a microorganism and has a property that cannot be easily obtained by cross breeding, mutagenesis, or natural recombination in a natural environment.

Examples of the techniques for producing the above-mentioned plants include conventional breeding techniques; genetic engineering techniques; genome breeding techniques; new breeding techniques; and genome editing techniques. Conventional breeding techniques are for obtaining a plant having a desirable property by mutation or crossing. Genetic engineering techniques include techniques for imparting a new property to a target organism by extracting a target gene (DNA) from another organism (for example, a microorganism) and introducing the target gene into the genome of the target organism. Genetic engineering techniques also include antisense techniques or RNA interference techniques for imparting a new or improved property by silencing another gene present in the plant. Genome breeding techniques are for improving breeding efficiency using genomic information, and examples of the genome breeding techniques include DNA marker (also called genomic marker or genetic marker) breeding techniques and genomic selection. For example, DNA marker breeding is a method in which a progeny having a target useful trait gene is selected from a large number of crossed progenies using a DNA marker that is a DNA sequence that serves as a marker of the location of the specific useful trait gene on the genome. In the method, the crossed progeny is analyzed when it is an infant plant using a DNA marker to effectively shorten the time required for the breeding.

Genomic selection is a technique in which a prediction formula is created from a phenotype and genomic information obtained in advance to predict the property from the prediction formula and the genomic information without evaluating the phenotype and is a technique that can contribute to improving breeding efficiency. The term "new breeding techniques" is a general term for breed improvement (breeding) techniques that combine molecular biological techniques. Examples of the new breeding techniques include cisgenesis/intragenesis, oligonucleotide-directed mutagenesis, RNA-dependent DNA methylation, genome editing, grafting on a GM rootstock or a scion, reverse breeding, agroinfiltration, and seed production technology (SPT). The genome editing technique is for converting genetic information in a sequence-specific manner, and it is possible to delete a base sequence, substitute an amino acid sequence, introduce a foreign gene, and the like using the technique. Examples of the tool include sequence-specific genome modification techniques such as a zinc finger nuclease capable of sequence-specific DNA cleavage (Zinc-Finger, ZFN), TALEN, CRISPR-Cas9, CRISPER-Cpf1, Meganuclease, and CAS9 Nickase and Target-AID created by modifying the aforementioned tools.

Examples of the above-mentioned plants include plants listed in the database of the registered genetically-modified crops (GM Approval Database) in the electronic information site of International Service for the Acquisition of Agri-biotech Applications (ISAAA) (http://www.isaaa.org/). More specific examples are herbicide-tolerant plants, pest-resistant plants, disease-resistant plants, plants modified in the quality (for example, with increase or decrease in the content or change in the composition) of the products (for example, starch, amino acids, and fatty acids), fertility trait-modified plants, abiotic stress-tolerant plants, and plants modified in the trait related to the growth or the yield.

Mechanisms of obtaining herbicide tolerance include reduction in the affinity between the agent and its target, rapid metabolism (decomposition, modification, and the like) of the agent by an expressed enzyme that inactivates the agent, or inhibition of incorporation or translocation of the agent in the plant body. Examples of the plants to which herbicide tolerance has been imparted by genetic engineering technique include plants to which tolerance has been imparted to 4-hydroxyphenylpyruvate dioxygenase (hereinafter abbreviated as HPPD) inhibitors such as isoxaflutole and mesotrione, acetolactate synthase (hereinafter abbreviated as ALS) inhibitors such as imidazolinone herbicides containing imazethapyr and sulfonylurea herbicides containing thifensulfuron-methyl, 5-enolpyruvylshikimate-3-phosphate synthase (hereinafter abbreviated as EPSP) inhibitors such as glyphosate, glutamine synthase inhibitors such as glufosinate, auxin herbicides such as 2,4-D and dicamba, and oxynyl herbicides containing bromoxynil. Preferable herbicide-tolerant transgenic plants treated by the combinations of the invention are cereals such as wheat, barley, rye, and oats, canola, sorghum, soybeans, rice, rape, sugar beet, sugar cane, grapes, lentils, sunflowers, alfalfa, pomaceous fruits, drupes, coffee, tea, strawberries, lawn grass, tomatoes, potatoes, cucumbers, and vegetables such as lettuces, and more preferable herbicide-tolerant transgenic plants are cereals such as wheat, barley, rye, and oats, soybeans, rice, vines, tomatoes, potatoes, and pomaceous fruits.

In one example, in order to obtain the glyphosate herbicide-tolerant plants one or more genes are introduced from: a glyphosate-tolerant EPSPS gene (CP4 epsps) from *Agrobacterium tumefaciens* strain CP4; a glyphosate metabolizing enzyme gene (gat4601, gat4621) in which the metabolic activity of the glyphosate metabolizing enzyme (glyphosate N-acetyltransferase) gene from *Bacillus licheniformis* is enhanced by a shuffling technique; a glyphosate metabolizing enzyme (glyphosate oxidase gene, goxv247) from *Ochrobacterum anthropi* strain LBAA; and EPSPS genes from maize having a glyphosate-tolerant mutation (mepsps, 2mepsps). Main examples of the plants are alfalfa (*Med-* icago sativa), Argentine canola (*Brassica napus*), cotton (*Gossypium hirsutum* L.), creeping bentgrass (*Agrostis stolonifera*), maize (*Zea mays* L.), polish canola (*Brassica rapa*), potato (*Solanum tuberosum* L.), soybean (*Glycine max* L.), sugar beet (*Beta vulgaris*), and wheat (*Triticum aestivum*). Some glyphosate-tolerant transgenic plants are commercially available. For example, the genetically-modified plant in which the glyphosate-tolerant EPSPS from the *Agrobacterium* is expressed is commercially available with a trade name such as "Roundup Ready®" the genetically-modified plant in which the glyphosate metabolizing enzyme that is from *Bacillus* and has the metabolic activity enhanced by a shuffling technique is expressed is commercially available with a trade name such as "Optimum® GAT®, or "Optimum® Gly canola", and the genetically-modified plant in which the EPSPS that is from maize and has glyphosate-tolerant mutation is expressed is commercially available with the trade name "GlyTol®".

In another example, in order to obtain the glufosinate herbicide-tolerant plants one or more genes are introduced from: a phosphinothricin N-acetyltransferase (PAT) gene (bar) that is a glufosinate metabolizing enzyme from *Streptomyces hygroscopicus*; a phosphinothricin N-acetyltransferase (PAT) enzyme gene (pat) that is a glufosinate metabolizing enzyme from *Streptomyces viridochromogenes*; and a synthesized pat gene (pat syn) from *Streptomyces viridochromogenes* strain Tu494. Main examples of the plants include Argentine canola (*Brassica napus*), chicory (*Cichorium intybus*), cotton (*Gossypium hirsutum* L.), maize (*Zea mays* L.), polish canola (*Brassica rapa*), rice (*Oryza sativa* L.), soybean (*Glycine max* L.), and sugar beet (*Beta vulgaris*). Some glufosinate-tolerant genetically-modified plants are commercially available. For example, a genetically-modified plant from a glufosinate metabolizing enzyme (bar) from *Streptomyces hygroscopicus* and from *Streptomyces viridochromogenes* is commercially available with trade names such as "LibertyLink®", "InVigor®", or "WideStrike®".

In another example, oxynil herbicide-tolerant plants are known. For example, bromoxynil-tolerant transgenic plants into which a nitrilase gene (bxn) is introduced from an oxynil herbicide metabolizing enzyme from *Klebsiella pneumoniae* subsp. *ozaenae*. Main examples of the plants are Argentine canola (*Brassica napus*), cotton (*Gossypium hirsutum* L.), and tobacco (*Nicotiana tabacum* L.). The plants are commercially available with a trade name such as "Navigator® canola" or "BXN®".

ALS herbicide-tolerant plants are also known. Examples include carnations (*Dianthus caryophyllus*), which are obtained by introduction of an ALS herbicide-tolerant ALS gene (surB) as a selection marker from tobacco (*Nicotiana tabacum*) and are commercially available with the trade names "Moondust®", "Moonshadow®", "Moonshade®", "Moonlite®", "Moonaqua®", "Moonvista®", "Moonique®", "Moonpearl®", "Moonberry®", and "Moonvelvet®"; flax (*Linum usitatissumum* L.), into which an ALS herbicide-tolerant ALS gene (als) from *Arabidopsis thaliana* is introduced is commercially available with the trade name "CDC Triffid Flax"; sulfonylurea herbicide-tolerant and an imidazolinone herbicide-tolerant maize (*Zea mays* L.) into which an ALS herbicide-tolerant ALS gene (zm-hra) from maize is introduced is commercially available with the trade name "Optimum® GAT™"; an imidazolinone herbicide-tolerant soybean into which an ALS herbicide-tolerant ALS gene (csr1-2) from *Arabidopsis thaliana* is introduced is commercially available with the trade name "Cultivance®"; and sulfonylurea herbicide-tolerant soybeans into which an ALS herbicide-tolerant ALS gene (gm-hra) from a soybean (*Glycine max*) is introduced are commercially available with the trade names "Treus®", "Plenish®", and "Optimum® GAT™". There is also cotton into which an ALS herbicide-tolerant ALS gene (S4-HrA) from tobacco (*Nicotiana tabacum* cv. *Xanthi*) is introduced.

HPPD herbicide-tolerant plants are also known. In one example, a soybean into which a mesotrione-tolerant HPPD gene (avhppd-03) from an oat (*Avena sativa*) and a phinothricin N-acetyltransferase (PAT) enzyme gene (pat) are simultaneously introduced. In another example, a soybean tolerant to mesotrione into which a glufosinate metabolizing enzyme from *Streptomyces viridochromogenes* is introduced is commercially available.

In another example, 2,4-D-tolerant plants include: maize into which an aryloxyalkanoate dioxygenase gene (aad-1) for a 2,4-D metabolizing enzyme from *Sphingobium herbicidovorans* is introduced is commercially available with the trade name "Enlist® Maize"; and soybean and cotton into which an aryloxyalkanoate dioxygenase gene (aad-12) for a 2,4-D metabolizing enzyme from Delftia *acidovorans* is introduced is commercially available with the trade name "Enlist® Soybean".

In another example, Dicamba-tolerant plants include: soybean and cotton into which a dicamba monooxygenase gene (dmo) having a dicamba metabolizing enzyme from *Stenotrophomonas maltophilia* strain DI-6 is introduced; and a soybean (*Glycine max* L.) into which a glyphosate-tolerant EPSPS gene (CP4 epsps) from *Agrobacterium tumefaciens* strain CP4 is introduced simultaneously with the above-mentioned gene is commercially available with the trade name "Genuity® Roundup Ready™ 2 Xtend®".

Further examples of the commercially available transgenic plants to which herbicide tolerance has been imparted include: the glyphosate-tolerant maize "Roundup Ready® Corn", "Roundup Ready® 2", "Agrisure® GT", "Agrisure® GT/CB/LL", "Agrisure® GT/RW", "Agrisure® 3000GT", "YieldGard™ VT™ Rootworm/RR2", and "YieldGard™ VT™ Triple"; the glyphosate-tolerant soybeans "Roundup Ready® Soybean" and "Optimum® GAT"; the glyphosate-tolerant cotton "Roundup Ready® Cotton" and "Roundup Ready® Flex"; the glyphosate-tolerant canola "Roundup Ready® Canola"; the glyphosate-tolerant alfalfa "Roundup Ready® Alfalfa", the glyphosate-tolerant rice "Roundup Ready® Rice"; the glufosinate-tolerant maize "Roundup Ready® 2", "LibertyLink®", "Herculex® 1", "Herculex® RW", "Herculex® Xtra", "Agrisure® GT/CB/LL", "Agrisure® CB/LL/RW", and "Bt10"; the glufosinate-tolerant cotton "FiberMax™ LibertyLink™"; the glufosinate-tolerant canola "InVigor®"; the glufosinate-tolerant rice "LibertyLink™ Rice" (manufactured by Bayer AG); the bromoxynil-tolerant cotton "BXN"; the bromoxynil-tolerant canola "Navigator®" and "Compass®"; and the glufosinate-tolerant canola "InVigor®". Additional plants modified with respect to a herbicide are widely known, and the examples of the plants include alfalfa, apples, barley, eucalyptuses, flax, grapes, lentils, rape, peas, potatoes, rice, sugar beet, sunflowers, tobacco, tomato, turfgrass, and wheat that are tolerant to glyphosate (see, for example, U.S. Pat. Nos. 4,940,835, 5,633,435, 5,804,425, and 5,627,061); beans, cotton, soybeans, peas, potatoes, sunflowers, tomatoes, tobacco, maize, sorghum, and sugar cane that are tolerant to dicamba (see, for example, WO2008051633, U.S. Pat. Nos. 7,105,724, and 5,670,454); soybeans, sugar beet, potatoes, tomatoes, and tobacco that are tolerant to glufosinate (see, for example, U.S. Pat. Nos. 6,376,754, 5,646,024, and 5,561,236); cotton, peppers, apples, tomatoes, sunflowers, tobacco, potatoes, maize, cucumbers, wheat, soybeans, sorghum, and cereals that are tolerant to 2,4-D (see, for example, U.S. Pat. Nos. 6,153,401, 6,100,446, WO2005107437, U.S. Pat. Nos. 5,608,147, and 5,670,454); and canola, maize, millet, barley, cotton, mustard, lettuces, lentils, melons, millet, oats, sword beans, potatoes, rice, rye, sorghum, soybeans, sugar beet, sunflowers, tobacco, tomatoes, and wheat that are tolerant to acetolactate synthase (ALS) inhibitor herbicide (for example, a sulfonylurea herbicide and an imidazolinone herbicide) (see, for example, U.S. Pat. No. 5,013,659, WO2006060634, U.S. Pat. Nos. 4,761,373, 5,304,732, 6,211,438, 6,211,439, and 6,222,100). The rice tolerant to an imidazolinone herbicide is especially known, and examples of the rice include rice having specific mutation (for example, S653N, S654K, A122T, S653(At)N, S654(At)K, and A122(At)T) in the acetolactate synthase gene (acetohydroxyacid synthase gene) (see, for example, US 2003/0217381, and WO000520673); and the examples include barley, sugar cane, rice, maize, tobacco, soybeans, cotton, rape, sugar beet, wheat, and potatoes that are tolerant to an HPPD inhibitor herbicide (for example, an isoxazole herbicide such as isoxaflutole, a triketone herbicide such as sulcotrione or mesotrione, a pyrazole herbicide such as pyrazolynate, or diketonitrile that is a decomposition product of isoxaflutole) (see, for example, WO2004/055191, WO199638567, WO1997049816, and U.S. Pat. No. 6,791, 014).

Examples of the plants to which herbicide tolerance has been imparted by a classical technique or a genome breeding technique include the rice "Clearfield® Rice", the wheat "Clearfield® Wheat", the sunflower "Clearfield® Sunflower", the lentil "Clearfield® lentils", and the canola "Clearfield® canola" (manufactured by BASF SE) that are tolerant to an imidazolinone-based ALS inhibitor herbicide such as imazethapyr or imazamox; the soybean "STS® soybean" that is tolerant to a sulfonyl-based ALS inhibitor herbicide such as thifensulfuron-methyl; the sethoxydim-tolerant maize "SR® corn" and 'Poast Protected® corn" that are tolerant to an acetyl-CoA carboxylase inhibitor such as a trionoxime herbicide or an aryloxy phenoxypropionic acid herbicide; the sunflower "ExpressSun®" that is tolerant to a sulfonylurea herbicide such as tribenuron; the rice "Provisia™ Rice" that is tolerant to an acetyl-CoA carboxylase inhibitor such as quizalofop; and the canola "Triazine Tolerant Canola" that is tolerant to a PSII inhibitor.

Examples of the plants to which herbicide tolerance has been imparted by a genome editing technique include the canola "SU Canola®" tolerant to a sulfonylurea herbicide in which a rapid variety development technique (Rapid Trait Development System, RTDS®) is used. RTDS® corresponds to oligonucleotide-directed mutagenesis of the genome editing technique, and by RTDS, it is possible to introduce mutation in a DNA in a plant via Gene Repair Oligonucleotide (GRON), that is, a chimeric oligonucleotide of the DNA and the RNA without cutting the DNA. In addition, examples of the plants include maize in which herbicide tolerance and phytic acid content have been reduced by deleting the endogenous gene IPK1 using zinc finger nuclease (see, for example, Nature 459, 437-441 2009); and rice to which herbicide tolerance has been imparted using CRISPR-Cas9 (see, for example, Rice, 7, 5 2014).

In the present invention, examples of the crop tolerant to a specific PPO inhibitor include crops to which PPO having a reduced affinity for the inhibitor is imparted by a genetic engineering technique. Alternatively, the crop may have a substance that detoxifies and decomposes the PPO inhibitor by cytochrome P450 monooxygenase alone or in combination with the above-mentioned PPO. The tolerant crops are described in, for example, patent documents such as WO2011085221, WO2012080975, WO2014030090, WO2015022640, WO2015022636, WO2015022639, WO2015092706, WO2016203377, WO2017198859, WO2018019860, WO2018022777, WO2017112589, WO2017087672, WO2017039969, and WO2017023778, and non-patent document Li & Nicholl in Pest Management Science (2005), Vol. 61, pgs. 277-285.

Examples of the plants to which herbicide tolerance has been imparted by a new breeding technique in which the property of a GM rootstock is imparted to a scion by a breeding technique in which grafting is used include the non-transgenic soybean scion to which glyphosate tolerance is imparted using the glyphosate-tolerant soybean Roundup Ready® as a rootstock (see Jiang, et al., in Weed Technology (2013) Vol. 27, pgs. 412-416).

The above-mentioned plants include strains to which two or more traits are imparted among abiotic stress tolerance, disease resistance, herbicide tolerance, pest resistance, a growth trait, a yield trait, nutrient uptake, product quality, a fertility trait, and the like as described above using a genetic engineering technique, a classical breeding technique, a genome breeding technique, a new breeding technique, a genome editing technique, or the like, and strains to which two or more of the properties of the parent strains are imparted by crossing plants having the same or different properties.

Examples of the commercially available plants to which tolerance to two or more herbicides are imparted include the cotton "GlyTol™ LibertyLink™" and "GlyTol™ LibertyLink™" that are tolerant to glyphosate and glufosinate; the maize "Roundup Ready™ LibertyLink™ Maize" that is tolerant to glyphosate and glufosinate; the soybean "Enlist™ Soybean" that is tolerant to glufosinate and 2,4-D; the soybean "Genuity® Roundup Ready (trademark) 2 Xtend (trademark)" that is tolerant to glyphosate and dicamba; the maize and the soybean "OptimumGAT™" that are tolerant to glyphosate and an ALS inhibitor; the genetically modified soybeans "Enlist E3™" and "Enlist™ Roundup Ready® 2 Yield" that are tolerant to three herbicides of glyphosate, glufosinate, and 2,4-D; the genetically modified maize "Enlist™ Roundup Ready® Corn 2" that is tolerant to glyphosate, 2,4-D, and an aryloxyphenoxypropionate (FDPs) herbicide; the genetically modified maize "Enlist™ Roundup Ready® Corn 2" that is tolerant to glyphosate, 2,4-D, and an aryloxyphenoxypropionate (FDPs) herbicide; the genetically modified cotton "Bollgard II® XtendFlex™ Cotton" that is tolerant to dicamba, glyphosate, and glufosinate; and the genetically modified cotton "Enlist™ Cotton" that is tolerant to three herbicides of glyphosate, glufosinate, and 2,4-D. In addition, the cotton tolerant to glufosinate and 2,4-D, the cotton tolerant to both glufosinate and dicamba, the maize tolerant to both glyphosate and 2,4-D, the soybean tolerant to both glyphosate and an HPPD herbicide, and the genetically modified maize tolerant to glyphosate, glufosinate, 2,4-D, an aryloxyphenoxypropionate (FDPs) herbicide, and a cyclohexanedione (DIMs) herbicide have been also developed.

Examples of the commercially available plants to which herbicide tolerance and pest resistance are imparted include the maize "YieldGard Roundup Ready®" and "YieldGard Roundup Ready® 2" that are tolerant to glyphosate and resistant to a corn borer; the maize "Agrisure® CB/LL" that is tolerant to glufosinate and resistant to a corn borer; the maize "Yield Gard® VT Root worm/RR2" that is tolerant to glyphosate and resistant to a corn rootworm; the maize "Yield Gard® VT Triple" that is tolerant to glyphosate and resistant to a corn rootworm and a corn borer; the maize "Herculex® I" that is tolerant to glufosinate and resistant to a lepidopteran maize pest (Cry1F) (for example, resistance to a western bean cutworm, a corn borer, a black cutworm, and a fall armyworm); the maize "YieldGard® Corn Rootworm/Roundup Ready® 2" that is tolerant to glyphosate and resistant to a corn rootworm; the maize "Agrisure® GT/RW" that is tolerant to glufosinate and resistant to a Coleoptera maize pest (Cry3A) (for example, resistant to a western corn rootworm, a northern corn rootworm, and a Mexican corn rootworm); the maize "Herculex® RW" that is tolerant to glufosinate and resistant to a Coleoptera maize pest (Cry34/35Ab1) (for example, resistant to a western corn rootworm, a northern corn rootworm, and a Mexican corn rootworm); the maize "Yield Gard® VT Root worm/RR2" that is tolerant to glyphosate and resistant to a corn rootworm; and the cotton "Bollgard XtendFlex®" that is tolerant to dicamba, glyphosate, and glufosinate and resistant to a lepidopteran cotton pest (for example, resistant to bollworms, a tobacco budworm, and armyworms).

In the present invention, a composition of the invention is applied to a place where weeds are growing or likely to grow. Examples of the method of applying the present composition include a method of spraying the present composition on soil and a method of spraying the present composition on weeds.

In some variations, the application rate of a composition of the invention is generally 1 to 10,000 g per 10,000 m$^2$, 2 to 5,000 g per 10,000 m$^2$, 5 to 2,000 g per 10,000 m$^2$, 1 to 1000 g per 10,000 m$^2$, 1 to 500 g per 10,000 m$^2$, 1 to 100 g per 10,000 m$^2$, 1 to 75 g per 10,000 m$^2$, 15 to 1000 g per 10,000 m$^2$, 15 to 100 g per 10,000 m$^2$, 15 to 75 g per 10,000 m$^2$, or 15 to 60 g per 10,000 m$^2$, in terms of the total amount of a compound of formula I, II, III or IV, or a salt thereof (including an agriculturally suitable salt thereof).

In one variation, the application rate of a composition of the invention is generally 1 to 10,000 g per 10,000 m$^2$, 2 to 5,000 g per 10,000 m$^2$, 5 to 2,000 g per 10,000 m$^2$, 1 to 1000 g per 10,000 m$^2$, 1 to 500 g per 10,000 m$^2$, 1 to 100 g per 10,000 m$^2$, 1 to 75 g per m$^2$, 15 to 1000 g per 10,000 m$^2$, 15 to 100 g per 10,000 m$^2$, 15 to 75 g per 10,000 m$^2$, or 15 to 60 g per 10,000 m$^2$, in terms of the total amount of a compound of formula I and the at least one compound selected from the group consisting of the herbicide compound group B and the safener group C.

In the present method, an adjuvant may be mixed in a composition of the invention, followed by application. The type of the adjuvant is not particularly limited, and examples of the adjuvant include oil-based adjuvants such as AgriDex® and methylated seed oil (MSO), non-ions (esters or ethers of polyoxyethylene) such as Induce, anions (substituted sulfonates) such as Gramine S, cations (polyoxyethylene amines) such as Genamin® T 200BM, and organic silicons such as Silwet® L77.

The pH and the hardness of the spray liquid prepared when a composition of the invention is applied are not particularly limited, and the pH is usually in the range of 5 to 9, and the hardness is usually in the range of 0 to 500.

The time period for applying a composition of the invention is not particularly limited, and is usually in the range of 5:00 AM to 9:00 PM, and the photon flux density is usually 10 to 2,500 μmol/m$^2$/s.

When a composition of the invention is applied to a crop field, it may be applied before sowing a crop seed, simultaneously with sowing a crop seed, and/or after sowing a crop seed. That is, the frequency of the application of a composition of the invention is once before, simultaneously with, or after sowing a crop seed, twice excluding before the sowing, excluding simultaneously with the sowing, or excluding after the sowing, or three times at all the timing.

When a composition of the invention is applied before sowing a crop seed, it is applied from 50 days before to immediately before the sowing, preferably from 30 days before to immediately before the sowing, more preferably from 20 days before to immediately before the sowing, and still more preferably from 10 days before to immediately before the sowing.

When a composition of the invention is applied after sowing a crop seed, it is usually applied from immediately after the sowing to before flowering. The composition is more preferably applied from immediately after the sowing to before the emergence, or from 1 to 6 leaf stages of the crop. The case where a composition of the invention is applied simultaneously with sowing a crop seed is the case where a sowing machine and a sprayer are integrated with each other.

In the step of applying a composition of the invention in a cultivation area, a compound of formula I or the compound and at least one additional compound selected from the group consisting of the herbicide compound group B and the safener group C are usually mixed with a carrier such as a solid carrier or a liquid carrier, and an auxiliary agent for formulation such as a surfactant is added if necessary to prepare a formulation. Preferable formulation types is aqueous liquid suspension formulations, oil-based suspension formulations, wettable powders, water dispersible granules, granules, water-based emulsions, oil-based emulsions, and emulsifiable concentrates, and more preferable formulation type is emulsifiable concentrates. Furthermore, a formulation containing a compound of formula I alone as an active ingredient and a formulation containing the at least one compound selected from the group consisting of the herbicide compound group B and the safener group C as an active ingredient may be used in combination. Furthermore, a formulation containing the present composition as active ingredients and a formulation containing another herbicide as an active ingredient may be used in combination.

Examples of the method of applying a composition of the invention in a cultivation area include a method of spraying it on the soil in the cultivation area and a method of spraying the present composition on a weeds that are growing. The composition is usually diluted with water, followed by spraying. The spray volume is not particularly limited, and is usually 50 to 1,000 L/ha, preferably 100 to 500 L/ha, and more preferably 140 to 300 L/ha.

Specific examples of the weed species to be controlled by the present composition include, but are not limited to, the weed species described below.

Urticaceae weeds to be controlled include *Urtica urens*.

Polygonaceae weeds to be controlled include *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius*, and *Rumex acetosa*.

Portulacaceae weeds to be controlled include *Portulaca oleracea*.

Caryophyllaceae weeds to be controlled include *Stellaria media, Stellaria aquatica, Cerastium holosteoides, Cerastium glomeratum, Spergula arvensis*, and *Silene gallica*.

Molluginaceae weeds to be controlled include *Mollugo verticillate*.

Chenopodiaceae weeds to be controlled include *Chenopodium album, Chenopodium ambrosioides, Kochia scoparia, Salsola kali*, and *Atriplex* spp.

Amaranthaceae weeds to be controlled include *Amaranthus retroflexus, Amaranthus viridis, Amaranthus lividus, Amaranthus spinosus, Amaranthus hybridus, Amaranthus palmeri, Amaranthus patulus*, Waterhemp (*Amaranthus tuberculatus, Amaranthus rudis*, or *Amaranthus tamariscinus*), *Amaranthus blitoides, Amaranthus deflexus, Amaranthus quitensis, Alternanthera philoxeroides, Alternanthera sessilis*, and *Alternanthera tenella*.

Papaveraceae weeds to be controlled include *Papaver rhoeas, Papaver dubium*, and *Argemone mexicana*.

Brassicaceae weeds to be controlled include *Raphanus raphanistrum, Raphanus sativus, Sinapis arvensis, Capsella bursa-pastoris, Brassica juncea, Brassica napus, Descurainia pinnata, Rorippa islandica, Rorippa sylvestris, Thlaspi arvense, Myagrum rugosum, Lepidium virginicum*, and *Coronopus didymus*.

Capparaceae weeds to be controlled include *Cleome affinis*.

Fabaceae weeds to be controlled include *Aeschynomene indica, Aeschynomene rudis, Sesbania exaltata, Cassia obtusifolia, Cassia occidentalis, Desmodium tortuosum, Desmodium adscendens, Desmodium illinoense, Trifolium repens, Pueraria lobata, Vicia angustifolia, Indigofera hirsuta, Indigofera truxillensis*, and *Vigna sinensis*.

Oxalidaceae weeds to be controlled include *Oxalis corniculata, Oxalis strica*, and *Oxalis oxyptera*.

Geraniaceae weeds to be controlled include *Geranium carolinense* and *Erodium cicutarium*.

Euphorbiaceae weeds to be controlled include *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis*, and *Ricinus communis*.

Malvaceae weeds to be controlled include *Abutilon theophrasti, Sida rhombifora, Sida cordifolia, Sida spinosa, Sida glaziovii, Sida santaremnensis, Hibiscus trionum, Anoda cristata*, and *Malvastrum coromandelianum*.

Onagraceae weeds to be controlled include *Ludwigia epilobioides, Ludwigia octovalvis, Ludwigia decurre, Oenothera biennis*, and *Oenothera laciniata*.

Sterculiaceae weeds to be controlled include *Waltheria indica*.

Violaceae weeds to be controlled include *Viola arvensis* and *Viola tricolor*.

Cucurbitaceae weeds to be controlled include *Sicyos angulatus, Echinocystis lobata*, and *Momordica charantia*.

Lythraceae weeds to be controlled include *Ammannia multiflora, Ammannia auriculata, Ammannia coccinea, Lythrum salicaria*, and *Rotala indica*.

Elatinaceae weeds to be controlled include *Elatine triandra* and *Elatine californica*.

Apiaceae weeds to be controlled include *Oenanthe javanica, Daucus carota*, and *Conium maculatum*.

Araliaceae weeds to be controlled include *Hydrocotyle sibthorpioides* and *Hydrocotyle ranunculoides*.

Ceratophyllaceae weeds to be controlled include *Ceratophyllum demersum*.

Cabombaceae weeds to be controlled include *Cabomba caroliniana*.

Haloragaceae weeds to be controlled include *Myriophyllum aquaticum, Myriophyllum verticillatum, Myriophyllum spicatum*, and *Myriophyllum heterophyllum*.

Sapindaceae weeds to be controlled include *Cardiospermum halicacahum*.

Primulaceae weeds to be controlled include *Anagallis arvensis*.

Asclepiadaceae weeds to be controlled include *Asclepias syriaca*, and *Ampelamus albidus*.

Rubiaceae weeds to be controlled include *Galium aparine, Galium spurium* var. *echinospermon, Spermacoce latifolia, Richardia brasiliensis*, and *Borreria alata*.

Convolvulaceae weeds to be controlled include *Ipomoea nil, Ipomoea hederacea, Ipomoea purpurea, Ipomoea hederacea* var. *integriuscula, Ipomoea lacunosa, Ipomoea triloba, Ipomoea acuminata, Ipomoea hederifolia, Ipomoea coccinea, Ipomoea qusimoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides*, and *Jacquemontia tamnifolia*.

Boraginaceae weeds to be controlled include *Myosotis arvensis*.

Lamiaceae weeds to be controlled include *Lamium purpureum, Lamium amplexicaule, Leonotis nepetaefolia, Hyptis suaveolens, Hyptis lophano, Leonurus sibiricus*, and *Stachys arvensis*.

Solanaceae weeds to be controlled include *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata*, and *Nicandra physaloides*.

Scrophulariaceae weeds to be controlled include *Veronica hederaefolia, Veronica persica, Veronica arvensis, Lindernia procumbens, Lindernia dubia, Lindernia angustifolia, Bacopa rotundifolia, Dopatrium junceum*, and *Gratiola japonica*.

Plantaginaceae weeds to be controlled include *Plantago asiatica, Plantago lanceolata, Plantago major*, and *Callitriche palustris*.

Asteraceae weeds to be controlled include *Xanthium pensylvanicum, Xanthium occidentale, Xanthium italicum, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parviflora, Senecio vulgaris, Senecio brasiliensis, Senecio grisebachii, Conyza bonariensis, Conyza smatrensis, Conyza canadensis, Ambrosia artemisiaefolia, Ambrosia trifida, Bidens tripartita, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampoclium perfoliatum, Emilia sonchifolia, Tagetes minuta, Blainvillea latifolia, Tridax procumbens, Porophyllum ruderale, Accmthosperinum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis, Eclipta prostrata, Eclipta alba*, and *Centipeda minima*.

Alismataceae weeds to be controlled include *Sagittaria pyginaea, Sagittaria trifolia, Sagittaria sagittifolia, Sagittaria niontevidensis, Sagittaria aginashi, Alisma canaliculatum*, and *Alisma plantago-aquatica*.

Limnocharitaceae weeds to be controlled include *Limnocharis flava*.

Hydrocharitaceae weeds to be controlled include *Limnobium spongia, Hydrilla verticillata,* and *Alajas guadalupensis.*

Araceae weeds to be controlled include *Pistia stratiotes.*

Lemnaceae weeds to be controlled include *Lemna aoukikusa, Spirodela polyrhiza,* and *Wolffia* spp.

Potamogetonaceae to be controlled include *Potamogeton distinctus, Potamogeton crispus, Potamogeton illinoensis,* and *Stuckenia pectinata.*

Liliaceae weeds to be controlled include *Allium canadense, Allium vineale,* and *Allium macrostemon.*

Pontederiaceae weeds to be controlled include *Eichhornia crassipes, Heteranthera limosa, Monochoria korsakowii,* and *Monochoria vaginalis.*

Commelinaceae weeds to be controlled include *Commelina communis, Commelina bengharensis, Commelina erecta,* and *Murdannia keisak.*

Poaceae weeds to be controlled include *Echinochloa crus-galli, Echinochloa oryzicola, Echinochloa crus-galli varformosensis, Echinochloa oryzoides, Echinochloa colona, Echinochloa crus-pavonis, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Poa trivialis, Poa pratensis, Alospecurus aequalis, Alopecurus myosuroides, Avena fatua, Sorghum halepense, Sorghum vulgare, Agropyron repens, Lohum multiflorum, Lolium perenne, Lohum rigidum, Bromus catharticus, Bromus sterilis, Bromus japonicus, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Chlorisvirgata, Eragrostis pilosa, Rhynchelitrum repens, Dactyloctenium aegyptium, Ischaenmm rugosum, Isachne globosa, Oryza sativa, Paspalum notatum, Paspalum maritimum, Paspalum distichum, Pennisetum clandestinum, Pennisetum setosum, Rottboelha cochinchinensis, Leptochloa chinensis, Leptochloa fascicularis, Leptochloa filiformis, Leptochloa panicoides, Leersia japonica, Leersia sayanuka, Leersia oryzoides, Glyceria leptorrhiza, Glyceria acutiflora, Glyceria maxima, Agrostis gigantea, Agrostis stolonifera, Cynodon dactylon, Dactylis glomerata, Eremochloa ophiuroides, Festuca arundinacea, Festuca rubra, Imperata cylindrica, Miscanthus sinensis, Panicum virgatum,* and *Zoysia japonica.*

Cyperaceae weeds to be controlled include *Cyperus microiria, Cyperus iria, Cyperus compressus, Cyperus difformis, Cyperus flaccidus, Cyperus globosus, Cyperus nipponics, Cyperus odorants, Cyperus serotinus, Cyperus rotundus, Cyperus esculentus, Kyllinga gracillima, Kyllinga brevifolia, Fimbristylis miliacea, Fimbristyhs dichotoma, Eleocharis acicularis, Eleocharis kuroguwai, Schoenoplectiella hotarui, Schoenoplectiella juncoides, Schoenoplectiella wallichii, Schoenoplectiella mucronatus, Schoenoplectiella triangulatus, Schoenoplectiella nipponicus, Schoenoplectiella triqueter, Bolboschoenus koshevnikovii,* and *Bolboschoenus fluviatilis.*

Equisetaceae weeds to be controlled include Equisetum *arvense,* and *Equisetum palustre.*

Salviniaceae weeds to be controlled include *Salvinia natans.*

Azollaceae weeds to be controlled include *Azolla japonica* and *Azolla imbricata.*

Marsileaceae weeds to be controlled include *Marsilea quadrifolia.*

Other weeds to be controlled include *Pithophora, Cladophora, Bryophyte, Marchantiophyta, Anthocerotophyta, Cyanobacteria, Pteridophyta,* sucker of perennial crops (pomaceous fruits, nut trees, citruses, *Humulus lupulus,* grapes, and the like).

In the above-mentioned weeds to be controlled, mutations within the species are not particularly limited. That is, the weeds include weeds having reduced sensitivity to a specific herbicide. The reduced sensitivity may be attributed to a mutation at a target site (target site mutation) or may be attributed to any factors other than the target site mutation (non-target site mutation). Examples of the factor of the reduced sensitivity due to a non-target site mutation include increased metabolism, malabsorption, translocation dysfunction, and excretion to out of system. Examples of the factor of the increased metabolism include the enhanced activity of a metabolizing enzyme such as cytochrome P450 monooxygenase, aryl acylamidase, esterase, or glutathione S-transferase. Examples of the excretion to out of system include transport to the vacuole by an ABC transporter. Examples of the weeds having reduced sensitivity due to a target site mutation include weeds having any one of or two or more of the following amino acid substitutions in the ALS gene: Ala122Thr, Ala122Val, Ala122Tyr, Pro197Ser, Pro197His, Pro197Thr, Pro197Arg, Pro197Leu, Pro197Gln, Pro197Ala, Pro197Ile, Ala205Val, Ala205Phe, Asp376Glu, Arg377His, Trp574Leu, Trp574Gly, Trp574Met, Ser653Thr, Ser653Thr, Ser653Asn, Ser635Ile, Gly654Glu, and Gly645Asp. Similarly, examples of the weeds having reduced sensitivity due to a target site mutation include weeds having any one of or two or more of the following amino acid substitutions in the ACCase gene: Ile1781Leu, Ile1781Val, Ile1781Thr, Trp1999Cys, Trp1999Leu, Ala2004Val, Trp2027Cys, Ile2041Asn, Ile2041Val, Asp2078Gly, Cys2088Arg, Gly2096Ala, and Gly2096Ser.

Similarly, as an example of the weeds having reduced sensitivity due to a target site mutation, PPO inhibitor-resistant weeds having one or more mutations selected from an Arg128Leu mutation, an Arg128Met mutation, an Arg128Gly mutation, an Arg128His mutation, a Gly210 deletion mutation, and a Gly399Ala mutation in PPO. The word "PPO" means protoporphyrinogen oxidase. Weeds usually have PPO1 and PPO2 in PPO, and the above-mentioned mutations may be present in either PPO1 or PPO2 or in both. The case where weeds have the mutations in PPO2 is preferable. For example, the word "Arg128Met" means that the mutation is present in the 128th (the number is standardized with PPO2 of *Amaranthus palmeri*) amino acid. In PPO2 of *Ambrosia artemisiaefolia,* the mutation corresponds to a mutation in the 98th amino acid (Rousonelos, et al., Weed Science (2012) Vol. 60, pgs. 335-344) and is known as Arg98Leu. In this case, Arg98 is equivalent to Arg128 according to the present invention. The Arg128Met mutation and the Arg128Gly mutation in the PPO of the weed to be controlled in the present invention are known in *Amaranthus palmeri* (Giacomini, et al., Pest Management Science (2017) Vol. 73, pgs. 1559-1563), the Arg128His mutation is known in *Lolium rigidum* (Fernandez-Moreno, et al., Weed Science Society of America (WSSA) annual meeting, 2018), and the Gly399Ala mutation is known in *Amaranthus palmeri* (Rangani, et al., WSSA annual meeting, 2018). In the present invention, the above-mentioned reported resistant weeds are particularly effectively controlled, but particularly effectively controlled weeds are not limited thereto. That is, other weeds having the amino acid mutation are similarly controlled. Not only *Amaranthus palmeri* having an Arg128Leu mutation, an Arg128Met mutation, an Arg128Gly mutation, an Arg128His mutation, a Gly210 deletion mutation, or a Gly399Ala mutation, but also, for example, waterhemp having the above-mentioned mutation, *Ambrosia artemisiaefolia* having the above-mentioned mutation, *Lolium rigidum* having the above-mentioned mutation, *Lolium multiflorum* having the above-mentioned mutation, and *Euphorbia heterophylla* having the above-mentioned mutation are effectively controlled.

Similarly, examples of the weeds having reduced sensitivity due to a target site mutation include weeds having an amino acid substitution such as Thr102Ile, Pro106Ser, Pro106Ala, or Pro106Leu in the EPSP gene. In particular, *Eleusine indica, Lolium multiflorum, Lolium rigidum, Digitaria insularis*, waterhemp, *Echinochloa colona*, and the like which are resistant to glyphosate and have one or both of the mutations are effectively controlled. Similarly, examples of the weeds having reduced sensitivity due to a target site include weeds having increased copies of the EPSP gene and *Amaranthus palmeri*, waterhemp, *Kochia scoparia*, and the like which are resistant to glyphosate and have the mutation are particularly effectively controlled. *Conyza canadensis, Conyza smatrensis*, and *Conyza bonariensis* which are resistant to glyphosate in which an ABC transporter is involved are also effectively controlled.

In the cultivation of a crop according to the present invention, plant nutritional management in general cultivation of a crop can be performed. The fertilization system may be based on Precision Agriculture or may be conventionally uniform one. In addition, a nitrogen-fixing bacterium or a mycorrhizal fungus can be inoculated in combination with seed treatment.

Combinations

In certain aspects, controlling effect on weeds is exhibited by using a compound of formula I and a specific compound in combination.

Accordingly, the present invention features—[1] A herbicidal composition including a compound of formula I and at least one compound selected from the group consisting of a herbicide compound group B and a safener group C, wherein a weight ratio of a compound of formula I to the at least one compound selected from the group consisting of the herbicide compound group B and the safener group C is 1:0.1 to 1:50, and the herbicide compound group B is a group consisting of the following B-1 to B-12:
B-1 acetolactate synthase inhibitors;
B-2 acetyl-CoA carboxylase inhibitors;
B-3 protoporphyrinogen IX oxidase inhibitors;
B-4 4-hydrophenylpyruvate dioxygenase inhibitors;
B-5 phytoene desaturase inhibitors;
B-6 photosystem II inhibitors;
B-7 very long chain fatty acid synthesis inhibitors;
B-8 microtubule formation inhibitors;
B-9 auxin herbicides;
B-10 enolpyruvylshikimate 3-phosphate synthase inhibitors;
B-11 glutamine synthase inhibitors; and
B-12 other herbicides (including agriculturally acceptable salts or derivatives for each of B-1 to B-12).

The present invention also features—[2] the herbicidal composition according to [1], wherein the B-1 is a group consisting of pyrithiobac, pyrithiobac-sodium salt, pyriminobac, pyriminobac-methyl, bispyribac, bispyribac-sodium salt, pyribenzoxim, pyrimisulfan, pyriftalid, triafamone, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, metazosulfuron, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron, trifloxysulfuron-sodium salt, chlorsulfuron, cinosulfuron, ethametsulfuron, ethametsulfuron-methyl, iodosulfuron, iodosulfuron-methyl-sodium, iofensulfuron, iofensulfuron-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, bencarbazone, flucarbazone, flucarbazone-sodium salt, propoxycarbazone, propoxycarbazone-sodium salt, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium salt, imazapic, imazapic-ammonium salt, imazapyr, imazapyr-isopropylammonium salt, imazaquin, imazaquin-ammonium, imazethapyr, and imazethapyr-ammonium salt (including agriculturally acceptable salts and derivatives thereof for each);

the B-2 is a group consisting of clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, and pinoxaden (including agriculturally acceptable salts and derivatives thereof for each);

the B-3 is a group consisting of azafenidin, oxadiazon, oxadiargyl, carfentrazone, carfentrazone-ethyl, saflufenacil, cinidon, cinidon-ethyl, sulfentrazone, pyraclonil, pyraflufen, pyraflufen-ethyl, butafenacil, fluazolate, fluthiacet, fluthiacet-methyl, flufenpyr, flufenpyr-ethyl, flumiclorac, flumiclorac-pentyl, flumioxazin, pentoxazone, oxyfluorfen, acifluorfen, acifluorfen-sodium salt, aclonifen, chlormethoxynil, chlornitrofen, nitrofen, bifenox, fluoroglycofen, fluoroglycofen-ethyl, fomesafen, fomesafen-sodium salt, lactofen, tiafenacil, and ethyl [3-[2-chl oro-4-fluoro-5-(1-methyl-6-trifluoromethyl-2,4-di oxo-1,2,3, 4-tetrahydropyrimidin-3-yl)phenoxy]-2-pyridyloxy] acetate (including agriculturally acceptable salts and derivatives thereof for each);

the B-4 is a group consisting of benzobicyclon, bicyclopyrone, mesotrione, sulcotrione, tefuryltrione, tembotrione, isoxachlortole, isoxaflutole, benzofenap, pyrasulfotole, pyrazolynate, pyrazoxyfen, fenquinotrione, topramezone, tolpyralate, lancotrione, lancotrione-sodium salt, 2-methyl-N-(5-methyl-1,3,4-oxadiazol-2-yl)-3-(methylsulfonyl)-4-(trifluoromethyl) benzamide (CAS Registry Number: 1400904-50-8), 2-chloro-N-(1-methyl-1H-tetrazol-5-yl)-3-(methylthio)-4-(trifluoromethyl)-benzamide (CAS Registry Number: 1361139-71-0), and 4-(4-fluorophenyl)-6-[(2-hydroxy-6-oxo-1-cyclohexene-1-yl)carbonyl]-2-methyl-1,2,4-triazine-3,5(2H,4H)-dione (CAS Registry Number: 1353870-34-4) (including agriculturally acceptable salts and derivatives thereof for each);

the B-5 is a group consisting of diflufenican, picolinafen, beflubutamid, norflurazon, fluridone, flurochloridone, and flurtamone (including agriculturally acceptable salts and derivatives thereof for each);

the B-6 is a group consisting of ioxynil, ioxynil-octanoate, bentazone, pyridate, bromoxynil, bromoxynil-octanoate, chlorotoluron, dimefuron, diuron, linuron, fluometuron, isoproturon, isouron, tebuthiuron, benzthiazuron, methabenzthiazuron, propanil, metobromuron, metoxuron, monolinuron, siduron, simazine, atrazine, propazine, cyanazine, ametryn, simetryn, dimethametryn, prometryn, terbumeton, terbuthylazine, terbutryn, trietazine, hexazinone, metamitron, metribuzin, amicarbazone, bromacil, lenacil, terbacil, chloridazon, desmedipham, and phenmedipham (including agriculturally acceptable salts and derivatives thereof for each);

the B-7 is a group consisting of propachlor, metazachlor, alachlor, acetochlor, metolachlor, S-metolachlor, butachlor, pretilachlor, thenylchlor, indanofan, cafenstrole, fentrazamide, dimethenamid, dimethenamid-P, mefenacet, pyroxasulfone, fenoxasulfone, naproanilide, napropamide, anilofos, flufenacet, and ipfencarbazone (including agriculturally acceptable salts and derivatives thereof for each);

the B-8 is a group consisting of trifluralin, pendimethalin, ethalfluralin, benfluralin, oryzalin, prodiamine, butamifos, dithiopyr, and thiazopyr (including agriculturally acceptable salts and derivatives thereof for each);

the B-9 is a group consisting of 2,4-DB [4-(2,4-dichlorophenoxy)butyric acid] and its salts or esters (dimethylammonium salt, isooctyl ester, and choline salt), MCPA and its salts or esters (dimethylammonium salt, 2-ethylhexyl ester, isooctyl ester, sodium salt, and choline salt), MCPB, mecoprop and its salts or esters (dimethylammonium salt, dioramine salt, ethadyl ester, 2-ethylhexyl ester, isooctyl ester, methyl ester, potassium salt, sodium salt, trolamine salt, and choline salt), mecoprop-P and its salts or esters (dimethylammonium salt, 2-ethylhexyl ester, isobutyl salt, potassium salt, and choline salt), dichlorprop and its salt or ester (butotyl ester, dimethylammonium salt, 2-ethylhexyl ester, isooctyl ester, methyl ester, potassium salt, sodium salt, and choline salt), dichlorprop-P, dichlorprop-P dimethylammonium, triclopyr and its salts or esters (butotyl ester, and triethylammonium salt), fluroxypyr, fluroxypyr-meptyl, picloram and its salts (potassium salt, tris(2-hydroxypropyl)ammonium salt, and choline salt), quinclorac, quinmerac, aminopyralid and its salts (potassium salt, tris(2-hydroxypropyl)ammonium salt, and choline salt), clopyralid and its salts (olamine salt, potassium salt, triethylammonium salt, and choline salt), clomeprop, aminocyclopyrachlor, halauxifen, halauxifen-methyl, florpyrauxifen, and florpyrauxifen-benzyl (including agriculturally acceptable salts and derivatives thereof for each);

the B-10 is a group consisting of glyphosate, glyphosate-isopropylammonium salt, glyphosate-trimesium salt, glyphosate-ammonium salt, glyphosate-diammonium salt, glyphosate-dimethylammonium salt, glyphosate-monoethanolamine salt, glyphosate-sodium salt, glyphosate-potassium salt, and glyphosate-guanidine salt (including agriculturally acceptable salts and derivatives thereof for each);

B-11 is a group consisting of glufosinate, glufosinate-ammonium salt, glufosinate-P, glufosinate-P-sodium salt, and bialaphos (including agriculturally acceptable salts and derivatives thereof for each); and the B-12 is a group consisting of isoxaben, dichlobenil, methiozolin, diallate, butylate, triallate, chlorpropham, asulam, phenisopham, benthiocarb, molinate, esprocarb, pyributicarb, prosulfocarb, orbencarb, EPTC, dimepiperate, swep, difenoxuron, methyldymron, bromobutide, daimuron, cumyluron, diflufenzopyr, diflufenzopyr-sodium salt, etobenzanid, tridiphane, amitrole, clomazone, 2-[(2,4-dichlorophenyl)methyl]-4,4-dimethylisoxazolidin-3-one (CAS Registry Number: 81777-95-9), (3S,4S)—N-(2-fluorophenyl)-1-methyl-2-oxo-4-[3-(trifluoromethyl)phenyl]-3-pyrrolidinecarboxamide (CA S Registry Number: 2053901-33-8), maleic hydrazide, oxaziclomefone, cinmethylin, benfuresate, ACN, dalapon, chlorthiamid, flupoxam, bensulide, paraquat, paraquat-dichloride, diquat, diquat-dibromide, MSMA, indaziflam, and triaziflam (including agriculturally acceptable salts and derivatives thereof for each).

The present invention also features—[3] the herbicidal composition according to [1] or [2], wherein the safener group C is a group consisting of benoxacor, cloquintocet, cyometrinil, cyprosulfamide, dichlormid, dicyclonone, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane, 2,2,5-trimethyl-3-(dichloroacetyl)-1,3-oxazolidine, and N-(2-methoxybenzoyl)-4-[(methylaminocarbonyl)amino]benzenesulfon-amide.

In one embodiment, the present invention includes—[4] the herbicidal composition according to [1], wherein B-1 is a group consisting of pyrithiobac, pyrithiobac-sodium salt, chlorimuron-ethyl, foramsulfuron, halosulfuron-methyl, nicosulfuron, primisulfuron-methyl, rimsulfuron, trifloxysulfuron-sodium salt, chlorsulfuron, iodosulfuron-methyl-sodium, iofensulfuron sodium, metsulfuron-methyl, prosulfuron, thifensulfuron-methyl, tribenuron-methyl, thiencarbazone-methyl, cloransulam-methyl, flumetsulam, imazamethabenz-methyl, imazamox-ammonium salt, imazapic-ammonium salt, imazapyr-isopropylammonium, imazaquin-ammonium salt, and imazethapyr-ammonium salt (including agriculturally acceptable salts and derivatives thereof for each).

In another embodiment, the present invention includes—[5] the herbicidal composition according to [1], wherein B-2 is a group consisting of fenoxaprop-ethyl, fenoxaprop-P-ethyl, fluazifop-butyl, fluazifop-P-butyl, quizalofop-ethyl, quizalofop-P-ethyl, clethodim, and sethoxydim (including agriculturally acceptable salts and derivatives thereof for each).

In another embodiment, the present invention includes—[6] the herbicidal composition according to [1], wherein B-3 is a group consisting of carfentrazone-ethyl, saflufenacil, sulfentrazone, pyraflufen-ethyl, fluthiacet-methyl, flufenpyr-ethyl, flumiclorac-pentyl, flumioxazin, oxyfluorfen, acifluorfen-sodium salt, fomesafen-sodium salt, lactofen, tiafenacil, and ethyl [(3-{2-chloro-4-fluoro-5-[3-methyl-4-(trifluoromethyl)-2,6-dioxo-1,2,3,6-tetrahydropyrimidine-1-yl]phenoxy}pyridin-2-yl)oxy]acetate (including agriculturally acceptable salts and derivatives thereof for each).

In another embodiment, the present invention includes—[7] the herbicidal composition according to [1], wherein B-4 is a group consisting of bicyclopyrone, mesotrione, tembotrione, isoxaflutole, fenquinotrione, topramezone, tolpyralate, lancotrione-sodium salt, 2-methyl-N-(5-methyl-1,3,4-oxadiazol-2-yl)-3-(methylsulfonyl)-4-(trifluoromethyl)benzamide (CAS Registry Number 1400904-50-8), 2-chloro-N-(1-methyl-1H-tetrazol-5-yl)-3-(methylthio)-4-

(trifluoromethyl)-benzamide (CAS Registry Number 1361139-71-0), and 4-(4-fluorophenyl)-6-[(2-hydroxy-6-oxo-1-cyclohexene-1-yl)carbonyl]-2-methyl-1,2,4-triazine-3,5-(2H,4H)-dione (CAS Registry Number 1353870-34-4) (including agriculturally acceptable salts and derivatives thereof for each).

In another embodiment, the present invention includes—
[8] the herbicidal composition according to [1], wherein B-5 is a group consisting of norflurazon and fluridone (including agriculturally acceptable salts and derivatives thereof for each).

In another embodiment, the present invention includes—
[9] the herbicidal composition according to [1], wherein B-6 is a group consisting of bentazone, bromoxynil octanoate, diuron, linuron, fluometuron, simazine, atrazine, ametryn, prometryn, and metribuzin (including agriculturally acceptable salts and derivatives thereof for each).

In another embodiment, the present invention includes—
the herbicidal composition according to [1], wherein B-7 is a group consisting of alachlor, acetochlor, metolachlor, S-metolachlor, dimethenamid, dimethenamid-P, pyroxasulfone, and flufenacet (including agriculturally acceptable salts and derivatives thereof for each).

In another embodiment, the present invention includes—
the herbicidal composition according to [1], wherein B-8 is a group consisting of trifluralin, pendimethalin, and ethalfluralin (including agriculturally acceptable salts and derivatives thereof for each).

In another embodiment, the present invention includes—
the herbicidal composition according to [1], wherein B-9 is a group consisting of 2,4-DB, fluroxypyr, fluroxypyr-meptyl, clopyralid-olamine salt, clopyralid-potassium salt, clopyralid-triethylammonium salt, halauxifen, halauxifen-methyl, florpyrauxifen, and florpyrauxifen-benzyl (including agriculturally acceptable salts and derivatives thereof for each).

In another embodiment, the present invention includes—
the herbicidal composition according to [1], wherein B-10 is a group consisting of a combination of two or more of glyphosate, glyphosate-isopropyl ammonium salt, glyphosate-ammonium salt, glyphosate-dimethyl amine salt, glyphosate-monoethanolamine salt, glyphosate-potassium salt, and glyphosate-guanidine salt (including agriculturally acceptable salts and derivatives thereof for each).

In another embodiment, the present invention includes—
the herbicidal composition according to [1], wherein the B-11 is a group consisting of glufosinate, glufosinate-ammonium salt, glufosinate-P, and glufosinate-P-sodium salt (including agriculturally acceptable salts and derivatives thereof for each).

In another embodiment, the present invention includes—
the herbicidal composition according to [1], wherein the B-12 is a group consisting of EPTC, diflufenzopyr, diflufenzopyr-sodium salt, clomazone, 2-[(2,4-dichlorophenyl) methyl]-4,4-dimethylisoxazolidin-3-one (CA S Registry Number: 81777-95-9), (3S,4,S)—N-(2-fluorophenyl)-1-methyl-2-oxo-4-[3-(trifluoromethyl)phenyl]-3-pyrrolidinecarboxamide (CAS Registry Number: 2053901-33-8), cinmethylin, MSMA, paraquat, paraquat dichloride, diquat, and diquat dibromide (including agriculturally acceptable salts and derivatives thereof for each).

In another embodiment, the present invention includes—
The herbicidal composition according to [1], wherein the safener group C is a group consisting of benoxacor, cyprosulfamide, and isoxadifen-ethyl (including agriculturally acceptable salts and derivatives thereof for each).

The present invention also features—A method for controlling weeds, the method including a step of applying a compound of formula I and at least one compound selected from the group consisting of the herbicide compound group B and the safener group C simultaneously or sequentially to a place where weeds are growing or to grow.

In one embodiment, the present invention includes—The method according to [18], wherein a compound of formula I and the at least one compound selected from the group consisting of the herbicide compound group B and the safener group C are used at a weight ratio of 1:0.1 to 1:50.

In another embodiment, the present invention includes—
The method according to or [19], wherein the place where weeds are growing or to grow is a crop field.

The present invention also features—A use of the herbicidal composition according to any one of [1] to [16], for controlling weeds.

Herbicidal compositions according to the present invention also include a compound of formula I and at least one compound selected from the group consisting of an herbicide compound group B and a safener group C.

The method for controlling weeds according to the present invention (hereinafter referred to as "present method") includes the step of applying the present composition to a place where weeds are growing or likely to grow in a crop field, a vegetable field, a land under perennial crops, a non-crop land, or the like. In a crop field and a vegetable field, the present composition may be applied before, simultaneously with, and/or after sowing a crop seed.

The present method includes the step of applying a compound of formula I and at least one compound selected from the group consisting of the herbicide compound group B and the safener group C simultaneously or sequentially to a place where weeds are growing or likely to grow. In the case of the sequential application, the order of the application is not particularly limited.

The present composition is usually a formulation prepared by mixing a compound of formula I and at least one compound selected from the group consisting of the herbicide compound group B and the safener group C with a carrier such as a solid carrier or a liquid carrier and adding an auxiliary agent for formulation such as a surfactant if necessary. Preferable formulation types of such a formulation are aqueous liquid suspension concentrates, wettable powders, water dispersible granules, granules, and emulsifiable concentrates. The present composition may be used in combination with a formulation containing another herbicide as an active ingredient.

The total content of a compound of formula I and the at least one compound selected from the group consisting of the herbicide compound group B and the safener group C in the present composition is within a range of 0.01 to 90% by weight, preferably 1 to 80% by weight.

Hereinafter, when the at least one compound selected from the group consisting of the herbicide compound group B is a salt (for example, glyphosate-potassium salt), the weight of the at least one compound is represented by the acid equivalent.

A mixing ratio of a compound of formula I to the at least one compound selected from the group consisting of the herbicide compound group B and the safener group C in the present composition is within a range of 1:0.05 to 1:100, preferably 1:0.1 to 1:50 by weight ratio.

A ratio of application rates of a compound of formula I to the at least one compound selected from the group consisting of the herbicide compound group B and the safener group C in the present method is within a range of 1:0.05 to 1:100, preferably 1:0.1 to 1:50 by weight ratio.

In some variations, the mixing ratio of a compound of formula I to the at least one compound selected from the group consisting of the herbicide compound group B and the safener group C in the present composition include about 1:0.1, about 1:0.2, about 1:0.3, about 1:0.5, about 1:0.7, about 1:1, about 1:2, about 1:3, about 1:5, about 1:7, about 1:10, about 1:15, about 1:20, about 1:30, and about 1:50 by weight ratio.

In some variations, the ratio of application rates of a compound of formula I to the at least one compound selected from the group consisting of the herbicide compound group B and the safener group C in the present method include about 1:0.1, about 1:0.2, about 1:0.3, about 1:0.5, about 1:0.6, about 1:0.7, about 1:0.8, about 1:1, about 1:1.2, about 1:1.4, about 1:1.6, about 1:1.8, about 1:2, about 1:2.2, about 1:2.4, about 1:2.6, about 1:2.8, about 1:3, about 1:5, about 1:7, about 1:10, about 1:15, about 1:20, about 1:30, and about 1:50 by weight ratio.

The word "about" in the preceding paragraph means that the specified ratio includes the ratio in the range increased or decreased by 10% by weight relative to the specified ratio. For example, a ratio of about 1:2 includes a range of 1:1.8 to 1:2.2.

In the present composition and the present method, particularly preferable examples of the combination of a compound of formula I and the at least one compound selected from the group consisting of the herbicide compound group B and the safener group C and the range of weight ratio thereof include, but are not limited to, the following combinations and the ranges:

a combination of a compound of formula I and pyrithiobac (1:0.1 to 1:20);
a combination of a compound of formula I and pyrithiobac-sodium salt (1:0.1 to 1:20);
a combination of a compound of formula I and chlorimuron-ethyl (1:0.1 to 1:20);
a combination of a compound of formula I and foramsulfuron (1:0.1 to 1:20);
a combination of a compound of formula I and halosulfuron-methyl (1:0.1 to 1:20);
a combination of a compound of formula I and nicosulfuron (1:0.1 to 1:20);
a combination of a compound of formula I and primisulfuron-methyl (1:0.1 to 1:20);
a combination of a compound of formula I and rimsulfuron (1:0.1 to 1:20);
a combination of a compound of formula I and trifloxysulfuron-sodium salt (1:0.1 to 1:20);
a combination of a compound of formula I and chlorsulfuron (1:0.1 to 1:20);
a combination of a compound of formula I and iodosulfuron-methyl-sodium (1:0.1 to 1:20);
a combination of a compound of formula I and iofensulfuron-sodium (1:0.1 to 1:20);
a combination of a compound of formula I and metsulfuron-methyl (1:0.1 to 1:20);
a combination of a compound of formula I and prosulfuron (1:0.1 to 1:20);
a combination of a compound of formula I and thifensulfuron-methyl (1:0.1 to 1:20);
a combination of a compound of formula I and tribenuron-methyl (1:0.1 to 1:20);
a combination of a compound of formula I and thiencarbazone-methyl (1:0.1 to 1:20);
a combination of a compound of formula I and cloransulam-methyl (1:0.1 to 1:20);
a combination of a compound of formula I and flumetsulam (1:0.1 to 1:20);
a combination of a compound of formula I and imazamethabenz-methyl (1:0.1 to 1:20);
a combination of a compound of formula I and imazamox-ammonium salt (1:0.1 to 1:20);
a combination of a compound of formula I and imazapic-ammonium salt (1:0.1 to 1:20);
a combination of a compound of formula I and imazapyr-isopropylammonium salt (1:0.1 to 1:20);
a combination of a compound of formula I and imazaquin-ammonium salt (1:0.1 to 1:20);
a combination of a compound of formula I and imazethapyr-ammonium salt (1:0.1 to 1:20);
a combination of a compound of formula I and fenoxaprop-ethyl (1:0.1 to 1:20);
a combination of a compound of formula I and fenoxaprop-P-ethyl (1:0.1 to 1:20);
a combination of a compound of formula I and fluazifop-butyl (1:0.1 to 1:20);
a combination of a compound of formula I and fluazifop-P-butyl (1:0.1 to 1:20);
a combination of a compound of formula I and quizalofop-ethyl (1:0.1 to 1:20);
a combination of a compound of formula I and quizalofop-P-ethyl (1:0.1 to 1:20);
a combination of a compound of formula I and clethodim (1:0.1 to 1:20);
a combination of a compound of formula I and sethoxydim (1:0.1 to 1:20);
a combination of a compound of formula I and carfentrazone-ethyl (1:0.1 to 1:20);
a combination of a compound of formula I and saflufenacil (1:0.1 to 1:20);
a combination of a compound of formula I and sulfentrazone (1:0.1 to 1:30);
a combination of a compound of formula I and pyraflufen-ethyl (1:0.1 to 1:30);
a combination of a compound of formula I and fluthiacet-methyl (1:0.1 to 1:20);
a combination of a compound of formula I and flufenpyr-ethyl (1:0.1 to 1:20);
a combination of a compound of formula I and flumiclorac-pentyl (1:0.1 to 1:20);
a combination of a compound of formula I and flumioxazin (1:0.1 to 1:20);
a combination of a compound of formula I and oxyfluorfen (1:0.1 to 1:30);
a combination of a compound of formula I and acifluorfen-sodium salt (1:0.1 to 1:30);
a combination of a compound of formula I and fomesafen-sodium salt (1:0.1 to 1:30);
a combination of a compound of formula I and lactofen (1:0.1 to 1:30);
a combination of a compound of formula I and tiafenacil (1:0.1 to 1:20);
a combination of a compound of formula I and ethyl [(3-{2-chloro-4-fluoro-5-[3-methyl-4-(trifluoromethyl)-2,6-dioxo-1,2,3,6-tetrahydropyrimidine-1-yl]phenoxy}pyridin-2-yl)oxy]acetate (1:0.1 to 1:20);
a combination of a compound of formula I and bicyclopyrone (1:0.1 to 1:20);
a combination of a compound of formula I and mesotrione (1:0.1 to 1:20);

a combination of a compound of formula I and tembotrione (1:0.1 to 1:20);
a combination of a compound of formula I and isoxaflutole (1:0.1 to 1:20);
a combination of a compound of formula I and fenquinotrione (1:0.1 to 1:20);
a combination of a compound of formula I and topramezone (1:0.1 to 1:20);
a combination of a compound of formula I and tolpyralate (1:0.1 to 1:20);
a combination of a compound of formula I and lancotrione-sodium salt (1:0.1 to 1:20);
a combination of a compound of formula I and 2-methyl-N-(5-methyl-1,3,4-oxadiazol-2-yl)-3-(methylsulfonyl)-4-(trifluoromethyl)benzamide (CAS Registry Number: 1400904-50-8) (1:0.1 to 1:20);
a combination of a compound of formula I and 2-chloro-N-(1-methyl-1H-tetrazol-5-yl)-3-(methylthio)-4-(trifluoromethyl)-benzamide (CAS Registry Number: 1361139-71-0) (1:0.1 to 1:20);
a combination of a compound of formula I and 4-(4-fluorophenyl)-6-[(2-hydroxy-6-oxo-1-cyclohexene-1-yl)carbonyl]-2-met-hyl-1,2,4-triazine-3,5(2H,4H)-dione (CAS Registry Number: 1353870-34-4) (1:0.1 to 1:20);
a combination of a compound of formula I and norflurazon (1:0.1 to 1:20);
a combination of a compound of formula I and fluridone (1:0.1 to 1:20);
a combination of a compound of formula I and bentazone (1:1 to 1:50);
a combination of a compound of formula I and bromoxynil octanoate (1:1 to 1:50);
a combination of a compound of formula I and diuron (1:1 to 1:50);
a combination of a compound of formula I and linuron (1:1 to 1:50);
a combination of a compound of formula I and fluometuron (1:1 to 1:50);
a combination of a compound of formula I and simazine (1:1 to 1:50);
a combination of a compound of formula I and atrazine (1:1 to 1:50);
a combination of a compound of formula I and ametryn (1:1 to 1:50);
a combination of a compound of formula I and prometryn (1:1 to 1:50);
a combination of a compound of formula I and metribuzin (1:1 to 1:50);
a combination of a compound of formula I and alachlor (1:1 to 1:50);
a combination of a compound of formula I and acetochlor (1:1 to 1:50);
a combination of a compound of formula I and metolachlor (1:1 to 1:50);
a combination of a compound of formula I and S-metolachlor (1:1 to 1:50);
a combination of a compound of formula I and dimethenamid (1:1 to 1:50);
a combination of a compound of formula I and dimethenamid-P (1:1 to 1:50);
a combination of a compound of formula I and pyroxasulfone (1:0.1 to 1:20);
a combination of a compound of formula I and flufenacet (1:0.1 to 1:20);
a combination of a compound of formula I and trifluralin (1:1 to 1:50);
a combination of a compound of formula I and pendimethalin (1:1 to 1:50);
a combination of a compound of formula I and ethalfluralin (1:1 to 1:50);
a combination of a compound of formula I and 2,4-DB (1:1 to 1:50);
a combination of a compound of formula I and fluroxypyr (1:1 to 1:50);
a combination of a compound of formula I and fluroxypyr-meptyl (1:1 to 1:50);
a combination of a compound of formula I and clopyralid-olamine salt (1:1 to 1:50);
a combination of a compound of formula I and clopyralid-potassium salt (1:1 to 1:50);
a combination of a compound of formula I and clopyralid-triethylammonium salt (1:1 to 1:50);
a combination of a compound of formula I and halauxifen (1:0.1 to 1:20);
a combination of a compound of formula I and halauxifen-methyl (1:0.1 to 1:20);
a combination of a compound of formula I and florpyrauxifen (1:0.1 to 1:20);
a combination of a compound of formula I and florpyrauxifen-benzyl (1:0.1 to 1:20);
a combination of a compound of formula I and glyphosate (1:1 to 1:50);
a combination of a compound of formula I and glyphosate-isopropylammonium salt (1:1 to 1:50);
a combination of a compound of formula I and glyphosate-ammonium salt (1:1 to 1:50);
a combination of a compound of formula I and glyphosate-dimethylamine salt (1:1 to 1:50);
a combination of a compound of formula I and glyphosate-monoethanolamine salt (1:1 to 1:50);
a combination of a compound of formula I and glyphosate-potassium salt (1:1 to 1:50);
a combination of a compound of formula I and glyphosate-guanidine salt (1:1 to 1:50);
a combination of a compound of formula I and glufosinate (1:1 to 1:50); 1:50);
a combination of a compound of formula I and glufosinate-ammonium salt (1:1 to 1:50);
a combination of a compound of formula I and glufosinate-P (1:1 to 1:50);
a combination of a compound of formula I and glufosinate-P-sodium salt (1:1 to 1:50);
a combination of a compound of formula I and EPTC (1:1 to 1:50);
a combination of a compound of formula I and diflufenzopyr (1:1 to 1:50);
a combination of a compound of formula I and diflufenzopyr-sodium salt (1:1 to 1:50);
a combination of a compound of formula I and clomazone (1:1 to 1:50);
a combination of a compound of formula I and 2-[(2,4-dichlorophenyl)methyl]-4,4-dimethylisoxazolidin-3-one (CAS Registry Number: 81777-95-9) (1:1 to 1:50);
a combination of a compound of formula I and (3S,4S)—N-(2-fluorophenyl)-1-methyl-2-oxo-4-[3-(trifluoromethyl)phenyl]-3-pyrrolidinecarboxamide (CAS Registry Number: 2053901-33-8) (1:1 to 1:50);
a combination of a compound of formula I and cinmethylin (1:1 to 1:50);
a combination of a compound of formula I and MSMA (1:1 to 1:50);
a combination of a compound of formula I and paraquat (1:1 to 1:50);
a combination of a compound of formula I and paraquat-dichloride (1:1 to 1:50);
a combination of a compound of formula I and diquat (1:1 to 1:50);

a combination of a compound of formula I and diquat-dibromide (1:1 to 1:50);

a combination of a compound of formula I and benoxacor (1:0.1 to 1:20);

a combination of a compound of formula I and cyprosulfamide (1:0.1 to 1:20); or a combination of a compound of formula I and isoxadifen-ethyl (1:0.1 to 1:20).

Before, simultaneously with, and/or after sowing a crop seed treated with one or more compounds selected from the group consisting of an insecticide compound, a nematicide compound, a fungicide compound, and the like, the present composition may be applied to the field in which the crop seed have been sown or is to be sown.

In some embodiments, the present composition may be used in combination with another pesticidally-active compound. Examples of the insecticide compound, the nematicide compound, and the fungicide compound which may be used in combination with the present composition include neonicotinoid compounds, diamide compounds, carbamate compounds, organophosphorus compounds, biological nematicide compounds, other insecticide compounds and nematicide compounds, azole compounds, strobilurin compounds, metalaxyl compounds, SDHI compounds, and other fungicide compounds and plant growth regulators.

EXAMPLES

The presently disclosed subject matter will be better understood by reference to the following Examples, which are provided as exemplary of the invention, and not by way of limitation.

Compound Synthesis and Characterization

Steps in the following Examples illustrate a procedure for each step in an overall synthetic transformation, and the starting material for each step may not have necessarily been prepared by a procedure described in other Examples or Steps. $^{1}$H-NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet. Mass spectra (MS) are reported as the molecular weight of the highest isotopic abundance parent ion (M+1) formed by addition of H$^{+}$ (molecular weight of 1) to the molecule, or (M−1) formed by the loss of H$^{+}$ (molecular weight of 1) from the molecule, observed by using liquid chromatography coupled to a mass spectrometer (LCMS) using either atmospheric pressure chemical ionization (AP+) where "amu" stands for unified atomic mass units or electrospray ionization (ES$^{+}$).

Example 1. Preparation of 2,2,7-trifluoro-6-(perfluorophenyl)-2H-benzo[b][1,4]oxazin-3(4H)-one (Compound 1) and 2,2,7-trifluoro-6-(perfluorophenyl)-4-(prop-2-yn-1-yl)-2H-benzo[b][1,4]oxazin-3(4H)-one (Compound 2)

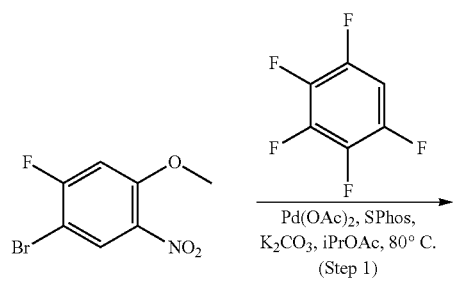

Scheme 3

As shown in Step 1 of Scheme 3, to a degassed mixture of 1-bromo-2-fluoro-4-methoxy-5-nitrobenzene (3.0 g, 12.0 mmol) in isopropyl acetate (50 mL) was added Pd(OAc)$_2$ (269 mg, 1.2 mmol), 2-dicyclohexylphosphino-2',6'-dimethoxybiphenyl (Sphos, 985 mg, 2.4 mmol) and K$_2$CO$_3$ (3.3 g, 24.0 mmol) under an atmosphere of nitrogen. The resulting mixture was stirred at room temperature for 5 mins, followed by the addition of a solution of pentafluorobenzene (4.0 g, 24.0 mmol) in isopropyl acetate (10 mL). The resulting mixture was stirred at 80° C. for 16 hours under nitrogen, cooled to room temperature, filtered, and concentrated under reduced pressure. The residue was purified by flash column chromatography (0-40% ethyl acetate in petroleum ether) to afford 2,2',3,4,5,6-hexafluoro-4'-methoxy-5'-nitro-1,1'-biphenyl (Compound 1001, 2.6 g, 64% yield) as a reddish solid: GCMS calculated for ($C_{13}H_5F_6NO_3$), 337.0; found, 337.0.

As shown in Step 2 of Scheme 3, to a stirred mixture of 2,2',3,4,5,6-hexafluoro-4'-methoxy-5'-nitro-1,1'-biphenyl (2.6 g, 7.71 mmol) in DCM (50 mL) was added boron tribromide (7.7 g, 30.84 mmol) dropwise at −78° C. under an atmosphere of nitrogen. The mixture was stirred at −78° C. for 1 hour, then slowly warmed to room temperature over 16 hours. The reaction was diluted with water and extracted with DCM. The combined organics were washed with brine, dried over anhydrous sodium sulfate, filtered, and concentrated under reduced pressure to afford 2,2',3',4',5',6'-hexafluoro-5-nitro-[1,1'-biphenyl]-4-ol (Compound 1002, 2.4 g, crude) as a yellow solid: MS (ESI) calculated for ($C_{72}H_3F_6NO_3$) [M−1]$^-$, 322.0; found, 322.1. This material was used in subsequent steps without further purification.

As shown in Step 3 of Scheme 3, to a stirred solution of 2,2',3',4',5',6'-hexafluoro-5-nitro-[1,1'-biphenyl]-4-ol (2.4 g, 7.42 mmol) in EtOH (20 mL) was added a solution of sodium hyposulfite (6.4 g, 37.1 mmol) in water (20 mL). The resulting mixture was refluxed for 1 hour, cooled to room temperature, concentrated under reduced pressure, diluted with water, and extracted with ethyl acetate. The combined organics were washed with brine, dried over anhydrous sodium sulfate, filtered, and concentrated under reduced pressure to afford 5-amino-2,2',3',4',5',6'-hexafluoro-[1,1'-biphenyl]-4-ol (Compound 1003, 2.0 g, crude) as a yellow solid: MS (ESI) calculated for ($C_{12}H_5F_6NO$) [M−1]$^-$, 292.1; found, 292.1. This material was used in subsequent steps without further purification.

As shown in Step 4 of Scheme 3, to a solution of 5-amino-2,2',3',4',5',6'-hexafluoro-[1,1'-biphenyl]-4-ol (1.0 g, 3.41 mmol) in EtOAc (10 mL) were added ethyl 2-bromo-2,2-difluoroacetate (690 mg, 3.41 mmol) and triethylamine (345 mg, 3.41 mmol). The mixture was stirred at 70° C. for 1 hour, cooled to room temperature, diluted with water, and extracted with EtOAc. The combined organic layers were washed with brine, dried over anhydrous sodium sulfate, filtered, concentrated under reduced pressure, and purified by flash chromatography (0-50% ethyl acetate in petroleum ether) to afford 2-bromo-2,2-difluoro-N-(2',3',4',5',6,6'-hexafluoro-4-hydroxy-[1,1'-biphenyl]-3-yl)acetamide (Compound 1004, 800 mg, 52% yield) as a yellow solid: MS (EST) calculated for ($C_{14}H_4BrF_8NO_2$) [M+1]$^+$, 450.1; found, 450.1.

As shown in Step 5 of Scheme 3, to a stirred solution of 2-bromo-2,2-difluoro-N-(2',3',4',5',6,6'-hexafluoro-4-hydroxy-[1,1'-biphenyl]-3-yl)acetamide (600 mg, 1.33 mmol) in DMF (6 mL) was added $K_2CO_3$ (276 mg, 2.00 mmol). The mixture was stirred at 50° C. for 16 hours, diluted with water, and extracted with ethyl acetate. The combined organic layers were washed with brine, dried over anhydrous sodium sulfate, filtered, concentrated under reduced pressure, and purified by flash chromatography (0-20% ethyl acetate in petroleum ether) to afford 2,2,7-trifluoro-6-(perfluorophenyl)-2H-benzo[b][1,4]oxazin-3(4H)-one (Compound 1, 320 mg, 64% yield) as a yellow solid: MS (ESI) calculated for ($C_{14}H_3F_8NO_2$) [M−1]$^-$, 368.1; found, 368.1.

As shown in Step 6 of Scheme 3, to a solution of 2,2,7-trifluoro-6-(perfluorophenyl)-2H-benzo[b][1,4]oxazin-3(4H)-one (200 mg, 0.54 mmol) in DMF (2 mL) were added $K_2CO_3$ (74 mg, 0.54 mmol) and 3-bromoprop-1-yne (70 mg, 0.54 mmol). The mixture was stirred at room temperature for 16 hours, diluted with water, and extracted with ethyl acetate. The combined organic layers were washed with brine, dried over anhydrous sodium sulfate, filtered, concentrated under reduced pressure, and purified by flash chromatography (0-30% ethyl acetate in petroleum ether) to afford 2,2,7-trifluoro-6-(perfluorophenyl)-4-(prop-2-yn-1-yl)-2H-benzo[b][1,4]oxazin-3(4H)-one (Compound 2, 120 mg, 54% yield) as an off-white solid: GCMS calculated for ($C_{17}H_5F_8NO_2$), 407.0; found, 407.0; $^1$H-NMR (400 MHz, DMSO-d$_6$) δ 7.81-7.67 (m, 2H), 4.88 (s, 2H), 3.45 (s, 1H); $^{19}$F-NMR (400 MHz, DMSO-d$_6$) δ −74.85, −115.56, −140.50, −153.03, −162.01.

The following compounds were produced by procedures analogous to that of Step 6 of Scheme 3 by reacting Compound 1 with the appropriate alkyl halide or alkyl triflate:

2,2,7-trifluoro-4-methyl-6-(perfluorophenyl)-2H-benzo[b][1,4]oxazin-3(4H)-one (Compound 24 mg, 23% yield) as a white solid: GCMS calculated for ($C_{15}H_5F_8NO_2$), 383.0; found, 383.0; $^1$H-NMR (400 MHz, DMSO-d$_6$) δ 7.87-7.62 (m, 2H), 3.43 (s, 3H); $^{19}$F-NMR (376 MHz, DMSO-d$_6$) δ −74.05, −116.55, −140.32, −153.34, −162.15;

4-benzyl-2,2,7-trifluoro-6-(perfluorophenyl)-2H-benzo[b][1,4]oxazin-3(4H)-one (Compound 26.3 mg, 30% yield) as a white solid: GCMS calculated for ($C_{21}H_9F_8NO_2$), 459.1; found, 459.0; $^1$H-NMR (400 MHz, methanol-d$_4$) δ 7.42-7.37 (m, 4H), 7.35-7.31 (m, 3H), 5.33 (s, 2H); $^{19}$F-NMR (376 MHz, methanol-d$_4$) δ −78.80, −116.83, −142.52, −155.24 −164.83;

4-allyl-2,2,7-trifluoro-6-(perfluorophenyl)-2H-benzo[b][1,4]oxazin-3(4H)-one (Compound 11, 29.6 mg, 44% yield) as a white solid. GCMS calculated for ($C_{17}H_7F_8NO_2$), 409.0; found, 409.0; $^1$H-NMR (400 MHz, DMSO-d$_6$) δ 7.79-7.74 (m, 1H), 7.62 (d, J=6.4 Hz, 1H), 5.88 (m, 1H), 5.27-5.14 (m, 2H), 4.68-4.62 (m, 2H); $^{19}$F-NMR (376 MHz, DMSO-d$_6$) δ −74.67, −116.18, −140.50, −153.27, −162.03;

4-ethyl-2,2,7-trifluoro-6-(perfluorophenyl)-2H-benzo[b][1,4]oxazin-3(4H)-one (Compound 12, 28.0 mg, 43% yield) as a white solid: GCMS calculated for ($C_{16}H_7F_8NO_2$), 397.0; found, 397.0; $^1$H-NMR (400 MHz, DMSO-d$_6$) δ 7.80 (d, J=6.4 Hz, 1H), 7.78-7.72 (m, 1H), 4.05 (m, 2H), 1.19 (t, J=7.2 Hz, 3H); $^{19}$F-NMR (376 MHz, DMSO-d$_6$) δ −74.60, −116.48, −140.36, −153.44, −162.15;

2,2,7-trifluoro-6-(perfluorophenyl)-4-propyl-2H-benzo[b][1,4]oxazin-3(4H)-one (Compound 13, 25 mg, 32% yield) as a white solid: GCMS calculated for ($C_{17}H_9F_8NO_2$), 411.1; found, 411.0; $^1$H-NMR (400 MHz, DMSO-d$_6$) δ 7.82-7.72 (m, 2H), 3.98 (t, J=7.2 Hz, 2H), 1.65-1.59 (m, 2H), 0.91 (t, J=6.8 Hz, 3H); $^{19}$F-NMR (400 MHz, DMSO-d$_6$) δ −74.70, −116.40, −140.10, −153.46, −162.12;

4-(3-cyclopropylprop-2-yn-1-yl)-2,2,7-trifluoro-6-(perfluorophenyl)-2H-benzo[b][1,4]oxazin-3(4H)-one (Compound 14, 28 mg, 33% yield) as a white solid: GCMS calculated for ($C_{20}H_9F_8NO_2$), 447.1; found, 447.1; $^1$H-NMR (400 MHz, DMSO-d$_6$) δ 7.76 (d, J=9.6 Hz, 1H), 7.71 (d, J=6.4 Hz, 1H), 4.80 (s, 2H), 1.32-1.24 (m, 1H), 0.80-0.69 (m, 2H), 0.58-0.50 (m, 2H); $^{19}$F-NMR (376 MHz, DMSO-d$_6$) δ −74.72, −115.70, −140.77, −153.12, −162.06;

4-(but-2-yn-1-yl)-2,2,7-trifluoro-6-(perfluorophenyl)-2H-benzo[b][1,4]oxazin-3(4H)-one (Compound 18, 31.0 mg, 37% yield) as a white solid: GCMS calculated for ($C_{18}H_7F_8NO_2$), 421.0; found, 421.1; $^1$H-NMR (400 MHz, DMSO-d$_6$) δ 7.78-7.73 (m, 2H), 4.83-4.78 (m, 2H), 1.78 (s, 3H); $^{19}$F-NMR (376 MHz, DMSO-d$_6$) δ −74.68, −115.65, −140.58, −153.09, −161.96;

2,2,7-trifluoro-4-(2-methylallyl)-6-(perfluorophenyl)-2H-benzo[b][1,4]oxazin-3(4H)-one (Compound 19, 250 mg, 72% yield) as a white solid: GCMS calculated for (C$_{18}$H$_9$F$_8$NO$_2$), 423.0; found, 423.0. $^1$H-NMR (400 MHz, DMSO-d$_6$) δ 7.77 (d, J=9.6 Hz, 1H), 7.53 (d, J=6.4 Hz, 1H), 4.92-4.88 (m, 1H), 4.72-4.66 (m, 1H), 4.56 (s, 2H), 1.75 (d, J=1.2 Hz, 3H); $^{19}$F-NMR (376 MHz, DMSO-d$_6$) δ −75.05, −116.00, −140.57, −153.23, −162.01;

2,2,7-trifluoro-6-(perfluorophenyl)-4-(2,2,2-trifluoroethyl)-2H-benzo[b][1,4]oxazin-3(4H)-one (Compound 20, 58 mg, 39% yield) as a white solid: GCMS calculated for (C$_{16}$H$_4$F$_{11}$NO$_2$), 451.0; found, 451.0; $^1$H-NMR (400 MHz, DMSO-d$_6$) δ 7.97 (d, J=6.4 Hz, 1H), 7.80 (d, J=9.2 Hz, 1H), 5.08-4.97 (m, 2H); $^{19}$F-NMR (400 MHz, DMSO-d$_6$) δ −67.95, −75.15, −115.30, −140.49, −152.81, −161.86;

2,2,7-trifluoro-4-(2-fluorobenzyl)-6-(perfluorophenyl)-2H-benzo[b][1,4]oxazin-3(4H)-one (Compound 23, 89 mg, 66% yield) as a white solid: MS (ESI) calculated for (C$_{21}$H$_8$F$_9$NO$_2$) [M+1]$^+$, 478.2; found, 477.9; $^1$H-NMR (400 MHz, DMSO-d6) δ 7.78 (d, J=9.6 Hz, 1H), 7.65 (d, J=6.4 Hz, 1H), 7.43-7.33 (m, 1H), 7.33-7.21 (m, 2H), 7.18-7.16 (m, 1H), 5.32 (s, 2H); $^{19}$F-NMR (400 MHz, DMSO-d6) δ −74.91, −115.69, −117.44, −140.68, −153.15, −162.02;

2,2,7-trifluoro-4-isopropyl-6-(perfluorophenyl)-2H-benzo[b][1,4] oxazin-3(4H)-one (Compound 24, 34.1 mg, 15% yield) as a light yellow solid: GCMS calculated for (C$_{17}$H$_9$F$_8$NO$_2$), 411.0; found, 411.0; $^1$H-NMR (400 MHz, DMSO-d6) δ 7.72-7.62 (m, 2H), −5.30 (m, 1H), 1.39 (d, J=6.4 Hz, 6H); $^{19}$F-NMR (400 MHz, DMSO-d6) δ −67.27, −112.83, −140.84, −153.73, −162.21.

Example 2. Preparation of 7-fluoro-6-(perfluorophenyl)-2H-benzo[b][1,4]oxazin-3(4H)-one (Compound 3) and 7-fluoro-6-(perfluorophenyl)-4-(prop-2-yn-1-yl)-2H-benzo[b][1,4]oxazin-3(4H)-one (Compound 4)

Scheme 4

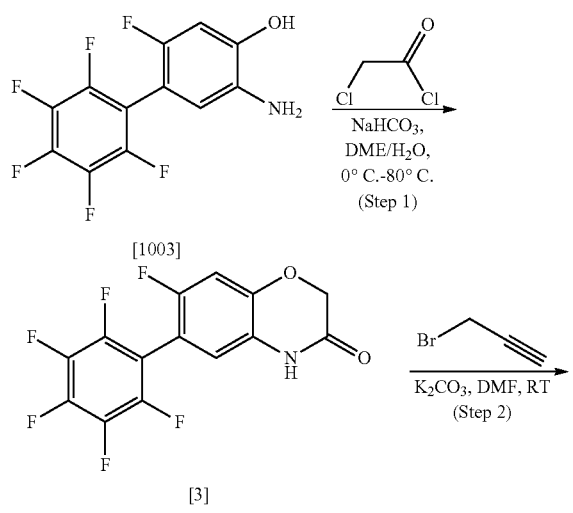

[1003]

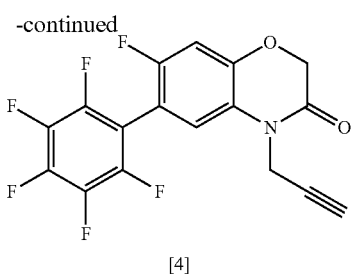

[4]

As shown in Step 1 of Scheme 4, to a solution of 5-amino-2,2',3',4',5',6'-hexafluoro-[1,1'-biphenyl]-4-ol (500 mg, 1.70 mmol) in dimethoxyethane (DME, 2.5 mL) and H$_2$O (2.5 mL) at 0° C. under an atmosphere of nitrogen was added NaHCO$_3$ (429 mg, 5.11 mmol) and chloroacetyl chloride (288 mg, 2.55 mmol). The mixture was stirred at 15° C. for minutes, then heated to 80° C. for 12 hours. After cooling, the suspension was filtered and the collected solid was washed with water and dried under vacuum to afford 7-fluoro-6-(perfluorophenyl)-2H-benzo[b][1,4]oxazin-3 (4H)-one (Compound 3, 350 mg, 60% yield) as a brown solid: MS (ESI) calculated for C$_{14}$H$_5$FNO$_2$ [M-H]$^-$=332.0, found, 332.0; $^1$H-NMR (400 MHz, DMSO-d$_6$) δ 10.93 (s, 1H), 7.18 (d, J=10.4 Hz, 1H), 6.96 (d, J=7.2 Hz, 1H), 4.71 (s, 2H); $^{19}$F-NMR (400 MHz, DMSO-d6) δ −119.20, −141.34, −154.32, −162.26.

As shown in Step 2 of Scheme 4, to a solution of 7-fluoro-6-(perfluorophenyl)-2H-benzo[b][1,4]oxazin-3 (4H)-one (60 mg, 0.18 mmol) in DMF (1 mL) were added K$_2$CO$_3$ (27 mg, 0.19 mmol) and 3-bromoprop-1-yne (23 mg, 0.19 mmol) at room temperature under nitrogen. The mixture was stirred at room temperature for 8 hours, diluted with water, and extracted with ethyl acetate. The combined organic layers were washed with brine, dried over anhydrous sodium sulfate, filtered, concentrated under reduced pressure, and purified by preparative reversed-phase HPLC using the following conditions—Column: XBridge Prep OBD C18 Column, 30×150 mm 5 um; Mobile Phase A: Water (10 mM NH$_4$HCO$_3$), Mobile Phase B: acetonitrile; Gradient: 45 B to 75 B, to afford 7-fluoro-6-(perfluorophenyl)-4-(prop-2-yn-1-yl)-2H-benzo[b][1,4]oxazin-3(4H)-one (Compound 4, 23 mg, 20% yield) as a white solid: GCMS calculated for (C$_{17}$H$_7$F$_6$NO), 371.0, found, 371.0; $^1$H-NMR (400 MHz, DMSO-d$_6$) δ 7.43 (d, J=6.8 Hz, 1H), 7.28 (d, J=9.6 Hz, 1H), 4.86 (s, 2H), 4.75 (s, 2H), 3.30 (s, 1H); $^{19}$F NMR (400 MHz, DMSO-d$_6$) δ −118.25, −140.71, −153.89, −162.21.

Example 3. Preparation of 7-fluoro-2,2-dimethyl-6-(perfluorophenyl)-2H-benzo[b][1,4]oxazin-3(4H)-one (Compound 6) and 7-fluoro-2,2-dimethyl-6-(perfluorophenyl)-4-(prop-2-yn-1-yl)-2H-benzo[b][1,4]oxazin-3(4H)-one (Compound 7)

Scheme 5

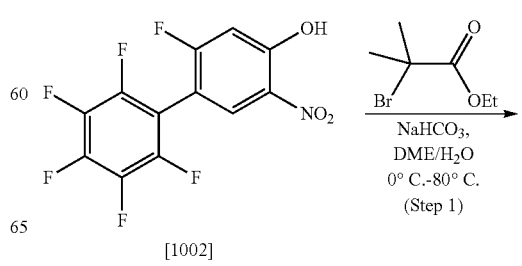

[1002]

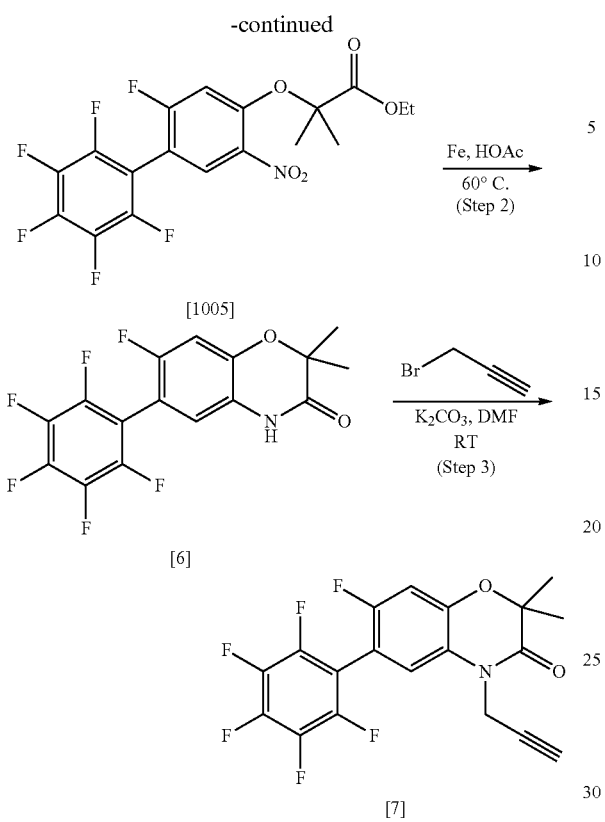

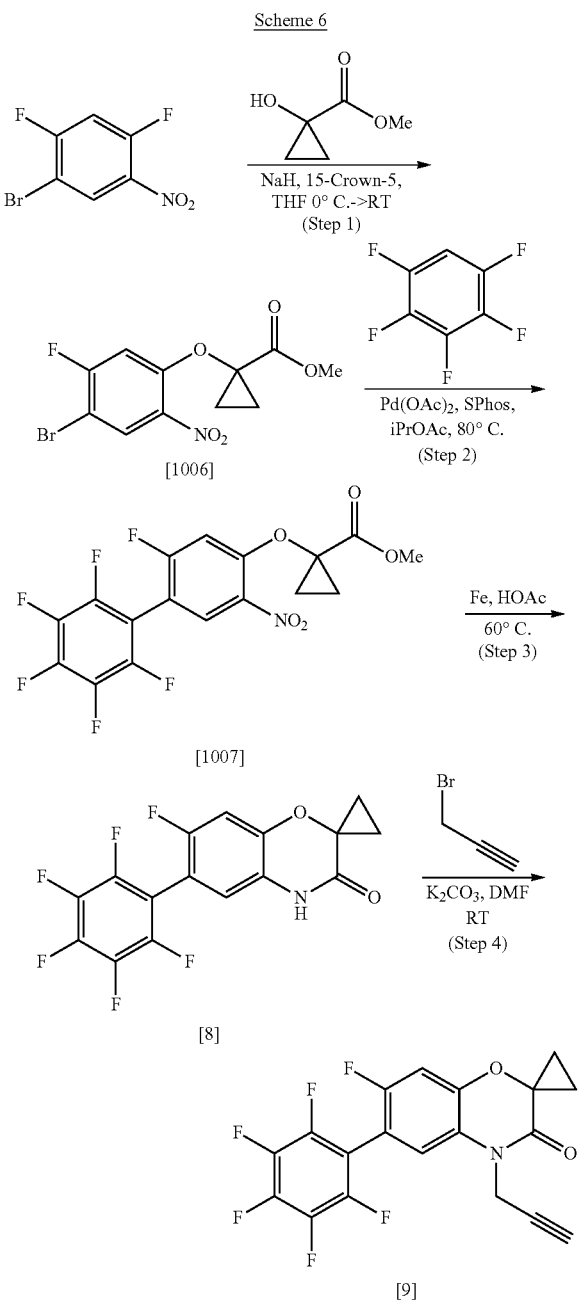

As shown in Step 1 of Scheme 5, to a solution of 2,2',3',4',5',6'-hexafluoro-5-nitro-[1,1'-biphenyl]-4-ol (500 mg, 1.54 mmol) in acetonitrile (5 mL) were added ethyl 2-bromo-2-methylpropanoate (362 mg, 1.85 mmol) and $K_2CO_3$ (427 mg, 3.09 mmol). The resulting solution was stirred at 80° C. for 2 hours before concentration under reduced pressure. The residue was purified by reversed-phase flash chromatography (5-35% acetonitrile in water) to afford ethyl 2-([2,2',3',4',5',6'-hexafluoro-5-nitro-[1,1'-biphenyl]-4-yl]oxy)-2-methylpropanoate (Compound 1005, 390 mg, 52% yield) as a yellow solid: $^1$H-NMR (400 MHz, DMSO-$d_6$) δ 8.34 (d, J=8.4 Hz, 1H), 7.18 (d, J=6.8 Hz, 1H), 4.20 (m, 2H), 1.62 (s, 6H), 1.19 (t, J=7.2 Hz, 3H).

As shown in Step 2 of Scheme 5, to a solution of ethyl 2-([2,2',3',4',5',6'-hexafluoro-5-nitro-[1,1'-biphenyl]-4-yl]oxy)-2-methylpropanoate (100 mg, 0.22 mmol) in acetic acid (1 mL) was added iron powder (63 mg, 1.14 mmol). The resulting mixture was stirred at 60° C. for 16 hours, cooled to room temperature, filtered, and concentrated under reduced pressure. The residue was purified by reversed-phase flash chromatography (20-70% acetonitrile in water) to afford 7-fluoro-2,2-dimethyl-6-(perfluorophenyl)-2H-benzo[b][1,4]oxazin-3(4H)-one (Compound 6, 35 mg, 40% yield) as a white solid: MS (ESI) calculated for $C_{16}H_9F_6NO_2$ [M-H]$^-$, 360.1; found, 360.0; $^1$H-NMR (400 MHz, DMSO-$d_6$) δ 10.88 (s, 1H), 7.16 (d, J=10.4 Hz, 1H), 6.97 (d, J=6.8 Hz, 1H), 1.47 (s, 6H); $^{19}$F-NMR (400 MHz, DMSO-$d_6$) δ −118.85, −141.24, −154.31, −162.25.

As shown in Step 3 of Scheme 5, to a solution of 7-fluoro-2,2-dimethyl-6-(perfluorophenyl)-2H-benzo[b][1,4]oxazin-3(4H)-one (100 mg, 0.27 mmol) in DMF (2 mL) were added $K_2CO_3$ (42 mg, 0.31 mmol) and propargyl bromide (36 mg, 0.31 mmol). The mixture was stirred at room temperature for 2 hours, diluted with water, and extracted with ethyl acetate. The combined organic layers were washed with brine, dried over anhydrous sodium sulfate, filtered, concentrated under reduced pressure, and purified by reversed-phase flash chromatography (5%-40% acetonitrile in water) to afford 7-fluoro-2,2-dimethyl-6-(perfluorophenyl)-4-(prop-2-yn-1-yl)-2H-benzo[b][1,4]oxazin-3(4H)-one (Compound 7, 35 mg, 30% yield) as a white solid: GCMS calculated for ($C_{19}H_{11}F_6NO_2$), 399.0; found, 399.0; $^1$H-NMR (400 MHz, DMSO-$d_6$) δ 7.43 (d, J=6.4 Hz, 1H), 7.25 (d, J=10.4 Hz, 1H), 4.75 (s, 2H), 3.30 (s, 1H), 1.49 (s, 6H); $^{19}$F-NMR (400 MHz, DMSO-$d_6$) δ −117.89, −140.62, −153.97, −162.25.

Example 4. Preparation of 7-fluoro-6-(perfluorophenyl)-4-(prop-2-yn-1-yl)spiro[benzo[b][1,4]oxazine-2,1'-cyclopropan]-3(4H)-one (Compound 9)

As shown in Step 1 of Scheme 6, to a solution of 1-bromo-2,4-difluoro-5-nitrobenzene (102 mg, 4.30 mmol) in THF (5 mL) at 0° C. was added NaH (60% oil dispersion, 206 mg, 5.16 mmol) in portions under an atmosphere in nitrogen. The mixture was stirred at room temperature for 10 minutes, followed by the addition of 15-crown-5 (94 mg, 0.43 mmol) and methyl 1-hydroxycyclopropane-1-carboxylate (500 mg, 4.30 mmol). The mixture was stirred at room temperature for 16 hours, cooled to 0° C., and diluted with water at 0° C., and extracted with ethyl acetate (3×15 mL). The combined organics were washed with brine, dried over anhydrous sodium sulfate, filtered, and concentrated under reduced pressure. The residue was purified by flash column chromatography (0-35% ethyl acetate in petroleum ether) to afford methyl 1-(4-bromo-5-fluoro-2-nitrophenoxy)cyclopropane-1-carboxylate (Compound 1006, 500 mg, 33% yield) as a yellow solid: GCMS calculated for $C_{11}H_9BrFNO_5$, 332.9; found, 332.9.

As shown in Step 2 of Scheme 6, to a solution of 1,2,3,4,5-pentafluorobenzene (503 mg, 2.99 mmol) in isopropyl acetate (5 mL) under an atmosphere of nitrogen were added $K_2CO_3$ (413 mg, 2.99 mmol), 2-dicyclohexylphosphino-2',6'-dimethoxybiphenyl (SPhos, 122 mg, 0.29 mmol) and Pd(OAc)$_2$ (33 mg, 0.15 mmol). The mixture was stirred at room temperature for 5 minutes, followed by the addition of methyl 1-(4-bromo-5-fluoro-2-nitrophenoxy)cyclopropane-1-carboxylate (500 mg, 1.49 mmol). The mixture was stirred at 80° C. for 12 hours under an atmosphere of nitrogen, cooled to room temperature, diluted with water, and extracted with ethyl acetate (3×10 mL). The combined organics were washed with brine, dried over anhydrous sodium sulfate, filtered, concentrated under reduced pressure, and purified by flash chromatography (0-20% ethyl acetate in petroleum ether) to afford methyl 1-((2,2',3',4',5',6'-hexafluoro-5-nitro-[1,1'-biphenyl]-4-yl)oxy)cyclopropane-1-carboxylate (Compound 1007, 400 mg, 71% yield) as a brown oil: GCMS calculated for $C_{17}H_9F_6NO_5$=421.0, found, 421.0.

As shown in Step 3 of Scheme 6, to a solution of methyl 1-((2,2',3',4',5',6'-hexafluoro-5-nitro-[1,1'-biphenyl]-4-yl)oxy)cyclopropane-1-carboxylate (200 mg, 0.47 mmol) in acetic acid (1 mL) was added iron powder (132 mg, 2.37 mmol). The mixture was stirred at 60° C. for 12 hours. The suspension was cooled to room temperature, filtered, and the filtrate concentrated under reduced pressure. The residue was purified by preparative reversed-phase HPLC using the following conditions—Waters XBridge C18 column (30 mm×150 mm, 5 um, 130 angstrom); mobile phase A: water (10 mM $NH_4HCO_3$); mobile phase B: acetonitrile; gradient: 55% to 66% B/A, to afford 7-fluoro-6-(2,3,4,5,6-pentafluorophenyl)-4H-spiro[1,4-benzoxazine-2,1'-cyclopropan]-3-one (Compound 8, 100 mg, 58% yield) as a white solid: MS (ESI) calculated for $C_{16}H_7F_6NO_2$ [M−1]$^-$, 358.0; found, 358.0; $^1$H-NMR (400 MHz, DMSO-d$_6$) δ 11.02 (s, 1H), 7.12 (d, J=10.4 Hz, 1H), 6.99 (d, J 6.8 Hz, 1H), 1.35-1.29 (m, 2H), 1.29-1.23 (m, 2H); $^{19}$F-NMR (400 MHz, DMSO-d$_6$) δ −118.92, −141.27, −154.15, −162.24.

As shown in Step 4 of Scheme 6, to a solution of 7-fluoro-6-(2,3,4,5,6-pentafluorophenyl)-4H-spiro[1,4-benzoxazine-2,1'-cyclopropan]-3-one (50 mg, 0.13 mmol) in DMF (1 mL) were added $K_2CO_3$ (21 mg, 0.15 mmol) and propargyl bromide (18 mg, 0.15 mmol). The mixture was stirred at room temperature for 2 hours, filtered, and the filtrate purified by preparative reversed-phase HPLC using the following conditions—Waters SunFire C18 column (30 mm×150 mm, 5 um); mobile phase A: water (0.1% TFA); mobile phase B: acetonitrile; gradient: 50% B/A to 90% B/A, to afford 7-fluoro-6-(perfluorophenyl)-4-(prop-2-yn-1-yl)spiro[benzo[b][1,4]oxazine-2,1'-cyclopropan]-3(4H)-one (Compound 9, 21 mg, 37% yield) as a white solid: GCMS calculated for $C_{19}H_9F_6NO_2$, 397.0; found, 397.0; $^1$H-NMR (400 MHz, methanol-d$_4$) δ 7.37 (d, J=6.4 Hz, 1H), 6.99 (d, J=9.6 Hz, 1H), 4.78 (d, J=2.4 Hz, 2H), 2.76 (t, J=2.4 Hz, 1H), 1.48-1.39 (m, 2H), 1.38-1.32 (m, 2H); $^{19}$F-NMR (400 MHz, DMSO-d$_6$) δ −119.24, −142.60, −157.13, −165.16.

Example 5. Preparation of 2,2-difluoro-6-(perfluorophenyl)-2H-benzo[b][1,4]oxazin-3(4H)-one (Compound 15) and 2,2-difluoro-6-(perfluorophenyl)-4-(prop-2-yn-1-yl)-2H-benzo[b][1,4]oxazin-3(4H)-one (Compound 16)

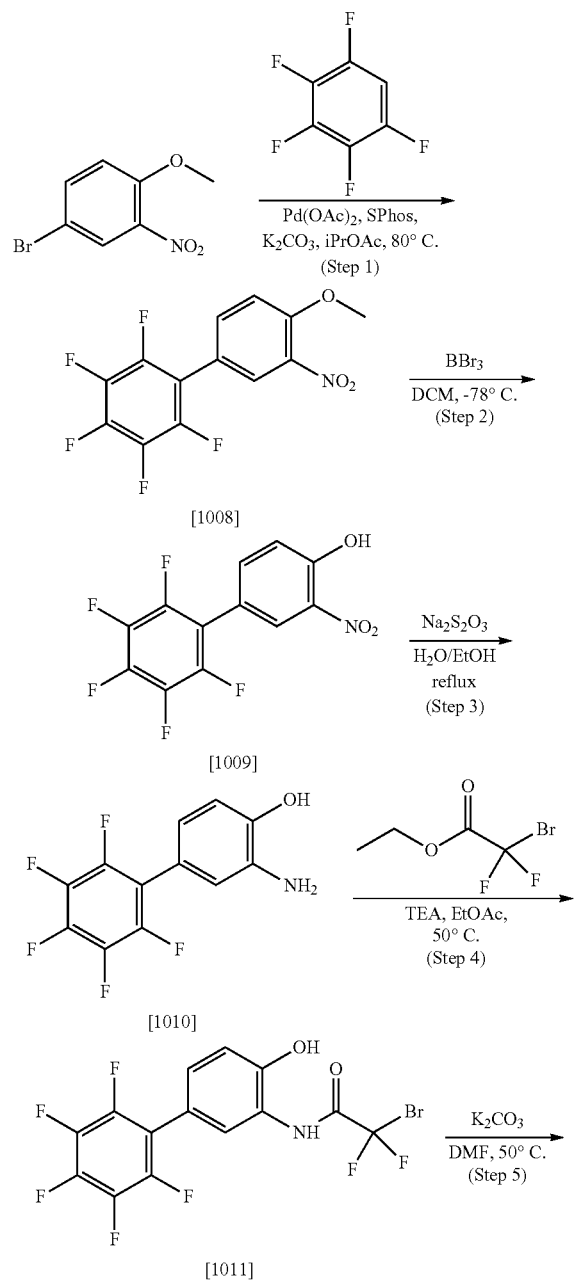

Scheme 7

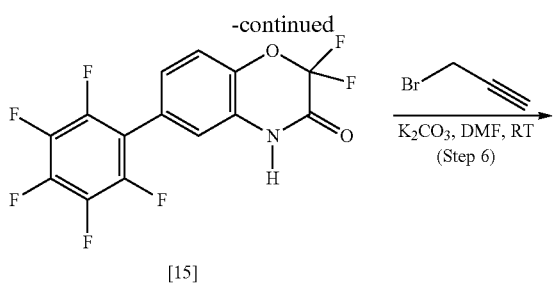

[15]

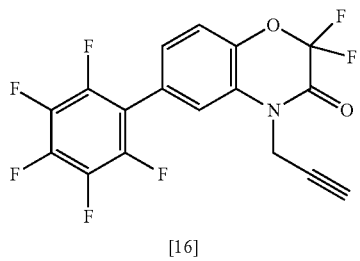

[16]

As shown in Step 1 of Scheme 7, to a degassed mixture of 4-bromo-1-methoxy-2-nitrobenzene (2.0 g, 8.62 mmol) in isopropyl acetate (10 mL) were added Pd(OAc)$_2$ (190 mg, mmol), Sphos (700 mg, 1.72 mmol), and K$_2$CO$_3$ (2.4 g, 17.2 mmol) under a nitrogen atmosphere. The mixture was stirred at room temperature for 5 minutes and a solution of pentafluorobenzene (2.9 g, 17.24 mmol) in isopropyl acetate (10 mL) was added. The resulting mixture was stirred at 80° C. for 16 hours under nitrogen, cooled to room temperature, filtered, and concentrated under reduced pressure. The residue was purified by flash chromatography (0%-45% ethyl acetate in petroleum ether) to afford 2,3,4,5,6-pentafluoro-4'-methoxy-3'-nitro-1, 1'-biphenyl (Compound 1008, 1.7 g, 54% yield) as a brown solid: GCMS calculated for (C$_{13}$H$_6$F$_5$NO$_3$), 319.0; found, 319.0.

As shown in Step 2 of Scheme 7, to a stirred solution of 2,3,4,5,6-pentafluoro-4-methoxy-3-nitro-1,1-biphenyl (1.3 g, 4.1 mmol) in DCM (10 mL) was added boron tribromide (5.1 g, 20.4 mmol) dropwise at −78° C. under a nitrogen atmosphere. The resulting mixture was stirred at −78° C. for 2 hours, then warmed to room temperature and stirred for an additional 16 hours. The reaction diluted with water, extracted with DCM, and the combined organics washed with brine, dried over anhydrous sodium sulfate, filtered, and concentrated under reduced pressure to afford 2',3',4', 5',6'-pentafluoro-3-nitro-[1,1'-biphenyl]-4-ol (Compound 1009, 1.2 g, crude) as a yellow solid: MS (ESI) calculated for (C$_{12}$H$_4$F$_5$NO$_3$) [M−1]$^-$, 304.0; found, 303.8. This material was used in subsequent reactions as is.

As shown in Step 3 of Scheme 7, to a stirred solution of 2',3',4',5',6'-pentafluoro-3-nitro-[1,1'-biphenyl]-4-ol (1.3 g, 4.2 mmol) in EtOH (6 mL) was added a solution of sodium hyposulfite (3.6 g, 20.8 mmol) in water (6 mL). The mixture was stirred at reflux for 1 hour, cooled to room temperature, and the volatiles removed under reduced pressure. The resulting mixture was diluted with water and extracted with ethyl acetate. The combined organic layers were washed with brine, dried over anhydrous sodium sulfate, filtered, and concentrated under reduced pressure to afford 3-amino-2',3',4',5',6'-pentafluoro-[1,1'-biphenyl]-4-ol (Compound 1010, 400 mg, crude) as a yellow solid: MS (ESI) calculated for (C$_{12}$H$_6$F$_5$NO) [M−1]$^-$, 274.0; found, 274.1. This material was used in subsequent reactions as is.

As shown in Step 4 of Scheme 7, to a solution of 3-amino-2',3',4',5',6'-pentafluoro-[1,1'-biphenyl]-4-ol (169 mg, 0.61 mmol) in ethyl acetate (2 mL) were added ethyl 2-bromo-2,2-difluoroacetate (140 mg, 0.69 mmol) and TEA (70 mg, 0.69 mmol). The mixture was stirred at 50° C. for 2 hours, cooled to room temperature, diluted with water, and extracted with ethyl acetate. The combined organic layers were washed with brine, dried over anhydrous sodium sulfate, filtered, and concentrated under reduced pressure to afford 2-bromo-2,2-difluoro-N-(2',3',4',5',6'-pentafluoro-4-hydroxy-[1,1'-biphenyl]-3-yl) acetamide (Compound 1011, 350 mg, crude) as a brown oil: MS (ESI) calculated for (C$_{14}$H$_5$BrF$_7$NO$_2$) [M−1]$^-$, 429.9; found, 431.9. This material was used in subsequent reactions as is.

As shown in Step 5 of Scheme 7, to a stirred solution of 2-bromo-2,2-difluoro-N-(2',3',4',5',6'-pentafluoro-4-hydroxy-[1,1'-biphenyl]-3-yl)acetamide (268 mg, 0.62 mmol) in DMF (3 mL) was added K$_2$CO$_3$ (129 mg, 0.93 mmol). The mixture was stirred at 50° C. for 16 hours, cooled to room temperature, diluted with water, and extracted with ethyl acetate. The combined organic layers were washed with brine, dried over anhydrous sodium sulfate, filtered, concentrated under reduced pressure, and purified by flash chromatography (0%-30% ethyl acetate in petroleum ether) to afford 2,2-difluoro-6-(perfluorophenyl)-2H-benzo[b][1,4]oxazin-3(4H)-one (Compound 15, 25 mg, 12% yield) as a white solid: MS (ESI) calculated for (C$_{14}$H$_4$F$_7$NO$_2$) [M−1]$^-$, 350.0; found, 350.0; $^1$H-NMR (400 MHz, DMSO-d$_6$) δ 12.15 (b, 1H), 7.49 (d, J=8.4 Hz, 1H), 7.33-7.23 (m, 1H), 7.21 (d, J=2.0 Hz, 1H); $^{19}$F-NMR (376 MHz, DMSO-d$_6$) δ −75.08, −143.46, −155.67, −162.52.

As shown in Step 6 of Scheme 7, to a stirred solution of 2,2-difluoro-6-(perfluorophenyl)-2H-benzo[b][1,4]oxazin-3 (4H)-one (78 mg, 0.22 mmol) in DMF (1 mL) were added 3-bromoprop-1-yne (29 mg, 0.24 mmol) and K$_2$CO$_3$ (37 mg, 0.27 mmol). The mixture was stirred at room temperature for 16 hours, diluted with water, and extracted with ethyl acetate. The combined organic layers were washed with brine, dried over anhydrous sodium sulfate, filtered, concentrated under reduced pressure, and purified by reversed-phase flash chromatography (5%-60% acetonitrile in water) to afford 2,2-difluoro-6-(perfluorophenyl)-4-(prop-2-yn-1-yl)-2H-benzo[b][1,4]oxazin-3(4H)-one (Compound 16, 30 mg, 35% yield) as a white solid: $^1$H-NMR (400 MHz, methanol-d$_4$) δ 7.67-7.57 (m, 1H), 7.48-7.44 (m, 1H), 7.42-7.36 (m, 1H), 4.92 (d, J=2.4 Hz, 2H), 2.91-2.81 (m, 1H); $^{19}$F-NMR (376 MHz, methanol-d$_4$) δ −78.89, −145.03, −157.96, −165.12.

Example 6. Preparation of 6-(2,3,4,5,6-pentafluorophenyl)-2,4-dihydro-1,4-benzoxazin-3-one (Compound 21) and 6-(perfluorophenyl)-4-(prop-2-yn-1-yl)-2H-benzo[b][1,4]oxazin-3(4H)-one (Compound 22)

Scheme 8

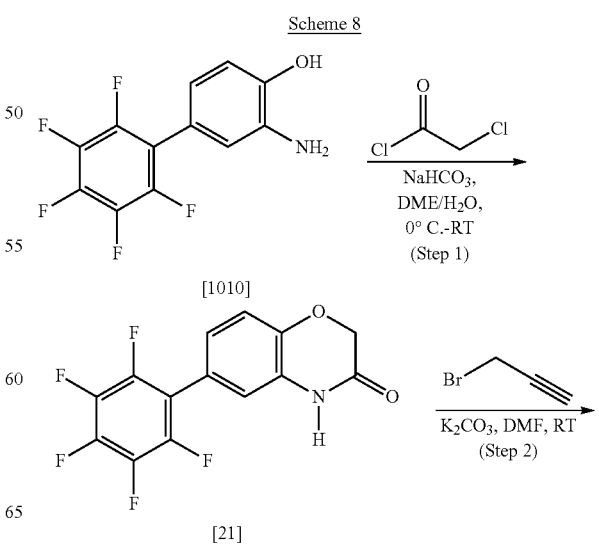

[1010]

[21]

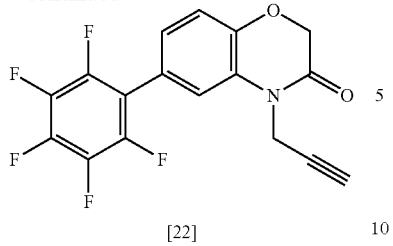

[22]

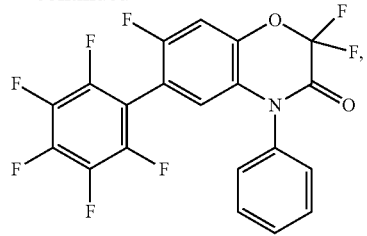

[17]

As shown in Step 1 of Scheme 8, to a stirred solution of 3-amino-2',3',4',5',6'-pentafluoro-[1,1'-biphenyl]-4-ol (5.0 g, 18.2 mmol) and NaHCO$_3$ (4.5 g, 54.5 mmol) in DME (25 mL) and H$_2$O (25 mL) was added chloroacetyl chloride (3.1 g, 27.25 mmol) dropwise at 0° C. under a nitrogen atmosphere. The mixture was stirred for 16 hours at room temperature under a nitrogen atmosphere, diluted with water, and extracted with ethyl acetate. The combined organic layers were washed with brine, drive over anhydrous sodium sulfate, concentrated under reduced pressure, and purified by flash chromatography (10%-60% ethyl acetate in petroleum ether) to afford 6-(2,3,4,5,6-pentafluorophenyl)-2,4-dihydro-1,4-benzoxazin-3-one (Compound 21, 3.4 g, 57% yield) as a brown solid: MS (ESI) calculated for (C$_{14}$H$_6$F$_5$NO$_2$) [M−1]$^-$, 315.2; found, 314.0; $^1$H-NMR (400 MHz, DMSO-d$_6$) S (s, 1H), 7.13 (d, J=8.4 Hz, 1H), 7.06 (d, J=8.4 Hz, 1H), 7.00 (s, 1H), 4.67 (s, 2H); $^{19}$F-NMR (400 MHz, DMSO-d$_6$) δ −143.63, −156.62, −162.75.

As shown in Step 2 of Scheme 8, to a stirred solution of 6-(2,3,4,5,6-pentafluorophenyl)-2,4-dihydro-1,4-benzoxazin-3-one (100 mg, 0.32 mmol) in DMF (1 mL) were added Cs$_2$CO$_3$ (124 mg, 0.38 mmol) and propargyl bromide (45 mg, 0.38 mmol). The resulting mixture was stirred at room temperature for 16 hours, then purified by preparative-HPLC using the following conditions—Column: X Bridge Shield RP18 OBD Column, 19 mm×250 mm, 10 μm; Mobile Phase A: water (10 mM NH$_4$HCO$_3$), Mobile Phase B: acetonitrile; Gradient: 75% B/A to 80% B/A, then 80% B/A to afford 6-(perfluorophenyl)-4-(prop-2-yn-1-yl)-2H-benzo[b][1,4]oxazin-3(4H)-one (Compound 22, 39 mg, 34%) as a white solid: MS (ESI) calculated for (C$_{17}$H$_8$F$_5$NO$_2$) [M+1]$^+$, 354.0; found, 354.1; $^1$H-NMR (400 MHz, DMSO-d$_6$) δ 7.42 (s, 1H), 7.22 (d, J=7.2 Hz, 2H), 4.93-4.70 (m, 4H), 3.30 (d, J=6.4 Hz, 1H); $^{19}$F-NMR (400 MHz, DMSO-d$_6$) δ −143.06, −156.10, −162.69.

Example 7. Preparation of 2,2,7-trifluoro-6-(perfluorophenyl)-4-phenyl-2H-benzo[b][1,4]oxazin-3 (4H)-one (Compound 17)

As shown in Scheme 9, to a stirred solution of 2,2,7-trifluoro-6-(perfluorophenyl)-2H-benzo[b][1,4]oxazin-3 (4H)-one (300 mg, 0.81 mmol) and phenylboronic acid (594 mg, 4.87 mmol) in THF (3 mL) were added 2-[bis(2-hydroxyethyl)amino]ethanol (986 mg, 9.75 mmol) and copper (II) acetate (118 mg, 0.65 mmol) under nitrogen. The mixture was stirred at 60° C. for 16 hours, cooled to room temperature, diluted with water, and extracted with ethyl acetate. The combined organic layers were washed with brine, dried over anhydrous sodium sulfate, filtered, concentrated under reduced pressure, and purified by reversed-phase flash chromatography (30%-80% acetonitrile in water), then further purified by preparative reversed-phase HPLC using the following conditions—Column: X Bridge Shield RP18 OBD Column, 30×150 mm, 5 μm; Mobile Phase A: Water (10 mM NH$_4$HCO$_3$); Mobile Phase B: acetonitrile; Gradient: 51% B/A to 73% B/A, then 73% B/A, to afford 2,2,7-trifluoro-6-(perfluorophenyl)-4-phenyl-2H-benzo[b][1,4]oxazin-3(4H)-one (Compound 17, 23 mg, 35%) as a white solid: GCMS calculated for (C$_{20}$H$_7$F$_8$NO$_2$), 445.0; found, 445.0; $^1$H-NMR (400 MHz, DMSO-d$_6$) δ 7.87-7.80 (m, 1H), 7.70-7.58 (m, 3H), 7.56-7.47 (m, 2H), 6.63 (d, J=6.4 Hz, 1H); $^{19}$F-NMR (376 MHz, DMSO-d$_6$) δ −73.83, −116.15, −141.22, −153.75, −162.19.

Example 8. Preparation of 7-fluoro-2-methyl-6-(perfluorophenyl)-2H-benzo[b][1,4]oxazin-3(4H)-one (Compound 25), (R)-7-fluoro-2-methyl-6-(perfluorophenyl)-4-(prop-2-yn-1-yl)-2H-benzo[b][1,4] oxazin-3(4H)-one (Compound 26), and (S)-7-fluoro-2-methyl-6-(perfluorophenyl)-4-(prop-2-yn-1-yl)-2H-benzo[b][1,4]oxazin-3(4H)-one (Compound 27)

Scheme 9

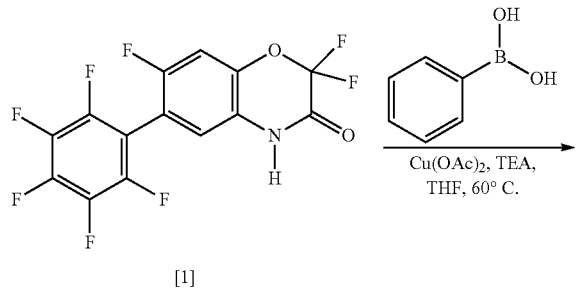

[1]

Scheme 10

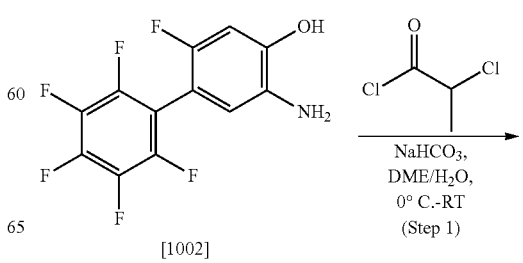

[1002]

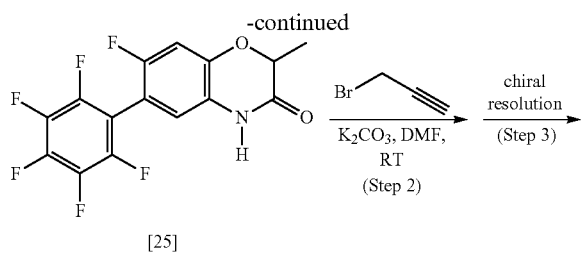

[25]

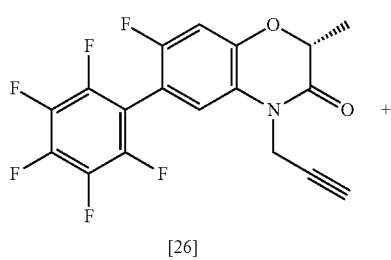

[26]

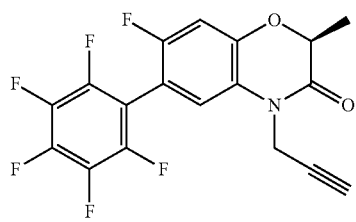

[27]

As shown in Step 1 of Scheme 10, to a stirred mixture of 5-amino-2,2',3',4',5',6'-hexafluoro-[1,1'-biphenyl]-4-ol (100 mg, 0.34 mmol) and NaHCO$_3$ (86 mg, 1.02 mmol) in DME (1.5 mL) and water (1.5 mL) was added 2-chloropropanoyl chloride (65 mg, 0.51 mmol) at 0° C. under a nitrogen atmosphere. The mixture was stirred at room temperature for 16 hours under a nitrogen atmosphere then concentrated under reduced pressure. The residue was dissolved in DMF (3 mL), K$_2$CO$_3$ (94 mg, 0.68 mmol) was added, and the resulting mixture stirred at 80° C. for 16 hours. After cooling to room temperature, the mixture was diluted with water and extracted with ethyl acetate. The combined organic layers were washed with water, dried over anhydrous sodium sulfate, concentrated under reduced pressure, and purified by reversed-phase flash chromatography (10%-60% acetonitrile in water) to afford 7-fluoro-2-methyl-6-(perfluorophenyl)-2H-benzo[b][1,4]oxazin-3(4H)-one (Compound 25, 38 mg, 32% yield) as a white solid: MS (ESI) calculated for (C$_{14}$H$_3$F$_8$NO$_2$) [M–1]$^−$, 346.2; found, 346.2; $^1$H-NMR (400 MHz, DMSO-d$_6$) δ 10.87 (s, 1H), 7.18 (d, J=Hz, 1H), 6.97 (d, J=7.2 Hz, 1H), 4.89-4.80 (m, 1H), 1.51-1.45 (m, 3H).

As shown in Step 2 of Scheme 10, to a stirred mixture of 7-fluoro-2-methyl-6-(perfluorophenyl)-2H-benzo[b][1,4]oxazin-3(4H)-one (390 mg, 1.12 mmol), K$_2$CO$_3$ (310 mg 2.25 mmol) in DMF (4 mL) was added propargyl bromide (401 mg, 3.37 mmol). The resulting mixture was stirred at 80° C. for 4 hours, cooled to room temperature, diluted with water, and extracted with ethyl acetate. The combined organics were washed with water, dried over anhydrous sodium sulfate, concentrated under reduced pressure, and purified by flash chromatography (0%-30% ethyl acetate in petroleum ether) to afford racemic 7-fluoro-2-methyl-6-(perfluorophenyl)-4-(prop-2-yn-1-yl)-2H-benzo[b][1,4]oxazin-3(4H)-one (300 mg, 69% yield) as a brown-yellow oil.

As shown in Step 3 of Scheme 10, racemic 7-fluoro-2-methyl-6-(2,3,4,5,6-pentafluorophenyl)-4-(prop-2-yn-1-yl)-2H-1,4-benzoxazin-3-one (150 mg) was resolved by Chiral Prep-HPLC using the following conditions—Column: CHIRALPAK AD-H, 2×25 cm, 5 μm; Mobile Phase A: Hexane, Mobile Phase B: 1:1 MeOH/EtOH; Gradient: 5% B/A to 5% B/A, to afford (R)-7-fluoro-2-methyl-6-(perfluorophenyl)-4-(prop-2-yn-1-yl)-2H-benzo[b][1,4]oxazin-3(4H)-one (Compound 26, 26 mg, 18% yield) as a white solid: MS (ESI) calculated for (C$_{18}$H$_9$F$_6$NO$_2$) [M+1]$^+$, 386.1; found, 386.1; $^1$H-NMR (400 MHz, DMSO-d$_6$) δ 7.44 (d, J=6.8 Hz, 1H), 7.27 (d, J=10.0 Hz, 1H), 4.96 (q, J=6.8 Hz, 1H), 4.77-4.72 (m, 2H), 3.28 (s, 1H), 1.51 (d, J=6.8 Hz, 3H); $^{19}$F-NMR (377 MHz, DMSO-d$_6$) δ −118.05, −140.67, −154.00, −162.27. Also recovered with a longer retention time was (S)-7-fluoro-2-methyl-6-(perfluorophenyl)-4-(prop-2-yn-1-yl)-2H-benzo[b][1,4]oxazin-3(4H)-one (Compound 27, 35 mg, 23% yield) as a white solid: MS (ESI) calculated for (C$_{18}$H$_9$F$_6$NO$_2$) [M+1]$^+$, 386.1; found, 386.1; $^1$H-NMR (400 MHz, DMSO-d$_6$) δ 7.43 (d, J=6.8 Hz, 1H), 7.28 (d, J=10.0 Hz, 1H), 4.96 (q, J=6.8 Hz, 1H), 4.75 (s, 2H), 3.28 (s, 1H), 1.50 (d, J=6.8 Hz, 3H); $^{19}$F-NMR (377 MHz, DMSO-d$_6$) δ −118.04, −140.67, −153.97, −162.25.

Example 9. Preparation of (S)-4-(but-3-yn-2-yl)-2,2,7-trifluoro-6-(perfluorophenyl)-2H-benzo[b][1,4]oxazin-3(4H)-one (Compound 28) and (R)-4-(but-3-yn-2-yl)-2,2,7-trifluoro-6-(perfluorophenyl)-2H-benzo[b][1,4]oxazin-3(4H)-one (Compound 29)

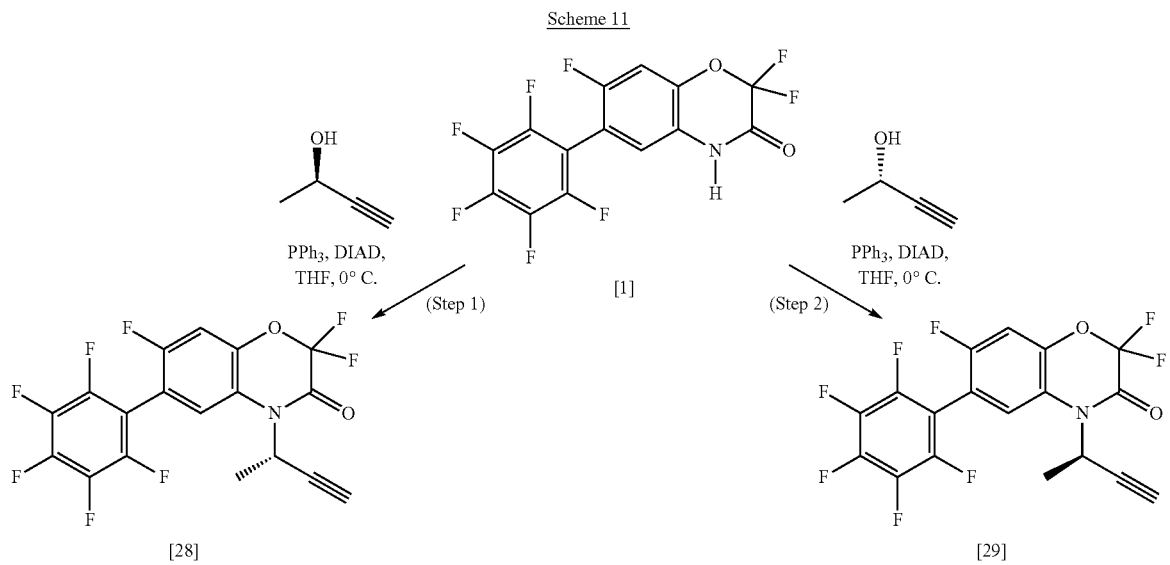

As shown in Step 1 of Scheme 11, to a stirred solution of (R)-but-3-yn-2-ol (200 mg, 2.86 mmol), 2,2,7-trifluoro-6-(perfluorophenyl)-2H-benzo[b][1,4]oxazin-3(4H)-one (703 mg, 1.90 mmol) and PPh$_3$ (749 mg, 2.86 mmol) in THF (5 mL) was added diisopropyl azodicarboxylate (DIAD, 578 mg, 2.86 mmol) dropwise at 0° C. under a nitrogen atmosphere. The mixture was stirred at room temperature for 2 hours under nitrogen atmosphere, diluted with water, and extracted with ethyl acetate. The combined organic layers were washed with water, dried over anhydrous sodium sulfate, concentrated under vacuum, and purified by preparative-TLC (1:10 EtOAc/Petroleum ether) to afford (S)-4-(but-3-yn-2-yl)-2,2,7-trifluoro-6-(perfluorophenyl)-2H-benzo[b][1,4]oxazin-3(4H)-one (Compound 28, 73 mg, 9% yield) as a white solid: GCMS calculated for ($C_{18}H_7F_8NO_2$), 421.0; found, 421.0; $^1$H-NMR (400 MHz, DMSO-d$_6$) δ 7.96 (d, J=6.4 Hz, 1H), 7.84-7.74 (m, 1H), 5.98-5.86 (m, 1H), 3.68 (d, J=2.4 Hz, 1H), 1.64 (d, J=7.2 Hz, 3H); $^{19}$F-NMR (376 MHz, DMSO-d$_6$) δ −74.63, −77.16, −115.34, −140.69, −153.45, −162.12.

Similarly, as shown in Step 2 of Scheme 11, the same procedure as described for Step 1 was employed, using (S)-but-3-yn-2-ol instead of (R)-but-3-yn-2-ol, to produce (R)-4-(but-3-yn-2-yl)-2,2,7-trifluoro-6-(perfluorophenyl)-2H-benzo[b][1,4]oxazin-3(4H)-one (Compound 29, 49 mg, 21% yield) as a white solid: GCMS calculated for ($C_{18}H_7F_8NO_2$), 421.0; found, 421.0; $^1$H-NMR (400 MHz, DMSO-d$_6$) δ 7.96 (d, J=6.4 Hz, 1H), 7.80 (d, J=9.6 Hz, 1H), 5.97-5.87 (m, 1H), 3.69 (d, J=2.4 Hz, 1H), 1.64 (d, J=7.2 Hz, 3H); $^{19}$F-NMR (376 MHz, DMSO-d$_6$) δ −74.75, −77.34, −115.34, −140.91, −153.37, −162.17.

Example 10. Preparation of 2,2,5,7-tetrafluoro-6-(perfluorophenyl)-2H-benzo[b][1,4]oxazin-3(4H)-one (Compound 30) and 2,2,5,7-tetrafluoro-6-(perfluorophenyl)-4-(prop-2-yn-1-yl)-2H-benzo[b][1,4]oxazin-3(4H)-one (Compound 31)

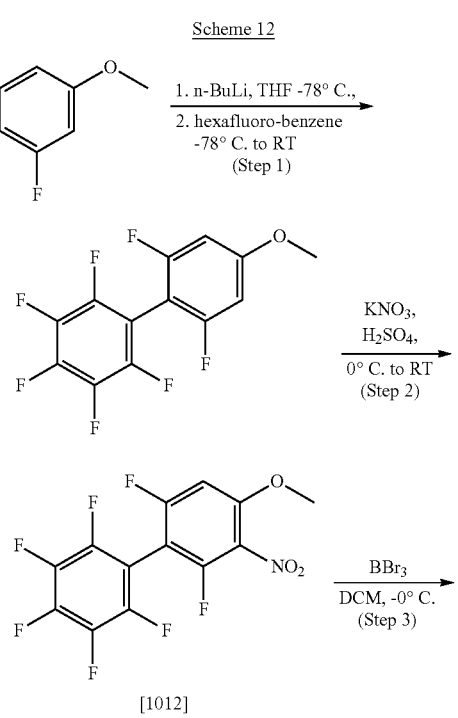

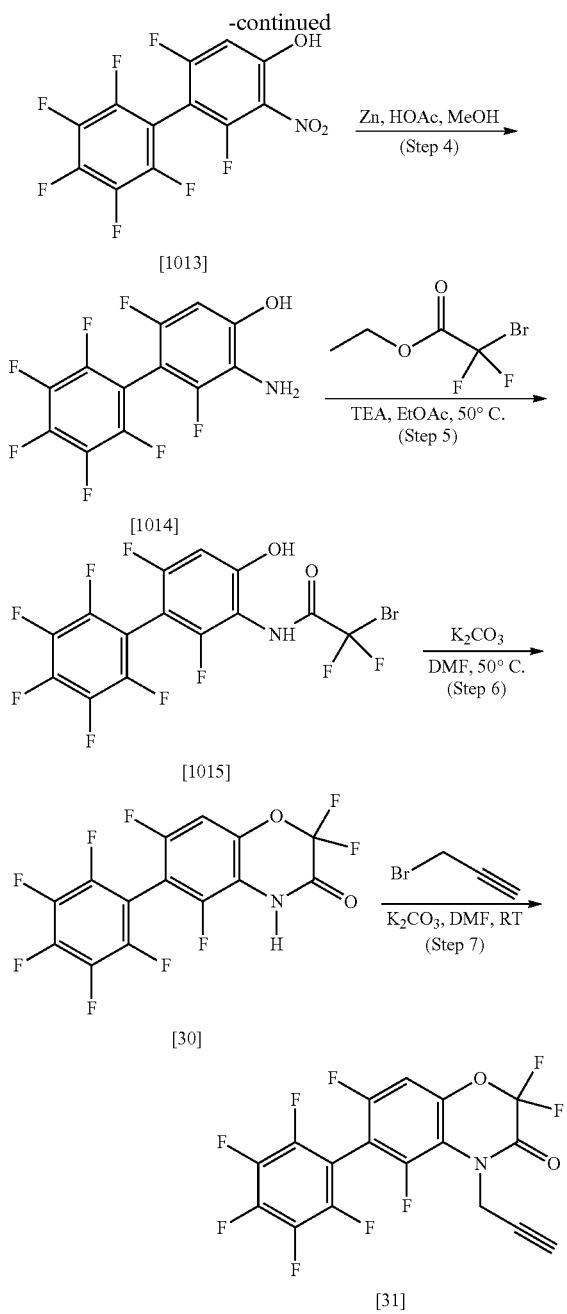

As shown in Step 1 of Scheme 12, to a stirred solution of 2-bromo-1,3-difluoro-5-methoxybenzene (20.0 g, 90.1 mmol) in anhydrous THF (200 mL) under an atmosphere of nitrogen was added n-BuLi (2.5 M in hexane, 39.6 mL, 99.1 mmol,) dropwise at −78° C. After addition was complete, stirring was continued at −78° C. for 15 minutes and hexafluorobenzene (25.1 g, 135.1 mmol) was added dropwise at −78° C. The resulting mixture was warmed to room temperature, stirred for 2 hours under nitrogen, diluted with water, and extracted with ethyl acetate. The combined organic layers were washed with brine, dried over anhydrous sodium sulfate, filtered, concentrated under reduced pressure, and purified by flash chromatography (0%-10% ethyl acetate in petroleum ether) to afford 2,2',3,4,5,6,6'-heptafluoro-4'-methoxy-1,1'-biphenyl (9.0 g, 26% yield) as a white solid: GCMS calculated for ($C_{13}H_5F_7O$), 310.0; found, 310.0.

As shown in Step 2 of Scheme 12, to a stirred solution of 2,2',3,4,5,6,6'-heptafluoro-4'-methoxy-1,1'-biphenyl (8.0 g, 25.8 mmol) in DCM (20 mL) and concentrated $H_2SO_4$ (80 mL) was added $KNO_3$ (2.6 g, 25.8 mmol) in portions at 0° C. The resulting solution was stirred at 20° C. for 16 hours under nitrogen, diluted with water, and extracted with ethyl acetate. The combined organic layers were washed with brine, dried over anhydrous sodium sulfate, filtered, concentrated under reduced pressure, and purified by flash chromatography (0%-25% ethyl acetate in petroleum ether) to afford 2,2',3,4,5,6,6'-heptafluoro-4'-methoxy-3'-nitro-1,1'-biphenyl (Compound 1012, 5.5 g, 54% yield) as a yellow solid: GCMS (ESI) calculated for ($C_{13}H_4F_7NO_3$), 355.0; found, 355.0.

As shown in Step 3 of Scheme 12, to a stirred solution of 2,2',3,4,5,6,6'-heptafluoro-4'-methoxy-3'-nitro-1,1'-biphenyl (5.5 g, 15.5 mmol) in DCM (70 mL) under a nitrogen atmosphere was added $BBr_3$ (19.4 g, 77.4 mmol) dropwise at 0° C. The solution was stirred at 0° C. for 2 hours under nitrogen, diluted with water, and extracted with ethyl acetate. The combined organic layers were washed with brine, dried over anhydrous sodium sulfate, filtered, and concentrated under reduced pressure to afford 2,2',3',4',5',6,6'-heptafluoro-3-nitro-[1,1'-biphenyl]-4-ol (Compound 1013, 4.9 g, crude) as yellow oil: MS (ESI) calculated for ($C_{12}H_2F_7NO_3$) [M−1]$^-$, 339.9; found, 339.9. This material was used as is in subsequent reactions.

As shown in Step 4 of Scheme 12, to a stirred solution of 2,2',3',4',5',6,6'-heptafluoro-3-nitro-[1,1'-biphenyl]-4-ol (4.9 g, 14.4 mmol) in EtOH (30 mL) and $H_2O$ (30 mL) was added $Na_2S_2O_4$ (12.5 g, 71.8 mmol) in portions at 20° C. The resulting mixture was stirred at 100° C. for 2 hours under nitrogen, diluted with water, and extracted with ethyl acetate. The combined organic layers were washed with brine, dried over anhydrous sodium sulfate, filtered, concentrated under reduced pressure, and purified by flash chromatography (0%-30% ethyl acetate in petroleum ether) to afford 3-amino-2,2',3',4',5',6,6'-heptafluoro-[1,1'-biphenyl]-4-ol (Compound 1014, 3.9 g, 78% yield) as a yellow solid: MS (ESI) calculated for ($C_{12}H_4F_7NO$) [M+1]$^+$, 312.0; found, 311.9.

As shown in Step 5 of Scheme 12, to a stirred solution of 3-amino-2,2',3',4',5',6,6'-heptafluoro-[1,1'-biphenyl]-4-ol (3.9 g, 12.5 mmol) and TEA (2.5 g, 25.1 mmol) in EtOAc (50 mL) was added ethyl 2-bromo-2,2-difluoroacetate (5.1 g, 25.1 mmol) in portions at 20° C. The resulting mixture was stirred at 50° C. for 16 hours under nitrogen, cooled to room temperature, diluted with water, and extracted with ethyl acetate. The combined organic layers were washed with brine, dried over anhydrous sodium sulfate, filtered, concentrated under vacuum, and purified by reversed-phase flash chromatography (5%-70% acetonitrile in water) to afford 2-bromo-2,2-difluoro-N-(2,2',3',4',5',6,6'-heptafluoro-4-hydroxy-[1,1'-biphenyl]-3-yl)acetamide (Compound 1015, 1.5 g, 17% yield): MS (ESI) calculated for ($C_{14}H_3BrF_9NO$) [M−1]$^-$, 465.9; found, 465.8.

As shown in Step 6 of Scheme 12, to a stirred solution of 2-bromo-2,2-difluoro-N-(2,2',3',4',5',6,6'-heptafluoro-4-hydroxy-[1,1'-biphenyl]-3-yl)acetamide (1.0 g, 2.1 mmol) in DMF (10 mL) was added $K_2CO_3$ (591 mg, 4.27 mmol) in portions at 20° C. The resulting mixture was stirred at 50° C. for 2 hours under nitrogen, diluted with water, and extracted with ethyl acetate. The combined organic layers were washed with brine, dried over anhydrous sodium sulfate, filtered, concentrated under reduced pressure, and purified by flash chromatography (0%-20% ethyl acetate in petroleum ether) to afford 2,2,5,7-tetrafluoro-6-(perfluorophenyl)-2H-benzo[b][1,4]oxazin-3(4H)-one (Compound 30, 590 mg, 71% yield) as a yellow solid: MS (ESI) calculated for ($C_{14}H_2F_9NO_2$) [M−1]⁻, 385.9; found, 385.9; $^1$H-NMR (400 MHz, DMSO-$d_6$) δ 12.53 (s, 1H), 7.63 (d, J=9.6 Hz, 1H); $^{19}$F-NMR (376 MHz, DMSO-$d_6$) δ −76.31, −116.25, −124.01, −139.00, −151.21, −161.25.

As shown in Step 7 of Scheme 12, to a stirred solution of 2,2,5,7-tetrafluoro-6-(perfluorophenyl)-2H-benzo[b][1,4]oxazin-3(4H)-one (50 mg, 0.13 mmol) in DMF (1 mL) were added propargyl bromide (17 mg, 0.14 mmol) and $K_2CO_3$ (20 mg, 0.14 mmol at 20° C. The resulting solution was stirred at 20° C. for 16 hours under nitrogen, then purified by reversed-phase preparative HPLC using the following conditions—Column: Xselect CSH C18 OBD Column 30×150 mm 5 μm; gradient: 60%-72% acetonitrile/0.1% aq. formic acid, to afford 2,2,5,7-tetrafluoro-6-(perfluorophenyl)-4-(prop-2-yn-1-yl)-2H-benzo[b][1,4]oxazin-3(4H)-one (Compound 31, 28 mg, 51% yield) as a white solid: GCMS calculated for ($C_{17}H_4F_9NO_2$), 425.0; found, 425.0; H-NMR (400 MHz, DMSO-$d_6$) δ 7.80 (d, J=9.2 Hz, 1H), 4.82 (d, J=2.8 Hz, 2H), 3.46 (s, 1H); $^{19}$F-NMR (376 MHz, DMSO-$d_6$) δ −78.21, −112.89, −117.49, −138.75, −150.73, −161.14.

Example 11. Preparation of 4-(3,3-difluoroallyl)-2,2,7-trifluoro-6-(perfluorophenyl)-2H-benzo[b][1,4]oxazin-3(4H)-one (Compound 32)

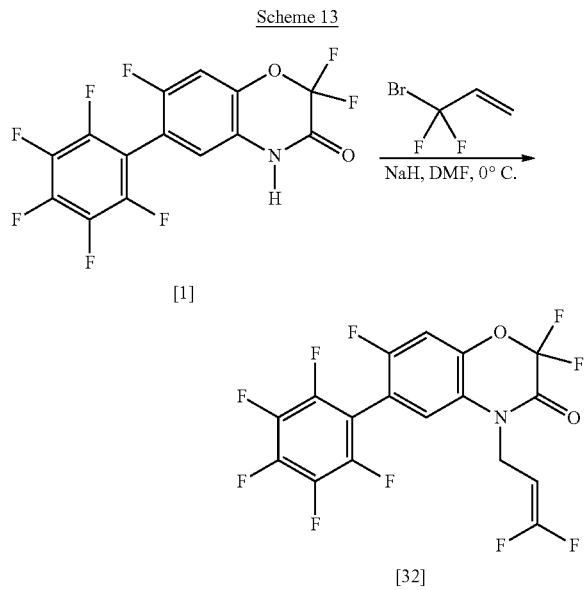

Scheme 13

[1]

[32]

As shown in Scheme 13, to a solution of 2,2,7-trifluoro-6-(perfluorophenyl)-2H-benzo[b][1,4]oxazin-3(4H)-one (500 mg, 1.35 mmol) in DMF (3 mL) was added NaH (60% in mineral oil, 49 mg, 1.22 mmol) in portions at 0° C. under a nitrogen atmosphere. The mixture was stirred at 0° C. for 30 minutes under a nitrogen atmosphere followed by the dropwise addition of 3-bromo-3,3-difluoroprop-1-ene (255 mg, 1.65 mmol) at 0° C. The mixture was warmed to room temperature, stirred for 16 hours under nitrogen, diluted with water, and extracted with ethyl acetate. The combined organic layers were washed with brine, dried over anhydrous sodium sulfate, filtered, concentrated under reduced pressure, and purified by reversed-phase flash chromatography (5%-55% acetonitrile in water) to afford 4-(3,3-difluoroallyl)-2,2,7-trifluoro-6-(perfluorophenyl)-2H-benzo[b][1,4]oxazin-3(4H)-one (Compound 32, 200 mg, 40% yield) as a white solid: GCMS calculated for ($C_{17}H_5F_{10}NO_2$), 445.0; found, 445.0; $^1$H-NMR (400 MHz, DMSO-$d_6$) δ 7.76 (d, J=9.6 Hz, 1H), 7.65 (d, J=6.4 Hz, 1H), 4.94-4.76 (m, 1H), 4.72-4.63 (m, 2H); $^{19}$F-NMR (376 MHz, DMSO-$d_6$) δ −74.97, −85.19, −115.92, −140.67, −153.18, −162.08.

Example 12. Preparation of 2,2,7-trifluoro-6-(perfluorophenyl)-4-phenethyl-2H-benzo[b][1,4]oxazin-3(4H)-one (Compound 33)

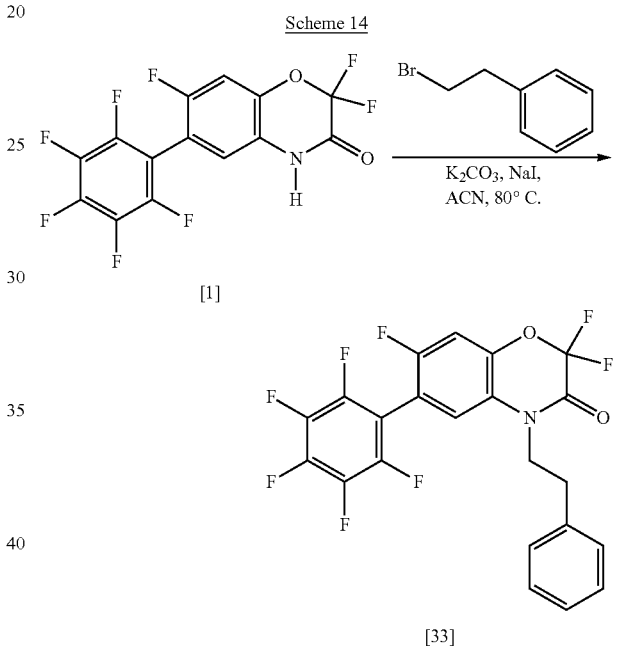

Scheme 14

[1]

[33]

As shown in Scheme 14, to a solution of 2,2,7-trifluoro-6-(perfluorophenyl)-2H-benzo[b][1,4]oxazin-3(4H)-one (200 mg, 0.54 mmol) and (2-bromoethyl)benzene (150 mg, 0.81 mmol) in acetonitrile (2 mL) was added $K_2CO_3$ (150 mg, 1.08 mmol) and NaI (41 mg, mmol) at 20° C. The resulting solution was stirred at 80° C. for 16 hours, cooled to room temperature, diluted with water, and extracted with ethyl acetate. The combined organic layers were washed with brine, dried over anhydrous sodium sulfate, filtered, concentrated under reduced pressure, and purified by flash chromatography (0%-25% ethyl acetate in petroleum ether) to afford 2,2,7-trifluoro-6-(perfluorophenyl)-4-phenethyl-2H-benzo[b][1,4]oxazin-3(4H)-one (Compound 33, 200 mg, 74% yield) as a white solid: MS (ESI) calculated for ($C_{22}H_{11}F_8NO_2$) [M+1]⁺, 474.0; found, 474.0; $^1$H-NMR (400 MHz, methanol-$d_4$) δ 7.37 (m, 2H), 7.26-7.16 (m, 5H), 4.33 (t, J=7.2 Hz, 2H), 3.03 (t, J=7.2 Hz, 2H); $^{19}$F-NMR (376 MHz, methanol-$d_4$) δ −79.18, −117.29, −142.37, −156.38, −164.90.

Example 13. Preparation of 2,2,7-trifluoro-4-(2-methylbut-3-yn-2-yl)-6-(perfluorophenyl)-2H-benzo[b][1,4]oxazin-3(4H)-one (Compound 34) and 2,2,7-trifluoro-4-(3-methylbuta-1,2-dien-1-yl)-6-(perfluorophenyl)-2H-benzo[b][1,4]oxazin-3(4H)-one (Compound 35)

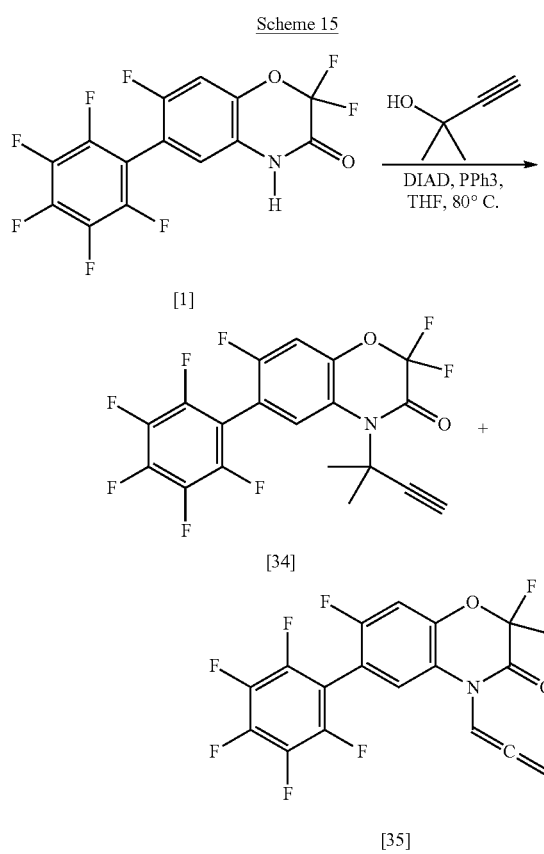

As shown in Scheme 15, to a stirred solution of 2,2,7-trifluoro-6-(perfluorophenyl)-2H-benzo[b][1,4]oxazin-3(4H)-one (300 mg, 0.81 mmol) and 2-methylbut-3-yn-2-ol (342 mg, 4.07 mmol) in tetrahydrofuran (4 mL) were sequentially added PPh$_3$ (1.1 g, 4.07 mmol) and DIAD (822 mg, 4.07 mmol) at 23° C. under nitrogen. The resulting solution was stirred at 80° C. for 16 hours under nitrogen, cooled to room temperature, diluted with water, and extracted with ethyl acetate. The combined organic layers were washed with brine, dried over anhydrous sodium sulfate, filtered, concentrated under reduced pressure, and purified by reversed-phase flash chromatography (5%-65% acetonitrile/water) to afford a mixture of compounds. The crude mixture was further purified by reversed-phase preparative HPLC using the following conditions—Column: XSelect CSH Prep C18 OBD Column, 19×250 mm, 5 µm; gradient: 80% to 90% MeOH/0.1% aq. formic acid, to afford 2,2,7-trifluoro-4-(2-methylbut-3-yn-2-yl)-6-(perfluorophenyl)-2H-benzo[b][1,4]oxazin-3(4H)-one (Compound 34, 25.3 mg, 7% yield) as a yellow semi-solid: GCMS calculated for (C$_{19}$H$_9$F$_8$NO$_2$), 435.0; found, 435.1; $^1$H-NMR (400 MHz, DMSO-d$_6$) δ 8.02 (d, J=6.8 Hz, 1H), 7.79 (d, J=9.2 Hz, 1H), 3.89 (s, 1H), 1.99 (s, 6H); $^{19}$F-NMR (377 MHz, DMSO-d$_6$) δ −78.25, −114.71, −140.13, 153.50, −162.20. Also recovered as a later eluting compounds was 2,2,7-trifluoro-4-(3-methylbuta-1,2-dien-1-yl)-6-(perfluorophenyl)-2H-benzo[b][1,4]oxazin-3(4H)-one (Compound 35, 81.5 mg, 22% yield) as a white semi-solid: GCMS calculated for (C$_{19}$H$_9$F$_8$NO$_2$), 435.0; found, 435.0; $^1$H-NMR (400 MHz, DMSO-d$_6$) δ 7.78 (d, J=9.6 Hz, 1H), 7.68 (d, J=6.4 Hz, 1H), 6.48 (s, 1H), 1.81 (s, 6H); $^{19}$F-NMR (377 MHz, DMSO-d$_6$) δ −74.90, −115.58, −140.75, 153.23, −162.07.

Example 14. Preparation of 2,2,7-trifluoro-6-(2,3,4,6-tetrafluorophenyl)-2H-benzo[b][1,4]oxazin-3(4H)-one (Compound 36) and 2,2,7-trifluoro-4-(prop-2-yn-1-yl)-6-(2,3,4,6-tetrafluorophenyl)-2H-benzo[b][1,4]oxazin-3(4H)-one (Compound 37)

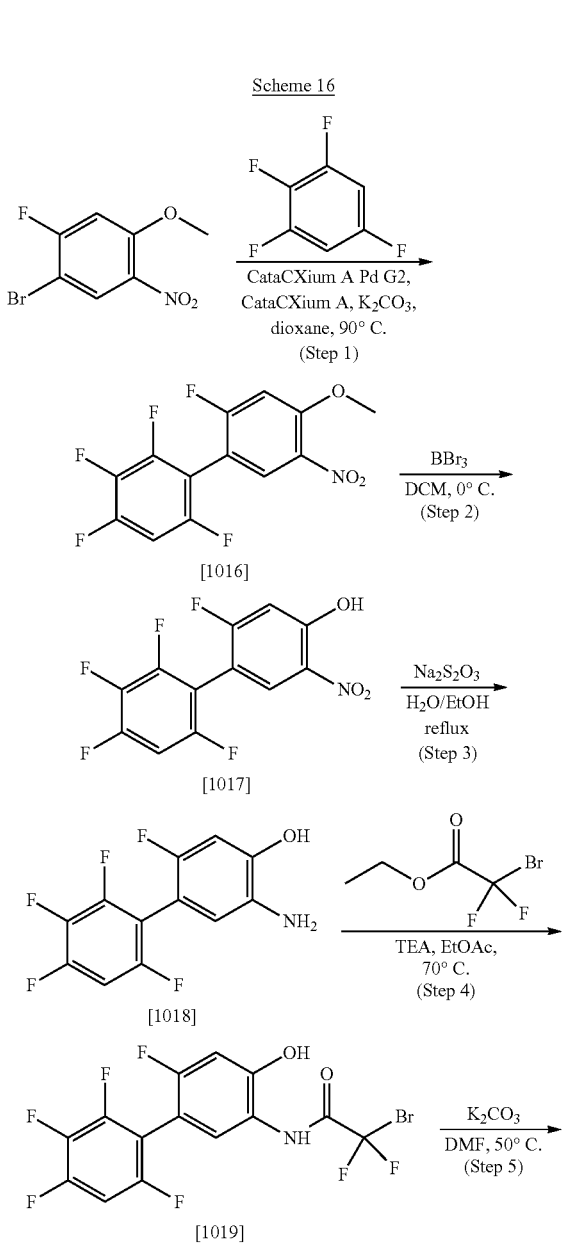

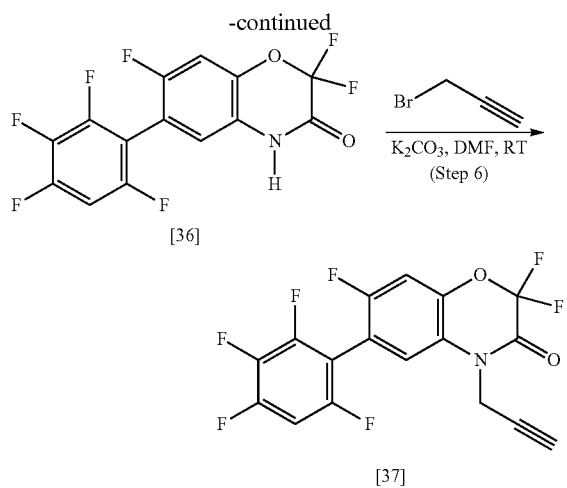

As shown in Step 1 of Scheme 16, to a solution of 1-bromo-2-fluoro-4-methoxy-(20.0 g, 80.0 mmol), 1,2,3,5-tetrafluorobenzene (36.0 g, 24.0 mmol), $K_3PO_4$ (33.9 g, 160 mmol), chloro[(diadamantan-1-yl)(n-butyl)phosphino][2-amino-1,1-biphenyl-2-yl]palladium(II) (CataCXium A Pd G2, 2.7 g, 4.0 mmol), bis(adamantan-1-yl)(butyl)phosphane (CataCXium A, 1.4 g, 4.0 mmol) in dioxane (150 mL) was stirred at for 16 hours under an atmosphere of nitrogen. The solvent was removed under reduced pressure and the residue purified by reversed-phase flash column chromatography (5%-52% acetonitrile/water) to afford 2,2',3,4,6-pentafluoro-4'-methoxy-5'-nitro-1,1'-biphenyl (Compound 1016, 11.0 g, 38% yield) as a light yellow solid: GCMS calculated for $C_{13}H_6F_5NO_3$, 319.0; found, 319.0.

As shown in Step 2 of Scheme 16, to a stirred mixture of 2,2',3,4,6-pentafluoro-4'-methoxy-5'-nitro-1,1'-biphenyl (1.0 g, 3.13 mmol) in DCM (10 mL) was added boron tribromide (3.9 g, 15.7 mmol) dropwise at 0° C. under an atmosphere of nitrogen. The mixture was stirred at 0° C. for 3 hours, diluted with water, and extracted with dichloromethane. The combined organic layers were washed with brine, dried over anhydrous sodium sulfate, filtered, and concentrated under reduced pressure to afford 2,2',3',4',6'-pentafluoro-5-nitro-[1,1'-biphenyl]-4-ol (Compound 1017, 790 mg, 74% yield) as a brown solid: MS (ESI) calculated for $(C_{12}H_4F_5NO_3)$ $[M-1]^-$, 304.0; found, 303.9.

As shown in Step 3 of Scheme 16, to a stirred solution of 2,2',3',4',6'-pentafluoro-5-nitro-[1,1'-biphenyl]-4-ol (790 mg, 2.58 mmol) in water (5 mL) and EtOH (5 mL) was added sodium hyposulfite (2.0 g, 12.94 mmol). The resulting mixture was stirred at 100° C. for 2 hours, cooled to room temperature, diluted with water, and extracted with dichloromethane. The combined organic layers were washed with brine, dried over anhydrous sodium sulfate, filtered, and concentrated under reduced pressure. The residue was purified by flash chromatography (0%-25% ethyl acetate/petroleum ether) to afford 5-amino-2,2',3',4',6'-pentafluoro-[1,1'-biphenyl]-4-ol (Compound 1018, 580 mg, 59% yield) as a yellow solid: MS (ESI) calculated for $(C_{12}H_6F_5NO)$ $[M-1]^-$, 274.0; found, 274.0.

As shown in Step 4 of Scheme 16, to a solution of 5-amino-2,2',3',4',6'-pentafluoro-[1,1'-biphenyl]-4-ol (580 mg, 2.10 mmol) and triethylamine (427 mg, 4.21 mmol) in EtOAc (5 mL) was added ethyl 2-bromo-2,2-difluoroacetate (856 mg, 4.21 mmol). The resulting mixture was stirred at 80° C. for 2 hours, cooled to room temperature, diluted with water, and extracted with dichloromethane. The combined organic layers were washed with brine, dried over anhydrous sodium sulfate, filtered, and concentrated under reduced pressure to afford 2-bromo-2,2-difluoro-N-(2',3',4',6,6'-pentafluoro-4-hydroxy-[1,1'-biphenyl]-3-yl)acetamide (Compound 1019, 800 mg, 75% yield) as a brown oil: MS (ESI) calculated for $(C_{14}H_5BrF_7NO_2)$ $[M-1]^-$, 429.9; found, 430.0.

As shown in Step 5 of Scheme 16, a stirred solution of 2-bromo-2,2-difluoro-N-(2',3',4',6,6'-pentafluoro-4-hydroxy-[1,1'-biphenyl]-3-yl)acetamide (870 mg, 2.01 mmol) and $K_2CO_3$ (417 mg, 3.02 mmol) in DMF (10 mL) was stirred at 50° C. for 2 hours, cooled to room temperature, diluted with water, and extracted with dichloromethane. The combined organic layers were washed with brine, dried over anhydrous sodium sulfate, filtered, and concentrated under reduced pressure. The residue was purified by reversed-phase flash chromatography (5%-80% acetonitrile/water) to afford 2,2,7-trifluoro-6-(2,3,4,6-tetrafluorophenyl)-2H-benzo[b][1,4]oxazin-3(4H)-one (Compound 36, 250 mg, 31% yield) as a brown solid: MS (ESI) calculated for $(C_{34}H_4F_7NO_2)$ $[M-1]^-$, 350.0; found, 350.2; $^1$H-NMR (400 MHz, DMSO-$d_6$) δ 12.14 (s, 1H), 7.71-7.65 (m, 1H), 7.62 (d, J=9.6 Hz, 1H), 7.20 (d, J=6.4 Hz, 1H); $^{19}$F-NMR (376 MHz, DMSO-$d_6$) δ −75.34, −115.87, −116.95, −131.54, −134.11, −164.81.

As shown in Step 6 of Scheme 16, to a solution of 2,2,7-trifluoro-6-(2,3,4,6-tetrafluorophenyl)-2H-benzo[b][1,4]oxazin-3(4H)-one (100 mg, 0.28 mmol) and $K_2CO_3$ (79 mg, 0.57 mmol) in DMF (1 mL) was added propargyl bromide (68 mg, 0.57 mmol). The resulting mixture was stirred at 25° C. for 16 hours then purified by reversed-phase flash chromatography (5%-70% acetonitrile/water) to afford 2,2,7-trifluoro-4-(prop-2-yn-1-yl)-6-(2,3,4,6-tetrafluorophenyl)-2H-benzo[b][1,4]oxazin-3(4H)-one (Compound 37, 47 mg, 42% yield) as a white solid: GCMS calculated for $(C_{17}H_6F_7NO_2)$, 389.0, found, 389.0; $^1$H-NMR (400 MHz, DMSO-$d_6$) δ 7.82-7.70 (m, 3H), 4.88 (d, J=2.4 Hz, 2H), 3.43 (t, J=2.4 Hz, 1H); $^{19}$F-NMR (376 MHz, DMSO-$d_6$) δ −74.99, −115.19, −115.78, −131.27, −133.64, −164.84.

Example 15. Preparation of 6-bromo-2,2,7-trifluoro-4-(4-methoxybenzyl)-2H-benzo[b][1,4]oxazin-3(4H)-one (Compound 1024)

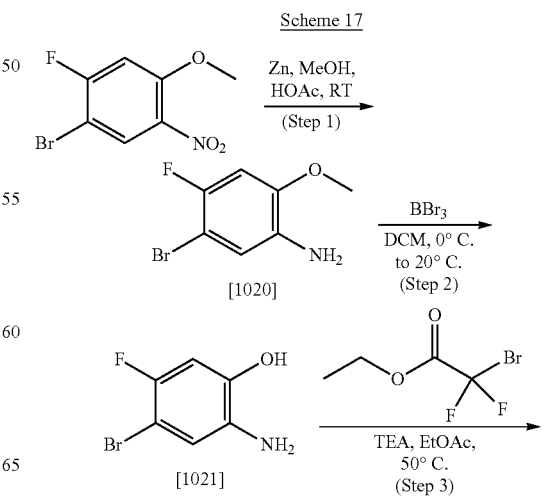

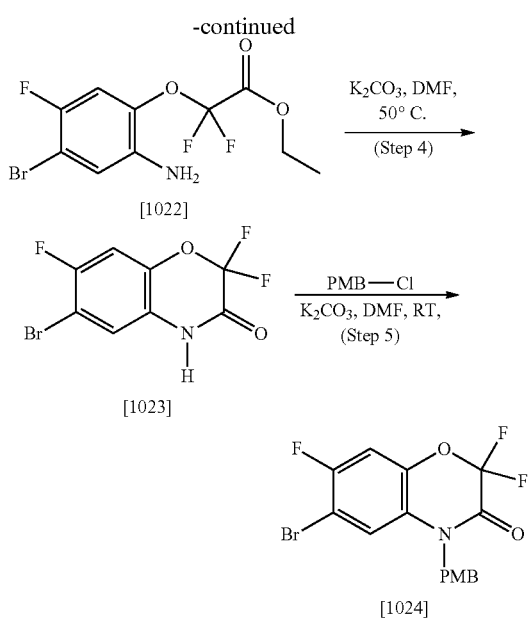

As shown in Step 1 of Scheme 17, to a solution of 1-bromo-2-fluoro-4-methoxy-5-nitrobenzene (30.0 g, 0.12 mol) in MeOH (300 mL) and acetic acid (30 mL, 0.52 mol) was added Zn powder (39.5 g, 0.6 mol) in portions at 0° C. The resulting solution was then stirred at 20° C. for 16 hours, filtered, diluted with water, and extracted with ethyl acetate. The combined organic layers were washed with brine, dried over anhydrous sodium sulfate, filtered, and concentrated under reduced pressure. The residue was purified by flash chromatography (0%-50% ethyl acetate/petroleum ether) to afford 5-bromo-4-fluoro-2-methoxyaniline (Compound 1020, 27.0 g, 78% yield) as a yellow solid: MS (ESI) calculated for ($C_7H_7BrFNO$) [M−1]⁻, 218.0; found, 218.0.

As shown in Step 2 of Scheme 17, to a solution of 5-bromo-4-fluoro-2-methoxyaniline (27.0 g, 122.70 mmol) in DCM (270 mL) was added $BBr_3$ (154 g, 614 mmol) in portions at 0° C. The resulting solution was stirred at 20° C. for 16 hours, diluted by the slow addition of ice/water, and extracted with ethyl acetate. The combined organic layers were washed with brine, dried over anhydrous sodium sulfate, filtered, concentrated under reduced pressure, and purified by flash chromatography (0%-60% ethyl acetate/petroleum ether) to afford 2-amino-4-bromo-5-fluorophenol (Compound 1021, 25.0 g, 89% yield) as a brown solid: MS (ESI) calculated for ($C_6H_5BrFNO$) [M−1]⁻, 204.0; found, 204.0.

As shown in Step 3 of Scheme 17, to a solution of 2-amino-4-bromo-5-fluorophenol (18.0 g, 87.4 mmol) and ethyl 2-bromo-2,2-difluoroacetate (35.5 g, 175 mmol) in EtOAc (180 mL) was added triethylamine (17.6 g, 175 mmol) at 20° C. The resulting solution was stirred at 50° C. for 2 hours, cooled to room temperature, diluted with water, and extracted with ethyl acetate. The combined organic layers were washed with brine, dried over anhydrous sodium sulfate, filtered, concentrated under reduced pressure, and purified by flash chromatography (0%-40% ethyl acetate/petroleum ether) to afford 2-bromo-N-(5-bromo-4-fluoro-2-hydroxyphenyl)-2,2-difluoroacetamide (Compound 1022, 11.0 g, 31% yield) as a brown solid: MS (ESI) calculated for ($C_8H_4Br_2F_3NO_2$) [M−1]⁻, 360.0; found, 360.0.

As shown in Step 4 of Scheme 17, to a solution of 2-bromo-N-(5-bromo-4-fluoro-2-hydroxyphenyl)-2,2-difluoroacetamide (7.0 g, 19.3 mmol) in DMF (70 mL) was added $K_2CO_3$ (5.3 g, 38.6 mmol) at 20° C. The resulting solution was stirred at 50° C. for 16 hours, cooled to room temperature, diluted with water, and extracted with ethyl acetate. The combined organic layers were washed with brine, dried over anhydrous sodium sulfate, filtered, concentrated under reduced pressure, and purified by flash chromatography (0%-30% ethyl acetate/petroleum ether) to afford 6-bromo-2,2,7-trifluoro-4H-1,4-benzoxazin-3-one (Compound 1023, 4.0 g, 66% yield) as a brown solid: MS (ESI) calculated for ($C_8H_3BrF_3NO_2$) [M−1]⁻, 280.0; found, 280.0.

As shown in Step 5 of Scheme 17, to a solution of 6-bromo-2,2,7-trifluoro-4H-1,4-benzoxazin-3-one (2.0 g, 7.09 mmol) in DMF (20 mL) were added p-methoxybenzyl chloride (1.6 g, 10.7 mmol) and $K_2CO_3$ (1.9 g, 14.2 mmol) at 20° C. The resulting solution was stirred at 20° C. for 16 hours, diluted with water, and extracted with ethyl acetate. The combined organic layers were washed with brine, dried over anhydrous sodium sulfate, filtered, concentrated under reduced pressure, and purified by flash column chromatography (0%-30% ethyl acetate/petroleum ether) to afford 6-bromo-2,2,7-trifluoro-4-[(4-methoxyphenyl)methyl]-1,4-benzoxazin-3-one (Compound 1024, 2.5 g, 78% yield) as a yellow solid: GCMS calculated for ($C_{16}H_{11}BrF_3NO_3$), 401.0; found, 401.0.

Example 16. Preparation of 2,2,7-trifluoro-4-(prop-2-yn-1-yl)-6-(2,3,4,6-tetrafluoro-5-methoxyphenyl)-2H-benzo[b][1,4]oxazin-3(4H)-one (Compound 38)

Scheme 18

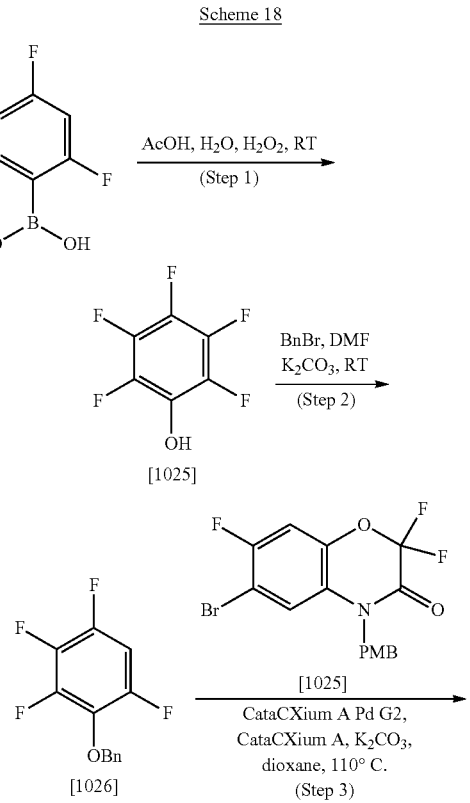

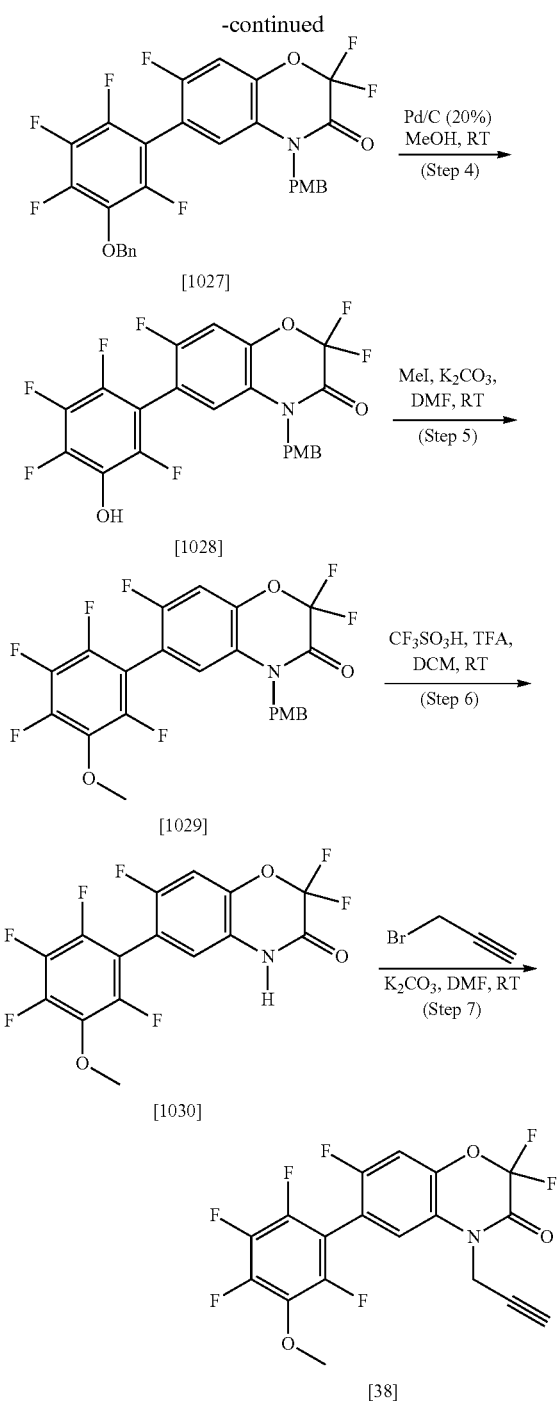

As shown in Step 1 of Scheme 18, a mixture of 2,3,4,6-tetrafluorophenylboronic acid (1.0 g, 5.15 mmol), $H_2O_2$ (30%) (877 mg, 25.8 mmol) in acetic acid (2 mL) and water (2 mL) was stirred at 25° C. for 16 hours under an atmosphere of nitrogen, diluted with water, and extracted with dichloromethane. The combined organic layers were washed with brine, dried over anhydrous sodium sulfate, filtered, and concentrated under reduced pressure to afford 2,3,4,6-tetrafluorophenol (Compound 1025, 800 mg) as a colorless oil: MS (ESI) calculated for $(C_6H_2F_4O)$ [M−1]$^-$, 165.0; found, 165.0. This material was used in subsequent reactions as is.

As shown in Step 2 of Scheme 18, to a stirred mixture of 2,3,4,6-tetrafluorophenol (800 mg, 4.81 mmol), $K_2CO_3$ (1.0 g, 7.23 mmol) in DMF (4 mL) was added benzyl bromide (0.90 g, 5.63 mmol) dropwise at 25° C. under an atmosphere of nitrogen. The resulting mixture was stirred at 25° C. for 16 hours under nitrogen, diluted with water, and extracted with dichloromethane. The combined organic layers were washed with brine, dried over anhydrous sodium sulfate, filtered, concentrated under reduced pressure, and purified by reversed-phase flash chromatography (5%-78% acetonitrile/water) to afford 2-(benzyloxy)-1,3,4,5-tetrafluorobenzene (Compound 1026, 480 mg, 38% yield) as a colorless oil: GCMS calculated for $(C_{13}H_8F_4O)$, 256.1; found, 256.0.

As shown in Step 3 of Scheme 18, to a solution of 2-(benzyloxy)-1,3,4,5-tetrafluorobenzene (669 mg, 2.61 mmol), 6-bromo-2,2,7-trifluoro-4-[(4-methoxyphenyl)methyl]-1,4-benzoxazin-3-one (700 mg, 1.74 mmol) and $K_2CO_3$ (481 mg, 3.48 mmol) in dioxane (2 mL) were added bis(adamantan-1-yl)(butyl)phosphane (62 mg, mmol) and chloro[(diadamantan-1-yl)(n-butyl)phosphino][2-amino-1,1-biphenyl-2-yl]palladium(II) (116 mg, 0.17 mmol) at 20° C. The mixture was stirred at 110° C. for 16 hours under nitrogen, cooled to room temperature, and purified by flash chromatography (0%-20% ethyl acetate/petroleum ether), then further purified by reversed-phase flash chromatography (5%-84% acetonitrile/water) to afford 6-[3-(benzyloxy)-2,4,5,6-tetrafluorophenyl]-2,2,7-trifluoro-4-[(4-methoxyphenyl)methyl]-1,4-benzoxazin-3-one (Compound 1027, 400 mg, 39% yield) as a brown solid: GCMS calculated for $(C_{29}H_{18}F_7NO_4)$, 577.1; found, 577.1.

As shown in Step 4 of Scheme 18, to a stirred mixture of 6-[3-(benzyl oxy)-2,4,5,6-tetrafluorophenyl]-2,2,7-trifluoro-4-[(4-methoxyphenyl)methyl]-1,4-benzoxazin-3-one (440 mg, 0.76 mmol) in methanol (10 mL) was added Pd/C (48.6 mg, 0.45 mmol) under an atmosphere of nitrogen. The atmosphere was evacuated and charged with hydrogen three times then stirred at 25° C. for 2 hours under a hydrogen atmosphere. After this time, the hydrogen atmosphere was removed, the mixture filtered, and the filter cake washed with MeOH. The filtrate was collected and concentrated under reduced pressure to afford 2,2,7-trifluoro-4-[(4-methoxyphenyl)methyl]-6-(2,3,4,6-tetrafluoro-5-hydroxyphenyl)-1,4-benzoxazin-3-one (Compound 1028, 380 mg, 95% yield) as a brown solid: MS (ESI) calculated for $(C_{22}H_{12}F_7NO_4)$ [M−1]$^-$, 486.1; found, 485.9.

As shown in Step 5 of Scheme 18, to a stirred mixture of 2,2,7-trifluoro-4-[(4-methoxyphenyl)methyl]-6-(2,3,4,6-tetrafluoro-5-hydroxyphenyl)-1,4-benzoxazin-3-one (340 mg, 0.69 mmol) in DMF (3 mL) were added methyl iodide (119 mg, 0.84 mmol) and $K_2CO_3$ (145 mg, 1.04 mmol) at 25° C. under an atmosphere of nitrogen. The resulting mixture was stirred at 25° C. for 2 hours under an atmosphere of nitrogen, diluted with water, and extracted with dichloromethane. The combined organic layers were washed with brine, dried over anhydrous sodium sulfate, filtered, concentrated under reduced pressure, and purified by reversed-phase flash chromatography (5%-28% acetonitrile/water) to afford 2,2,7-trifluoro-4-[(4-methoxyphenyl)methyl]-6-(2,3,4,6-tetrafluoro-5-methoxyphenyl)-1,4-benzoxazin-3-one (Compound 1029, 300 mg, 85% yield) as a colorless oil: GCMS calculated for $(C_{23}H_{14}F_7NO_4)$, 501.1; found, 501.1.

As shown in Step 6 of Scheme 18, to a mixture of 2,2,7-trifluoro-4-[(4-methoxyphenyl)methyl]-6-(2,3,4,6-tetrafluoro-5-methoxyphenyl)-1,4-benzoxazin-3-one (300 mg, 0.59 mmol) in DCM (2 mL) were added trifluoromethanesulfonic acid (898 mg, 6.0 mmol) and TFA (682 mg, 6.0 mmol). The resulting mixture was stirred at 20° C. for 2 hours under an atmosphere of nitrogen, diluted with water, and extracted with ethyl acetate. The combined organic layers were washed with brine, dried over anhydrous sodium sulfate, filtered, concentrated under reduced pressure, and purified by reversed-phase flash chromatography (5%-55% acetonitrile/water) to afford 2,2,7-trifluoro-6-(2,3,4,6-tetrafluoro-(Compound 1030, 200 mg, 83% yield) as a yellow oil: MS (ESI) calculated for ($C_{15}H_6F_7NO_3$) [M–1]$^-$, 381.0; found, 381.0.

As shown in Step 7 of Scheme 18, a mixture of 2,2,7-trifluoro-6-(2,3,4,6-tetrafluoro-5-methoxyphenyl)-4H-1,4-benzoxazin-3-one (180 mg, 0.47 mmol), propargyl bromide (84.2 mg, 0.71 mmol) and $K_2CO_3$ (131 mg, 0.94 mmol) in DMF (1 mL) was stirred at 25° C. for 2 hours under an atmosphere of nitrogen, diluted with water, and extracted with ethyl acetate. The combined organic layers were washed with brine, dried over anhydrous sodium sulfate, filtered, concentrated under reduced pressure, and purified by reversed-phase flash chromatography (5%-64% acetonitrile/water) to afford 2,2,7-trifluoro-4-(prop-2-yn-1-yl)-6-(2,3,4,6-tetrafluoro-5-methoxyphenyl)-1,4-benzoxazin-3-one (Compound 38, 150 mg, 80% yield) as a yellow oil: GCMS calculated for ($C_{18}H_8F_7NO_3$), 419.0; found, 419.0; $^1$H-NMR (400 MHz, DMSO-d$_6$) δ 7.7-7.71 (m, 2H), 4.88 (d, J=2.4 Hz, 2H), 4.02 (s, 3H), 3.44 (s, 1H); $^{19}$F NMR (377 MHz, DMSO-d$_6$) δ –74.94, –115.60, –134.37, –142.53, –148.47, –163.57.

Example 17. Preparation of 2,2,7-trifluoro-4-(prop-2-yn-1-yl)-6-(2,3,5,6-tetrafluoro-4-hydroxyphenyl)-2H-benzo[b][1,4]oxazin-3(4H)-one (Compound 39)

Scheme 19

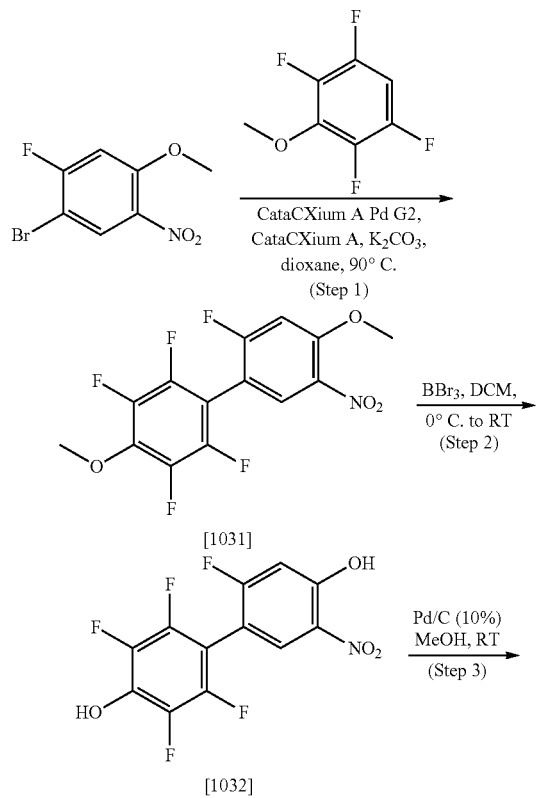

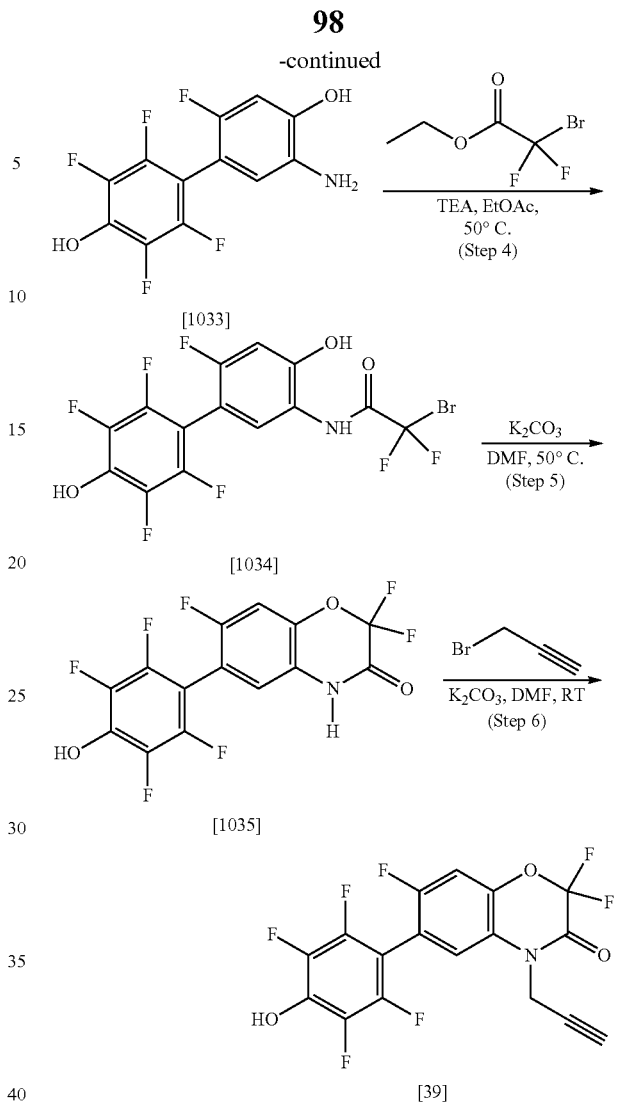

As shown in Step 1 of Scheme 19, to a stirred solution of 1-bromo-2-fluoro-4-methoxy-5-nitrobenzene (10.0 g, 40.0 mmol) in dioxane (100 mL) were added 2,3,5,6-tetrafluoroanisole (10.8 g, 60.00 mmol), chloro[(diadamantan-1-yl)(n-butyl)phosphino][2-amino-1,1-biphenyl-2-yl]palladium (II) (1.3 g, 2.0 mmol), bis(adamantan-1-yl)(butyl)phosphane (0.70 g, 2.0 mmol), and $K_2CO_3$ (11.1 g, 80.0 mmol). The resulting mixture was stirred at 90° C. for 16 hours under an atmosphere of nitrogen, cooled to room temperature, diluted with water, and extracted with ethyl acetate. The combined organic layers were washed with brine, dried over anhydrous sodium sulfate, filtered, concentrated under reduced pressure, and purified by flash chromatography (0%-10% ethyl acetate/petroleum ether) to afford 2,2',3,5,6-pentafluoro-4,4'-dimethoxy-5'-nitro-1,1'-biphenyl (Compound 1031, 10.0 g, 72% yield) as a yellow solid: CGMS calculated for ($C_{14}H_8F_5NO_4$), 349.0; found, 349.0.

As shown in Step 2 of Scheme 19, to a stirred solution of 2,2',3,5,6-pentafluoro-4,4'-dimethoxy-5'-nitro-1,1'-biphenyl (5.0 g, 14.3 mmol) in DCM (100 mL) was added BBr$_3$ (17.9 g, 71.6 mmol) dropwise at 0° C. The resulting mixture was stirred at 20° C. for 2 hours under an atmosphere of nitrogen, quenched with MeOH at 0° C., diluted with water, extracted with ethyl acetate, and the combined organics concentrated under reduced pressure. The residue was purified by flash chromatography (0%-5% MeOH/DCM) to afford 2,2',3,5,6-pentafluoro-5'-nitro-[1,1'-biphenyl]-4,4'-diol (Compound 1032, 4.0 g, 87% yield) as a yellow solid: MS (ESI) calculated for $(C_{12}H_4F_5NO_4)$ [M−1]⁻, 320.0; found, 320.0.

As shown in Step 3 of Scheme 19, to a stirred solution of 2,2',3,5,6-pentafluoro-5'-nitro-[1,1'-biphenyl]-4,4'-diol (4.5 g, 14.01 mmol) in MeOH (50 mL) was added Pd/C (450 mg, 4.23 mmol) under an atmosphere of nitrogen. The atmosphere was replaced with hydrogen and the resulting mixture stirred at 20° C. for 2 hours under a hydrogen atmosphere. After removal of the hydrogen atmosphere, the mixture was filtered and the filter cake washed with MeOH. The filtrate was concentrated under reduced pressure to afford 5'-amino-2,2',3,5,6-pentafluoro-[1,1'-biphenyl]-4,4'-diol (Compound 1033, 4.0 g, 98% yield) as a dark green solid: MS (ESI) calculated for $(C_{12}H_6F_5NO_2)$ [M−1]⁻, 290.0; found, 290.0.

As shown in Step 4 of Scheme 19, to a stirred solution of 5'-amino-2,2',3,5,6-pentafluoro-[1,1'-biphenyl]-4,4'-diol (4.0 g, 13.7 mmol) in MeOH (40 mL) were added ethyl 2-bromo-2,2-difluoroacetate (8.4 g, 41.21 mmol) and triethylamine (4.2 g, 41.2 mmol). The resulting mixture was stirred at 50° C. for 16 hours under an atmosphere of nitrogen, cooled to room temperature, diluted with water, and extracted with ethyl acetate. The combined organics were dried over anhydrous sodium sulfate, filtered, concentrated under reduced pressure, and purified by flash chromatography (0%-7% MeOH/DCM) to afford 2-bromo-2,2-difluoro-N-{2',3',5',6,6'-pentafluoro-4,4'-dihydroxy-[1,1'-biphenyl]-3-yl}acetamide (Compound 1034, 3.3 g, 53% yield) as a yellow solid: MS (ESI) calculated for $(C_{14}H_5BrF_7NO_3)$ [M−1]⁻, 446.0; found, 446.0.

As shown in Step 5 of Scheme 19, to a stirred solution of 2-bromo-2,2-difluoro-N-{2',3',5',6,6'-pentafluoro-4,4'-dihydroxy-[1,1'-biphenyl]-3-yl}acetamide (3.3 g, 7.37 mmol) in DMF (20 mL) was added $K_2CO_3$ (1.5 g, 11.05 mmol). The resulting mixture was stirred at for 2 hours under an atmosphere of nitrogen, cooled to room temperature, diluted with water, and extracted with ethyl acetate. The combined organics were dried over sodium sulfate, filtered, concentrated under reduced pressure, and purified by reversed-phase flash column chromatography (5%-50% acetonitrile/water) to afford 2,2,7-trifluoro-6-(2,3,5,6-tetrafluoro-4-hydroxyphenyl)-4H-1,4-benzoxazin-3-one (Compound 1035, 1.5 g, 56% yield) as a yellow solid: MS (ESI) calculated for $(C_{14}H_4F_7NO_3)$ [M−1]⁻, 366.0; found, 366.0.

As shown in Step 6 of Scheme 19, to a stirred mixture of 2,2,7-trifluoro-6-(2,3,4,6-tetrafluoro-5-hydroxyphenyl)-4H-1,4-benzoxazin-3-one (50 mg, 0.14 mmol) in DMF (2 mL) was added propargyl bromide (16.2 mg, 0.14 mmol) dropwise at 0° C. under an atmosphere of nitrogen. The resulting mixture was stirred at 25° C. for 2 hours under an atmosphere of nitrogen, diluted with water, and extracted with ethyl acetate. The combined organics were dried over sodium sulfate, filtered, concentrated under reduced pressure, and purified by flash chromatography (0%-28% ethyl acetate/petroleum ether) to afford 2,2,7-trifluoro-4-(prop-2-yn-1-yl)-6-(2,3,4,6-tetrafluoro-5-hydroxyphenyl)-1,4-benzoxazin-3-one (Compound 39, 26 mg, 51% yield) as an off-white solid: MS (ESI) calculated for $(C_{17}H_6F_7NO_3)$ [M−1]⁻, 404.0; found, 403.9; ¹H-NMR (400 MHz, DMSO-$d_6$) δ 11.94 (s, 1H), 7.74-7.68 (m, 2H), 4.88 (d, J=2.4 Hz, 2H), 3.43 (t, J=2.4 Hz, 1H). ¹⁹F-NMR (377 MHz, DMSO-$d_6$) δ −75.03, −115.61, −143.82, −161.43. Also isolated from the chromatographic purification were 2,2,7-trifluoro-6-(2,3,5,6-tetrafluoro-4-(prop-2-yn-1-yloxy)phenyl)-2H-benzo[b][1,4]oxazin-3(4H)-one (Compound 67): MS (ESI) calculated for $(C_{17}H_6F_7NO_3)$ [M−1]⁻ 404.0, found 403.9; ¹H-NMR (400 MHz, DMSO-$d_6$) δ 12.08 (s, 1H), 7.67-7.64 (m, 1H), 7.28-7.22 (m, 1H), 5.08 (s, 2H), 3.81 (s, 1H). ¹⁹F-NMR (377 MHz, DMSO-$d_6$) δ −75.23, −116.77, −142.59, −155.59 and 2,2,7-trifluoro-4-(prop-2-yn-1-yl)-6-(2,3,5,6-tetrafluoro-4-(prop-2-yn-1-yloxy)phenyl)-2H-benzo[b][1,4]oxazin-3(4H)-one (Compound 68) GCMS calculated for $(C_{20}H_8F_7NO_3)$ 443.0, found 443.1; ¹H-NMR (400 MHz, DMSO-$d_6$) δ 7.86-7.67 (m, 2H), 5.10 (s, 2H), 4.88 (s, 2H), 3.81 (s, 1H), 3.45 (s, 1H); ¹⁹F-NMR (376 MHz, DMSO-$d_6$) δ −74.86, −115.59, −141.92, −155.51.

Example 18. Preparation of 2,2,7-trifluoro-6-(2,3,5,6-tetrafluorophenyl)-2H-benzo[b][1,4]oxazin-3(4H)-one (Compound 40) and 2,2,7-trifluoro-4-(prop-2-yn-1-yl)-6-(2,3,4,6-tetrafluorophenyl)-2H-benzo[b][1,4]oxazin-3(4H)-one (Compound 41)

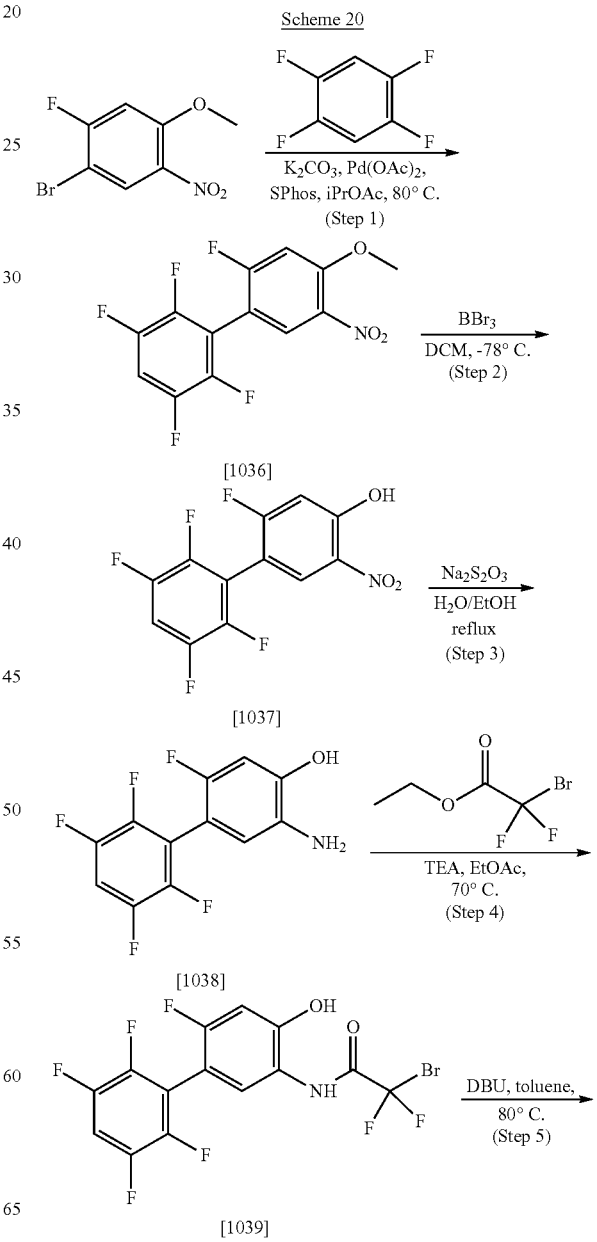

Scheme 20

-continued

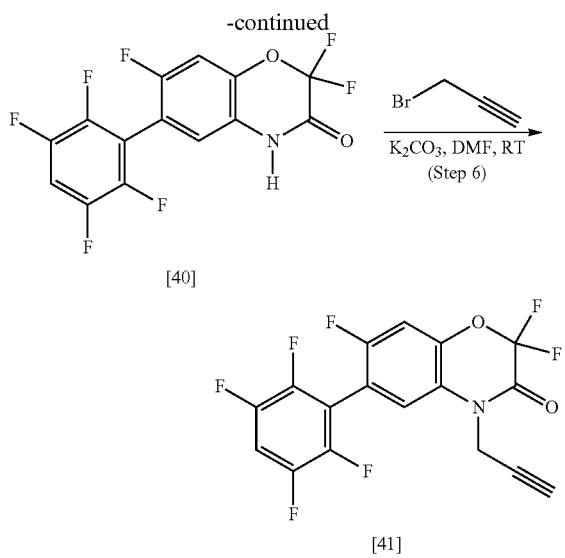

[40]

[41]

As shown in Step 1 of Scheme 20, to a stirred mixture of dicyclohexyl(2',6'-dimethoxy[1,1'-biphenyl]-2-yl)phosphane (Sphos, 990 mg, 2.40 mmol), Pd(OAc)$_2$ (270 mg, 1.20 mmol) and K$_2$CO$_3$ (3.3 g, 24.0 mmol) in isopropyl acetate (20 mL) was added 1,2,4,5-tetrafluorobenzene (3.6 g, 24.0 mmol) at room temperature under an atmosphere of nitrogen. The resulting mixture was stirred at room temperature for 10 minutes under an atmosphere of nitrogen and 1-bromo-2-fluoro-4-methoxy-5-nitrobenzene (3.0 g, 12.0 mmol) in isopropyl acetate (10 mL) was added dropwise over 0.5 hours at 80° C. The mixture was stirred at 80° C. for additional 2 hours, the volatiles removed under reduced pressure, and the residue purified by flash chromatography (0%-40% EtOAc/petroleum ether) to afford 2,2',3,5,6-pentafluoro-4'-methoxy-5'-nitro-1,1'-biphenyl (Compound 1036, 1.5 g, 35% yield) as a purple solid: GCMS calculated for (C$_{13}$H$_6$F$_5$NO$_3$), 319.0; found, 319.0.

As shown in Step 2 of Scheme 20, to a mixture of 2,2',3,5,6-pentafluoro-4'-methoxy-5'-nitro-1,1'-biphenyl (1.5 g, 4.69 mmol) in DCM (15 mL) at −78° C. was added BBr$_3$ (5.8 g, 23.49 mmol) dropwise. The resulting mixture was stirred at −78° C. for 3 hours under an atmosphere of nitrogen, diluted with water at room temperature, and extracted with CH$_2$Cl$_2$. The combined organics were dried over sodium sulfate, filtered, and concentrated to about 20% volume under reduced pressure, filtered again, and the filtrate concentrated under reduced pressure to afford 2,2', 3',5',6'-pentafluoro-5-nitro-[1,1'-biphenyl]-4-ol (Compound 1037, 1.3 g) as a brown solid: MS (ESI) calculated for (C$_{12}$H$_4$F$_5$NO$_3$) [M−1]$^-$, 304.0; found, 304.0. This material was used in subsequent steps without further purification.

As shown in Step 3 of Scheme 20, to a stirred solution of 2,2',3',5',6'-pentafluoro-5-nitro-[1,1'-biphenyl]-4-ol (1.4 g, 4.58 mmol) in EtOH (10 mL) and H$_2$O (3 mL) was added sodium hyposulfite (3.9 g, 22.91 mmol) in portions. The resulting mixture was stirred at 100° C. for 1 hour under an atmosphere of nitrogen, cooled to room temperature, diluted with water, and extracted with ethyl acetate. The combined organics dried over sodium sulfate, filtered, and concentrated under reduced pressure to afford 5-amino-2,2',3',5',6'-pentafluoro-[1,1'-biphenyl]-4-ol (Compound 1038, 1.2 g) as a yellow solid: MS (ESI) calculated for (C$_{12}$H$_5$F$_6$NO) [M−1]$^-$, 292.1; found, 292.1. This material was used as is in subsequent reactions.

As shown in Step 4 of Scheme 20, to a solution of 5-amino-2,2',3',5',6'-pentafluoro-[1,1'-biphenyl]-4-ol (500 mg, 1.81 mmol) and triethylamine (184 mg, 1.81 mmol) in EtOAc (5 mL) was added ethyl 2-bromo-2,2-difluoroacetate (369 mg, 1.81 mmol). The resulting mixture was stirred at 80° C. for 5 hours under an atmosphere of nitrogen, cooled to room temperature diluted with water, and extracted with ethyl acetate. The combined organic layers were washed with brine, dried over anhydrous sodium sulfate, filtered, concentrated under reduced pressure, and purified by flash chromatography (0%-38% EtOAc/petroleum ether) to afford 2-bromo-2,2-difluoro-N-(2',3',5',6,6'-pentafluoro-4-hydroxy-[1,1'-biphenyl]-3-yl) acetamide (Compound 1039, 300 mg, 38% yield) as a brown solid: MS (ESI) calculated for (C$_{14}$H$_5$BrF$_7$NO$_2$) [M+1]$^+$, 431.9; found, 431.9.

As shown in Step 5 of Scheme 20, a solution of 2-bromo-2,2-difluoro-N-[2',3',5',6,6'-pentafluoro-4-hydroxy-[1,1'-biphenyl]-3-yl] acetamide (500 mg, 1.15 mmol) and 1,8-diazabicyclo[5.4.0]undec-7-ene (DBU, 178 mg, 1.16 mmol) in toluene (5 ml) were stirred at 80° C. for 2 hours under an atmosphere of nitrogen, cooled to room temperature, diluted with water, and extracted with ethyl acetate. The combined organic layers were washed with brine, dried over anhydrous sodium sulfate, filtered, concentrated under reduced pressure, and purified by flash chromatography (0%-30% ethyl acetate/petroleum ether) to afford 2,2,7-trifluoro-6-(2,3,5,6-tetrafluorophenyl)-2H-benzo[b][1,4] oxazin-3(4H)-one (Compound 40, 230 mg, 55% yield) as a brown solid: MS (ESI) calculated for (C$_{14}$H$_4$F$_7$NO$_2$) [M−1]$^-$, 350.0; found, 350.0; $^1$H-NMR (400 MHz, DMSO-d$_6$) δ 12.20 (s, 1H), 8.07 (m, 1H), 7.70-7.62 (m, 1H), 7.24 (d, J=6.4 Hz, 1H); $^{19}$F-NMR (376 MHz, DMSO-d$_6$) δ −75.21, −116.80, −138.87, −141.58.

As shown in Step 6 of Scheme 20, to a solution of 2,2,7-trifluoro-6-(2,3,5,6-tetrafluorophenyl)-4H-1,4-benzoxazin-3-one (50 mg, 0.14 mmol) and K$_2$CO$_3$ (22 mg, 0.15 mmol) in DMF (1 mL) was added propargyl bromide (19 mg, 0.15 mmol). The resulting mixture was stirred at room temperature for 2 hours under an atmosphere of nitrogen followed by purification via reversed-phase HPLC (53% to 68% acetonitrile/10 mM aqueous NH$_4$HCO$_3$) to afford 2,2, 7-trifluoro-4-(prop-2-yn-1-yl)-6-(2,3,5,6-tetrafluorophenyl)-2H-benzo[b][1,4]oxazin-3(4H)-one (Compound 41, 42.1 mg, 75% yield) as a yellow oil: GCMS calculated for (C$_{17}$H$_6$F$_7$NO$_2$), 389.0; found, 389.0; H-NMR (400 MHz, DMSO-d$_6$) δ 8.18-8.05 (m, 1H), 7.83-7.74 (m, 2H), 4.87 (d, J=2.4 Hz, 2H), 3.45 (t, J=2.4 Hz, 1H); $^{19}$F-NMR (376 MHz, DMSO-d$_6$) δ −74.83, −115.67, −138.83, −141.01.

Example 19. Preparation of 2,2,7-trifluoro-6-(2,3,4, 6-tetrafluoro-5-methylphenyl)-2H-benzo[b][1,4] oxazin-3(4H)-one (Compound 42) and 2,2,7-trifluoro-4-(prop-2-yn-1-yl)-6-(2,3,4,6-tetrafluoro-5-methylphenyl)-2H-benzo[b][1,4]oxazin-3(4H)-one (Compound 43)

Scheme 21

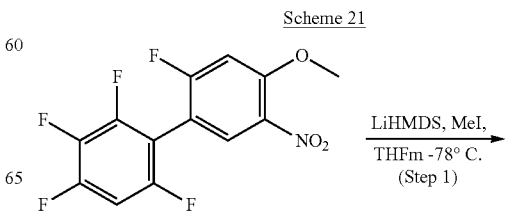

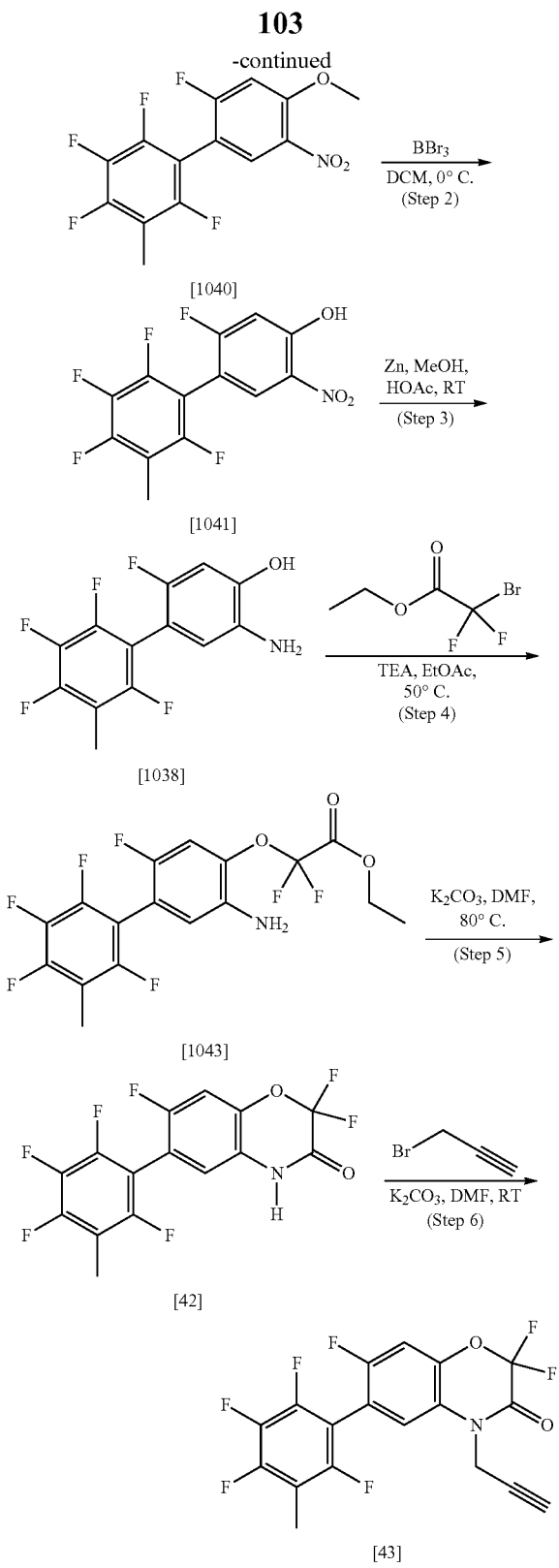

methyl iodide (0.7 g, 4.70 mmol) was added at −78° C. under an atmosphere of nitrogen. The mixture was stirred at −78° C. for 4 hours under nitrogen, diluted with water, and extracted with ethyl acetate. The combined organic layers were washed with brine, dried over anhydrous sodium sulfate, filtered, concentrated under reduced pressure, and purified by flash chromatography (0%-50% ethyl acetate/petroleum ether) to afford 2,2',3,4,6-pentafluoro-4'-methoxy-5-methyl-5'-nitro-1,1'-biphenyl (Compound 1040, 800 mg, 77% yield) as a yellow solid: GCMS calculated for ($C_{14}H_8F_5NO_3$), 333.0; found, 333.0.

As shown in Step 2 of Scheme 21, to a stirred mixture of 2,2',3,4,6-pentafluoro-4'-methoxy-5-methyl-5'-nitro-1,1'-biphenyl (800 mg, 2.40 mmol) in DCM (20 mL) was added boron tribromide (3.7 g, 12.00 mmol) dropwise at 0° C. under an atmosphere of nitrogen. The resulting mixture was stirred at 0° C. for 2 hours, diluted with water, and extracted with ethyl acetate. The combined organic layers were washed with brine, dried over anhydrous sodium sulfate, filtered, concentrated under reduced pressure, and purified by flash chromatography (0%-50% ethyl acetate/petroleum ether) to afford methyl 2-(6-amino-2,2,7-trifluoro-3-oxo-2,3-dihydro-4H-benzo[b][1,4]oxazin-4-yl)acetate (Compound 1041, 710.0 mg, 93% yield) as a yellow oil: MS (ESI) calculated for ($C_{13}H_6F_5NO_3$) [M−1]⁻, 318.0; found, 318.0.

As shown in Step 3 of Scheme 21, to a stirred mixture of 2,2',3',4',6'-pentafluoro-5'-methyl-5-nitro-[1,1'-biphenyl]-4-ol (710 mg, 2.22 mmol) in acetic acid (0.2 mL) and MeOH (20 mL) was added zinc powder (727 mg, 11.1 mmol). The resulting mixture was stirred at room temperature for 2 hours under an atmosphere of nitrogen, filtered, diluted with water, and extracted with ethyl acetate. The combined organic layers were washed with $NaHCO_3$, dried over anhydrous sodium sulfate, filtered, concentrated under reduced pressure, and purified by flash chromatography (0%-50% ethyl acetate/petroleum ether) to afford 5-amino-2,2',3',4',6'-pentafluoro-5'-methyl-[1,1'-biphenyl]-4-ol (Compound 1042, 560 mg, 87% yield) as a brown solid: MS (ESI) calculated for ($C_{13}H_8F_5NO$) [M−1]⁻, 288.0; found, 288.0.

As shown in Step 4 of Scheme 21, to a stirred mixture of 5-amino-2,2',3',4',6'-pentafluoro-5'-methyl-[1,1'-biphenyl]-4-ol (600 mg, 2.08 mmol) in ethyl acetate (15 mL) were added ethyl 2-bromo-2,2-difluoroacetate (632 mg, 3.11 mmol) and triethylamine (420 mg, 4.15 mmol). The resulting mixture was stirred at 50° C. for 16 hours under an atmosphere of nitrogen, cooled to room temperature, diluted with water, and extracted with ethyl acetate. The combined organic layers were washed with brine, dried over anhydrous sodium sulfate, filtered, concentrated under reduced pressure, and purified by flash chromatography (0%-50% ethyl acetate/petroleum ether) to afford 2-bromo-2,2-difluoro-N-(2',3',4',6,6'-pentafluoro-4-hydroxy-5'-methyl-[1,1'-biphenyl]-3-yl)acetamide (Compound 1043, 550 mg, 59% yield) as a brown solid: MS (ESI) calculated for ($C_{15}H_7BrF_7NO_2$) [M−1]⁻, 444.0; found, 444.0.

As shown in Step 5 of Scheme 21, to a stirred mixture of 2-bromo-2,2-difluoro-N-(2',3',4',6,6'-pentafluoro-4-hydroxy-5'-methyl-[1,1'-biphenyl]-3-yl)acetamide (550 mg, 1.23 mmol) in DMF (10 mL) was added $K_2CO_3$ (511 mg, 3.70 mmol). The resulting mixture was stirred at 80° C. for 2 hours under an atmosphere of nitrogen, cooled to room temperature, diluted with water, and extracted with ethyl acetate. The combined organic layers were washed with brine, dried over anhydrous sodium sulfate, filtered, concentrated under reduced pressure, and purified by flash chromatography (0%-50% ethyl acetate/petroleum ether) to As shown in Step 1 of Scheme 21, to a stirred mixture of 2,2',3,4,6-pentafluoro-4'-methoxy-5'-nitro-1,1'-biphenyl (1.0 g, 3.13 mmol) in THF (20 mL) was added lithium bis(trimethylsilyl)amide (LiHMDS, 6.27 mmol, 1M in THF) dropwise at −78° C. under an atmosphere of nitrogen. The resulting mixture was stirred at −78° C. for 30 minutes and afford 2,2,7-trifluoro-6-(2,3,4,6-tetrafluoro-5-methylphenyl)-2H-benzo[b][1,4]oxazin-3(4H)-one (Compound 42, 360 mg, 80% yield) as a brown solid; MS (ESI) calculated for ($C_{15}H_6F_7NO_2$) [M−1]⁻, 364.0; found, 364.0; ¹H-NMR (400 MHz, DMSO-$d_6$) δ 12.17 (s, 1H), 7.64 (d, J=9.6 Hz, 1H), 7.18 (d, J=6.4 Hz, 1H), 2.24 (s, 3H); ¹⁹F-NMR (376 MHz, DMSO-$d_6$) δ −75.25, −116.88, −120.24, −135.31, −138.86, −165.49.

As shown in Step 6 of Scheme 21, to a stirred solution of 2,2,7-trifluoro-6-(2,3,4,6-tetrafluoro-5-methylphenyl)-2H-benzo[b][1,4]oxazin-3(4H)-one (180.0 mg, 0.49 mmol) in DMF (6 mL) were added propargyl bromide (70.4 mg, 0.59 mmol) and $K_2CO_3$ (204.4 mg, 1.48 mmol). The resulting mixture was stirred at room temperature for 2 hours under an atmosphere of nitrogen, diluted with water, and extracted with ethyl acetate. The combined organic layers were washed with brine, dried over anhydrous sodium sulfate, filtered, concentrated under reduced pressure, and purified by reversed-phase flash chromatography (5%-50% acetonitrile/water) to afford 2,2,7-trifluoro-4-(prop-2-yn-1-yl)-6-(2,3,4,6-tetrafluoro-5-methylphenyl)-2H-benzo[b][1,4]oxazin-3(4H)-one (Compound 43, 148.0 mg, 75% yield) as a colorless oil: GCMS calculated for ($C_{18}H_8F_7NO_2$), 403.0; found, 403.0; ¹H-NMR (400 MHz, DMSO-$d_6$) δ 7.77-7.69 (m, 2H), 4.88 (s, 2H), 3.45-3.43 (m, 1H), 2.28-2.23 (m, 3H); ¹⁹F-NMR (400 MHz, DMSO-$d_6$) δ −74.98, −115.72, −119.75, −134.88, −138.34, −165.51.

Example 20. Preparation of 4-benzyl-2,2,7-trifluoro-6-(2,3,5,6-tetrafluorophenyl)-2H-benzo[b][1,4]oxazin-3(4H)-one (Compound 44)

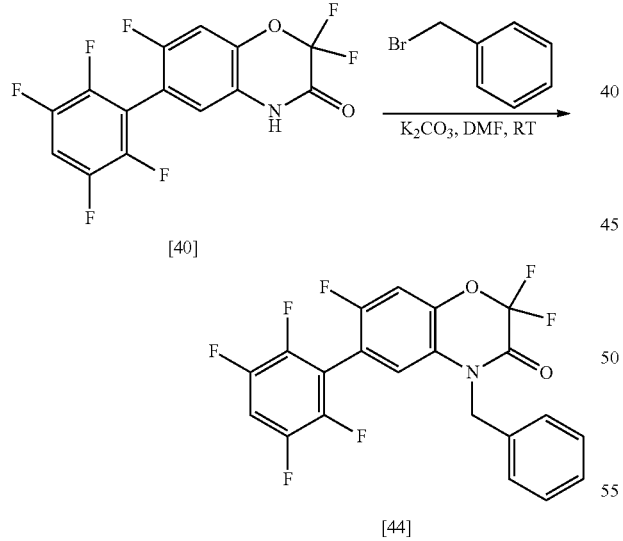

As shown in Scheme 22, to a mixture of 2,2,7-trifluoro-6-(2,3,5,6-tetrafluorophenyl)-2H-benzo[b][1,4] oxazin-3 (4H)-one (50 mg, 0.14 mmol) and $K_2CO_3$ (39 mg, 0.28 mmol) in DMF (1 mL) was added benzyl bromide (29 mg, 0.17 mmol). The resulting mixture was stirred at room temperature for 16 hours under an atmosphere of nitrogen, then purified by reversed-phase HPLC (60% to 72% acetonitrile/10 mM aqueous $NH_4HCO_3$) to afford 4-benzyl-2,2,7-trifluoro-6-(2,3,5,6-tetrafluorophenyl)-2H-benzo[b][1,4]oxazin-3(4H)-one (Compound 44, 43 mg, 68% yield) as a white solid: GCMS calculated for ($C_{21}H_{10}F_7NO_2$), 441.1; found, 441.1; ¹H-NMR (400 MHz, DMSO-$d_6$) δ 8.07 (m, 1H), 7.78-7.75 (m, 1H), 7.73-7.68 (m, 1H), 7.39-7.26 (m, 5H), 5.28 (s, 2H); ¹⁹F-NMR (376 MHz, DMSO-$d_6$) δ −74.87, −115.89, −138.90, −141.20.

Example 21. Preparation of 2,2,7-trifluoro-4-methyl-6-(2,3,4,6-tetrafluoro-5-methoxyphenyl)-2H-benzo[b][1,4]oxazin-3(4H)-one (Compound 45) and 2,2,7-trifluoro-4-methyl-6-(2,3,4,6-tetrafluoro-5-hydroxyphenyl)-2H-benzo[b][1,4]oxazin-3(4H)-one (Compound 46)

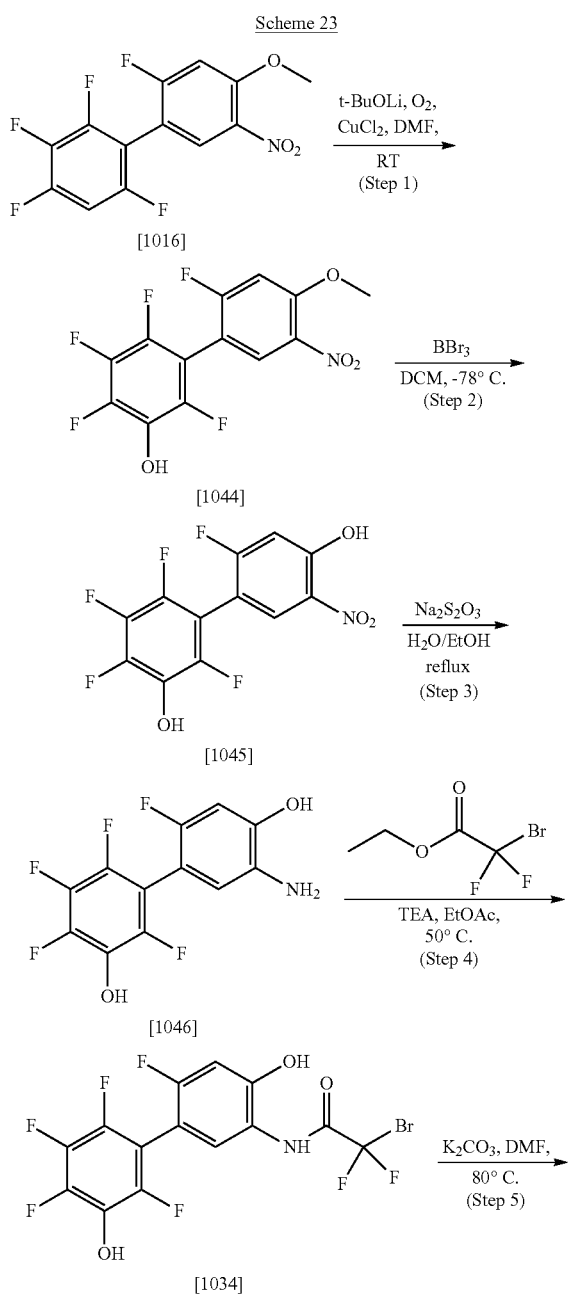

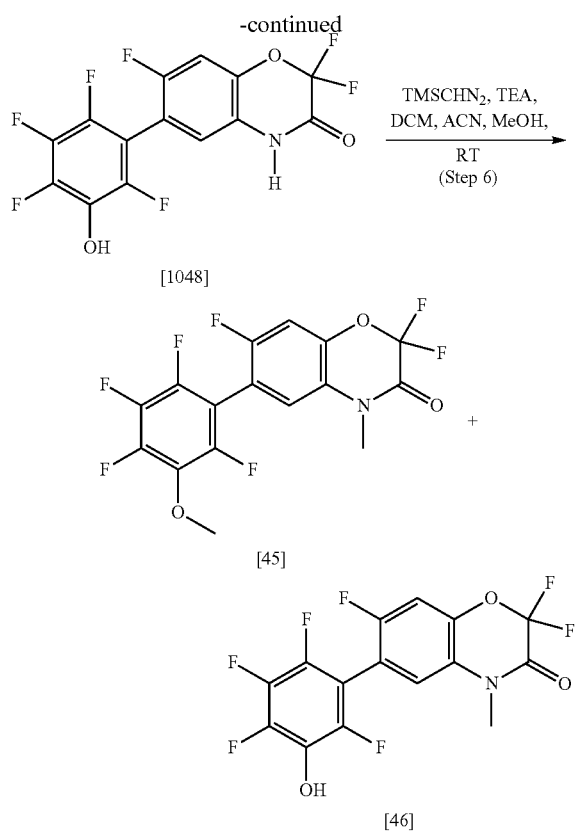

[1048]

[45]

[46]

As shown in Step 1 of Scheme 23, to a degassed mixture of 2,2',3,4,6-pentafluoro-4'-methoxy-5'-nitro-1,1'-biphenyl (3.0 g, 9.40 mmol) in DMF (30 mL) were added CuCl$_2$ (0.6 g, 4.70 mmol) and t-BuOLi (1.5 g, 18.80 mmol) under an oxygen atmosphere. The mixture was stirred at room temperature for 16 hours under an O$_2$ atmosphere, diluted with water, acidified to pH 2-4 with formic acid, and extracted with ethyl acetate. The combined organics were washed with brine, dried over anhydrous sodium sulfate, filtered, concentrated under reduced pressure, and purified by reversed-phase flash chromatography (30%-50% acetonitrile/water) to afford 2,2',4,5,6-pentafluoro-4'-methoxy-5'-nitro-[1,1'-biphenyl]-3-ol (Compound 1044, 850 mg, 25% yield) as a yellow solid: MS (ESI) calculated for (C$_{13}$H$_6$F$_5$NO$_4$) [M−1]$^−$, 334.0; found, 334.0.

As shown in Step 2 of Scheme 23, to a solution of 2,2',4,5,6-pentafluoro-4'-methoxy-5'-nitro-[1,1'-biphenyl]-3-ol (850 mg, 2.54 mmol) in DCM (10 mL) was added boron tribromide (3.2 g, 12.7 mmol) dropwise at −78° C. under an atmosphere of nitrogen. The resulting mixture was stirred at −78° C. for 3 hours under an atmosphere of nitrogen, warmed to room temperature, then stirred for additional 2 hours. The mixture was diluted with water and extracted with ethyl acetate. The combined organic layers were washed with brine, dried over anhydrous sodium sulfate, filtered, and concentrated under reduced pressure to afford 2,2',4,5,6-pentafluoro-5'-nitro-[1,1'-biphenyl]-3,4'-diol (Compound 1045, 850 mg, 78% yield) as a yellow solid. MS (ESI) calculated for (C$_{12}$H$_4$F$_5$NO$_4$) [M−1]$^−$, 320.0; found, 319.8.

As shown in Step 3 of Scheme 23, to a solution of 2,2',4,5,6-pentafluoro-5'-nitro-[1,1'-biphenyl]-3,4'-diol (850 mg, 2.70 mmol) in ethanol (9 mL) and H$_2$O (3 mL) was added sodium hyposulfite (2.4 g, 14.01 mmol). The resulting mixture was stirred at 100° C. for 2 hours, cooled to room temperature, diluted with water, and extracted with ethyl acetate. The combined organic layers were washed with brine, dried over anhydrous sodium sulfate, filtered, and concentrated under reduced pressure to afford 5'-amino-2,2',4,5,6-pentafluoro-[1,1'-biphenyl]-3,4'-diol (Compound 1046, 850 mg) as a yellow solid: MS (ESI) calculated for (C$_{12}$H$_6$F$_5$NO$_2$) [M−1]$^−$, 290.0; found, 289.9. This material was used in subsequent reactions as is.

As shown in Step 4 of Scheme 23, to a mixture of 5'-amino-2,2',4,5,6-pentafluoro-[1,1'-biphenyl]-3,4'-diol (850 mg, 2.92 mmol) in ethyl acetate (10 mL) were added triethylamine (325 mg, 3.21 mmol) and ethyl 2-bromo-2,2-difluoroacetate (652 mg, 3.21 mmol) under an atmosphere of nitrogen. The resulting mixture was stirred at 50° C. for 3 hours under nitrogen, cooled to room temperature, diluted with water, and extracted with ethyl acetate. The combined organic layers were washed with brine, dried over anhydrous sodium sulfate, filtered, and concentrated under reduced pressure to afford 2-bromo-2,2-difluoro-N-(2',3',4',6,6'-pentafluoro-4,5'-dihydroxy-[1,1'-biphenyl]-3-yl) acetamide (Compound 1047, 950 mg, crude) as a yellow oil. MS (ESI) calculated for (C$_{14}$H$_5$BrF$_7$NO$_3$) [M−1]$^−$, 445.9; found, 445.9.

As shown in Step 5 of Scheme 23, to a mixture of 2-bromo-2,2-difluoro-N-(2',3',4',6,6'-pentafluoro-4,5'-dihydroxy-[1,1'-biphenyl]-3-yl) acetamide (950 mg, 2.12 mmol) in DMF (10 mL) was added K$_2$CO$_3$ (879 mg, 6.36 mmol). The resulting mixture was stirred at 80° C. for 2 hours under a nitrogen atmosphere, cooled to room temperature, diluted with water, acidified to pH 1-3 with formic acid, and extracted with ethyl acetate. The combined organic layers were washed with brine, dried over anhydrous sodium sulfate, filtered, concentrated under reduced pressure, and purified by flash chromatography (20%-60% acetonitrile/water) to afford 2,2,7-trifluoro-6-(2,3,4,6-tetrafluoro-5-hydroxyphenyl)-2H-benzo[b][1,4]oxazin-3(4H)-one (Compound 1048, 150 mg, 19% yield) as a brown yellow solid: MS (ESI) calculated for (C$_{14}$H$_4$F$_7$NO$_3$) [M−1]$^−$, 366.0; found, 366.0; $^1$H-NMR (400 MHz, DMSO-d$_6$) δ 12.14 (s, 1H), 11.03 (s, 1H), 7.63 (d, J=9.6 Hz, 1H), 7.17 (d, J=6.8 Hz, 1H); $^{19}$F-NMR (376 MHz, DMSO-d6) δ −75.27, −116.82, −138.63, −150.19, −152.90, −165.02.

As shown in Step 6 of Scheme 23, to a solution of 2,2,7-trifluoro-6-(2,3,4,6-tetrafluoro-5-hydroxyphenyl)-2H-benzo[b][1,4] oxazin-3(4H)-one (150 mg, 0.41 mmol) and triethylamine (54 mg, 0.53 mmol) in DCM (1 mL), MeOH (0.1 mL) and acetonitrile (1 mL) was added trimethylsilyldiazomethane (0.49 mL, 2 M in hexane) at 0° C. under an atmosphere of nitrogen. The resulting mixture was stirred at room temperature for 16 hours, concentrated under reduced pressure, and purified by reversed-phase flash chromatography (20%-40% acetonitrile/water) to afford 2,2,7-trifluoro-4-methyl-6-(2,3,4,6-tetrafluoro-5-methoxyphenyl)-2H-benzo[b][1,4]oxazin-3(4H)-one (Compound 45, 31 mg, 20% yield) as a yellow oil: GCMS calculated for (C$_{16}$H$_8$F$_7$NO$_3$), 395.0; found, 395.1; $^1$H-NMR (400 MHz, DMSO-d$_6$) δ 7.85-7.65 (m, 2H), 4.02 (s, 3H), 3.42 (s, 3H). Also isolated was 2,2,7-trifluoro-4-methyl-6-(2,3,4,6-tetrafluoro-5-hydroxyphenyl)-2H-benzo[b][1,4]oxazin-3 (4H)-one (Compound 46, 6.7 mg, 4%) as a yellow oil: GCMS calculated for (C$_{15}$H$_6$F$_7$NO$_3$), 380.0; found, 379.9; $^1$H-NMR (300 MHz, DMSO-d$_6$) δ 7.79-7.66 (m, 2H), 3.63 (s, 3H).

Example 22. Preparation of 2,2,7-trifluoro-4-(prop-2-yn-1-yl)-6-(2,3,4,6-tetrafluoro-5-vinylphenyl)-2H-benzo[b][1,4]oxazin-3(4H)-one (Compound 47)

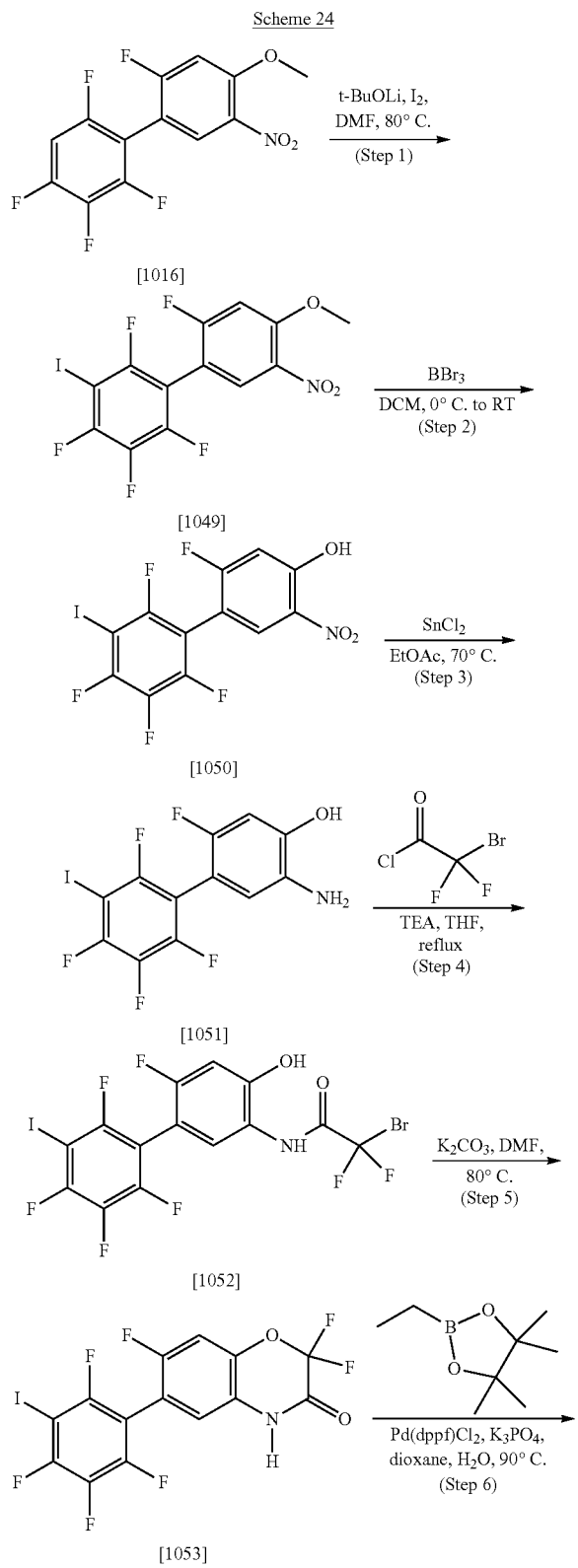

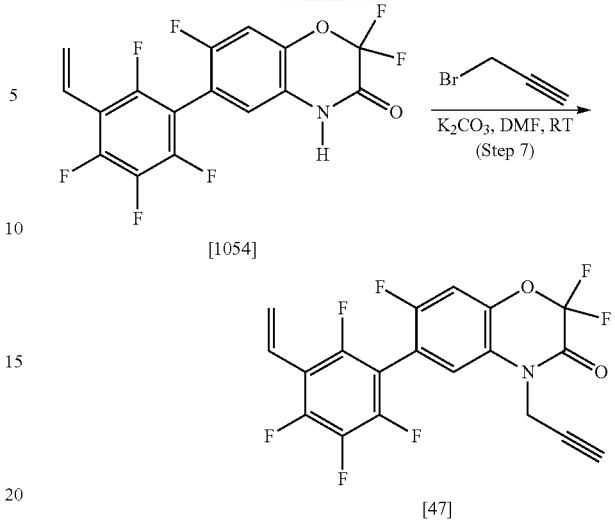

As shown in Step 1 of Scheme 24, to a stirred mixture of 2,2',3,4,6-pentafluoro-4'-methoxy-5'-nitro-1,1'-biphenyl (1.0 g, 3.13 mmol) in DMF (10 mL) were added t-BuOLi (0.30 g, 3.76 mmol) and iodine (0.80 g, 3.13 mmol). The mixture was stirred at 80° C. for 2 hours under an atmosphere of nitrogen, cooled to room temperature, diluted with water, and extracted with ethyl acetate. The combined organic layers were washed with brine, dried over anhydrous sodium sulfate, filtered, concentrated under reduced pressure, and purified by reversed-phase flash chromatography (0%-70% acetonitrile/water) to afford 2,2',3,4,6-pentafluoro-5-iodo-4'-methoxy-5'-nitro-1,1'-biphenyl (Compound 1049, 660 mg, 47% yield) as a yellow solid: GCMS calculated for ($C_{13}H_5F_5INO_3$), 444.9; found, 444.9.

As shown in Step 2 of Scheme 24, to a stirred mixture of 2,2',3,4,6-pentafluoro-5-iodo-4'-methoxy-5'-nitro-1,1'-biphenyl (660 mg, 1.48 mmol) in DCM (15 mL) was added boron tribromide (1.8 g, 7.41 mmol) dropwise at 0° C. under an atmosphere of nitrogen. The resulting mixture was stirred at 0° C. for 2 hours, diluted with water, and extracted with ethyl acetate. The combined organic layers were washed with brine, dried over anhydrous sodium sulfate, filtered, concentrated under reduced pressure, and purified by flash chromatography (0%-15% ethyl acetate/petroleum ether) to afford 2,2',3',4',6'-pentafluoro-5'-iodo-5-nitro-[1,1'-biphenyl]-4-ol (Compound 1050, 580 mg, 90% yield) as a brown oil: MS (ESI) calculated for ($C_{12}H_3F_5INO_3$) [M−1]$^−$, 430.0; found, 430.0.

As shown in Step 3 of Scheme 24, to a stirred mixture of 2,2',3',4',6'-pentafluoro-(580 mg, 1.32 mmol) in EtOAc (20 mL) was added $SnCl_2$ (1.3 g, 7.14 mmol). The mixture was stirred at 70° C. for 2 hours under an atmosphere of nitrogen, cooled to room temperature, diluted with water, and extracted with ethyl acetate. The combined organic layers were washed with 1M HCl and water, dried over anhydrous sodium sulfate, filtered, concentrated under reduced pressure, and purified by flash chromatography (0%-35% ethyl acetate/petroleum ether) to afford 5-amino-2,2',3',4',6'-pentafluoro-5'-iodo-[1,1'-biphenyl]-4-ol (Compound 1051, 330 mg, 56% yield) as a yellow solid: MS (ESI) calculated for ($C_{12}H_5F_5INO$) [M−1]$^−$, 400.0; found, 400.0.

As shown in Step 4 of Scheme 24, to a stirred mixture of 5-amino-2,2',3',4',6'-pentafluoro-5'-iodo-[1,1'-biphenyl]-4-ol (280 mg, 0.69 mmol) in THF (10 mL) were added bromodifluoroacetyl chloride (203 mg, 1.04 mmol) and triethylamine (141 mg, 1.39 mmol). The mixture was stirred at 100° C. for 1 hour under an atmosphere of nitrogen, cooled to room temperature, diluted with water, and extracted with ethyl acetate. The combined organic layers were washed with brine, dried over anhydrous sodium sulfate, filtered, concentrated under reduced pressure, and purified by flash column chromatography (0%-35% ethyl acetate/petroleum ether) to afford 2-bromo-2,2-difluoro-N-(2',3',4',6,6'-pentafluoro-4-hydroxy-5'-iodo-[1,1'-biphenyl]-3-yl)acetamide (Compound 1052, 340 mg, 87% yield) as a yellow solid: MS (ESI) calculated for ($C_{14}H_4BrF_7INO_2$) [M−1]⁻, 556.0; found, 556.0.

As shown in Step 5 of Scheme 24, to a stirred mixture of 2-bromo-2,2-difluoro-N-(2',3',4',6,6'-pentafluoro-4-hydroxy-5'-iodo-[1,1'-biphenyl]-3-yl)acetamide (310 mg, 0.56 mmol) in DMF (10 mL) was added $K_2CO_3$ (230 mg, 1.66 mmol). The mixture was stirred at for 2 hours, cooled to room temperature, diluted with water, and extracted with ethyl acetate. The combined organic layers were washed with brine, dried over anhydrous sodium sulfate, filtered, concentrated under reduced pressure, and purified by flash column chromatography (0%-35% ethyl acetate/petroleum ether) to afford 2,2,7-trifluoro-6-(2,3,4,6-tetrafluoro-5-iodophenyl)-2H-benzo[b][1,4]oxazin-3(4H)-one (Compound 1053, 200 mg, 75% yield) as a yellow oil: MS (ESI) calculated for ($C_{14}H_3F_7INO_2$) [M−1]⁻, 476.0; found, 476.0.

As shown in Step 6 of Scheme 24, to a stirred mixture of 2,2,7-trifluoro-6-(2,3,4,6-tetrafluoro-5-iodophenyl)-2H-benzo[b][1,4]oxazin-3(4H)-one (100 mg, 0.21 mmol) in dioxane (5 mL) and $H_2O$ (0.5 mL) were added 2-ethenyl-4,4,5,5-tetramethyl-1,3,2-dioxaborolane (39 mg, 0.25 mmol), Pd(dppf)Cl₂ (15 mg, 0.02 mmol), and $K_3PO_4$ (133 mg, mmol). The mixture was stirred at 80° C. for 16 hours under an atmosphere of nitrogen, cooled to room temperature, diluted with water, and extracted with ethyl acetate. The combined organic layers were washed with brine, dried over anhydrous sodium sulfate, filtered, concentrated under reduced pressure, and purified by preparative-TLC (1:5 EtOAc/petroleum ether) to afford 2,2,7-trifluoro-6-(2,3,4,6-tetrafluoro-5-vinylphenyl)-2H-benzo[b][1,4]oxazin-3(4H)-one (Compound 1054, 70 mg, 88% yield) as a yellow oil: MS (ESI) calculated for ($C_{16}H_6F_7NO_2$) [M−1]⁻, 376.0; found, 376.0.

As shown in Step 7 of Scheme 24, to a stirred solution of 2,2,7-trifluoro-6-(2,3,4,6-tetrafluoro-5-vinylphenyl)-2H-benzo[b][1,4]oxazin-3(4H)-one (60 mg, 0.16 mmol) in DMF (3 mL) were added propargyl bromide (23 mg, 0.19 mmol) and $K_2CO_3$ (66 mg, 0.48 mmol). The resulting mixture was stirred at room temperature for 2 hours, diluted with water, and extracted with ethyl acetate. The combined organic layers were washed with brine, dried over anhydrous sodium sulfate, filtered, concentrated under reduced pressure, and purified by flash column chromatography (0%-15% ethyl acetate/petroleum ether) to afford 2,2,7-trifluoro-4-(prop-2-yn-1-yl)-6-(2,3,4,6-tetrafluoro-5-vinylphenyl)-2H-benzo[b][1,4]oxazin-3(4M-one (Compound 47, 37 mg, 56% yield) as a light oil: GCMS calculated for ($C_{19}H_8F_7NO_2$), 415.0; found, 415.0; ¹H-NMR (400 MHz, DMSO-d₆) δ 7.76-7.74 (m, 2H), 6.78-6.66 (m, 1H), 6.05 (d, J=17.6 Hz, 1H), 5.81 (d, J=11.6 Hz, 1H), 4.87 (s, 2H), 3.44 (s, 1H); ¹⁹F-NMR (376 MHz, DMSO-d₆) δ −74.96, −115.67, −119.12, −135.03, −135.41, −164.64.

Example 23. Preparation of 6-(3-ethyl-2,4,5,6-tetrafluorophenyl)-2,2,7-trifluoro-4-(prop-2-yn-1-yl)-2H-benzo[b][1,4]oxazin-3(4H)-one (Compound 48)

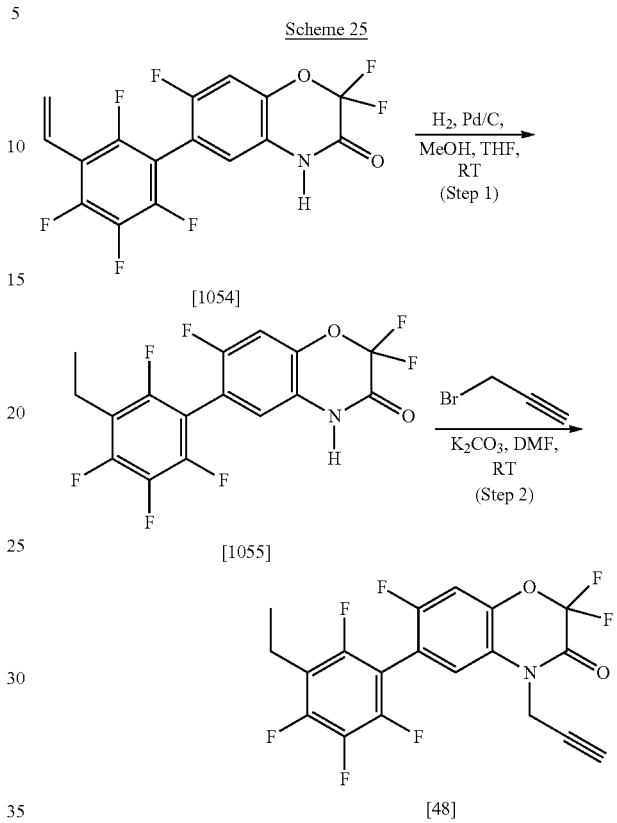

As shown in Step 1 of Scheme 25, to a stirred mixture of 2,2,7-trifluoro-6-(2,3,4,6-tetrafluoro-5-vinylphenyl)-2H-benzo[b][1,4]oxazin-3(4H)-one (80 mg, 0.21 mmol) in MeOH (2 mL) and THF (2 mL) was added Pd/C (10%, 20 mg) under nitrogen. The atmosphere was replaced with hydrogen and the mixture stirred at room temperature for 4 hours. After removal of the hydrogen atmosphere, the solids were filtered out through a Celite pad, the filtrate collected, and the volatiles removed under reduced pressure to afford 6-(3-ethyl-2,4,5,6-tetrafluorophenyl)-2,2,7-trifluoro-2H-benzo[b][1,4]oxazin-3(4H)-one (Compound 1055, 50 mg, 60% yield) as a brown oil: MS (ESI) calculated for ($C_{16}H_8F_7NO_2$) [M−1]⁻, 378.0; found, 378.0.

As shown in Step 2 of Scheme 25, to a stirred solution of 6-(3-ethyl-2,4,5,6-tetrafluorophenyl)-2,2,7-trifluoro-2H-benzo[b][1,4]oxazin-3(4H)-one (50 mg, 0.13 mmol) in DMF (2 mL) were added propargyl bromide (19 mg, 0.15 mmol) and $K_2CO_3$ (55 mg, 0.39 mmol). The resulting mixture was stirred at 25° C. for 2 hours under an atmosphere of nitrogen, diluted with water, and extracted with ethyl acetate. The combined organic layers were washed with brine, dried over anhydrous sodium sulfate, filtered, concentrated under reduced pressure, and purified by reversed-phase flash column chromatography (20%-70% acetonitrile/water to afford 6-(3-ethyl-2,4,5,6-tetrafluorophenyl)-2,2,7-trifluoro-4-(prop-2-yn-1-yl)-2H-benzo[b][1,4]oxazin-3(4H)-one (Compound 48, 13 mg, 24% yield) as a colorless oil: GCMS calculated for ($C_{19}H_{10}F_7NO_2$), 417.1; found, 417.0; ¹H-NMR (400 MHz, methanol-d₄) δ 7.59-7.57 (m, 1H), 7.40-7.36 (m, 1H), 4.91-4.89 (m, 2H), 2.87 (s, 1H), 2.88-2.77 (m, 2H), 1.29-1.24 (m, 3H); ¹⁹F-NMR (376 MHz, methanol-d₄) δ −78.88, −116.82, −123.84, −139.44, −139.86, −167.94.

Example 24. Preparation of 2,2,7-trifluoro-4-(prop-2-yn-1-yl)-6-(2,3,5,6-tetrafluoro-4-(methylthio)phenyl)-2H-benzo[b][1,4]oxazin-3(4H)-one (Compound 49)

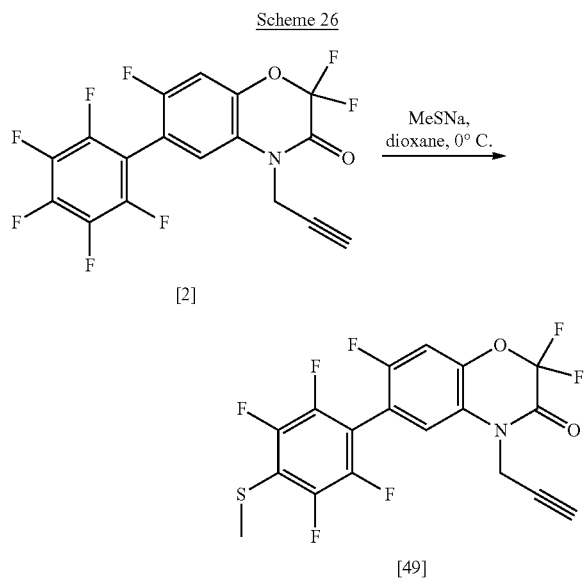

Scheme 26

[2]

[49]

As shown in Scheme 26, to a stirred solution of 2,2,7-trifluoro-6-(perfluorophenyl)-4-(prop-2-yn-1-yl)-2H-benzo[b][1,4]oxazin-3(4H)-one (200 mg, 0.49 mmol) in dioxane (3 mL) was added sodium thiomethoxide (34.0 mg, 0.49 mmol). The resulting mixture was stirred at 20° C. for 2 hours, diluted with water, and extracted with ethyl acetate. The combined organics were dried over sodium sulfate, filtered, concentrated under reduced pressure, and purified by flash chromatography (0%-10% ethyl acetate/petroleum ether) to afford 2,2,7-trifluoro-4-(prop-2-yn-1-yl)-6-(2,3,5,6-tetrafluoro-4-(methylthio)phenyl)-2H-benzo[b][1,4]oxazin-3(4H)-one (Compound 49, 40 mg, 19% yield) as a white solid: GCMS calculated for ($C_{18}H_8F_7NO_2S$) 435.0; found 434.9; $^1$H-NMR (400 MHz, chloroform-d) δ 7.32 (d, J=6.0 Hz, 1H), 7.18 (d, J=8.8 Hz, 1H), 4.82 (d, J=2.4 Hz, 2H), 2.62 (s, 3H), 2.39 (s, 1H); $^{19}$F-NMR (376 MHz, chloroform-d) δ −77.00, −113.18, −134.54, −140.64.

Example 25. Preparation of 2,2,7-trifluoro-4-(prop-2-yn-1-yl)-6-(2,3,5,6-tetrafluoro-4-methoxyphenyl)-2H-benzo[b][1,4]oxazin-3(4H)-one (Compound 50)

Scheme 27

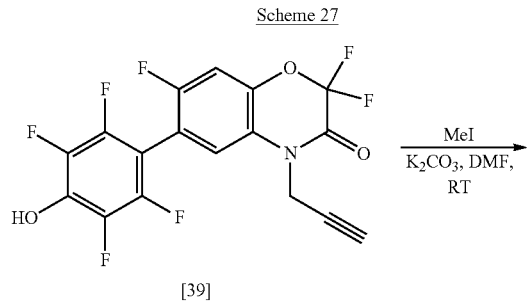

[39]

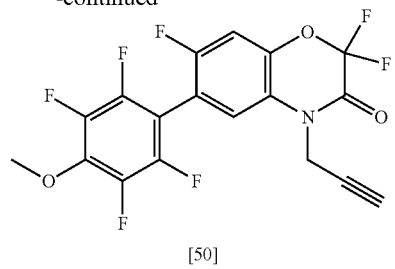

[50]

As shown in Scheme 27, to a stirred solution of 2,2,7-trifluoro-4-(prop-2-yn-1-yl)-6-(2,3,5,6-tetrafluoro-4-hydroxyphenyl)-2H-benzo[b][1,4]oxazin-3(4H)-one (50 mg, 0.12 mmol) in DMF (2 mL) were added methyl iodide (21 mg, 0.15 mmol) and $K_2CO_3$ (26 mg, mmol). The mixture was stirred at room temperature for 2 hours under a nitrogen atmosphere, diluted with water, and extracted with ethyl acetate. The combined organic layers were washed with brine, dried over anhydrous sodium sulfate, filtered, concentrated under reduced pressure, and purified by preparative—TLC (25% EtOAc/petroleum ether) and further purified by reversed-phase flash chromatography with (5%-60% acetonitrile in water) to afford 2,2,7-trifluoro-4-(prop-2-yn-1-yl)-6-(2,3,5,6-tetrafluoro-4-methoxyphenyl)-2H-benzo[b][1,4]oxazin-3(4H)-one (Compound 50) (13 mg, 25% yield) as a white solid: MS (ESI) calculated for ($C_{18}H_8F_7NO_3$) [M+1]$^+$, 420.0; found 420.0; $^1$H-NMR (400 MHz, DMSO-$d_6$) δ 7.87-7.64 (m, 2H), 4.88 (s, 2H), 4.15 (s, 3H), 3.38 (s, 1H); $^{19}$F-NMR (376 MHz, DMSO-$d_6$) δ −74.92, −115.62, −142.27, −157.65.

Example 26. Preparation of 6-(4-ethoxy-2,3,5,6-tetrafluorophenyl)-2,2,7-trifluoro-4-(prop-2-yn-1-yl)-2H-benzo[b][1,4]oxazin-3(4H)-one (Compound 51)

Scheme 28

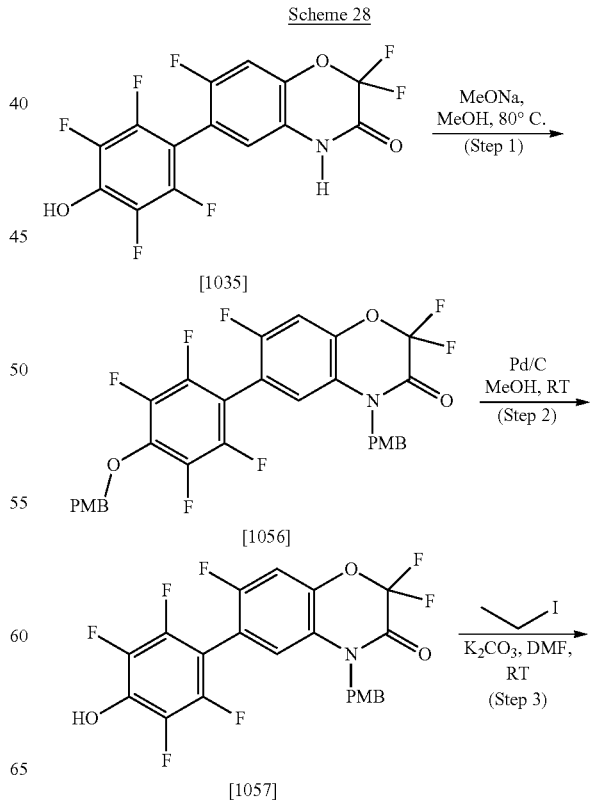

[1035]

[1056]

[1057]

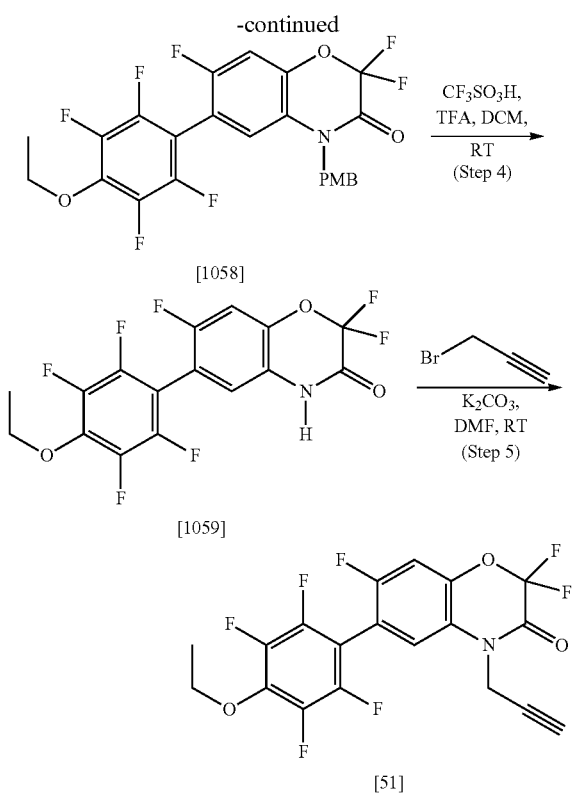

As shown in Step 1 of Scheme 28, to a solution of 2,2,7-trifluoro-6-(2,3,5,6-tetrafluoro-4-hydroxyphenyl)-2H-benzo[b][1,4]oxazin-3(4H)-one (1.0 g, 2.72 mmol) in DMF (10 mL) were added $K_2CO_3$ (1.1 g, 8.16 mmol) and 4-methoxybenzyl chloride (1.0 g, 6.8 mmol). The mixture was stirred at 20° C. for 2 hours under a nitrogen atmosphere, diluted with water, and extracted with ethyl acetate. The combined organic layers were washed with brine, dried over anhydrous sodium sulfate, filtered, concentrated under reduced pressure, and purified by flash chromatography (0%-50% ethyl acetate in petroleum ether) to afford 2,2,7-trifluoro-4-(4-methoxybenzyl)-6-(2,3,5,6-tetrafluoro-44(4-methoxybenzyl)oxy)phenyl)-2H-benzo[b][1,4]oxazin-3(4H)-one (Compound 1056, 804 mg, 48% yield) as a white solid: MS (ESI) calculated for $(C_{30}H_{20}F_7NO_5)$ [M−1]⁻, 606.0; found 606.2.

As shown in Step 2 of Scheme 15, to a solution of 2,2,7-trifluoro-4-(4-methoxybenzyl)-6-(2,3,5,6-tetrafluoro-4-((4-methoxybenzyl)oxy)phenyl)-2H-benzo[b][1,4]oxazin-3(4H)-one (804 mg, 1.41 mmol) in methanol (10 mL) was added Pd/C (161 mg, 20% wt/wt) under a nitrogen atmosphere. The atmosphere was replaced with hydrogen gas and the mixture was stirred at 20° C. for 2 hours under hydrogen. The hydrogen was removed, the mixture filtered, and the filtrated concentrated under reduced pressure to afford 2,2,7-trifluoro-4-(4-methoxybenzyl)-6-(2,3,5,6-tetrafluoro-4-hydroxyphenyl)-2H-benzo[b][1,4]oxazin-3(4H)-one (Compound 1057, 750 mg, crude) as a yellow solid: MS (ESI) calculated for $(C_{22}H_{12}F_7NO_4)$ [M−1]⁻, 486.0; found 486.1.

As shown in Step 3 of Scheme 15, to a solution of 2,2,7-trifluoro-4-(4-methoxybenzyl)-6-(2,3,5,6-tetrafluoro-4-hydroxyphenyl)-2H-benzo[b][1,4]oxazin-3(4H)-one (200 mg, 0.44 mmol) in DMF (3 mL) were added iodoethane (84 mg, 0.53 mmol) and $K_2CO_3$ (93 mg, 0.66 mmol). The mixture was stirred at 20° C. for 1 hour under a nitrogen atmosphere, diluted with water, and extracted with ethyl acetate. The combined organic layers were washed with brine, dried over anhydrous sodium sulfate, filtered, concentrated under reduced pressure, and purified by flash chromatography (0%-50% ethyl acetate in petroleum ether) to afford 6-(4-ethoxy-2,3,5,6-tetrafluorophenyl)-2,2,7-trifluoro-4-(4-methoxybenzyl)-2H-benzo[b][1,4]oxazin-3(4H)-one (Compound 1058. 160 mg, 97% yield) as a yellow solid: MS (ESI) calculated for $(C_{24}H_{16}F_7NO_4)$ [M−1]⁻, 514.1; found 514.0.

As shown in Step 4 of Scheme 15, to a solution of 6-(4-ethoxy-2,3,5,6-tetrafluorophenyl)-2,2,7-trifluoro-4-(4-methoxybenzyl)-2H-benzo[b][1,4]oxazin-3(4H)-one (150 mg, 0.29 mmol) in DCM (2 mL) were added trifluoroacetic acid (332 mg, 2.91 mmol) and trifluoromethanesulfonic acid (437 mg, 2.91 mmol). The mixture was stirred at 20° C. for 1 hour under a nitrogen atmosphere, diluted with water, and extracted with ethyl acetate. The combined organic layers were washed with brine, dried over anhydrous sodium sulfate, filtered, concentrated under reduced pressure, and purified by flash chromatography (0%-70% ethyl acetate in petroleum ether) to afford 6-(4-ethoxy-2,3,5,6-tetrafluorophenyl)-2,2,7-trifluoro-2H-benzo[b][1,4]oxazin-3(4H)-one (Compound 1059, 70 mg, 60% yield) as a yellow oil: MS (ESI) calculated for $(C_{16}H_8F_7NO_3)$ [M−1]⁻, 394.0; found 394.0.

As shown in Step 5 of Scheme 15, to a solution of 6-(4-ethoxy-2,3,5,6-tetrafluorophenyl)-2,2,7-trifluoro-2H-benzo[b][1,4]oxazin-3(4H)-one (68 mg, 0.17 mmol) in DMF (2 mL) were added $K_2CO_3$ (48 mg, 0.34 mmol) and propargyl bromide (31 mg, 0.25 mmol). The mixture was stirred at 20° C. for 2 hours under a nitrogen atmosphere, diluted with water, and extracted with ethyl acetate. The combined organic layers were washed with brine, dried over anhydrous sodium sulfate, filtered, concentrated under reduced pressure, and purified by reversed-phase flash chromatography (5%-70% acetonitrile in water) to afford 6-(4-ethoxy-2,3,5,6-tetrafluorophenyl)-2,2,7-trifluoro-4-(prop-2-yn-1-yl)-2H-benzo[b][1,4]oxazin-3(4H)-one (Compound 51, 59 mg, 78% yield) as a white solid: GCMS calculated for $(C_{19}H_{10}F_7NO_3)$, 433.0; found, 433.1; ¹H-NMR (400 MHz, DMSO-d₆) δ 7.80-7.72 (m, 2H), 4.88 (d, J=2.4 Hz, 2H), 4.40 (q, J=7.2 Hz, 2H), 3.45 (s, 1H), 1.39 (t, J=7.2 Hz, 3H); ¹⁹F-NMR (376 MHz, DMSO-d₆) δ −74.88, −115.55, −142.21, −156.98.

Example 27. Preparation of 7-fluoro-4-(prop-2-yn-1-yl)-6-(2,3,4,6-tetrafluorophenyl)-2H-benzo[b][1,4]oxazin-3(4H)-one (Compound 52)

Scheme 29

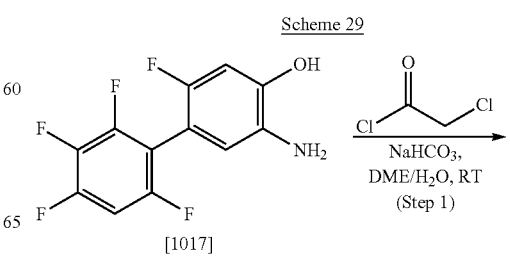

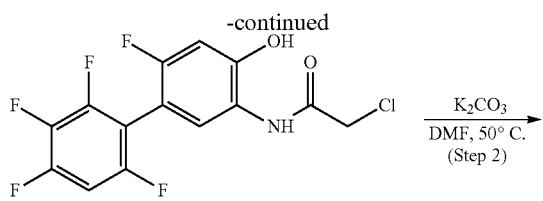

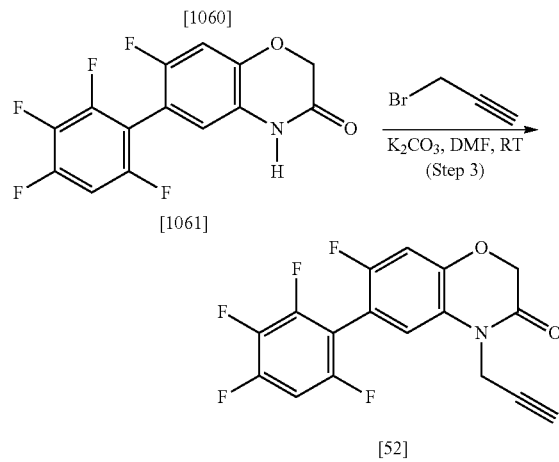

As shown in Step 1 of Scheme 29, to a solution of 5-amino-2,2',3',4',6'-pentafluoro-[1,1'-biphenyl]-4-ol (250 mg, 0.91 mmol) in DME (1.5 mL) and H$_2$O (1.5 mL) was added NaHCO$_3$ (229 mg, 2.73 mmol) at room temperature under a nitrogen atmosphere, followed by the dropwise addition of chloroacetyl chloride (154 mg, 1.36 mmol) at 0° C. The reaction was stirred at room temperature for 3 hours and concentrated under reduced pressure to afford 2-chloro-N-(2',3',4',6,6'-pentafluoro-4-hydroxy-[1,1'-biphenyl]-3-yl)acetamide (Compound 1060, 250 mg, crude) as a brown solid: MS (ESI) calculated for (C$_{14}$H$_7$ClF$_5$NO$_2$) [M−1]$^-$, 350.0; found, 350.0. This material was used as is in subsequent reactions.

As shown in Step 2 of Scheme 29, a mixture of 2-chloro-N-(2',3',4',6,6'-pentafluoro-4-hydroxy-[1,1'-biphenyl]-3-yl)acetamide (250 mg, 0.71 mmol) and K$_2$CO$_3$ (198 mg, 1.42 mmol) in DMF (3 mL) was stirred at 50° C. for 1 hour under a nitrogen atmosphere, cooled to room temperature, diluted with water, and extracted with ethyl acetate. The combined organic layers were washed with brine, dried over anhydrous sodium sulfate, filtered, concentrated under reduced pressure, and purified by flash chromatography (0%-20% ethyl acetate in petroleum ether) to afford 7-fluoro-6-(2,3,4,6-tetrafluorophenyl)-2H-benzo[b][1,4]oxazin-3(4H)-one (Compound 1061, 210 mg, 94% yield) as a yellow solid: MS (ESI) calculated for (C$_{14}$H$_6$F$_5$NO$_2$) [M−1]$^-$, 314.0; found, 314.0.

As shown in Step 3 of Scheme 29, to a stirred mixture of 7-fluoro-6-(2,3,4,6-tetrafluorophenyl)-2H-benzo[b][1,4]oxazin-3(4H)-one (50 mg, 0.16 mmol) and K$_2$CO$_3$ (33 mg, 0.24 mmol) in DMF (1 mL) was added propargyl bromide (23 mg, 0.19 mmol). The mixture was stirred at room temperature for 2 hours under a nitrogen atmosphere then purified by reversed-phase flash chromatography (5%-65% acetonitrile in water) to afford 7-fluoro-4-(prop-2-yn-1-yl)-6-(2,3,4,6-tetrafluorophenyl)-2H-benzo[b][1,4]oxazin-3 (4H)-one (Compound 52, 27 mg, 48% yield) as a white solid: MS (ESI) calculated for (C$_{17}$H$_8$F$_5$NO$_2$) [M+1]$^+$, 354.0; found, 354.0; $^1$H-NMR (400 MHz, DMSO-d$_6$) δ 7.77-7.67 (m, 1H), 7.40 (d, J=6.8 Hz, 1H), 7.23 (d, J=9.6 Hz, 1H), 4.84 (d, J=1.2 Hz, 2H), 4.75 (d, J=2.4 Hz, 2H), 3.33 (s, 1H); $^{19}$F-NMR (377 MHz, DMSO-d$_6$) δ −115.26, −118.50, −132.08, −133.75, −165.01.

Example 28. Preparation of 2,2,7-trifluoro-4-(prop-2-yn-1-yl)-6-(2,3,4,5-tetrafluorophenyl)-2H-benzo[b][1,4]oxazin-3 (4M-one (Compound 53)

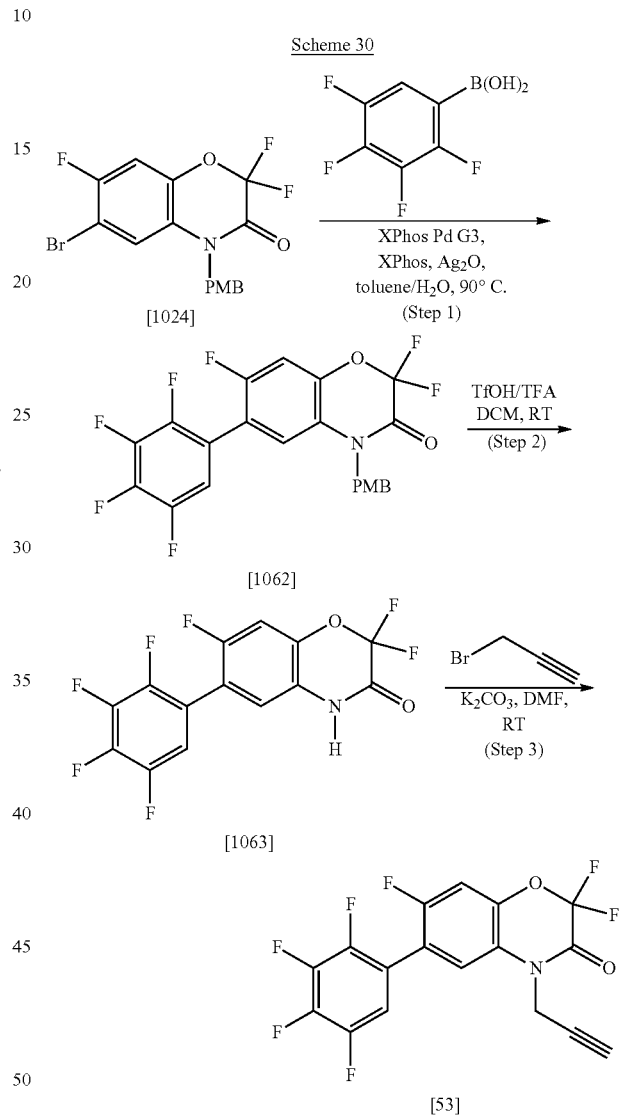

As shown in Step 1 of Scheme 30, to a degassed solution of 6-bromo-2,2,7-trifluoro-4-(4-methoxybenzyl)-2H-benzo[b][1,4]oxazin-3(4H)-one (300.0 mg, 0.74 mmol) in toluene (5 mL) and water (1 mL) were added 2,3,4,5-tetrafluorophenylboronic acid (434 mg, 2.23 mmol), XPhos Pd G3 (126 mg, 0.14 mmol), XPhos (71 mg, 0.14 mmol), Ag$_2$O (346 mg, 1.49 mmol) at 20° C. The resulting mixture was stirred for 16 hours at 90° C. under a nitrogen atmosphere followed by quenching by the addition of water. The aqueous layer was extracted with ethyl acetate, the combined organics dried over sodium sulfate, filtered, concentrated under reduced pressure, and purified by reversed-phase flash chromatography (5%-70% acetonitrile in water) to afford 2,2,7-trifluoro-4-(4-methoxybenzyl)-6-(2,3,4,5-tetrafluorophenyl)-2H-benzo[b][1,4]oxazin-3(4H)-one (Compound 1062, 20 mg, 5% yield) as a yellow solid: GCMS calculated for ($C_{22}H_{12}F_7NO_3$) 471.0, found 471.0; $^1$H-NMR (400 MHz, methanol-d4) δ 7.31-7.28 (m, 2H), 7.29-7.19 (m, 2H), 7.18-7.06 (m, 1H), 6.95-6.83 (m, 2H), 5.26 (s, 2H), 3.76 (s, 3H); $^{19}$F-NMR (376 MHz, methanol-$d_4$) δ −78.77, −78.85, −118.25, −141.39, −141.46, −158.09.

As shown in Step 2 of Scheme 30, To a solution of 2,2,7-trifluoro-4-(4-methoxybenzyl)-6-(2,3,4,5-tetrafluorophenyl)-2H-benzo[b][1,4]oxazin-3(4H)-one (50 mg, 0.11 mmol) in DCM (2.5 mL) were added TFA (121 mg, 1.06 mmol) and $CF_3SO_3H$ (159 mg, 1.06 mmol). The resulting mixture was stirred at 20° C. for 2 h before removal of the volatiles under reduced pressure. The residue was purified by silica gel column chromatography (0%-26% ethyl acetate in petroleum ether) and further purified by preparative-HPLC using the following conditions—Column: XSelect CSH C18 OBD Column 30×150 mm 5 µm; Mobile Phase A: ACN, Mobile Phase B: Water (0.1% formic acid); Flow rate: 60 mL/min; Gradient: 53% B to 63% B in 10 min, then 63% B to afford 2,2,7-trifluoro-6-(2,3,4,5-tetrafluorophenyl)-2H-benzo[b][1,4]oxazin-3(4H)-one (Compound 1063, 11 mg, 28% yield) as an off-white solid: MS (ESI) calculated for ($C_{14}H_4F_7NO_2$) [M−1]$^-$ 350.0, found 349.9; $^1$H-NMR (400 MHz, DMSO-$d_6$) δ 7.71-7.56 (m, 2H), 7.14 (d, J=6.9 Hz, 1H); $^{19}$F-NMR (376 MHz, DMSO-$d_6$) δ −75.54, −118.23, −139.87, −140.13, −155.38, −155.84.

As shown in Step 3 of Scheme 30, to a solution of 2,2,7-trifluoro-6-(2,3,4,5-tetrafluorophenyl)-2H-benzo[b][1,4]oxazin-3(4H)-one (70 mg, 0.20 mmol) in DMF (2 mL) were added propargyl bromide (36 mg, 0.30 mmol) and $K_2CO_3$ (55 mg, 0.39 mmol). The resulting mixture was stirred for 16 hours at 20° C. followed by purification by reversed-phase flash chromatography (5%-60% acetonitrile in water) to afford 2,2,7-trifluoro-4-(prop-2-yn-1-yl)-6-(2,3,4,5-tetrafluorophenyl)-2H-benzo[b][1,4]oxazin-3(4H)-one (Compound 53, 33 mg, 41% yield) as colorless oil: CGMS calculated for ($C_{17}H_6F_7NO_2$) 389.0, found 389.1; $^1$H-NMR (400 MHz, $CD_3OD$) δ 7.61-7.55 (m, 1H), 7.44-7.33 (m, 2H), 4.93 (s, 2H), 3.32 (s, 1H); $^{19}$F-NMR (376 MHz, $CD_3OD$) δ −78.93, −117.98, −141.37, −141.54, −157.99, −158.37.

Example 29. Preparation of 7-fluoro-4-(prop-2-yn-1-yl)-6-(2,3,4,5-tetrafluorophenyl)-2H-benzo[b][1,4]oxazin-3(4H)-one (Compound 54)

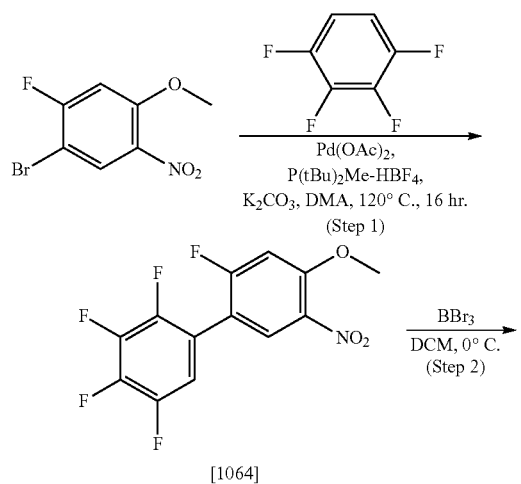

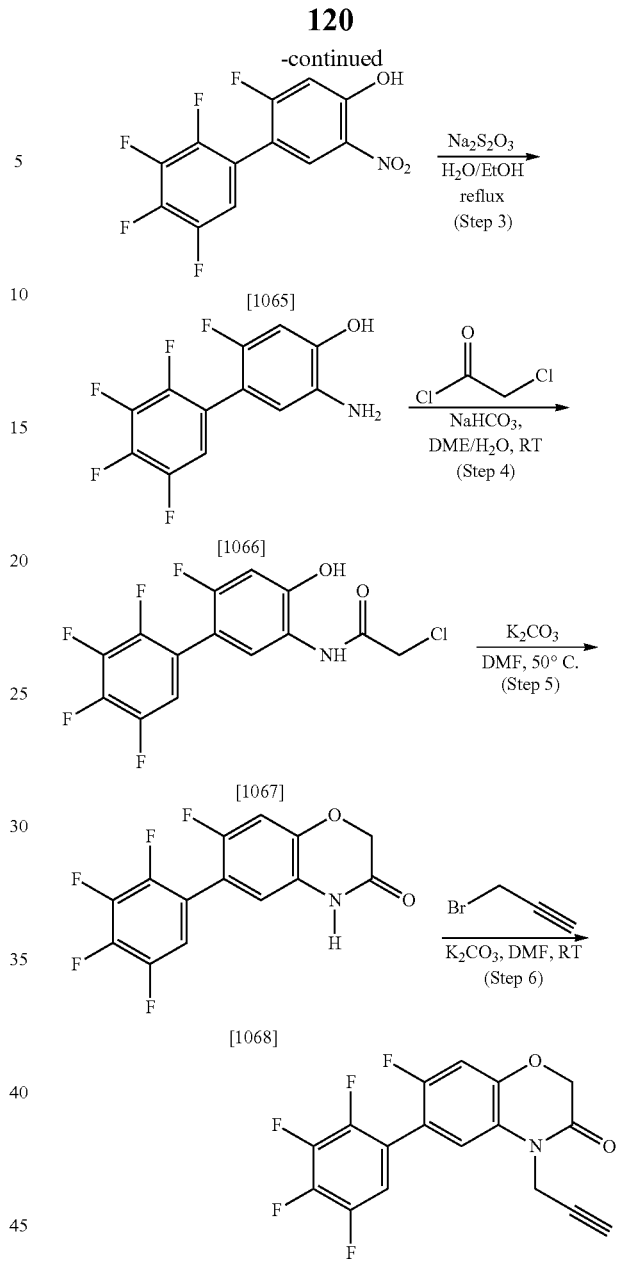

As shown in Step 1 of Scheme 31, a mixture of 1,2,3,4-tetrafluorobenzene (3 equiv.), 1-bromo-2-fluoro-4-methoxy-5-nitrobenzene (1 equiv.), Pd(OAc)$_2$) (0.1 equiv.), di-tert-butylmethylphosphine (0.1 equiv.), and $K_2CO_3$ (1 equiv.) in dioxane are heated to 90° C. for 16 hours, cooled to room temperature, diluted with water, and extracted with EtOAc. The combined extracts are washed with brine, dried over anhydrous sodium sulfate, filtered, and concentrated under reduced pressure. The residue is purified by reversed-phase flash chromatography to yield 2,2',3,4,5-pentafluoro-4'-methoxy-5'-nitro-1,1'-biphenyl (Compound 1064).

As shown in Step 2 of Scheme 31, to a stirred mixture of 2,2',3,4,5-pentafluoro-4'-methoxy-5'-nitro-1,1'-biphenyl (1 equiv.) in DCM is added boron tribromide (5 equiv.) dropwise at 0° C. under an atmosphere of nitrogen. The mixture is stirred at 0° C. for 3 hours, diluted with water, and extracted with dichloromethane. The combined organic layers are washed with brine, dried over anhydrous sodium sulfate, filtered, and concentrated under reduced pressure to afford 2,2',3',4',5'-pentafluoro-5-nitro-[1,1'-biphenyl]-4-ol (Compound 1065).

As shown in Step 3 of Scheme 31, to a stirred solution of 2,2',3',4',5'-pentafluoro-(1 equiv) in 1:1 water/EtOH is added sodium hyposulfite (5 equiv.). The resulting mixture is stirred at 100° C. for 2 hours, cooled to room temperature, diluted with water, and extracted with dichloromethane. The combined organic layers are washed with brine, dried over anhydrous sodium sulfate, filtered, and concentrated under reduced pressure. The residue is purified by flash chromatography to afford 5-amino-2,2',3',4',5'-pentafluoro-[1,1'-biphenyl]-4-ol (Compound 1066).

As shown in Step 4 of Scheme 31, to a solution 5-amino-2,2',3',4',5'-pentafluoro-[1,1'-biphenyl]-4-ol (1 equiv.) in 1:1 DME/H$_2$O is added NaHCO$_3$ (3 equiv.) at room temperature under a nitrogen atmosphere, followed by the dropwise addition of chloroacetyl chloride (1.5 equiv.) at 0° C. The reaction is stirred at room temperature for 3 hours and concentrated under reduced pressure to afford 2-chloro-N-(2',3',4',5',6-pentafluoro-4-hydroxy-[1,1'-biphenyl]-3-yl)acetamide (Compound 1067).

As shown in Step 5 of Scheme 31, a mixture of 2-chloro-N-(2',3',4',5',6-pentafluoro-4-hydroxy-[1,1'-biphenyl]-3-yl) acetamide (1 equiv.) and K$_2$CO$_3$ (2 equiv.) in DMF (3 mL) is stirred at 50° C. for 1 hour under a nitrogen atmosphere, cooled to room temperature, diluted with water, and extracted with ethyl acetate. The combined organic layers are washed with brine, dried over anhydrous sodium sulfate, filtered, concentrated under reduced pressure, and purified by flash chromatography to afford 7-fluoro-6-(2,3,4,5-tetrafluorophenyl)-2H-benzo[b][1,4]oxazin-3(4H)-one (Compound 1068).

As shown in Step 6 of Scheme 31, to a stirred mixture of 7-fluoro-6-(2,3,4,5-tetrafluorophenyl)-2H-benzo[b][1,4] oxazin-3(4H)-one (1 equiv.) and K$_2$CO$_3$ (1.5 equiv.) in DMF is added propargyl bromide (1.2 equiv.). The mixture is stirred at room temperature for 2 hours under a nitrogen atmosphere then purified by reversed-phase flash chromatography to afford 7-fluoro-4-(prop-2-yn-1-yl)-6-(2,3,4,5-tetrafluorophenyl)-2H-benzo[b][1,4]oxazin-3(4H)-one (Compound 54).

Example 30. Preparation of 2,2-dichloro-7-fluoro-6-(perfluorophenyl)-4-(prop-2-yn-1-yl)-2H-benzo[b][1,4]oxazin-3(4H)-one (Compound 55)

Scheme 32

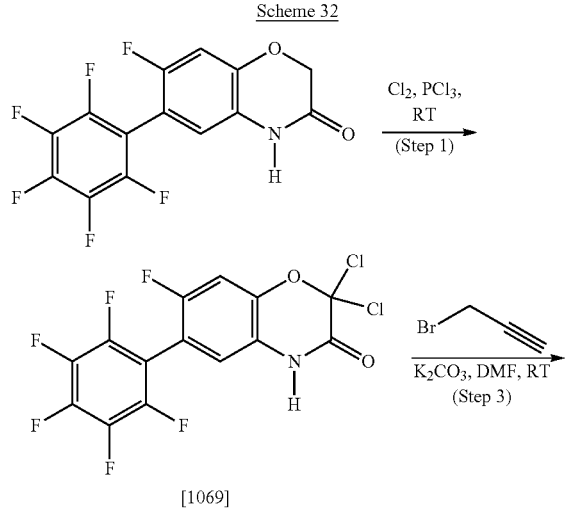

[1069]

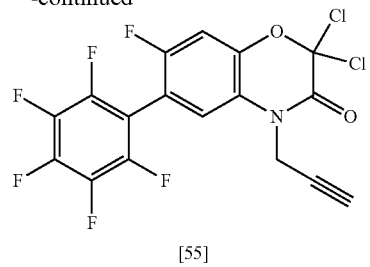

[55]

As shown in Step 1 of Scheme 32, chlorine gas (about 2 equiv.) is introduced into a stirred suspension of 7-fluoro-6-(perfluorophenyl)-2H-benzo[b][1,4]oxazin-3(4H)-one (1 equiv.) in PCl$_3$ (6 equiv.). After 2 hours at room temperature, the volatiles are removed at atmospheric pressure via distillation to afford 2,2-dichloro-7-fluoro-2H-benzo[b][1,4] oxazin-3(4H)-one (Compound 1069).

As shown in Step 2 of Scheme 32, to a solution of 2,2-dichloro-7-fluoro-2H-benzo[b][1,4]oxazin-3(4H)-one (1 equiv.) in DMF are added K$_2$CO$_3$ (1.05 equiv.) and 3-bromoprop-1-yne (1.05 equiv.) at room temperature under nitrogen. The mixture is stirred at room temperature for 8 hours, diluted with water, and extracted with ethyl acetate. The combined organic layers are washed with brine, dried over anhydrous sodium sulfate, filtered, concentrated under reduced pressure, and purified by preparative reversed-phase HPLC to afford 2,2-dichloro-7-fluoro-6-(perfluorophenyl)-4-(prop-2-yn-1-yl)-2H-benzo[b][1,4]oxazin-3(4H)-one (Compound 55).

Example 31. Preparation of 7-chloro-2,2-difluoro-6-(perfluorophenyl)-4-(prop-2-yn-1-yl)-2H-benzo[b] [1,4]oxazin-3(4H)-one (Compound 56)

Scheme 33

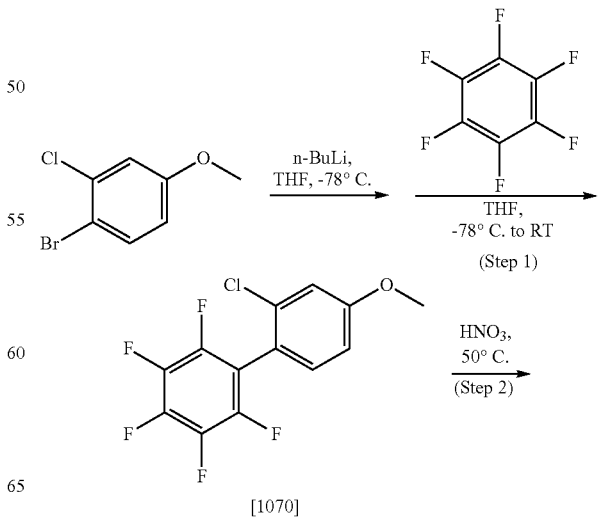

[1070]

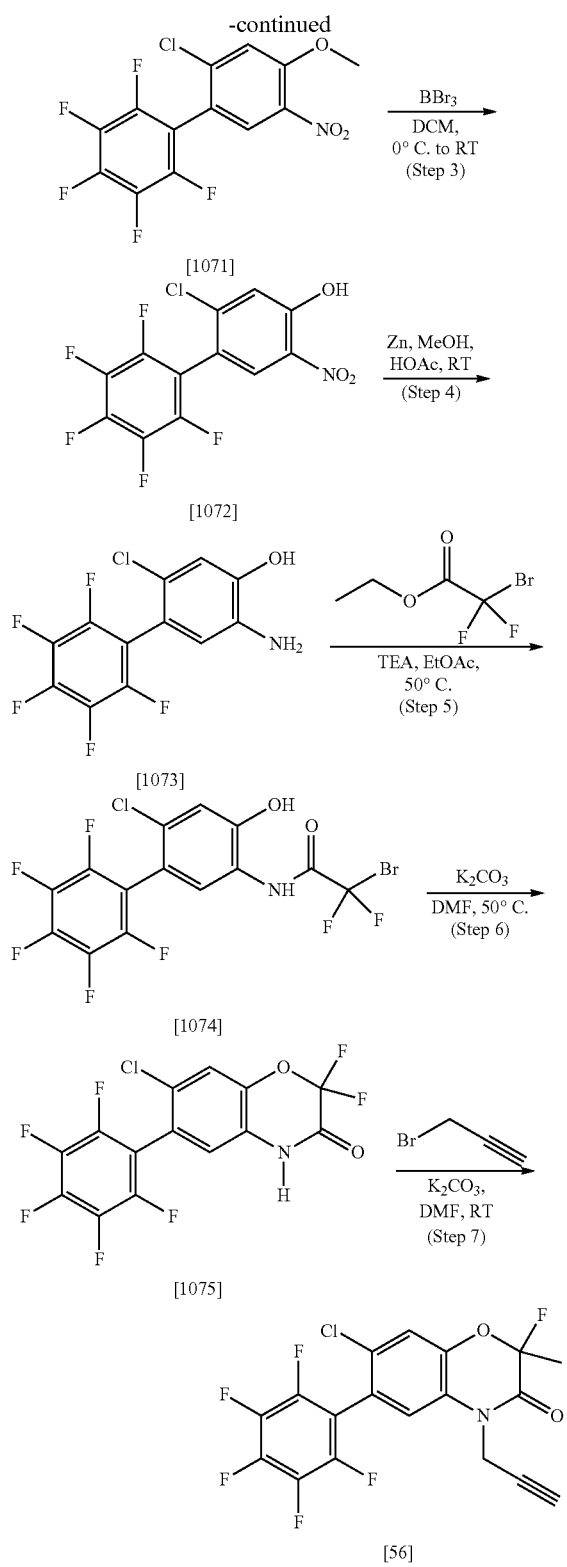

room temperature, stirred for 2 hours under nitrogen, diluted with water, and extracted with ethyl acetate. The combined organic layers are washed with brine, dried over anhydrous sodium sulfate, filtered, concentrated under reduced pressure, and purified by flash chromatography to afford 2'-chloro-2,3,4,5,6-pentafluoro-4'-methoxy-1,1'-biphenyl (Compound 1070).

As shown in Step 2 of Scheme 33, a solution of 2'-chloro-2,3,4,5,6-pentafluoro-4'-methoxy-1,1'-biphenyl in nitric acid is stirred at 50° C. for 4 hours, diluted with water, and extracted with ethyl acetate. The combined organic layers are washed with brine, dried over anhydrous sodium sulfate, filtered, concentrated under reduced pressure, and purified by flash chromatography to afford 2'-chloro-2,3,4,5,6-pentafluoro-4'-methoxy-5'-nitro-1,1'-biphenyl (Compound 1071).

As shown in Step 3 of Scheme 33, to a solution of 5-bromo-4-chloro-2-methoxyaniline (1 equiv.) in DCM is added $BBr_3$ (5 equiv.) in portions at 0° C. The resulting solution is stirred at 20° C. for 16 hours, diluted by the slow addition of ice/water, and extracted with ethyl acetate. The combined organic layers are washed with brine, dried over anhydrous sodium sulfate, filtered, concentrated under reduced pressure, and purified by flash chromatography to afford 2-chloro-2',3',4',5',6'-pentafluoro-5-nitro-[1,1'-biphenyl]-4-ol (Compound 1072).

As shown in Step 4 of Scheme 33, to a solution of 2-chloro-2',3',4',5',6'-pentafluoro-5-nitro-[1,1'-biphenyl]-4-ol (1 equiv.) in MeOH and acetic acid (4 equiv.) is added Zn powder (5 equiv.) in portions at 0° C. The resulting solution is stirred at 20° C. for 16 hours, filtered, diluted with water, and extracted with ethyl acetate. The combined organic layers are washed with brine, dried over anhydrous sodium sulfate, filtered, concentrated under reduced pressure, and purified by flash chromatography to afford 5-amino-2-chloro-2',3',4',5',6'-pentafluoro-[1,1'-biphenyl]-4-ol (Compound 1073).

As shown in Step 5 of Scheme 33, to a solution of 5-amino-2-chloro-2',3',4',5',6'-pentafluoro-[1,1'-biphenyl]-4-ol (1 equiv.) and ethyl 2-bromo-2,2-difluoroacetate (2 equiv.) in MeOH (180 mL) is added triethylamine (2 equiv.) at 20° C. The resulting solution is stirred at 50° C. for 2 hours, cooled to room temperature, diluted with water, and extracted with ethyl acetate. The combined organic layers are washed with brine, dried over anhydrous sodium sulfate, filtered, concentrated under reduced pressure, and purified by flash chromatography (0%-40% ethyl acetate/petroleum ether) to afford 2-bromo-N-(6-chloro-2',3',4',5',6'-pentafluoro-4-hydroxy-[1,1'-biphenyl]-3-yl)-2,2-difluoroacetamide (Compound 1074).

As shown in Step 6 of Scheme 33, to a solution of 2-bromo-N-(6-chloro-2',3',4',5',6'-pentafluoro-4-hydroxy-[1,1'-biphenyl]-3-yl)-2,2-difluoroacetamide (1 equiv.) in DMF is added $K_2CO_3$ (2 equiv.) at 20° C. The resulting solution is stirred at 50° C. for 16 hours, cooled to room temperature, diluted with water, and extracted with ethyl acetate. The combined organic layers are washed with brine, dried over anhydrous sodium sulfate, filtered, concentrated under reduced pressure, and purified by flash chromatography to afford 7-chloro-2,2-difluoro-6-(perfluorophenyl)-2H-benzo[b][1,4]oxazin-3(4H)-one (Compound 1075).

As shown in Step 7 of Scheme 33, to a solution of 7-chloro-2,2-difluoro-6-(perfluorophenyl)-2H-benzo[b][1,4]oxazin-3(4H)-one (50 mg, 0.13 mmol) in DMF (1 mL) is added $K_2CO_3$ (1.5 equiv.) and the mixture is stirred at 25° C. for 10 minutes, followed by the dropwise addition of propargyl bromide (1.5 equiv.) at room temperature. The mixture is stirred at room temperature for 2 hours followed by purification by preparative reversed-phase HPLC to afford 7-chloro-2,2-difluoro-6-(perfluorophenyl)-4-(prop-2-yn-1-yl)-2H-benzo[b][1,4]oxazin-3(4H)-one (Compound 56).

Example 32. Preparation of 6-(4-amino-2,3,5,6-tetrafluorophenyl)-2,2,7-trifluoro-4-(prop-2-yn-1-yl)-2H-benzo[b][1,4]oxazin-3(4H)-one (Compound 57) and N-acetyl-N-(2,3,5,6-tetrafluoro-4-(2,2,7-trifluoro-3-oxo-4-(prop-2-yn-1-yl)-3,4-dihydro-2H-benzo[b][1,4]oxazin-6-yl)phenyl)acetamide (Compound 58)

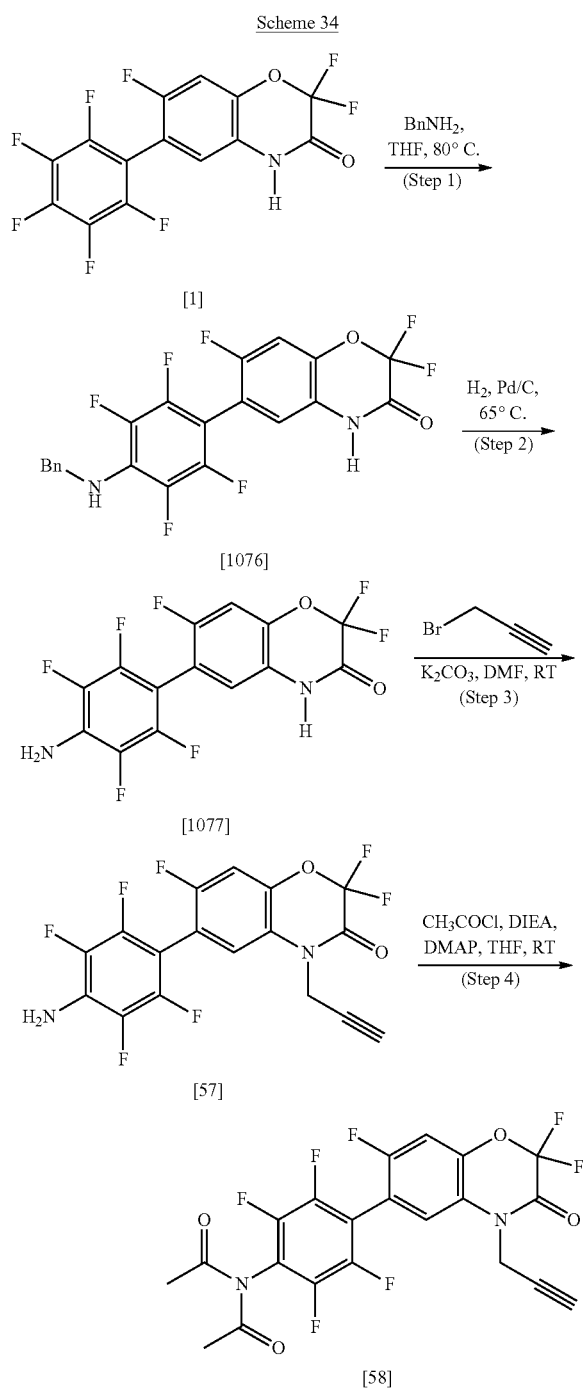

Scheme 34

As shown in Step 1 of Scheme 34, to solution of 2,2,7-trifluoro-6-(perfluorophenyl)-2H-benzo[b][1,4]oxazin-3(4H)-one (380 mg, 1.03 mmol) in THF (4 mL) was added benzylamine (441 mg, 4.11 mmol). The reaction mixture was stirred at 80° C. for 16 hours under a nitrogen atmosphere, cooled to room temperature, diluted with water, and extracted with ethyl acetate. The combined organic layers were washed with brine, dried over anhydrous sodium sulfate, filtered, concentrated under reduced pressure, and purified by reversed-phase flash chromatography (5%-60% acetonitrile in water) to afford 6-(4-(benzylamino)-2,3,5,6-tetrafluorophenyl)-2,2,7-trifluoro-2H-benzo[b][1,4]oxazin-3(4H)-one (Compound 1076, 220 mg, 42% yield) as a yellow solid: MS (ESI) calculated for ($C_{21}H_{11}F7N_2O_2$) $[M+1]^+$ 457.1, found 457.1.

As shown in Step 2 of Scheme 34, to a solution of 6-(4-(benzylamino)-2,3,5,6-tetrafluorophenyl)-2,2,7-trifluoro-2H-benzo[b][1,4]oxazin-3(4H)-one (100 mg, 0.22 mmol) in MeOH (5 mL) was added Pd/C (12 mg, 0.11 mmol) under nitrogen. The nitrogen atmosphere was replaced with hydrogen and the resulting solution stirred at 65° C. for 3 hours. The suspension was cooled, filtered and the filtrate collected and concentrated under reduced pressure. The residue was purified by reversed-phase flash chromatography (5%-53% acetonitrile in water) to afford 6-(4-amino-2,3,5,6-tetrafluorophenyl)-2,2,7-trifluoro-2H-benzo[b][1,4]oxazin-3(4H)-one (Compound 1077, 70 mg, 87% yield) as a yellow solid: MS (ESI) calculated for ($C_{14}H_5F_7N_2O_2$) $[M+1]^+$ 367.0, found 367.0.

As shown in Step 3 of Scheme 34, to a solution of 6-(4-amino-2,3,5,6-tetrafluorophenyl)-2,2,7-trifluoro-2H-benzo[b][1,4]oxazin-3(4H)-one (50 mg, 0.13 mmol) in DMF (1 mL) was added $K_2CO_3$ (28 mg, 0.20 mmol) and the mixture was stirred at 25° C. for minutes, followed by the dropwise addition of propargyl bromide (24 mg, 0.20 mmol) at room temperature. The mixture was stirred at room temperature for 2 hours followed by purification by preparative HPLC using the following conditions—Column: Xselect CSH C18 OBD Column 30×150 mm 5 μm; Mobile Phase A: ACN, Mobile Phase B: Water (0.1% FA); Gradient: 54% B to 62% B in 10 minutes, then 62% B, to afford 6-(4-amino-2,3,5,6-tetrafluorophenyl)-2,2,7-trifluoro-4-(prop-2-yn-1-yl)-2H-benzo[b][1,4]oxazin-3(4H)-one (Compound 57, 20 mg, 35% yield) as a white solid: GCMS calculated for ($C_{17}H_7F_7N_2O_2$) 404.0, found 404.0; $^1$H-NMR (400 MHz, DMSO-$d_6$) δ 7.76-7.50 (m, 2H), 6.33 (s, 2H), 4.89 (d, J=2.4 Hz, 2H), 3.43 (s, 1H); $^{19}$F-NMR (376 MHz, DMSO-$d_6$) δ −75.13, −115.56, −144.93, −161.62.

As shown in Step 4 of Scheme 34, to a stirred mixture of 6-(4-amino-2,3,5,6-tetrafluorophenyl)-2,2,7-trifluoro-4-(prop-2-yn-1-yl)-2H-benzo[b][1,4]oxazin-3(4H)-one (20 mg, 0.05 mmol) and DIEA (6.4 mg, 0.05 mmol) in THF (1 mL) was added acetyl chloride (4 mg, 0.05 mmol) at 0° C. under a nitrogen atmosphere. The resulting mixture was stirred at room temperature for 16 hours. The reaction was quenched by the addition of water and the aqueous layer was extracted with ethyl acetate. The combined organic layers were washed with brine, dried over anhydrous sodium sulfate, filtered, and concentrated under reduced pressure. The residue was dissolved in DMF (1 mL) and applied to a C-18 column and purified by reversed-phase flash chromatography (5%-65% acetonitrile in water) to afford N-acetyl-N-(2,3,5,6-tetrafluoro-4-(2,2,7-trifluoro-3-oxo-4-(prop-2-yn-1-yl)-3,4-dihydro-2H-benzo[b][1,4]oxazin-6-yl)phenyl)acetamide (Compound 58, 8 mg, 34% yield) as a yellow oil: MS (ESI) calculated for ($C_{21}H_{11}F_7N_2O_4$) $[M+1]^+$ 89.1, found 489.0; $^1$H-NMR (400 MHz, DMSO-$d_6$) δ 7.89 (d, J=6.4 Hz, 1H), 7.86-7.74 (m, 1H), 4.88 (d, J=2.4 Hz, 2H), 3.50 (s, 1H), 2.44 (s, 6H); $^{19}$F-NMR (376 MHz, DMSO-d$_6$) δ −74.64, −115.17, −140.00, −145.66.

Example 33. Preparation of 2,2,7-trifluoro-4-(prop-2-yn-1-yl)-6-(2,3,5,6-tetrafluoro-4-(methylamino)phenyl)-2H-benzo[b][1,4]oxazin-3(4H)-one (Compound 59) and N-methyl-N-(2,3,5,6-tetrafluoro-4-(2,2,7-trifluoro-3-oxo-4-(prop-2-yn-1-yl)-3,4-dihydro-2H-benzo[b][1,4]oxazin-6-yl)phenyl) acetamide (Compound 60)

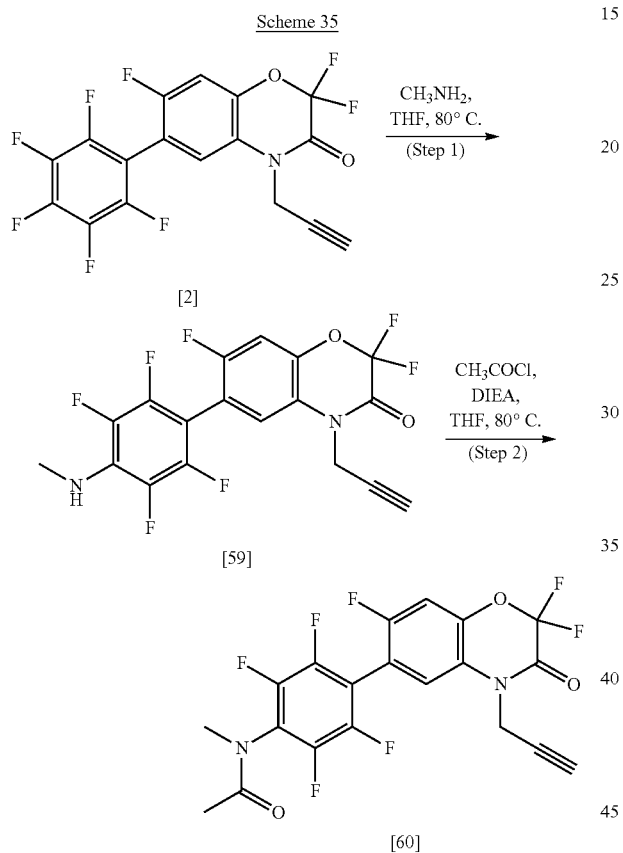

As shown in Step 1 of Scheme 35, a solution of 2,2,7-trifluoro-6-(perfluorophenyl)-4-(prop-2-yn-1-yl)-2H-benzo[b][1,4]oxazin-3(4H)-one (200 mg, 0.49 mmol) in methylamine (2M in THF) (3 mL) was stirred at 80° C. for 2 h under a nitrogen atmosphere. The resulting mixture was concentrated under reduced pressure and purified by preparative-HPLC using the following conditions: X Bridge Prep Phenyl OBD Column (19×250 mm, 5 μm); Mobile Phase A, Water (0.1% formic acid), Mobile Phase B, ACN; Flow rate: 25 mL/min; Gradient: 55% B to 75% B in 10 min, then 75% B; Wavelength: 254 nm to produce 2,2,7-trifluoro-4-(prop-2-yn-1-yl)-6-(2,3,5,6-tetrafluoro-4-(methylamino) phenyl)-2H-benzo[b][1,4]oxazin-3(4H)-one (Compound 59, 105 mg, 51% yield) as a white solid: MS (ESI) calc'd for (C$_{18}$H$_9$F$_7$N$_2$O$_2$) [M−1]$^-$ 417.0, found 417.0; $^1$H-NMR (400 MHz, DMSO-d$_6$) δ 7.76-7.58 (m, 2H), 6.36-6.21 (m, 1H), 4.88 (d, J=2.4 Hz, 2H), 3.48 (s, 1H), 3.11-2.96 (m, 3H); $^{19}$F-NMR (377 MHz, DMSO-d$_6$) δ −75.10, −115.55, −144.56, −161.54.

As shown in Step 2 of Scheme 35, to a solution of 2,2,7-trifluoro-4-(prop-2-yn-1-yl)-6-(2,3,5,6-tetrafluoro-4-(methylamino)phenyl)-2H-benzo[b][1,4]oxazin-3(4H)-one (40 mg, mmol) in THF (2 mL) were added acetyl chloride (15 mg, 0.19 mmol) and DIEA (25 mg, 0.19 mmol) at 0° C. The resulting solution was stirred at 80° C. for 16 hours under a nitrogen atmosphere, then concentrated under reduced pressure. The residue was purified by reversed-phase flash chromatography (5%-55% acetonitrile in water) to afford N-methyl-N-(2,3,5,6-tetrafluoro-4-(2,2,7-trifluoro-3-oxo-4-(prop-2-yn-1-yl)-3,4-dihydro-2H-benzo[b][1,4] oxazin-6-yl)phenyl)acetamide (Compound 60, 30 mg, 68% yield) as a white solid: MS (ESI) calc'd for (C$_{20}$H$_{11}$F$_7$N$_2$O$_3$) [M+1]$^+$ 461.0, found 461.0; $^1$H-NMR (400 MHz, DMSO-d$_6$) δ 7.91-7.68 (m, 2H), 4.88 (d, J=2.4 Hz, 2H), 3.53-3.39 (m, 3H), 3.19 (s, 1H), 2.35-1.90 (m, 3H); $^{19}$F-NMR (376 MHz, DMSO-d$_6$) δ −74.74, −115.35, −141.16, −145.4.

Example 34. Preparation of 6-(4-(dimethylamino)-2,3,5,6-tetrafluorophenyl)-2,2,7-trifluoro-4-(prop-2-yn-1-yl)-2H-benzo[b][1,4]oxazin-3(4H)-one (Compound 61)

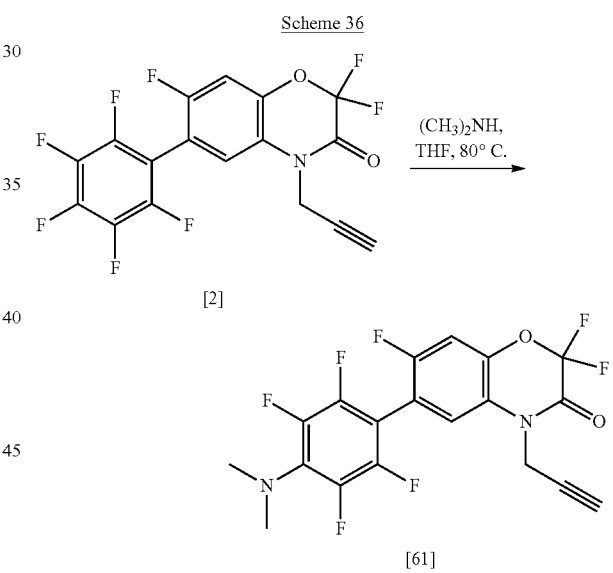

As shown in Scheme 36, a solution of 2,2,7-trifluoro-6-(perfluorophenyl)-4-(prop-2-yn-1-yl)-2H-benzo[b][1,4] oxazin-3(4H)-one (100 mg, 0.25 mmol) in methylamine (2M in THF) (3 mL) was stirred at 80° C. for 2 h under a nitrogen atmosphere. The resulting mixture was concentrated under reduced pressure and purified by reversed-phase flash chromatography (5%-60% acetonitrile in water) to afford 6-(4-(dimethylamino)-2,3,5,6-tetrafluorophenyl)-2,2, 7-trifluoro-4-(prop-2-yn-1-yl)-2H-benzo[b][1,4]oxazin-3 (4H)-one (Compound 61) (56 mg, 53% yield) as a white solid: MS (ESI) calc'd for (C$_{19}$H$_{11}$F$_7$N$_2$O$_2$) [M+1]$^+$ 433.0, found 432.9; $^1$H-NMR (400 MHz, DMSO-d$_6$) δ 7.80-7.60 (m, 2H), 4.88 (d, J=2.4 Hz, 2H), 3.50-3.42 (m, 1H), 3.06-2.93 (m, 6H); $^{19}$F-NMR (377 MHz, DMSO-d$_6$) δ −74.97, −115.58, −143.29, −151.61.

Example 35. Preparation of 6-(4-(benzylamino)-2,3,5,6-tetrafluorophenyl)-2,2,7-trifluoro-2H-benzo[b][1,4]oxazin-3(4H)-one (Compound 62)

Scheme 37

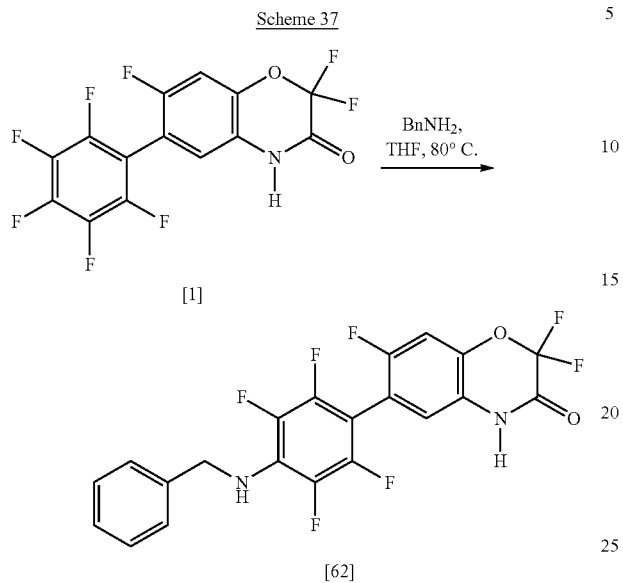

As shown in Scheme 37, To a stirred solution of 2,2,7-trifluoro-6-(perfluorophenyl)-2H-benzo[b][1,4]oxazin-3(4H)-one (100 mg, 0.27 mmol) in THF (1.5 mL) was added phenylmethanamine (116 mg, 1.08 mmol) at room temperature under a nitrogen atmosphere. The resulting mixture was stirred at 80° C. for 16 hours under a nitrogen atmosphere then concentrated under reduced pressure. The residue was applied to a C18 column and purified by reversed-phase flash chromatography (5%-65% acetonitrile in water), then further purified by preparative-HPLC using the following conditions: Column: XSelect CSH F-phenyl OBD Column, 19×250 mm, 5 μm; Mobile Phase A=water (0.05% formic acid), Mobile Phase B=ACN; Flow rate=25 mL/min; eluted with 60% B to afford 6-(4-(benzylamino)-2,3,5,6-tetrafluorophenyl)-2,2,7-trifluoro-2H-benzo[b][1,4]oxazin-3(4H)-one (Compound 62, 29.5 mg, 24% yield) as a white solid: MS (ESI) calculated for ($C_{21}H_{11}F_7N_2O_2$) [M+1]$^+$ 457.1, found 457.1; $^1$H-NMR (400 MHz, DMSO-$d_6$) δ 12.09 (br, 1H), 7.57 (d, J=9.6 Hz, 1H), 7.36-7.34 (m, 4H), 7.30-7.21 (m, 1H), 7.12 (d, J=6.8 Hz, 1H), 6.99 (s, 1H), 4.54 (d, J=6.0 Hz, 2H); $^{19}$F-NMR (376 MHz, DMSO-$d_6$) δ −75.38, −116.61, −144.64, −144.70, −159.97.

Example 36. Preparation of 6-(4-cyclopropoxy-2,3,5,6-tetrafluorophenyl)-2,2,7-trifluoro-2H-benzo[b][1,4]oxazin-3(4H)-one (Compound 63) and 6-(4-cyclopropoxy-2,3,5,6-tetrafluorophenyl)-2,2,7-trifluoro-4-(prop-2-yn-1-yl)-2H-benzo[b][1,4]oxazin-3(4H)-one (Compound 64)

Scheme 38

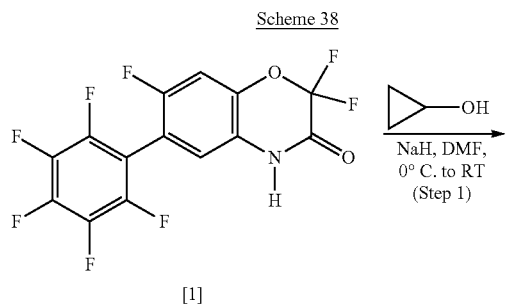

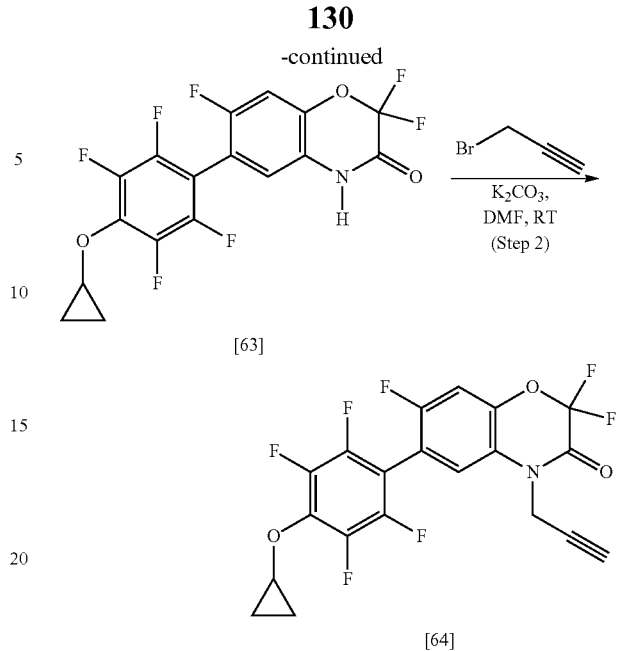

As shown in Step 1 of Scheme 38, to a solution of cyclopropanol (63 mg, 1.08 mmol) in DMF (2 mL) was added NaH (43 mg, 1.08 mmol, 60%) at 0° C. The reaction mixture was stirred at 0° C. for 30 min under a nitrogen atmosphere and 2,2,7-trifluoro-6-(2,3,4,5,6-pentafluorophenyl)-4H-1,4-benzoxazin-3-one (200 mg, 0.54 mmol) in DMF (1 mL) was added dropwise at 0° C. under a nitrogen atmosphere. The resulting mixture was stirred at 20° C. for 2 hours under a nitrogen atmosphere, followed by quenching the reaction with water at 0° C. The aqueous layer was extracted with ethyl acetate, the combined organics dried over sodium sulfate, filtered, and concentrated under reduced pressure. The residue was purified by silica gel column chromatography (0%-26% ethyl acetate in petroleum ether) and further purified by reversed-phase flash chromatography (5%-50% acetonitrile in water) to afford 6-(4-cyclopropoxy-2,3,5,6-tetrafluorophenyl)-2,2,7-trifluoro-2H-benzo[b][1,4]oxazin-3 (4H)-one (Compound 63, 70.0 mg, 35% yield) as a white solid: MS (ESI) calc'd for ($C_{17}H_8F_7NO_3$) [M−1]$^-$ 406.0, found 405.9; $^1$H-NMR (400 MHz, methanol-$d_4$) δ 7.31 (d, J=9.6 Hz, 1H), 7.16 (d, J=6.4 Hz, 1H), 4.47-4.39 (m, 1H), 0.96-0.89 (m, 2H), 0.81-0.72 (m, 2H); $^{19}$F-NMR (376 MHz, methanol-$d_4$) δ −78.94, −117.66, −144.45, −158.76.

As shown in Step 2 of Scheme 38, To a stirred solution of 6-(4-cyclopropoxy-2,3,5,6-tetrafluorophenyl)-2,2,7-trifluoro-2H-benzo[b][1,4]oxazin-3(4H)-one (70 mg, 0.17 mmol) in DMF (1 mL) were added $K_2CO_3$ (36 mg, 0.26 mmol) and propargyl bromide (25 mg, 0.20 mmol). The reaction mixture was stirred at room temperature for 2 hours under a nitrogen atmosphere, quenched with water, and the aqueous solution was extracted with ethyl acetate. The combined organic layers were washed with brine, dried over anhydrous sodium sulfate, filtered, and concentrated under vacuum. The residue was purified by reversed-phase flash chromatography (5%-68% acetonitrile in water to afford 6-(4-cyclopropoxy-2,3,5,6-tetrafluorophenyl)-2,2,7-trifluoro-4-(prop-2-yn-1-yl)-2H-benzo[b][1,4]oxazin-3(4H)-one (Compound 64, 23 mg, 29% yield) as a white solid: GCMS calculated for ($C_{20}H_{10}F_7NO_3$) 445.0, found 445.0;

$^1$H-NMR (400 MHz, DMSO-d$_6$) δ 7.88-7.59 (m, 2H), 4.87 (d, J=2.4 Hz, 2H), 4.51-4.42 (m, 1H), 3.46-3.43 (m, 1H), 0.94-0.88 (m, 2H), 0.81-0.73 (m, 2H); $^{19}$F-NMR (377 MHz, DMSO-d$_6$) δ −74.89, −115.55, −141.88, −156.42.

Example 37. Preparation of 2,2,7-trifluoro-6-(2,3,4,6-tetrafluoro-5-(2-hydroxyethyl)phenyl)-2H-benzo[b][1,4]oxazin-3(4H)-one (Compound 65) and 2,2,7-trifluoro-4-(prop-2-yn-1-yl)-6-(2,3,4,6-tetrafluoro-5-(2-hydroxy ethyl)phenyl)-2H-benzo[b][1,4]oxazin-3(4H)-one (Compound 66)

Scheme 39

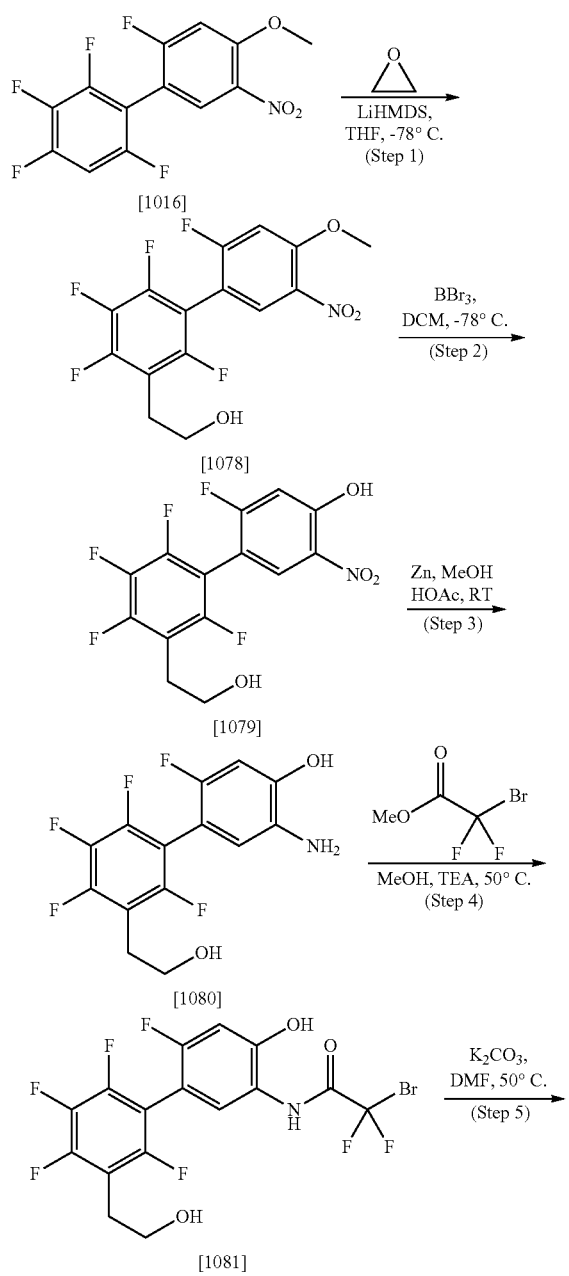

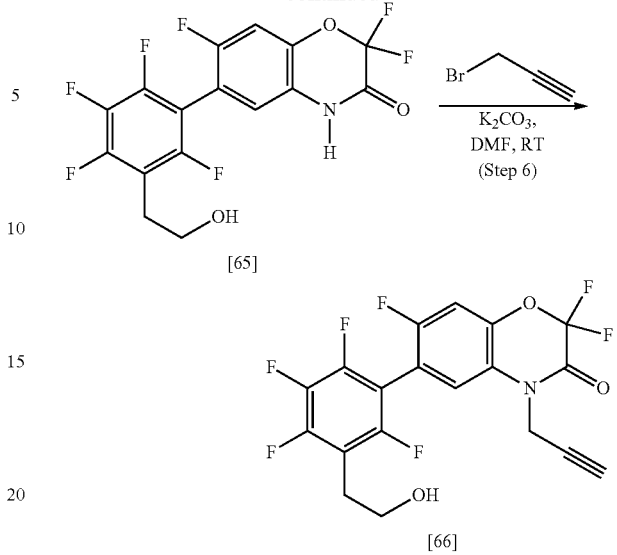

As shown in Step 1 of Scheme 39, To a solution of 2,2',3,4,6-pentafluoro-4'-methoxy-(3.5 g, 10.92 mmol) and 12 mmol equivalents of oxirane in THF (45 mL) was added lithium hexamethyldisilazide (27.4 mL, 27.37 mmol) dropwise at −78° C. After addition was complete, the resulting mixture was warmed to room temperature and stirred for 12 h under a nitrogen atmosphere. The reaction was quenched by the addition of water and extracted with ethyl acetate. The combined organic layers were washed with brine, dried over anhydrous sodium sulfate, filtered, and concentrated under vacuum, and purified by silica gel column chromatography, (0%-50% ethyl acetate in petroleum ether) to afford 2-(2,2',4,5,6-pentafluoro-4'-methoxy-5'-nitro-[1,1'-biphenyl]-3-yl)ethan-1-ol (Compound 1078, 1.7 g, 42% yield) as a yellow oil: GCMS calculated for (C$_{15}$H$_{10}$F$_5$NO$_4$) 363.1, found 363.1.

As shown in Step 2 of Scheme 39, To a solution of 2-(2,2',4,5,6-pentafluoro-4'-methoxy-5'-nitro-[1,1'-biphenyl]-3-yl)ethan-1-ol (1.7 g, 4.6 mmol) in DCM (15 mL) was added BBr$_3$ (2.2 mL, 23.0 mmol) dropwise at 0° C. The resulting mixture was stirred at 0° C. for 2 hours under a nitrogen atmosphere. The reaction mixture was quenched by the addition of water and extracted with ethyl acetate. The combined organic layers were washed with brine, dried over anhydrous sodium sulfate, filtered, and concentrated under reduced pressure. The residue was purified by silica gel column chromatography (0%-30% ethyl acetate in petroleum ether) to afford 2,2',3',4',6'-pentafluoro-5'-(2-hydroxyethyl)-5-nitro-[1,1'-biphenyl]-4-ol (Compound 1079, 690 mg, 42% yield) as a yellow solid: MS (ESI) calculated for (C$_{14}$H$_8$F$_5$NO$_4$) [M−1]$^−$ 348.0, found 348.0.

As shown in Step 3 of Scheme 39, To a stirred solution of 2,2',3',4',6'-pentafluoro-5'-(2-hydroxyethyl)-5-nitro-[1,1'-biphenyl]-4-ol (690 mg, 1.97 mmol) in AcOH (0.5 mL) and MeOH (5 mL) was added Zn dust (642.5 mg, 9.88 mmol) in portions at 0° C. under a nitrogen atmosphere. The resulting mixture was stirred at 25° C. for 2 hours under a nitrogen atmosphere, quenched by the addition of water, extracted with ethyl acetate, and washed with saturated NaHCO$_3$ three times. The combined organic layers were washed with brine, dried over anhydrous sodium sulfate, filtered, and concentrated under reduced pressure. The residue was purified by silica gel column chromatography (0%-50% ethyl acetate in petroleum ether) to afford 5-amino-2,2',3',4',6'-pentafluoro-5'-(2-hydroxyethyl)-[1,1'-biphenyl]-4-ol (Compound 1080, 450 mg, 71% yield) as a yellow solid: MS (ESI) calculated for ($C_{14}H_{10}F_5NO_2$) [M−1]⁻ 318.1, found 318.1.

As shown in Step 4 of Scheme 39, To a stirred solution of 5-amino-2,2',3',4',6'-pentafluoro-5'-(2-hydroxyethyl)-[1,1'-biphenyl]-4-ol (450 mg, 1.41 mmol) and methyl 2-bromo-2,2-difluoroacetate (346 mg, 1.83 mmol) in MeOH (5 mL) was added TEA (143 mg, 1.41 mmol) at 25° C. under a nitrogen atmosphere. The resulting mixture was stirred at 50° C. for 2 hours under a nitrogen atmosphere. The resulting reaction mixture was allowed to cool down to room temperature and quenched with water. The aqueous layer was extracted with ethyl acetate and the combined organic layers washed with brine, dried over anhydrous sodium sulfate, filtered, and concentrated under reduced pressure. The residue was purified by silica gel column chromatography (0%-30% ethyl acetate in petroleum ether) to afford 2-bromo-2,2-difluoro-N-(2',3',4',6,6'-pentafluoro-4-hydroxy-5'-(2-hydroxyethyl)-[1,1'-biphenyl]-3-yl)acetamide (Compound 1081, 110 mg, 16% yield) as a yellow oil. MS (ESI) calculated for ($C_{16}H_9BrF_7NO_3$) [M−1]⁻ 474.1; found 474.1.

As shown in Step 5 of Scheme 39, To a stirred solution of 2-bromo-2,2-difluoro-N-[2',3',4',6,6'-pentafluoro-4-hydroxy-5'-(2-hydroxyethyl)-[1,1'-biphenyl]-3-yl]acetamide (110 mg, 0.23 mmol) in DMF (1 mL) was added and $K_2CO_3$ (64 mg, 0.46 mmol) at 25° C. under a nitrogen atmosphere. The resulting mixture was stirred at 50° C. for 2 hours under a nitrogen atmosphere, followed by purification by reversed-phase flash chromatography (0-66% ACN in water) to afford 2,2,7-trifluoro-6-(2,3,4,6-tetrafluoro-5-(2-hydroxyethyl)phenyl)-2H-benzo[b][1,4]oxazin-3(4H)-one (Compound 65, 70.0 mg, 77% yield) as a yellow solid: MS (ESI) calculated for ($C_{16}H_8F_7NO_3$) [M−1]⁻ 394.0, found 393.9; ¹H-NMR (400 MHz, DMSO-$d_6$) δ 7.02-6.99 (m, 1H), 6.76-6.75 (m, 1H), 4.98-4.84 (m, 1H), 3.61-3.58 (t, J=6.4 Hz, 2H), 2.84 (t, J=6.8 Hz, 2H); ¹⁹F-NMR (377 MHz, DMSO-d6) δ −72.13, −120.85, −125.77, −137.97, −138.05, −166.14.

As shown in Step 6 of Scheme 39, to a stirred solution of 2,2,7-trifluoro-6-(2,3,4,6-tetrafluoro-5-(2-hydroxyethyl)phenyl)-2H-benzo[b][1,4]oxazin-3(4H)-one (30 mg, 0.07 mmol) and $K_2CO_3$ (16 mg, 0.11 mmol) in DMF (1 mL) was added 3-bromoprop-1-yne (11 mg, 0.09 mmol) at 25° C. under a nitrogen atmosphere. The resulting mixture was stirred at 25° C. for 2 hours under a nitrogen atmosphere, applied to a C18 column, and purified by reversed-phase flash chromatography (0%-70% ACN in water) to afford 2,2,7-trifluoro-4-(prop-2-yn-1-yl)-6-(2,3,4,6-tetrafluoro-5-(2-hydroxyethyl)phenyl)-2H-benzo[b][1,4]oxazin-3(4H)-one (Compound 66, 7 mg, 20% yield) as a white solid: ¹H-NMR (400 MHz, DMSO-$d_6$) δ 7.77-7.67 (m, 2H), 4.98-4.84 (m, 3H), 3.62 (t, J=6.4 Hz, 2H), 3.48-3.40 (m, 1H), 2.87 (t, J=6.8 Hz, 2H); ¹⁹F-NMR (377 MHz, DMSO-$d_6$) δ −75.02, −115.61, −120.43, −135.10, −137.54, −165.54.

BIOLOGICAL EXAMPLES

Example B 1. Testing the Herbicidal Activity of Compounds of the Invention

Protoporphyrinogen oxidase (PPO) inhibition was monitored by the change in fluorescence during the conversion of protoporphyrinogen IX (PPGIX) to protoporphyrin IX (PPIX) (Excitation=550 nm, Emission=625 nm) by PPO.
Cloning of pET28b_PPO_CHis
The coding sequence of AmPPO was optimized for *E. coli* expression and assembled from synthetic oligonucleotides. Synthetic fragments were introduced into a pET28b vector (Novagen) using restriction-less "Hot Fusion" cloning process (Fu C., et al., 'Hot Fusion: An Efficient Method to Clone Multiple DNA Fragments as Well as Inverted Repeats without Ligase,' *PLoS One* (2014) Vol. 9(12), page e115318). The resulting DNA was sequence-verified. Construct encoding mutant version (ΔG210-AmPPO) of the enzyme was produced via PCR-based mutagenesis using Q5 mutagenesis kit (NEB).
*Amaranthus tuberculatum* Protoporphyrinogen Oxidase (AmPPO) Expression
Lysogeny broth (LB media, 10 mL) supplemented with 100 μg/mL kanamyci was inoculated with a single colony of BL21(DE3) competent *E. coli* transformed with pET28b_PPO_CHis. [Is pET28b_PPO_CHis. The culture was grown at 37° C. with shaking at 230 rpm overnight. This culture was then used to inoculate 1 L of autoinduction media (AIM) prepared by the method of Fox, B. G., & Blommel, P. G. (2009), Autoinduction of protein expression, 'Current Protocols in Protein Science,' Chapter 5, Unit-5.23. The resulting culture was grown at 37° C. with shaking at 230 rpm for 4 to 6 hours and an additional 40 to 48 hours at 18° C. The culture was collected and centrifuged. The resulting AmPPO enzyme-containing cell pellets were frozen and stored at −80° C. for future use.
Mutant AmPPO ΔG210 PPO Expression
The same procedure used to produce AmPPO was used to produce mutant ΔG210-AmPPO (a PPO mutant in which the glycine at position 210 is absent), except *E. coli* used was transformed with pET28b_ΔG210 PPO_CHis.
AmPPO and Mutant ΔG210-AmPPO Purifications
A detergent solution was prepared by mixing together the following: 175 mL of B-PER Thermo Scientific); 75 mL of Y-PER (Thermo Scientific); 15 mL of 1M TRIS buffer, pH 9.0, 15 mL of 5M NaCl; 50 mL of glycerol; 2.5 mL of Triton-X100; and 1 mg of Flavin Adenine Dinucleotide (FAD). A portion of this solution (about 80 mL-100 mL) is set aside and supplemented with imidazole to a final concentration of 10 mM and a pH of pH 8.0. The remainder of detergent solution was supplemented with Hen Egg White Lysozyme (Gold Bio, 1 mg/mL) and *Serratia* endonuclease (produced in house) and added to about 45 g of frozen enzyme-containing cell pellets, which were allowed to thaw in the lysis solution with vigorous stirring for 30 minutes at room temperature, then briefly sonicated (30 seconds on 50% power using a VWR brand sonic disruptor). Incubation was continued with stirring for additional 15-30 minutes at 4° C. The lysate was clarified for 35 minutes by centrifugation at 14,000 RPM. The resulting clarified lysate was incubated for 1 hour at 4° C. with gentle stirring with His-SELECT® resin (Sigma, 20 mL of 50% slurry in 20% ethanol, washed 2× with 30 mM TRIS pH 8.1, 10% glycerol, 220 mM NaCl). The resin slurry was transferred to a disposable plastic column and washed with 10 mM Imidazole, 250 mM NaCl, 30 mM TRIS pH 8.5, 10% glycerol until the bound protein was deemed sufficiently washed away from lysate components (about 6-8 column volumes). The resin was then washed thoroughly (about 3 column volumes) with the previously set-aside detergent I-10 final buffer, followed by elution with the same buffer supplemented with 250 mM imidazole, pH 8.1. Enzyme-containing fractions were collected and pooled based on SDS-PAGE analysis. Pooled fractions were diluted with pure glycerol to final concentration of 50% and the AmPPO enzyme or mutant ΔG210-AmPPO was stored at −20° C. in liquid form.
PPO In Vitro Assay
Protoporphyrinogen IX (PPGIX) is prepared by reduction of protoporphyrin IX (PPIX) with a sodium amalgam as described by Jacobs and Jacobs, *Enyzme* 28: 206 (1982).

Once prepared, the PPGIX solution is kept in the dark and all subsequent manipulations of it are performed in the dark.

The Base Buffer for the assay was 50 mM TRIS pH 8.5, 160 mM NaCl, 2 mM DTT, 0.01% Triton X-100. An antifoam solution was prepared by two serial 1 to 10 dilutions of Antifoam B Emulsion (SigmaAldrich) with Milli-Q water. Buffer A was freshly prepared by diluting AmPPO or mutant ΔG210-AmPPO in Base Buffer to 3-8 ug/ml concentration of enzyme. Buffer B was prepared by adding 2 ml of reduced 2 mM PPIX to 60 ml of Base Buffer and adjusting the pH back to 8.5 using glacial acetic acid. Finally, antifoam B (Sigma) was added to 0.01% final concentration. Buffer B is unstable, must be protected from light, and should be used within the next 3 hours.

A 384 well, clear bottom plate was used for the assay (black plate is preferred for the fluorescent assay). Each test compound dissolved in DMSO to a concentration of 30 mM. The test compounds, tested in triplicate, butafenacil control, and a DMSO control were dispensed as 1.2 μL drops into a well of the plate. The wells were diluted with 60 μL of Buffer A and serially diluted 1 volume to 3 volumes over 7 dilutions by removing 20 ?IL from the first well, mixing well with 40 μL if Buffer A in a second well, removing 20 μL from the second well, and continuing the dilutions in this manner until there were 8 test wells. To initiate the reaction, 40 μL of Buffer B was added to each well and the wells gently mixed at least 2 times. The plate was centrifuged at 2000 rpm for 1 minute and the absorbance or fluorescence were read at ambient temperature using a plate reader. $IC_{50}$'s were calculated using a nonlinear regression Sigmoidal dose-response model (GraphPad Prism, variable slope) with curve bottoms constrained to zero and curve tops constrained to plate-specific $V_{average}$.

Each of Compounds 1 to 38 and 40 to 52 had an $IC_{50}$ of less than 100 nM.

Example B2. Testing the Post-Emergence Herbicidal Activity of Compounds of the Invention Selected compounds of the invention were screened at 100 ppm concentration against *Amaranthus retroflexus* (AMARE), *Setaria italica* (SETIT), and *Kochia/Bassia scoparia* (KCHSC).

Accordingly, PPO susceptible weed seeds were sown in 5"×5" pots by quadrant containing Miracle-Gro potting mix (Scotts Miracle-Gro Company, Marysville, OH, USA) and grown in a Conviron growth chamber with appropriate growth conditions (temperature of 26/22° C. with photoperiod 16/8 h light day/night and light intensity of 300 μmol $m^{-2}$ $s^{-1}$ supplemented by LED lamps). Relative humidity in the growth chamber was maintained at around 65%. Plants were grown until 2-4 leaf stage and thinned to 5-8 plants per quadrant per species.

Compounds were formulated in 25% Acetone, 1% Crop oil concentrate (COC-Agridex), 0.1% Tween-20, and 2.5% Ammonium sulphate (AMS). Three replicate pots were treated with each compound. Treatment consisting of the above formulation excluding active compound was applied as a treatment control (TC). Plants were treated with the test compound solution in a laboratory spray chamber fitted with 8003 flat fan nozzles calibrated to deliver 187-200 L $ha^{-1}$ at 269 kPa. Plants were placed back in the growth chamber and evaluated for % visual injury compared to TC 7 days after treatment (DAT). The data presented in Table 3 in which A represents a percentage control, where 100% control indicates complete inhibition of weed growth.

Representative compounds 2, 37, and 52 showed excellent herbicidal activity against weed species at a concentration of 100 parts per million (PPM), as shown in Table 3.

TABLE 3

| Post-emergence herbicidal activity of selected compounds of the invention 7 days after the compound application | | | |
|---|---|---|---|
| Cmpd. | Post-emergence % control (100 PPM) | | |
| No. | AMARE | SETIT | KCHSC |
| 2 | 98 | 58 | 75 |
| 37 | 100 | 58 | 92 |
| 52 | 100 | 72 | 93 |

Example B3. Testing Leaf Penetration and Translocation with and without Crop Oil Concentrate Adjuvant (COC)

Selected compounds of the invention, along with compounds 920-4 and 920-6 from Japanese Patent Application No. 06321920, were tested for leaf penetration, translocation, and herbicidal activity in a grass weed species when applied with or without an adjuvant to increase the compound cuticle penetration.

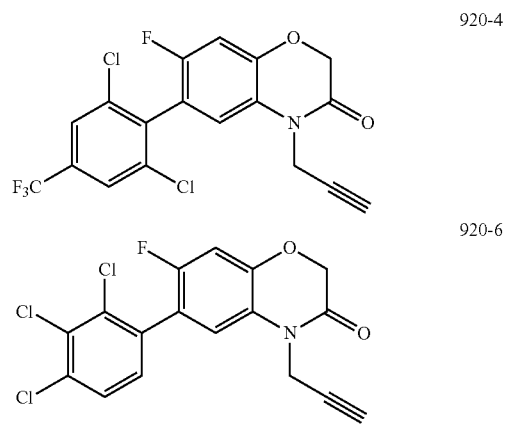

Four to five PPO susceptible *Setaria italica* (Foxtail millet) seed (Ernst Conservation Seeds, Meadville, PA) were sown in each of the 1.5×1.5-inch 6 cell plug inserts containing Miracle-Gro™ potting mix (Scotts Miracle-Gro Company, Marysville, OH, USA) and grown in a Conviron growth chamber with appropriate growth conditions (temperature of 26/22° C. with photoperiod 16/8 h light day/night and light intensity of 300 μmol $m^{-2}$ $s^{-1}$ supplemented by LED lamps). Relative humidity in the growth chamber was maintained at around 65%. Plants were grown until 1-2 leaf stage (one expanded leaf and one emerging leaf) and thinned to single plant per cell.

Test compounds were formulated to a final concentration of 1.5 mM in 25% Acetone, 0.1% Tween-20 and 2.5% Ammonium sulphate (AMS) with or without the addition of 1% v/v Crop oil concentrate (COC, Agridex). A total of 6 μL was applied as 3×2 μL droplets on the adaxial surface of an emerged *Setaria italica* leaf for each of the two compound solutions (with and without COC). Six replicate plants were treated with each compound. Treatment consisting of the above formulation excluding active compound was applied as a treatment control (TC). Plants were placed back in the growth chamber and, seven days after treatment, were evaluated for overall % visual injury compared to TC. Plants were also evaluated for rapid necrosis representative of PPO inhibition at the site of, acropetal to, and basipetal to the droplet application site to estimate the general, xylem, and phloem compound mobility, respectively. In general, compounds with necrosis only at the site of action were considered to be poorly mobile whereas necrosis in the emerging leaf indicates symplastic phloem movement and necrosis from leaf base to tip only on the applied leaf indicates apoplastic xylem movement.

The data are presented in Table 4 are relative to the TC treatment for which the plant and leaf injury percent is consider 0%. "A" represents a percentage leaf or plant injury between 80 and 100%; "B" represents a percentage leaf or plant injury of 20-80%; "C" represents a percentage control below 20%.

As seen in Table 4, Compound Nos. 2, 37, and 52 of the invention surprisingly showed significant improved leaf translocation compared to compounds 920-4 and 920-6.

TABLE 4

Xylem, and phloem mobility for compounds tested.

| Compound | Xylem mobility | | Phloem mobility | |
|---|---|---|---|---|
| No. | COC | No-COC | COC | No-COC |
| 2 | A | A | A | A |
| 37 | A | A | A | A |
| 52 | A | A | A | A |
| 920-4 | A | C | A | C |
| 920-6 | A | C | A | C |

Compounds 920-4 and 920-6 were also assessed for herbicidal activity as described above in Example 34 and compared with compounds of the invention as shown in Table 5. An unexpected improvement in herbicidal activity for the compounds of the invention was observed.

TABLE 5

Herbicidal activity of Compounds 920-4 and 920-6 from Japanese Patent Application No. 06321920 compared to Compounds 2, 37, and 52

| Cmpd. | Post-emergence % control (100 PPM) | | |
|---|---|---|---|
| No. | AMARE | SETIT | KCHSC |
| 920-4 | 89 | 38 | 52 |
| 920-6 | 85 | 18 | 21 |
| 2 | 98 | 58 | 75 |
| 37 | 100 | 58 | 92 |
| 52 | 100 | 72 | 93 |

Example B4. Control of PPO-Resistant Weeds Having a dG210 Mutation

A field experiment was conducted to evaluate the efficacy of Compound 2 controlling a PPO dG210 mutant Tall Waterhemp (*Amaranthus tuberculatus*) population. The field location was selected because of historical documentation of several commercial PPO herbicides failing to control this weed population. The field was prepared by a standard conventional till practice and different herbicide treatments were applied with a backpack carbon dioxide pressurized sprayer at 190 L/ha volume. The applications were made to soybean at pre-emergence stage (1 day after planting) in 10 meters long by 3 meters wide plots arranged in a randomized complete block layout replicated four times. Herbicides were surface applied to the vegetation free soil.

Herbicide treatments included Compound 2 formulated as 10% emulsified concentrate, plus the following commercially available herbicides: Flumioxazin 51, a 51% wettable granule formulation of Flumioxazin (RedEagle International LLC); Zidua SC, a 41% suspension concentrate formulation of Pyroxasulfone (BASF Corporation); and Spartan, a 40% dry flowable formulation of Sulfentrazone (FMC Corporation).

Figure 2A:
FIG. 2A is a photograph showing Compound 2 (60 g ai/ha) PPO dG210 mutant Tall Waterhemp (*Amaranthus tuberculatus*) residual control.
Figure 2B:
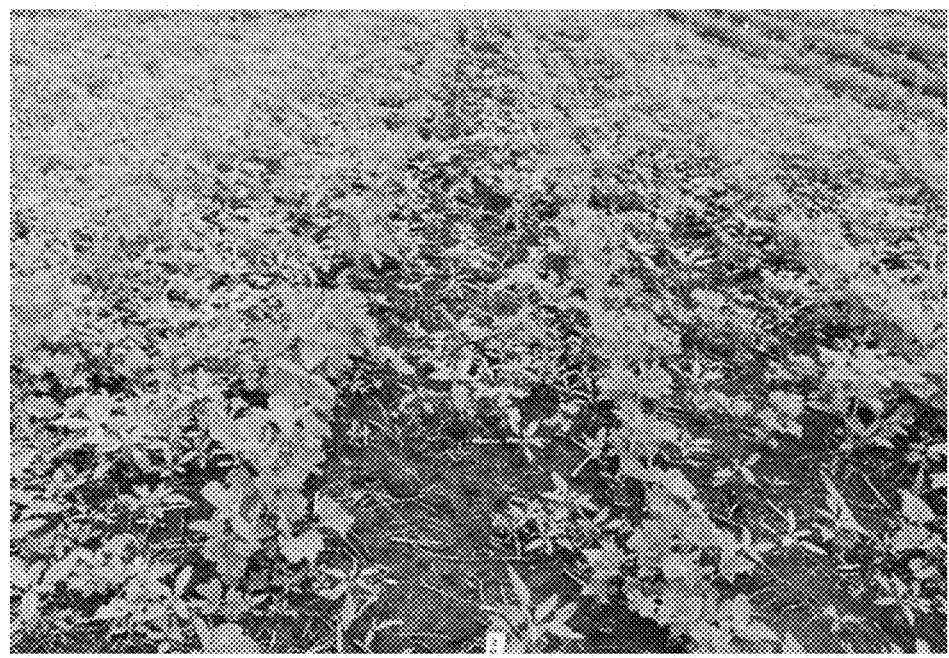
FIG. 2B is a photograph showing Flumioxazin (70 g ai/ha) PPO dG210 resistant Tall Waterhemp (*Amaranthus tuberculatus*) residual control.

Different weed species emergence and development were evaluated four weeks after the herbicide application and quantified as percent of growth control relative to the untreated control treatment, where total absence of control was equal to 0% and complete control was equal to 100%. Table 6 shows the degree of control for the different herbicide treatments and the significant improved biological activity of Compound 2 relative to Flumioxazin, Sulfentrazone, and Pyroxasulfone. The data in the table indicate that Compound 2 was more effective at resistant weed control than the other commercially available herbicides investigated in the experiment. Also see FIGS. 2A and 2B.

TABLE 6

| Compound | Rate (gai/ha) | Weed growth control (%) |
|---|---|---|
| Untreated control | — | 0 |
| Compound 2 | 30 | 65 |
| Compound 2 | 60 | 97 |
| Compound 2 | 90 | 100 |
| Flumioxazin | 70 | 43 |
| Sulfentrazone | 140 | 81 |
| Pyroxasulfone | 280 | 64 |

Further embodiments of the present invention are evident from the claims, the description, and the examples. It is to be understood that the features mentioned above and still to be illustrated below of the subject matter of the invention can be applied not only in the combination given in each particular case but also in other combinations, without leaving the scope of the invention.

What is claimed is:

1. A compound having the structure:

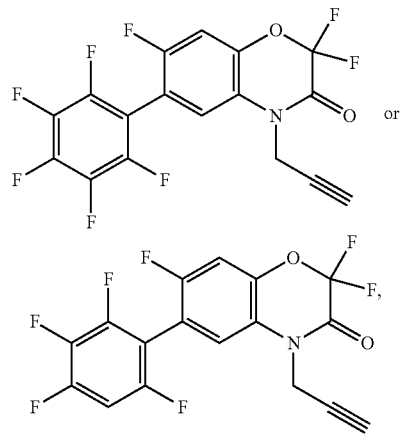

or a salt thereof.

2. The compound of claim 1, wherein the compound is

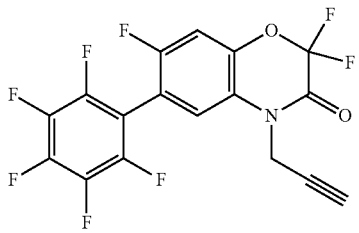

or a salt thereof.

3. The compound of claim 1, wherein the compound is

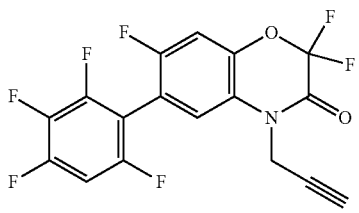 [SMILES: C#CCN1C(=O)C(F)(F)Oc2cc(F)c(-c3c(F)cc(F)c(F)c3F)cc21]

or a salt thereof.

4. An agricultural composition, comprising:
a compound of claim 1, or a salt thereof; and
at least one additional component that serves as a carrier.

5. The agricultural composition of claim 4, wherein the compound is

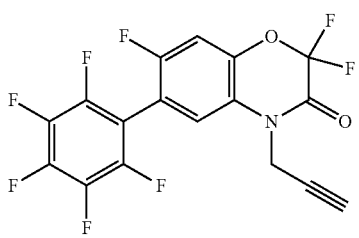

or a salt thereof.

6. The agricultural composition of claim 5, wherein the at least one additional component is a surfactant, a solid diluent, or a liquid diluent.

7. The agricultural composition of claim 4, wherein the compound is

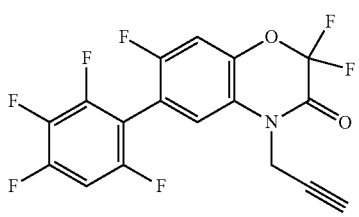 [SMILES: C#CCN1C(=O)C(F)(F)Oc2cc(F)c(-c3c(F)cc(F)c(F)c3F)cc21]

or a salt thereof.

8. The agricultural composition of claim 7, wherein the at least one additional component is a surfactant, a solid diluent, or a liquid diluent.

9. A method of controlling undesired vegetation, comprising contacting the undesired vegetation or its environment with an herbicidally effective amount of a compound of claim 1, or a salt thereof.

10. The method of claim 9, wherein the compound is

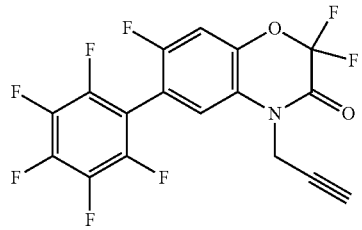 [SMILES: C#CCN1C(=O)C(F)(F)Oc2cc(F)c(-c3c(F)c(F)c(F)c(F)c3F)cc21]

or a salt thereof.

11. The method of claim 10, wherein the undesired vegetation comprises weeds.

12. The method of claim 10, wherein the undesired vegetation comprises protoporphyrinogen IX oxidase (PPO) inhibitor-resistant weeds.

13. The method of claim 12, wherein the PPO inhibitor-resistant weeds have a dG210 mutation.

14. The method of claim 10, wherein the compound or a salt thereof is applied at a rate of 1 to 100 g per 10,000 m$^2$.

15. The method of claim 10, wherein contacting the undesired vegetation or its environment with the compound or a salt thereof leads to postemergence control and/or preemergence control of the undesired vegetation.

16. The method of claim 10, wherein the undesired vegetation is at least 60% controlled.

17. The method of claim 9, wherein the compound is

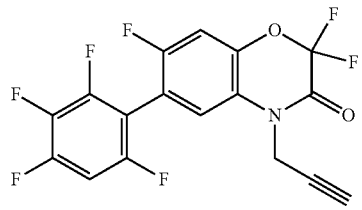 [SMILES: C#CCN1C(=O)C(F)(F)Oc2cc(F)c(-c3c(F)cc(F)c(F)c3F)cc21]

or a salt thereof.

18. The method of claim 17, wherein the undesired vegetation comprises weeds.

19. The method of claim 17, wherein the undesired vegetation comprises protoporphyrinogen IX oxidase (PPO) inhibitor-resistant weeds.

20. The method of claim 19, wherein the PPO inhibitor-resistant weeds have a dG210 mutation.

21. The method of claim 17, wherein the compound or a salt thereof is applied at a rate of 1 to 100 g per 10,000 m$^2$.

22. The method of claim 17, wherein contacting the undesired vegetation or its environment with the compound or a salt thereof leads to postemergence control and/or preemergence control of the undesired vegetation.

23. The method of claim 17, wherein the undesired vegetation is at least 60% controlled.

24. The method of claim 10, wherein contacting the undesired vegetation or its environment with the compound or a salt thereof leads to preemergence control of the undesired vegetation.

25. The method of claim 17, wherein contacting the undesired vegetation or its environment with the compound or a salt thereof leads to preemergence control of the undesired vegetation.

* * * * *